United States Patent
Kym et al.

(10) Patent No.: US 9,567,322 B2
(45) Date of Patent: Feb. 14, 2017

(54) SUBSTITUTED TETRAHYDROPYRANS AND METHOD OF USE

(71) Applicants: AbbVie S.á.r.l., Luxembourg (LU); Galapagos NV, Mechelen (BE)

(72) Inventors: Philip R. Kym, Libertyville, IL (US); Bo Liu, Waukegan, IL (US); Xenia B. Searle, Grayslake, IL (US); Xueqing Wang, Northbrook, IL (US); Ming C. Yeung, Grayslake, IL (US)

(73) Assignees: AbbVie S.á.r.l., Luxembourg (LU); Galapagos NV, Mechelen (BE)

( * ) Notice: Subject to any disclaimer, the term of this patent is extended or adjusted under 35 U.S.C. 154(b) by 0 days.

(21) Appl. No.: 14/926,727

(22) Filed: Oct. 29, 2015

(65) Prior Publication Data
US 2016/0122331 A1    May 5, 2016

Related U.S. Application Data

(60) Provisional application No. 62/073,586, filed on Oct. 31, 2014.

(51) Int. Cl.
| | | |
|---|---|---|
| *C07D 407/12* | (2006.01) | |
| *A61K 45/06* | (2006.01) | |
| *A61K 31/357* | (2006.01) | |

(52) U.S. Cl.
CPC ........... *C07D 407/12* (2013.01); *A61K 31/357* (2013.01); *A61K 45/06* (2013.01)

(58) Field of Classification Search
CPC .............................. C07D 407/12; A61K 45/06
See application file for complete search history.

(56) References Cited

U.S. PATENT DOCUMENTS

| | | |
|---|---|---|
| 2005/0148648 A1 | 7/2005 | Ruah et al. |
| 2010/0022543 A1 | 1/2010 | Melvin et al. |
| 2013/0296379 A1 | 11/2013 | Keshavarz-Shokri et al. |
| 2013/0317020 A1 | 11/2013 | Ruah et al. |

FOREIGN PATENT DOCUMENTS

| | | |
|---|---|---|
| WO | 2014/160440 A1 | 10/2014 |
| WO | 2014160440 A1 | 10/2014 |

OTHER PUBLICATIONS

International Search Report and Written Opinion issued in PCT Application No. PCT/US15/58043, mailed Feb. 2, 2016, 7 pages.
PCT International Search Report and Written Opinion, PCT/US2015/058043, Feb. 2, 2016, 10 pages.

*Primary Examiner* — Noble Jarrell
*Assistant Examiner* — John S Kenyon
(74) *Attorney, Agent, or Firm* — Quarles & Brady LLP

(57) ABSTRACT

Compounds of formula (I)

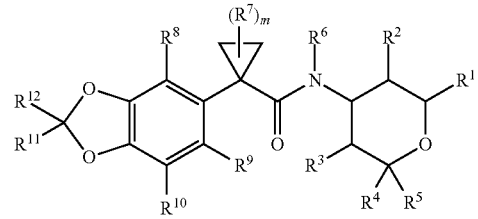

and pharmaceutically acceptable salts or radiolabelled forms thereof, wherein $R^1$, $R^2$, $R^3$, $R^4$, $R^5$, $R^6$, $R^7$, $R^8$, $R^9$, $R^{10}$, $R^{11}$, $R^{12}$ and m are as defined in the specification, are useful in treating conditions or disorders prevented by or ameliorated by the Cystic Fibrosis Transmembrane Conductance Regulator (CFTR) protein. Methods for making the compounds are described. Also described are pharmaceutical compositions of compounds of formula (I), and methods for using such compounds and compositions.

98 Claims, No Drawings

SUBSTITUTED TETRAHYDROPYRANS AND METHOD OF USE

This application claims priority to U.S. Provisional Patent Application No. 60/073,586, filed Oct. 31, 2014, which is incorporated herein by reference for all purposes.

BACKGROUND OF THE INVENTION

Technical Field

The invention relates to substituted tetrahydropyran compounds that are modulators of the Cystic Fibrosis Transmembrane Conductance Regulator (CFTR) protein, useful in treating diseases and conditions mediated and modulated by CFTR. Additionally, the invention relates to compositions containing compounds of the invention and processes for their preparation.

Description of Related Technology

Cystic fibrosis (CF), one of the most common autosomal recessive genetic diseases in the Caucasian population, is caused by loss of function mutations in the Cystic Fibrosis Transmembrane Conductance Regulator (CFTR) gene, which is located on chromosome 7 (http://www.cff.org/AboutCF/; Rowe S. M et al. (2005); *N Eng J Med.* (352), 1992-2001). Approximately 1:3500 and 1:3000 infants born in the United States and in Europe, respectively, are affected by CF, resulting in ~75,000 cases worldwide, ~30,000 of which are in the United State. Approximately 1,000 new cases of CF are diagnosed each year, with more than 75% of patients being diagnosed by 2 years of age. Nearly half the CF population is currently 18 years of age and older. The CFTR protein (Gregory, R. J. et al. (1990) Nature 347:382-386; Rich, D. P. et al. (1990) Nature 347:358-362), (Riordan, J. R. et al. (1989) Science 245:1066-1073) is a cAMP/ATP-mediated ion channel expressed in a variety of cell types, including secretory and absorptive epithelial cells. CFTR regulates chloride and bicarbonate anion flux across the cell membrane, maintaining electro neutrality and osmolarity across the epithelial membrane (Quinton, P. M. (1990), *FASEB J.* 4: 2709-2727). CFTR is also responsible for regulating the activity of other ion channels and proteins (Guggino, W. B. et al. (2006), *Nat Revs Molecular Cell Biology* 7, 426-436).

Aberrations in CFTR function result in imbalance of the airway surface liquid, leading to mucus dehydration, inflammation, recurrent bacterial infection and irreversible lung damage, which lead to premature death in affected patients. Besides respiratory disease, CF patients suffer from gastrointestinal problems and pancreatic insufficiency. The majority of males (95%) with cystic fibrosis are infertile as a result of azoospermia caused by altered vas deferens; which may be absent, atrophic, or fibrotic. Fertility is also decreased among females with cystic fibrosis due to abnormal cervical mucus.

The F508del mutation, the most common of the approximately 1900 identified polymorphisms in CFTR, results in defective processing of CFTR in the endoplasmic reticulum (ER) (http://www.cftr2.org/index.php). Approximately 90% of the CF patients carry at least one copy of the F508del mutation (deletion of a phenylalanine on position 508), and 50%-60% of the patients are homozygous for this mutation. The defective processing of CFTR results in early CFTR degradation, which leads to reduced trafficking or absence of the protein on the membrane. As there have been over 100 CF disease-causing mutations identified, they have been classified according to their phenotypic consequences and belong to synthesis, maturation, regulation, conductance, reduced number due to quantity and reduced number due to stability classifications.

Current CF drug discovery efforts focus upon developing two classes of compounds to modulate CFTR. One class, called Correctors, helps to overcome the folding defects of the mutated CFTR protein to promote its maturation resulting in higher cell surface expression. The other classes of compounds, called Potentiators, help overcome the defective regulation and/or conductance of the protein by increasing the probability of channel opening on the membrane surface.

In addition, as the modulation of CFTR protein mutations to promote proper protein folding is beneficial for CF, there are other diseases mediated by CFTR. For example, Sjögren's Syndrome (SS), an autoimmune disorder that results in symptoms of xerostomia (dry mouth) and keratoconjunctivitis sicca (KCS, dry eyes) may result from dysregulation of moisture producing glands throughout the body. Chronic obstructive lung disease (COLD), or chronic obstructive airway disease (COAD), which is a progressive and irreversible airflow limitation in the airways, is result of several physiologic abnormalities, including mucus hyper secretion and impaired mucociliary secretion. Increasing the anion secretion by CFTR potentiators has been suggested to overcome these phenotypic complexities with Sjögren's Syndrome by increasing the corneal hydration and by overcoming the impaired mucociliary secretion in COAD (Bhowmik A, et al. (2009); Vol. 103(4), 496-502. Sloane P, et al. PLOS One (2012); Vol 7(6), 239809 (1-13)).

Accordingly, there is a need for novel compounds able to modulate CFTR. In particular, the present invention discloses compounds that may act as CFTR modulators for the treatment of cystic fibrosis. The present invention also provides methods for the preparation of these compounds, pharmaceutical compositions comprising these compounds and methods for the treatment of cystic fibrosis by administering the compounds of the invention.

SUMMARY

The invention is directed to tetrahydropyrans having a structure of formula (I)

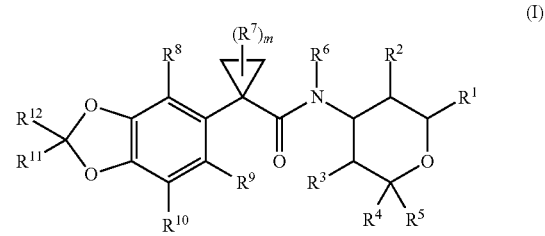

or a pharmaceutically acceptable salt thereof, wherein:
$R^1$ is phenyl, phenyl fused to a $C_3$-$C_6$cycloalkyl, or phenyl fused to a 4-6-membered heterocycle, wherein the phenyl, the phenyl of phenyl fused to a $C_3$-$C_6$cycloalkyl, or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)

$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^A$;

wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^1$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$;

wherein the $C_3$-$C_6$cycloalkyl of phenyl fused to a $C_3$-$C_6$cycloalkyl or the 4-6-membered heterocycle of phenyl fused to a 4-6-membered heterocycle are each optionally substituted with 1, 2 or 3 independently selected $R^s$ groups;

m is 0, 1, 2, or 3;

$R^s$ and $R^t$, at each occurrence, are each independently $C_1$-$C_6$alkyl, halogen, —CN, oxo, —$NO_2$, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, or $G^C$, wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^D$;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —OC(O)N($R^j$)$_2$, —$SR^j$, —C(O)$OR^j$, —C(O)N($R^j$)$_2$, —N($R^j$)$_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —OC(O)N($R^j$)$_2$, —$SR^j$, —C(O)$OR^j$, —C(O)N($R^j$)$_2$, —N($R^j$)$_2$, —CN, and $G^E$;

$R^2$ and $R^3$ are each independently hydrogen, $C_1$-$C_6$haloalkyl, or $C_1$-$C_6$alkyl;

$R^4$ and $R^5$ are each independently hydrogen, $C_1$-$C_6$haloalkyl, $C_1$-$C_6$alkyl or $G^F$, wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), and —N($R^h$)C(O)N($R^h$)$_2$; or $R^4$ and $R^5$ together with the carbon atom to which they are attached, form a $C_3$-$C_6$cycloalkyl or a 4-6-membered heterocycle; wherein the $C_3$-$C_6$cycloalkyl and the 4-6-membered heterocycle are each optionally substituted with 1, 2, or 3 independently selected $R^t$ groups;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, $G^C$, $G^D$, $G^E$, and $G^F$ at each occurrence, are each independently cycloalkyl, cycloalkenyl, heterocycle, aryl, or heteroaryl, each of which is independently unsubstituted or substituted with 1, 2, or 3 independently selected $R^u$ groups; wherein, $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —OC(O)$R^k$, —OC(O)N($R^j$)$_2$, —$SR^j$, —S(O)$_2R^j$, —S(O)$_2$N($R^j$)$_2$, —C(O)$R^k$, —C(O)$OR^j$, —C(O)N($R^j$)$_2$, —N($R^j$)$_2$, —N($R^j$)C(O)$R^k$, —N($R^j$)S(O)$_2R^k$, —N($R^j$)C(O)O($R^k$), —N($R^j$)C(O)N($R^j$)$_2$, —($C_1$-$C_6$alkylenyl)-$OR^j$, —($C_1$-$C_6$alkylenyl)-OC(O)$R^k$, —($C_1$-$C_6$alkylenyl)-OC(O)N($R^j$)$_2$, —($C_1$-$C_6$alkylenyl)-$SR^j$, —($C_1$-$C_6$alkylenyl)-S(O)$_2R^k$, —($C_1$-$C_6$alkylenyl)-S(O)$_2$N($R^j$)$_2$, —($C_1$-$C_6$alkylenyl)-C(O)$R^k$, —($C_1$-$C_6$alkylenyl)-C(O)$OR^j$, —($C_1$-$C_6$alkylenyl)-C(O)N($R^j$)$_2$, —($C_1$-$C_6$alkylenyl)-N($R^j$)$_2$, —($C_1$-$C_6$alkylenyl)-N($R^j$)C(O)$R^k$, —($C_1$-$C_6$alkylenyl)-N($R^j$)S(O)$_2R^k$, —($C_1$-$C_6$alkylenyl)-N($R^j$)C(O)O($R^k$), —($C_1$-$C_6$alkylenyl)-N($R^j$)C(O)N($R^j$)$_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

Another aspect of the invention relates to pharmaceutical compositions comprising compounds of the invention or pharmaceutically acceptable salts thereof, and a pharmaceutical carrier. Such compositions can be administered in accordance with a method of the invention, typically as part of a therapeutic regimen for treatment or prevention of conditions and disorders related to Cystic Fibrosis Transmembrane Conductance Regulator activity. In a particular aspect, the pharmaceutical compositions may additionally comprise further one or more therapeutically active ingredients suitable for use in combination with the compounds of the invention. In a more particular aspect, the further therapeutically active ingredient is an agent for the treatment of cystic fibrosis.

Moreover, the compounds of the invention or pharmaceutically acceptable salts thereof, useful in the pharmaceutical compositions and treatment methods disclosed herein, are pharmaceutically acceptable as prepared and used.

Yet another aspect of the invention relates to a method of correcting the folding defects of the mutated CFTR protein(s) to promote its maturation resulting in higher cell surface expression. The method is useful for treating, or preventing conditions and disorders related to Cystic Fibrosis Transmembrane Conductance Regulator activity in mammals. More particularly, the method is useful for treating or preventing conditions and disorders related to cystic fibrosis, Sjögren's syndrome, pancreatic insufficiency, chronic obstructive lung disease, or chronic obstructive airway disease. Accordingly, the compounds and compositions of the invention are useful as a medicament for treating or preventing Cystic Fibrosis Transmembrane Conductance Regulator modulated disease.

The compounds, compositions comprising the compounds or pharmaceutically acceptable salts thereof, methods for making the compounds, and methods for treating or preventing conditions and disorders by administering the compounds are further described herein.

In a particular aspect, the compounds of the invention or pharmaceutically acceptable salts thereof are provided for use in the treatment of cystic fibrosis. In a particular aspect, the compounds of the invention or pharmaceutically acceptable salts thereof are provided for use in the treatment of cystic fibrosis caused by class I, II, III, IV, V, and/or VI mutations.

The present invention also provides pharmaceutical compositions comprising a compound of the invention or pharmaceutically acceptable salts thereof, and a suitable pharmaceutical carrier for use in medicine. In a particular aspect, the pharmaceutical composition is for use in the treatment of cystic fibrosis.

In an alternative embodiment, certain compounds of the invention have a corrector activity.

These and other objects of the invention are described in the following paragraphs. These objects should not be deemed to narrow the scope of the invention.

DETAILED DESCRIPTION OF THE INVENTION

Compounds of formula (I) are described in this invention

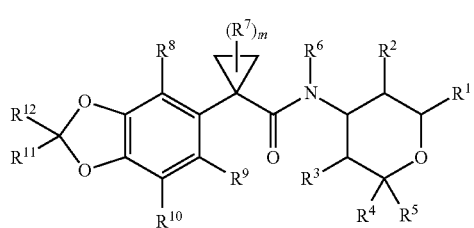

(I)

wherein $R^1$, $R^2$, $R^3$, $R^4$, $R^5$, $R^6$, $R^7$, $R^8$, $R^9$, $R^{10}$, $R^{11}$, $R^{12}$, and m are as defined above in the Summary. Compositions comprising such compounds and methods for treating conditions and disorders using such compounds and compositions are also described.

In various embodiments, the invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds which can be isolated from a reaction mixture.

DEFINITION OF TERMS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

Certain terms as used in the specification are intended to refer to the following definitions, as detailed below.

The term "alkenyl" as used herein, means a straight or branched hydrocarbon chain containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond.

Representative examples of alkenylene include, but are not limited to, —CH=CH—, —CH=CH$_2$CH$_2$—, and —CH=C(CH$_3$)CH$_2$—.

The term "alkyl" as used herein, means a straight or branched, saturated hydrocarbon chain containing from 1 to 10 carbon atoms. The term "lower alkyl" or "$C_1$-$C_6$alkyl" means a straight or branched chain hydrocarbon containing from 1 to 6 carbon atoms. The term "$C_1$-$C_3$alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" or "alkylenyl" denotes a divalent group derived from a straight or branched chain hydrocarbon containing from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the invention can be unsubstituted or substituted.

The term "carbonyl" as used herein means a —C(=O)— group.

The term "cyano" as used herein, means a —CN group.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group, or a bridged monocyclic ring system in which two non-adjacent carbon atoms of the monocyclic ring are linked by an alkylene bridge containing one, two, three, or four carbon atoms. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "cycloalkyl" or "cycloalkane" as used herein, means a monocyclic, a bicyclic, a tricyclic, or a spirocyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo [3.1.1]heptane, bicyclo[2.2.1]heptane, bicyclo[2.2.2]octane, bicyclo[3.2.2]nonane, bicyclo[3.3.1]nonane, and bicyclo [4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1. 0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The spirocyclic cycloalkyl groups of the invention can be appended to the parent molecular moiety through any substitutable carbon atom of the groups.

The term "halo" or "halogen" as used herein, means Cl, Br, I, or F.

The term "haloalkyl" as used herein, means an alkyl group, as defined herein, in which one, two, three, four, five, six, seven or eight hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the invention can be substituted or unsubstituted and are connected to the parent molecular moiety through any carbon atom or any nitrogen atom contained within the ring systems.

The term "heterocycle" or "heterocyclic" as used herein, means a monocyclic heterocycle, a bicyclic heterocycle, a tricyclic heterocycle, or a spirocyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), oxa-adamantane (2-oxatricyclo[3.3.1.1$^{3,7}$]decane), and octahydro-1H-4,7-epiminoisoindole. The spirocyclic heterocycles are exemplified by a monocyclic heterocycle as defined herein wherein one carbon atom of the monocyclic heterocycle is bridged by two ends of an alkylene chain. In the spirocyclic heterocycle, one or more carbon atoms in the bridging alkylene chain may be replaced with a heteroatom. Examples of spirocyclic heterocycles include, but are not limited to, 4,7-diazaspiro[2.5]octane, 2-oxa-6-azaspiro[3.3]heptane, 2,6-diazaspiro[3.3]heptane, 2-oxa-5,8-diazaspiro[3.5]nonane, 2,7-diazaspiro[3.5]nonane, 1,4-dioxa-8-azaspiro[4.5]decane, 1,6-diazaspiro[3.3]heptane, 1-azaspiro[4.4]nonane, 7-azaspiro[3.5]nonane, 1,4-dioxa-7-azaspiro[4.4]nonane, 5,8-diazaspiro[3.5]nonane, 5,8-dioxa-2-azaspiro[3.4]octane, 2-oxa-6-azaspiro[3.4]octane, 6-oxa-1-azaspiro[3.3]heptane, 6-oxa-2-azaspiro[3.4]octane, 6-oxa-2-azaspiro[3.5]nonane, and 7-oxa-2-azaspiro[3.5]nonane. The monocyclic, bicyclic, tricyclic, and spirocyclic heterocycles are connected to the parent molecular moiety through any carbon atom or any nitrogen atom contained within the rings, and can be unsubstituted or substituted.

The term "4-6-membered heterocycle" as used herein, means a 4, 5, or 6 membered monocyclic heterocycle as defined herein above. Examples of 4-6-membered heterocycle include azetidinyl, pyrrolidinyl, tetrahydrofuranyl, tetrahydropyranyl, piperazinyl, piperidinyl, thiomorpholinyl, 1,3-dioxolanyl and morpholinyl. The 4-6-membered heterocycles, including exemplary rings, are optionally substituted unless indicated otherwise.

The term "heteroatom" as used herein, means a nitrogen, oxygen, or sulfur atom.

The term "hydroxyl" or "hydroxy" as used herein, means an —OH group.

The term "oxo" as used herein means (=O).

In some instances, the number of carbon atoms in a hydrocarbyl substituent (e.g., alkyl, alkenyl, alkynyl, or cycloalkyl) is indicated by the prefix "$C_x$-$C_y$", wherein x is the minimum and y is the maximum number of carbon atoms in the substituent. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In preferred embodiments, the subject is a human.

The term 'one or more' refers to one to four. In one embodiment it refers to one or three. In another embodiment it refers to one to three. In a further embodiment it refers to one to two. In yet other embodiment it refers to two. In yet other further embodiment it refers to one.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G; G1349D; S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5](5T allele), c.S3140-26A>G (3272-26A>G), c.3850-2477C>T (3849+10kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326dellTC, or 4279insA mutations. More particularly, Class VI mutation(s) refers to Rescued F508del mutations.

Compounds of the Invention

Compounds of the invention can have the formula (I) as described in the Summary.

Particular values of variable groups in compounds of formula (I) are as follows. Such values can be used where appropriate with any of the other values, definitions, claims or embodiments defined hereinbefore or hereinafter.

In one embodiment, $R^1$ is phenyl, phenyl fused to a $C_3$-$C_6$cycloalkyl, or phenyl fused to a 4-6-membered heterocycle, wherein the phenyl, the phenyl of phenyl fused to a $C_3$-$C_6$cycloalkyl, or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$;
wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;
wherein the $C_3$-$C_6$cycloalkyl of phenyl fused to a $C_3$-$C_6$cycloalkyl or the 4-6-membered heterocycle of phenyl fused to a 4-6-membered heterocycle are each optionally substituted with 1, 2 or 3 independently selected $R^s$ groups.

In one embodiment, $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$.
wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$.

In one embodiment, $R^1$ is phenyl, wherein the phenyl is optionally substituted with one, two or three $R^x$ groups, wherein each $R^x$ group is independently selected from $C_1$-$C_6$alkyl, halogen, —C(O)R$^i$, and —C(O)OR$^h$,
wherein the $C_1$-$C_6$alkyl is optionally substituted with one, two or three substituents independently selected from the group consisting of fluorine, and —OR$^h$.

In one embodiment, $R^1$ is phenyl fused to a $C_3$-$C_6$cycloalkyl, wherein the phenyl of phenyl fused to a $C_3$-$C_6$cycloalkyl is optionally substituted with one, two, or three $R^x$ groups, wherein each $R^x$ group is independently selected, at each occurrence, from $C_1$-$C_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$;
wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;
wherein the $C_3$-$C_6$cycloalkyl of phenyl fused to a $C_3$-$C_6$cycloalkyl is optionally substituted with 1, 2 or 3 independently selected $R^s$ groups.

In one embodiment, $R^1$ is phenyl fused to a $C_3$-$C_6$cycloalkyl, wherein the phenyl of phenyl fused to a $C_3$-$C_6$cycloalkyl is optionally substituted with one, two or three $R^x$ groups, wherein each $R^x$ group is independently selected from $C_1$-$C_6$alkyl, halogen, —C(O)R$^i$, and —C(O)OR$^h$,
wherein the $C_1$-$C_6$alkyl is optionally substituted with one, two or three substituents independently selected from the group consisting of fluorine and —OR$^h$;
wherein the $C_3$-$C_6$cycloalkyl of phenyl fused to a $C_3$-$C_6$cycloalkyl is optionally substituted with 1, 2 or 3 independently selected $R^s$ groups.

In one embodiment, $R^1$ is phenyl fused to a 4-6-membered heterocycle, wherein the phenyl of phenyl fused to a 4-6-membered heterocycle is optionally substituted with one, two, or three $R^x$ groups, wherein each $R^x$ group is independently selected, at each occurrence, from $C_1$-$C_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$;
wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;
wherein the 4-6-membered heterocycle of phenyl fused to a 4-6-membered heterocycle is optionally substituted with 1, 2 or 3 independently selected $R^s$ groups.

In one embodiment, $R^1$ is phenyl fused to a 4-6-membered heterocycle, wherein the phenyl of phenyl fused to a 4-6-membered heterocycle is optionally substituted with one $R^x$ group, wherein the $R^x$ group is selected from $C_1$-$C_6$alkyl, halogen, —C(O)R$^i$, and —C(O)OR$^h$, wherein the $C_1$-$C_6$alkyl is optionally substituted with one, two or three substituents independently selected from the group consisting of fluorine and —$OR^h$;

wherein the 4-6-membered heterocycle of phenyl fused to a $C_3$-$C_6$cycloalkyl is optionally substituted with 1, 2 or 3 independently selected $R^s$ groups.

In one embodiment, m is 0, 1, 2, or 3.
In one embodiment, m is 0, 1, or 2.
In one embodiment, m is 0 or 1.
In one embodiment, m is 0.
In one embodiment, m is 1.
In one embodiment, m is 2.
In one embodiment, m is 3.

In one embodiment, $R^s$ and $R^t$, at each occurrence, are each independently $C_1$-$C_6$alkyl, halogen, —CN, oxo, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, or $G^C$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^D$.

In one embodiment, $R^s$ is $C_1$-$C_6$alkyl, halogen, —CN, oxo, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, or $G^C$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^D$.

In one embodiment, $R^s$ is $C_1$-$C_6$alkyl or halogen, wherein the $C_1$-$C_6$alkyl is optionally substituted with one, two or three substituents independently selected from the group consisting of fluorine and —$OR^h$.

In one embodiment, $R^t$ is $C_1$-$C_6$alkyl or halogen, wherein the $C_1$-$C_6$alkyl is optionally substituted with one, two or three substituents independently selected from the group consisting of fluorine and —$OR^h$.

In one embodiment, $R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$.

In one embodiment, $R^h$, at each occurrence, is independently hydrogen, $C_1$-$C_6$haloalkyl, or $C_1$-$C_6$alkyl.

In one embodiment, $R^h$ is hydrogen.
In one embodiment, $R^h$ is $C_1$-$C_6$haloalkyl.
In one embodiment, $R^h$ is $C_1$-$C_6$alkyl.

In one embodiment, $R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$.

In one embodiment, $R^i$, at each occurrence, is independently $C_1$-$C_6$haloalkyl or $C_1$-$C_6$alkyl.

In one embodiment, $R^i$ is $C_1$-$C_6$haloalkyl.

In one embodiment, $R^i$ is $C_1$-$C_6$alkyl.

In one embodiment, $R^2$ and $R^3$ are each independently hydrogen, $C_1$-$C_6$haloalkyl, or $C_1$-$C_6$alkyl.

In one embodiment, $R^2$ is hydrogen.
In one embodiment, $R^2$ is $C_1$-$C_6$haloalkyl.
In one embodiment, $R^2$ is $C_1$-$C_6$alkyl.
In one embodiment, $R^3$ is hydrogen.
In one embodiment, $R^3$ is $C_1$-$C_6$haloalkyl.
In one embodiment, $R^3$ is $C_1$-$C_6$alkyl.

In one embodiment, $R^4$ and $R^5$ are each independently hydrogen, $C_1$-$C_6$haloalkyl, $C_1$-$C_6$alkyl or $G^F$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$.

In one embodiment, $R^4$ and $R^5$ are each independently hydrogen, $C_1$-$C_6$haloalkyl or $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$.

In one embodiment, $R^4$ and $R^5$ are each hydrogen.

In one embodiment, $R^4$ and $R^5$ are each $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$.

In one embodiment, $R^4$ and $R^5$ are each $C_1$-$C_6$alkyl.

In one embodiment, $R^4$ is hydrogen and $R^5$ is $G^F$, wherein $G^F$ is cycloalkyl, cycloalkenyl, heterocycle, aryl, or heteroaryl unsubstituted or substituted with 1, 2, or 3 independently selected $R^u$ groups.

In one embodiment, $R^4$ is hydrogen and $R^5$ is $G^F$, wherein $G^F$ is $C_3$-$C_6$cycloalkyl unsubstituted or substituted with 1, 2, or 3 independently selected $R^u$ groups.

In one embodiment, $R^4$ is hydrogen and $R^5$ is $G^F$, wherein $G^F$ is cyclopropyl.

In one embodiment, $R^4$ is hydrogen and $R^5$ is $G^F$, wherein $G^F$ is aryl or heteroaryl unsubstituted or substituted with 1, 2, or 3 independently selected $R^u$ groups.

In one embodiment, $R^4$ is hydrogen and $R^5$ is $G^F$, wherein $G^F$ is aryl unsubstituted or substituted with 1, 2, or 3 independently selected $R^u$ groups.

In one embodiment, $R^4$ is hydrogen and $R^5$ is $G^F$, wherein $G^F$ is phenyl unsubstituted or substituted with 1, 2, or 3 independently selected $R^u$ groups.

In one embodiment, $R^4$ is hydrogen and $R^5$ phenyl.

In one embodiment, $R^4$ and $R^5$ together with the carbon atom to which they are attached, form a $C_3$-$C_6$cycloalkyl or a 4-6-membered heterocycle; wherein the $C_3$-$C_6$cycloalkyl and the 4-6-membered heterocycle are each optionally substituted with 1, 2, or 3 independently selected $R^t$ groups.

In one embodiment, $R^4$ and $R^5$ together with the carbon atom to which they are attached, form a $C_3$-$C_6$cycloalkyl; wherein the $C_3$-$C_6$cycloalkyl is optionally substituted with 1, 2, or 3 independently selected $R^t$ groups.

In one embodiment, $R^4$ and $R^5$ together with the carbon atom to which they are attached, form a 4-6-membered heterocycle; wherein the 4-6-membered heterocycle is optionally substituted with 1, 2, or 3 independently selected $R^t$ groups.

In one embodiment, $R^6$ is hydrogen, $C_1$-$C_6$haloalkyl, or $C_1$-$C_6$alkyl.

In one embodiment, $R^6$ is hydrogen.

In one embodiment, $R^6$ is $C_1$-$C_6$haloalkyl.

In one embodiment, $R^6$ is $C_1$-$C_6$alkyl.

In one embodiment, $R^7$ is an optional substituent on the cyclopropyl ring, and at each occurrence, is independently halogen, $C_1$-$C_6$haloalkyl, or $C_1$-$C_6$alkyl.

In one embodiment, $R^7$ is an optional substituent on the cyclopropyl ring, and at each occurrence, is halogen.

In one embodiment, $R^7$ is an optional substituent on the cyclopropyl ring, and at each occurrence, is $C_1$-$C_6$haloalkyl.

In one embodiment, $R^7$ is an optional substituent on the cyclopropyl ring, and at each occurrence, is $C_1$-$C_6$alkyl.

In one embodiment, $R^8$, $R^9$, and $R^{10}$ are each independently hydrogen, halogen, —$OR^j$, $C_1$-$C_6$haloalkyl, or $C_1$-$C_6$alkyl.

In one embodiment, $R^8$ is hydrogen, halogen, —$OR^j$, $C_1$-$C_6$haloalkyl, or $C_1$-$C_6$alkyl.

In one embodiment, $R^8$ is hydrogen.

In one embodiment, $R^9$ is hydrogen, halogen, —$OR^j$, $C_1$-$C_6$haloalkyl, or $C_1$-$C_6$alkyl.

In one embodiment, $R^9$ is hydrogen.

In one embodiment, $R^{10}$ is hydrogen, halogen, —$OR^j$, $C_1$-$C_6$haloalkyl, or $C_1$-$C_6$alkyl.

In one embodiment, $R^{10}$ is hydrogen.

In one embodiment, $R^{11}$ and $R^{12}$ are each independently hydrogen, $C_1$-$C_3$alkyl, or halogen.

In one embodiment, $R^{11}$ and $R^{12}$ are each hydrogen.

In one embodiment, $R^{11}$ and $R^{12}$ are each $C_1$-$C_3$alkyl.

In one embodiment, $R^{11}$ and $R^{12}$ are each halogen.

In one embodiment, $R^{11}$ and $R^{12}$ are each fluorine.

In one embodiment, $G^A$, $G^B$, $G^C$, $G^D$, $G^E$, and $G^F$ at each occurrence, are each independently cycloalkyl, cycloalkenyl, heterocycle, aryl, or heteroaryl, each of which is independently unsubstituted or substituted with 1, 2, or 3 independently selected $R^u$ groups.

In one embodiment, $G^A$ is cycloalkyl, cycloalkenyl, heterocycle, aryl, or heteroaryl unsubstituted or substituted with 1, 2, or 3 independently selected $R^u$ groups.

In one embodiment, $G^B$ is cycloalkyl, cycloalkenyl, heterocycle, aryl, or heteroaryl unsubstituted or substituted with 1, 2, or 3 independently selected $R^u$ groups.

In one embodiment, $G^C$ is cycloalkyl, cycloalkenyl, heterocycle, aryl, or heteroaryl unsubstituted or substituted with 1, 2, or 3 independently selected $R^u$ groups.

In one embodiment, $G^D$ is cycloalkyl, cycloalkenyl, heterocycle, aryl, or heteroaryl unsubstituted or substituted with 1, 2, or 3 independently selected $R^u$ groups.

In one embodiment, $G^E$ is cycloalkyl, cycloalkenyl, heterocycle, aryl, or heteroaryl unsubstituted or substituted with 1, 2, or 3 independently selected $R^u$ groups.

In one embodiment, $G^F$ is cycloalkyl, cycloalkenyl, heterocycle, aryl, or heteroaryl unsubstituted or substituted with 1, 2, or 3 independently selected $R^u$ groups.

In one embodiment, $G^A$ is phenyl unsubstituted or substituted with 1, 2, or 3 independently selected $R^u$ groups.

In one embodiment, $G^B$ is phenyl unsubstituted or substituted with 1, 2, or 3 independently selected $R^u$ groups.

In one embodiment, $G^C$ is phenyl unsubstituted or substituted with 1, 2, or 3 independently selected $R^u$ groups.

In one embodiment, $G^D$ is phenyl unsubstituted or substituted with 1, 2, or 3 independently selected $R^u$ groups.

In one embodiment, $G^E$ is phenyl unsubstituted or substituted with 1, 2, or 3 independently selected $R^u$ groups.

In one embodiment, $G^F$ is phenyl unsubstituted or substituted with 1, 2, or 3 independently selected $R^u$ groups.

In one embodiment, $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$alkylenyl)-$OR^j$, —($C_1$-$C_6$alkylenyl)-$OC(O)R^k$, —($C_1$-$C_6$alkylenyl)-$OC(O)N(R^j)_2$, —($C_1$-$C_6$alkylenyl)-$SR^j$, —($C_1$-$C_6$alkylenyl)-$S(O)_2R^j$, —($C_1$-$C_6$alkylenyl)-$S(O)_2N(R^j)_2$, —($C_1$-$C_6$alkylenyl)-$C(O)R^k$, —($C_1$-$C_6$alkylenyl)-$C(O)OR^j$, —($C_1$-$C_6$alkylenyl)-$C(O)N(R^j)_2$, —($C_1$-$C_6$alkylenyl)-$N(R^j)_2$, —($C_1$-$C_6$alkylenyl)-$N(R^j)C(O)R^k$, —($C_1$-$C_6$alkylenyl)-$N(R^j)S(O)_2R^k$, —($C_1$-$C_6$alkylenyl)-$N(R^j)C(O)O(R^k)$, —($C_1$-$C_6$alkylenyl)-$N(R^j)C(O)N(R^j)_2$, or —($C_1$-$C_6$alkylenyl)-CN.

In one embodiment, $R^u$, at each occurrence, is independently $C_1$-$C_6$alkyl, halogen, $C_1$-$C_6$haloalkyl, —CN, oxo, —$NO_2$, —$OR^j$, —$S(O)_2R^j$, —$S(O)_2N(R^j)_2$, —$C(O)R^k$, —$C(O)OR^j$, —$C(O)N(R^j)_2$, —$N(R^j)C(O)R^k$, or —$N(R^j)S(O)_2R^k$.

In one embodiment, $R^u$, at each occurrence, is independently $C_1$-$C_6$alkyl, halogen, $C_1$-$C_6$haloalkyl, —$OR^j$, —$C(O)R^k$, or —$C(O)OR^j$.

In one embodiment, $R^j$, at each occurrence, is independently hydrogen, $C_1$-$C_6$alkyl, or $C_1$-$C_6$haloalkyl.

In one embodiment, $R^j$ is hydrogen.

In one embodiment, $R^j$ is $C_1$-$C_6$alkyl.

In one embodiment, $R^j$ is $C_1$-$C_6$haloalkyl.

In one embodiment, $R^k$, at each occurrence, is independently $C_1$-$C_6$alkyl or $C_1$-$C_6$haloalkyl.

In one embodiment, $R^k$ is $C_1$-$C_6$alkyl.

In one embodiment, $R^k$ is $C_1$-$C_6$haloalkyl.

In one embodiment, in a compound or pharmaceutically acceptable salt of formula (I), $R^1$ is phenyl, phenyl fused to a $C_3$-$C_6$cycloalkyl, or phenyl fused to a 4-6-membered heterocycle, wherein the phenyl, the phenyl of phenyl fused to a $C_3$-$C_6$cycloalkyl, or the phenyl of phenyl fused to a 4-6-membered heterocycle are independently optionally substituted with one two or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;

wherein the $C_3$-$C_6$cycloalkyl of phenyl fused to a $C_3$-$C_6$cycloalkyl or the 4-6-membered heterocycle of phenyl fused to a 4-6-membered heterocycle are each optionally substituted with 1, 2 or 3 independently selected $R^s$ groups;

m is 0, 1, 2, or 3;

$R^s$ and $R^t$, at each occurrence, are each independently $C_1$-$C_6$alkyl, halogen, —CN, oxo, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C$ (O)N($R^h$)$_2$, or $G^C$, wherein the $C_1$-$C_6$alkyl is optionally substituted with one, two or three substituents independently selected from the group consisting of fluorine, —O$R^h$, —OC(O)$R^i$, —OC(O)N($R^h$)$_2$, —S$R^h$, —S(O)$_2$$R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2$$R^i$, —N($R^h$)C(O)O($R^i$), —N($R^h$)C(O)N($R^h$)$_2$, and $G^D$;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —O$R^j$, —OC(O)N($R^j$)$_2$, —S$R^j$, —C(O)O$R^j$, —C(O)N($R^j$)$_2$, —N($R^j$)$_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —O$R^j$, —OC(O)N($R^j$)$_2$, —S$R^j$, —C(O)O$R^j$, —C(O)N($R^j$)$_2$, —N($R^j$)$_2$, —CN, and $G^E$;

$R^2$ and $R^3$ are each hydrogen;

$R^4$ and $R^5$ are each hydrogen;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —O$R^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, G, $G^D$, $G^E$, and $G^F$ at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —NO$_2$, —O$R^j$, —OC(O)$R^k$, —OC(O)N($R^j$)$_2$, —S$R^j$, —S(O)$_2$$R^j$, —S(O)$_2$N($R^j$)$_2$, —C(O)$R^k$, —C(O)O$R^j$, —C(O)N($R^j$)$_2$, —N($R^j$)$_2$, —N($R^j$)C(O)$R^k$, —N($R^j$)S(O)$_2$$R^k$, —N($R^j$)C(O)O($R^k$), —N($R^j$)C(O)N($R^j$)$_2$, —($C_1$-$C_6$alkylenyl)-O$R^j$, —($C_1$-$C_6$alkylenyl)-OC(O)$R^k$, —($C_1$-$C_6$alkylenyl)-OC(O)N($R^j$)$_2$, —($C_1$-$C_6$alkylenyl)-S$R^j$, —($C_1$-$C_6$alkylenyl)-S(O)$_2$$R^j$, —($C_1$-$C_6$alkylenyl)-S(O)$_2$N($R^j$)$_2$, —($C_1$-$C_6$alkylenyl)-C(O)$R^k$, —($C_1$-$C_6$alkylenyl)-C(O)O$R^j$, —($C_1$-$C_6$alkylenyl)-C(O)N($R^j$)$_2$, —($C_1$-$C_6$alkylenyl)-N($R^j$)$_2$, —($C_1$-$C_6$alkylenyl)-N($R^j$)C(O)$R^k$, —($C_1$-$C_6$alkylenyl)-N($R^j$)S(O)$_2$$R^k$, —($C_1$-$C_6$alkylenyl)-N($R^j$)C(O)O($R^k$), —($C_1$-$C_6$alkylenyl)-N($R^j$)C(O)N($R^j$)$_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (I), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —NO$_2$, —O$R^h$, —OC(O)$R^i$, —OC(O)N($R^h$)$_2$, —S$R^h$, —S(O)$_2$$R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2$$R^i$, —N($R^h$)C(O)O($R^i$), —N($R^h$)C(O)N($R^h$)$_2$, and $G^A$;

wherein the $C_1$-$C_6$alkyl is optionally substituted with one, two or three substituents independently selected from the group consisting of fluorine, —O$R^h$, —OC(O)$R^i$, —OC(O)N($R^h$)$_2$, —S$R^h$, —S(O)$_2$$R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2$$R^i$, —N($R^h$)C(O)O($R^i$), —N($R^h$)C(O)N($R^h$)$_2$, and -$G^B$;

m is 0, 1, 2, or 3;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —O$R^j$, —OC(O)N($R^j$)$_2$, —S$R^j$, —C(O)O$R^j$, —C(O)N($R^j$)$_2$, —N($R^j$)$_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —O$R^j$, —OC(O)N($R^j$)$_2$, —S$R^j$, —C(O)O$R^j$, —C(O)N($R^j$)$_2$, —N($R^j$)$_2$, —CN, and $G^E$;

$R^2$ and $R^3$ are each hydrogen;

$R^4$ and $R^5$ are each hydrogen;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —O$R^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —NO$_2$, —O$R^j$, —OC(O)$R^k$, —OC(O)N($R^j$)$_2$, —S$R^j$, —S(O)$_2$$R^j$, —S(O)$_2$N($R^j$)$_2$, —C(O)$R^k$, —C(O)O$R^j$, —C(O)N($R^j$)$_2$, —N($R^j$)$_2$, —N($R^j$)C(O)$R^k$, —N($R^j$)S(O)$_2$$R^k$, —N($R^j$)C(O)O($R^k$), —N($R^j$)C(O)N($R^j$)$_2$, —($C_1$-$C_6$alkylenyl)-O$R^j$, —($C_1$-$C_6$alkylenyl)-OC(O)$R^k$, —($C_1$-$C_6$alkylenyl)-OC(O)N($R^j$)$_2$, —($C_1$-$C_6$alkylenyl)-S$R^j$, —($C_1$-$C_6$alkylenyl)-S(O)$_2$$R^j$, —($C_1$-$C_6$alkylenyl)-S(O)$_2$N($R^j$)$_2$, —($C_1$-$C_6$alkylenyl)-C(O)$R^k$, —($C_1$-$C_6$alkylenyl)-C(O)O$R^j$, —($C_1$-$C_6$alkylenyl)-C(O)N($R^j$)$_2$, —($C_1$-$C_6$alkylenyl)-N($R^j$)$_2$, —($C_1$-$C_6$alkylenyl)-N($R^j$)C(O)$R^k$, —($C_1$-$C_6$alkylenyl)-N($R^j$)S(O)$_2$$R^k$, —($C_1$-$C_6$alkylenyl)-N($R^j$)C(O)O($R^k$), —($C_1$-$C_6$alkylenyl)-N($R^j$)C(O)N($R^j$)$_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (I), $R^1$ is phenyl, wherein the phenyl is optionally substituted with one, two, or three $R^x$ groups, wherein the $R^x$ group is independently selected from $C_1$-$C_6$alkyl, halogen, —O$R^h$, —C(O)$R^i$, and —C(O)O$R^h$, wherein the $C_1$-$C_6$alkyl is optionally substituted with one, two or three substituents independently selected from the group consisting of fluorine and —O$R^h$;

m is 0, 1, 2, or 3;

$R^h$, at each occurrence, is independently hydrogen, $C_1$-$C_6$haloalkyl or $C_1$-$C_6$alkyl;

$R^i$ is $C_1$-$C_6$haloalkyl, or $C_1$-$C_6$alkyl;

$R^2$ and $R^3$ are each hydrogen;

$R^4$ and $R^5$ are each hydrogen;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen; and $R^j$, at each occurrence, is independently hydrogen, $C_1$-$C_6$alkyl, or $C_1$-$C_6$haloalkyl.

In one embodiment, in a compound or pharmaceutically acceptable salt of formula (I), $R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$;

m is 0;

$R^h$, at each occurrence, is independently hydrogen, $C_1$-$C_6$haloalkyl or $C_1$-$C_6$alkyl;

$R^i$ is $C_1$-$C_6$haloalkyl, or $C_1$-$C_6$alkyl;

$R^2$ and $R^3$ are each hydrogen;

$R^4$ and $R^5$ are each hydrogen;

$R^6$ is hydrogen;

$R^8$, $R^9$, and $R^{10}$ are each hydrogen; and $R^{11}$ and $R^{12}$ are each halogen.

In one embodiment, in a compound or pharmaceutically acceptable salt of formula (I), $R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$;

m is 0;

$R^h$, at each occurrence, is independently hydrogen, $C_1$-$C_6$haloalkyl or $C_1$-$C_6$alkyl;

$R^i$ is $C_1$-$C_6$haloalkyl, or $C_1$-$C_6$alkyl;

$R^2$ and $R^3$ are each hydrogen;

$R^4$ and $R^5$ are each hydrogen;

$R^6$ is hydrogen;

$R^8$, $R^9$, and $R^{10}$ are each hydrogen; and $R^{11}$ and $R^{12}$ are each fluorine.

In one embodiment, the compound or pharmaceutically acceptable salt is a cis diastereomer of formula (II), wherein

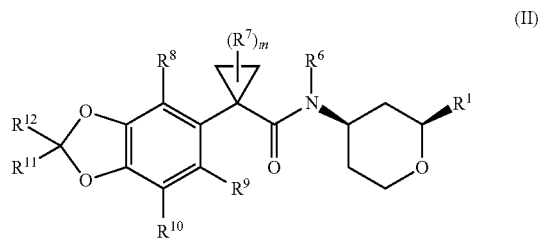

(II)

$R^1$ is phenyl or phenyl fused to a 4-6-membered heterocycle, wherein the phenyl or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;

wherein the 4-6-membered heterocycle of phenyl fused to a 4-6-membered heterocycle is optionally substituted with 1, 2 or 3 independently selected $R^s$ groups;

m is 0, 1, 2, or 3;

$R^s$, at each occurrence, is independently $C_1$-$C_6$alkyl, halogen, —CN, oxo, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, or $G^C$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^D$;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, $G^C$, $G^D$, and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$alkylenyl)-$OR^j$, —($C_1$-$C_6$alkylenyl)-$OC(O)R^k$, —($C_1$-$C_6$alkylenyl)-$OC(O)N(R^j)_2$, —($C_1$-$C_6$alkylenyl)-$SR^j$, —($C_1$-$C_6$alkylenyl)-$S(O)_2R^j$, —($C_1$-$C_6$alkylenyl)-$S(O)_2N(R^j)_2$, —($C_1$-$C_6$alkylenyl)-$C(O)R^k$, —($C_1$-$C_6$alkylenyl)-$C(O)OR^j$, —($C_1$-$C_6$alkylenyl)-$C(O)N(R^j)_2$, —($C_1$-$C_6$alkylenyl)-$N(R^j)_2$, —($C_1$-$C_6$alkylenyl)-$N(R^j)C(O)R^k$, —($C_1$-$C_6$alkylenyl)-$N(R^j)S(O)_2R^k$, —($C_1$-$C_6$alkylenyl)-$N(R^j)C(O)O(R^k)$, —($C_1$-$C_6$alkylenyl)-$N(R^j)C(O)N(R^j)_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (II), $R^1$ is phenyl fused to a 4-6-membered heterocycle, wherein the phenyl of phenyl fused to a 4-6-membered heterocycle is independently optionally substituted with one, two, or three $R^x$ groups, wherein each $R^x$ group is independently selected, at each occurrence, from $C_1$-$C_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$,
 wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;
 wherein the 4-6-membered heterocycle of phenyl fused to a 4-6-membered heterocycle is optionally substituted with 1, 2 or 3 independently selected $R^s$ groups;
 m is 0, 1, 2, or 3;
 $R^s$, at each occurrence, is independently $C_1$-$C_6$alkyl, halogen, —CN, oxo, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, or G$^C$, wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^D$;
 $R^h$, at each occurrence, is independently hydrogen, $C_1$-$C_6$haloalkyl, $C_1$-$C_6$alkyl, or G$^A$, wherein the $C_1$-$C_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;
 $R^i$, at each occurrence, is independently $C_1$-$C_6$haloalkyl, $C_1$-$C_6$alkyl, or G$^A$, wherein the $C_1$-$C_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;
 $R^6$ is hydrogen, $C_1$-$C_6$haloalkyl, or $C_1$-$C_6$alkyl;
 $R^7$ is an optional substituent on the cyclopropyl ring, and at each occurrence, is independently halogen, $C_1$-$C_6$haloalkyl, or $C_1$-$C_6$alkyl;
 $R^8$, $R^9$, and $R^{10}$ are each independently hydrogen, halogen, —OR$^j$, $C_1$-$C_6$haloalkyl, or $C_1$-$C_6$alkyl;
 $R^{11}$ and $R^{12}$ are each independently hydrogen, $C_1$-$C_3$alkyl, or halogen;
 G$^A$, G$^B$, G$^C$, G$^D$, and G$^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein
 $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;
 $R^j$, at each occurrence, is independently hydrogen, $C_1$-$C_6$alkyl, or $C_1$-$C_6$haloalkyl; and
 $R^k$, at each occurrence, is independently $C_1$-$C_6$alkyl or $C_1$-$C_6$haloalkyl.

In one embodiment, in a compound or pharmaceutically acceptable salt of formula (II), $R^1$ is phenyl fused to a 4-6-membered heterocycle, wherein the phenyl of phenyl fused to a 4-6-membered heterocycle is optionally substituted with one, two, or three $R^x$ groups, wherein each $R^x$ group is independently selected from $C_1$-$C_6$alkyl, halogen, —OR$^h$, —C(O)R$^i$, and —C(O)OR$^h$;
 wherein the $C_1$-$C_6$alkyl is optionally substituted with one, two or three substituents independently selected from the group consisting of fluorine and —OR$^h$;
 wherein the 4-6-membered heterocycle of phenyl fused to a 4-6-membered heterocycle is optionally substituted with 1, 2 or 3 independently selected $R^s$ groups;
 m is 0;
 $R^s$, at each occurrence, is independently $C_1$-$C_6$alkyl, halogen, —CN, oxo, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, or G$^C$, wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^D$;
 $R^h$, at each occurrence, is independently hydrogen, $C_1$-$C_6$haloalkyl, or $C_1$-$C_6$alkyl;
 $R^i$, at each occurrence, is independently $C_1$-$C_6$haloalkyl, $C_1$-$C_6$alkyl, or G$^A$, wherein the $C_1$-$C_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;
 $R^6$ is hydrogen;
 $R^8$, $R^9$, and $R^{10}$ are each hydrogen;
 $R^{11}$ and $R^{12}$ are each halogen;
 G$^A$, G$^C$, G$^D$, and G$^E$ at each occurrence, are each independently cycloalkyl, cycloalkenyl, heterocycle, aryl, or heteroaryl, each of which is independently unsubstituted or substituted with 1, 2, or 3 independently selected $R^u$ groups; wherein
 $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

In one embodiment, in a compound or pharmaceutically acceptable salt of formula (II), R$^1$ is phenyl fused to a 4-6-membered heterocycle, wherein the phenyl of phenyl fused to a 4-6-membered heterocycle is optionally substituted with one, two, or three R$^x$ groups, wherein each R$^x$ group is independently selected from C$_1$-C$_6$alkyl, halogen, —OR$^h$, —C(O)R$^i$, and —C(O)OR$^h$;

wherein the C$_1$-C$_6$alkyl is optionally substituted with one, two or three substituents independently selected from the group consisting of fluorine and —OR$^h$;

wherein the 4-6-membered heterocycle of phenyl fused to a 4-6-membered heterocycle is optionally substituted with 1, 2 or 3 independently selected R$^s$ groups;

m is 0;

R$^s$, at each occurrence, is independently C$_1$-C$_6$alkyl, halogen, —CN, oxo, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, or G$^C$, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^D$;

R$^h$, at each occurrence, is independently hydrogen, C$_1$-C$_6$haloalkyl, or C$_1$-C$_6$alkyl;

R$^i$, at each occurrence, is independently C$_1$-C$_6$haloalkyl, C$_1$-C$_6$alkyl, or G$^A$, wherein the C$_1$-C$_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;

R$^6$ is hydrogen;

R$^8$, R$^9$, and R$^{10}$ are each hydrogen;

R$^{11}$ and R$^{12}$ are each fluorine;

G$^C$, G$^D$, and G$^E$ at each occurrence, are each independently cycloalkyl, cycloalkenyl, heterocycle, aryl, or heteroaryl, each of which is independently unsubstituted or substituted with 1, 2, or 3 independently selected R$^u$ groups; wherein R$^u$, at each occurrence, is independently C$_1$-C$_6$alkyl, C$_2$-C$_6$alkenyl, C$_2$-C$_6$alkynyl, halogen, C$_1$-C$_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

In one embodiment, the compound or pharmaceutically acceptable salt is an enantiomer of formula (IIa).

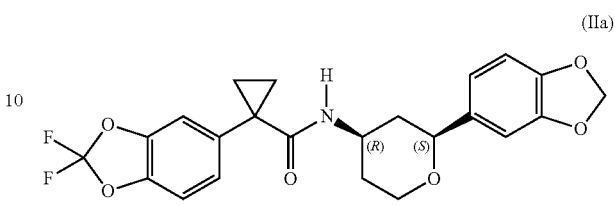

(IIa)

In one embodiment, the compound or pharmaceutically acceptable salt is an enantiomer of formula (IIb).

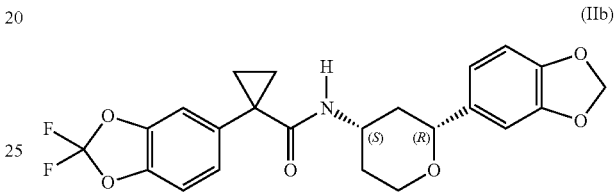

(IIb)

In one embodiment, in a compound or pharmaceutically acceptable salt of formula (II), R$^1$ is phenyl, wherein the phenyl is optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;

m is 0, 1, 2, or 3;

R$^h$, at each occurrence, is independently hydrogen, C$_1$-C$_6$haloalkyl, C$_1$-C$_6$alkyl, or G$^A$, wherein the C$_1$-C$_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;

R$^i$, at each occurrence, is independently C$_1$-C$_6$haloalkyl, C$_1$-C$_6$alkyl, or G$^A$, wherein the C$_1$-C$_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;

R$^6$ is hydrogen, C$_1$-C$_6$haloalkyl, or C$_1$-C$_6$alkyl;

R$^7$ is an optional substituent on the cyclopropyl ring, and at each occurrence, is independently halogen, C$_1$-C$_6$haloalkyl, or C$_1$-C$_6$alkyl;

R$^8$, R$^9$, and R$^{10}$ are each independently hydrogen, halogen, —OR$^j$, C$_1$-C$_6$haloalkyl, or C$_1$-C$_6$alkyl;

R$^{11}$ and R$^{12}$ are each independently hydrogen, C$_1$-C$_3$alkyl, or halogen;

$G^A$, $G^B$ and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —OC(O)$R^k$, —OC(O)N($R^j$)$_2$, —$SR^j$, —S(O)$_2R^j$, —S(O)$_2$N($R^j$)$_2$, —C(O)$R^k$, —C(O)O$R^j$, —C(O)N($R^j$)$_2$, —N($R^j$)$_2$, —N($R^j$)C(O)$R^k$, —N($R^j$)S(O)$_2R^k$, —N($R^j$)C(O)O($R^k$), —N($R^j$)C(O)N($R^j$)$_2$, —($C_1$-$C_6$alkylenyl)-$OR^j$, —($C_1$-$C_6$alkylenyl)-OC(O)$R^k$, —($C_1$-$C_6$alkylenyl)-OC(O)N($R^j$)$_2$, —($C_1$-$C_6$alkylenyl)-$SR^j$, —($C_1$-$C_6$alkylenyl)-S(O)$_2R^j$, —($C_1$-$C_6$alkylenyl)-S(O)$_2$N($R^j$)$_2$, —($C_1$-$C_6$alkylenyl)-C(O)$R^k$, —($C_1$-$C_6$alkylenyl)-C(O)O$R^j$, —($C_1$-$C_6$alkylenyl)-C(O)N($R^j$)$_2$, —($C_1$-$C_6$alkylenyl)-N($R^j$)$_2$, —($C_1$-$C_6$alkylenyl)-N($R^j$)C(O)$R^k$, —($C_1$-$C_6$alkylenyl)-N($R^j$)S(O)$_2R^k$, —($C_1$-$C_6$alkylenyl)-N($R^j$)C(O)O($R^k$), —($C_1$-$C_6$alkylenyl)-N($R^j$)C(O)N($R^j$)$_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (II), $R^1$ is phenyl, wherein the phenyl is optionally substituted with one, two, or three $R^x$ groups, wherein each $R^x$ group is independently selected from $C_1$-$C_6$alkyl, halogen, —$OR^h$, —C(O)$R^i$ and —C(O)O$R^h$, wherein the $C_1$-$C_6$alkyl is optionally substituted with one, two or three substituents independently selected from the group consisting of fluorine and —$OR^h$;

m is 0;

$R^h$, at each occurrence, is independently hydrogen, $C_1$-$C_6$haloalkyl, or $C_1$-$C_6$alkyl;

$R^i$ is $C_1$-$C_6$haloalkyl, or $C_1$-$C_6$alkyl;

$R^6$ is hydrogen;

$R^8$, $R^9$, and $R^{10}$ are each hydrogen; and $R^{11}$ and $R^{12}$ are each halogen.

In one embodiment, in a compound or pharmaceutically acceptable salt of formula (II), $R^1$ is phenyl, wherein the phenyl is optionally substituted with one, two, or three $R^x$ groups, wherein each $R^x$ group is independently selected from $C_1$-$C_6$alkyl, halogen, —$OR^h$, —C(O)$R^i$ and —C(O)O$R^h$, wherein the $C_1$-$C_6$alkyl is optionally substituted with one, two or three substituents independently selected from the group consisting of fluorine and —$OR^h$;

m is 0;

$R^h$, at each occurrence, is independently hydrogen, $C_1$-$C_6$haloalkyl, or $C_1$-$C_6$alkyl;

$R^i$ is $C_1$-$C_6$haloalkyl, or $C_1$-$C_6$alkyl;

$R^6$ is hydrogen;

$R^8$, $R^9$, and $R^{10}$ are each hydrogen; and $R^{11}$ and $R^{12}$ are each fluorine.

In one embodiment, the compound or pharmaceutically acceptable salt is an enantiomer of formula (IIc), wherein

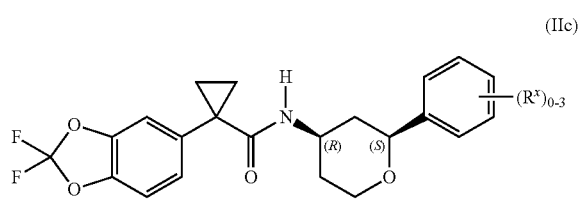

(IIc)

each $R^x$ is an optional substituent independently selected from $C_1$-$C_6$alkyl, halogen, —$OR^h$, —C(O)$R^i$, and —C(O)O$R^h$, wherein, the $C_1$-$C_6$alkyl is optionally substituted with one, two or three substituents independently selected from the group consisting of fluorine and —$OR^h$;

$R^h$ is hydrogen, $C_1$-$C_6$haloalkyl, or $C_1$-$C_6$alkyl; and $R^i$ is $C_1$-$C_6$haloalkyl, or $C_1$-$C_6$alkyl.

In one embodiment, the compound or pharmaceutically acceptable salt is an enantiomer of formula (IId), wherein

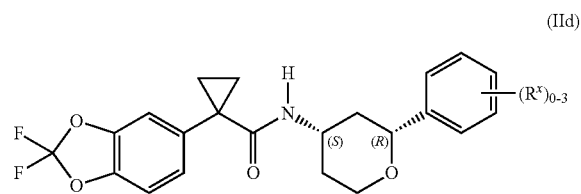

(IId)

each $R^x$ is an optional substituent independently selected from $C_1$-$C_6$alkyl, halogen, —$OR^h$, —C(O)$R^i$, and —C(O)O$R^h$, wherein, the $C_1$-$C_6$alkyl is optionally substituted with one, two or three substituents independently selected from the group consisting of fluorine and —$OR^h$;

$R^h$ is hydrogen, $C_1$-$C_6$haloalkyl, or $C_1$-$C_6$alkyl; and $R^i$ is $C_1$-$C_6$haloalkyl, or $C_1$-$C_6$alkyl In one embodiment, the compound or pharmaceutically acceptable salt is a trans diastereomer of formula (III), wherein,

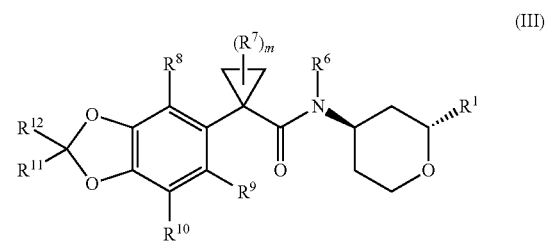

(III)

$R^1$ is phenyl or phenyl fused to a 4-6-membered heterocycle, wherein the phenyl or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —$NO_2$, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^A$, wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$;

wherein the 4-6-membered heterocycle of phenyl fused to a 4-6-membered heterocycle is optionally substituted with 1, 2 or 3 independently selected $R^s$ groups;

m is 0, 1, 2, or 3;

$R^s$, at each occurrence, is independently $C_1$-$C_6$alkyl, halogen, —CN, oxo, —$NO_2$, —$OR^h$, —OC(O)$R^i$, —OC(O)

$N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, or $G^C$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^D$;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, $G^C$, $G^D$ and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$alkylenyl)-$OR^j$, —($C_1$-$C_6$alkylenyl)-$OC(O)R^k$, —($C_1$-$C_6$alkylenyl)-$OC(O)N(R^j)_2$, —($C_1$-$C_6$alkylenyl)-$SR^j$, —($C_1$-$C_6$alkylenyl)-$S(O)_2R^j$, —($C_1$-$C_6$alkylenyl)-$S(O)_2N(R^j)_2$, —($C_1$-$C_6$alkylenyl)-$C(O)R^k$, —($C_1$-$C_6$alkylenyl)-$C(O)OR^j$, —($C_1$-$C_6$alkylenyl)-$C(O)N(R^j)_2$, —($C_1$-$C_6$alkylenyl)-$N(R^j)_2$, —($C_1$-$C_6$alkylenyl)-$N(R^j)C(O)R^k$, —($C_1$-$C_6$alkylenyl)-$N(R^j)S(O)_2R^k$, —($C_1$-$C_6$alkylenyl)-$N(R^j)C(O)O(R^k)$, —($C_1$-$C_6$alkylenyl)-$N(R^j)C(O)N(R^j)_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, the compound is a trans diastereomer or pharmaceutically acceptable salt of formula (III), wherein, $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;

m is 0, 1, 2, or 3;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$ and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$alkylenyl)-$OR^j$, —($C_1$-$C_6$alkylenyl)-$OC(O)R^k$, —($C_1$-$C_6$alkylenyl)-$OC(O)N(R^j)_2$, —($C_1$-$C_6$alkylenyl)-$SR^j$, —($C_1$-$C_6$alkylenyl)-$S(O)_2R^j$, —($C_1$-$C_6$alkylenyl)-$S(O)_2N(R^j)_2$, —($C_1$-$C_6$alkylenyl)-$C(O)R^k$, —($C_1$-$C_6$alkylenyl)-$C(O)OR^j$, —($C_1$-$C_6$alkylenyl)-$C(O)N(R^j)_2$, —($C_1$-$C_6$alkylenyl)-$N(R^j)_2$, —($C_1$-$C_6$alkylenyl)-$N(R^j)C(O)R^k$, —($C_1$-$C_6$alkylenyl)-$N(R^j)S(O)_2R^k$, —($C_1$-$C_6$alkylenyl)-$N(R^j)C(O)O(R^k)$, —($C_1$-$C_6$alkylenyl)-$N(R^j)C(O)N(R^j)_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, the compound is a trans diastereomer or pharmaceutically acceptable salt of formula (III), wherein, $R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$;

m is 0;

$R^h$ is hydrogen, $C_1$-$C_6$haloalkyl, or $C_1$-$C_6$alkyl;

$R^i$ is $C_1$-$C_6$haloalkyl, or $C_1$-$C_6$alkyl;

$R^6$ is hydrogen;

$R^8$, $R^9$, and $R^{10}$ are each hydrogen; and $R^{11}$ and $R^{12}$ are each halogen.

In one embodiment, the compound is a trans diastereomer or pharmaceutically acceptable salt of formula (III), wherein, $R^1$ is phenyl, wherein the phenyl is optionally substituted with one, two, or three $R^x$ groups, wherein each $R^x$ group is independently selected from $C_1$-$C_6$alkyl, halogen, —$OR^h$, —C(O)$R^i$, and —C(O)O$R^h$, wherein the $C_1$-$C_6$alkyl is optionally substituted with one, two or three substituents independently selected from the group consisting of fluorine and —$OR^h$;

m is 0;

$R^h$ is hydrogen, $C_1$-$C_6$haloalkyl, or $C_1$-$C_6$alkyl;

$R^i$ is $C_1$-$C_6$haloalkyl, or $C_1$-$C_6$alkyl;

$R^6$ is hydrogen;

$R^8$, $R^9$, and $R^{10}$ are each hydrogen; and $R^{11}$ and $R^{12}$ are each fluorine.

In one embodiment, the compound or pharmaceutically acceptable salt is an enantiomer of formula (IIIa), wherein

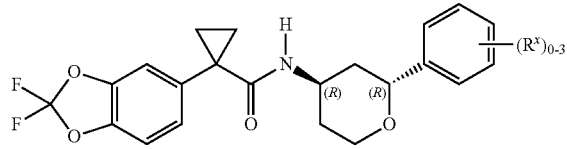

(IIIa)

each $R^x$ is an optional substituent independently selected from $C_1$-$C_6$alkyl, halogen, —$OR^h$, —C(O)$R^i$, and —C(O)O$R^h$, wherein, the $C_1$-$C_6$alkyl is optionally substituted with one, two or three substituents independently selected from the group consisting of fluorine and —$OR^h$;

$R^h$ is hydrogen, $C_1$-$C_6$haloalkyl, or $C_1$-$C_6$alkyl; and $R^i$ is $C_1$-$C_6$haloalkyl, or $C_1$-$C_6$alkyl.

In one embodiment, the compound or pharmaceutically acceptable salt is an enantiomer of formula (IIIb), wherein

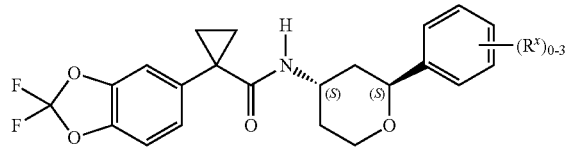

(IIIb)

each $R^x$ is an optional substituent independently selected from $C_1$-$C_6$alkyl, halogen, —$OR^h$, —C(O)$R^i$, and —C(O)O$R^h$, wherein, the $C_1$-$C_6$alkyl is optionally substituted with one, two or three substituents independently selected from the group consisting of fluorine and —$OR^h$;

$R^h$ is hydrogen, $C_1$-$C_6$haloalkyl, or $C_1$-$C_6$alkyl; and $R^i$ is $C_1$-$C_6$haloalkyl, or $C_1$-$C_6$alkyl.

In one embodiment, in a compound or pharmaceutically acceptable salt of formula (I), $R^1$ is phenyl, phenyl fused to a $C_3$-$C_6$cycloalkyl, or phenyl fused to a 4-6-membered heterocycle, wherein the phenyl, the phenyl of phenyl fused to a $C_3$-$C_6$cycloalkyl, or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —$NO_2$, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^A$, wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$;

wherein the $C_3$-$C_6$cycloalkyl of phenyl fused to a $C_3$-$C_6$cycloalkyl or the 4-6-membered heterocycle of phenyl fused to a 4-6-membered heterocycle are each optionally substituted with 1, 2 or 3 independently selected $R^s$ groups;

m is 0, 1, 2, or 3;

$R^s$, at each occurrence, is independently $C_1$-$C_6$alkyl, halogen, —CN, oxo, —$NO_2$, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, or $G^C$, wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^D$;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —OC(O)N($R^j$)$_2$, —$SR^j$, —C(O)O$R^j$, —C(O)N($R^j$)$_2$, —N($R^j$)$_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —OC(O)N($R^j$)$_2$, —$SR^j$, —C(O)O$R^j$, —C(O)N($R^j$)$_2$, —N($R^j$)$_2$, —CN, and $G^E$;

$R^2$ and $R^3$ are each hydrogen;

$R^4$ is hydrogen;

$R^5$ is $G^F$, wherein $G^F$ is $C_3$-$C_7$cycloalkyl, $C_5$-$C_7$cycloalkenyl, heterocycle, aryl or heteroaryl, each of which is independently unsubstituted or substituted with 1, 2, or 3 independently selected $R^u$ groups;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, $G^C$, $G^D$, and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —OC(O)$R^k$, —OC(O)N($R^j$)$_2$, —$SR^j$, —S(O)$_2R^j$, —S(O)$_2$N($R^j$)$_2$, —C(O)$R^k$, —C(O)O$R^j$, —C(O)N($R^j$)$_2$, —N($R^j$)$_2$, —N($R^j$)C(O)$R^k$, —N($R^j$)S(O)$_2R^k$, —N($R^j$)C(O)O($R^k$), —N($R^j$)C(O)N($R^j$)$_2$, —($C_1$-$C_6$alkylenyl)-$OR^j$, —($C_1$-$C_6$alkylenyl)-OC(O)$R^k$, —($C_1$-

$C_6$alkylenyl)-OC(O)N($R^j$)$_2$, —($C_1$-$C_6$alkylenyl)-S$R^j$, —($C_1$-$C_6$alkylenyl)-S(O)$_2R^j$, —($C_1$-$C_6$alkylenyl)-S(O)$_2$N($R^j$)$_2$, —($C_1$-$C_6$alkylenyl)-C(O)$R^k$, —($C_1$-$C_6$alkylenyl)-C(O)O$R^j$, —($C_1$-$C_6$alkylenyl)-C(O)N($R^j$)$_2$, —($C_1$-$C_6$alkylenyl)-N($R^j$)$_2$, —($C_1$-$C_6$alkylenyl)-N($R^j$)C(O)$R^k$, —($C_1$-$C_6$alkylenyl)-N($R^j$)S(O)$_2R^k$, —($C_1$-$C_6$alkylenyl)-N($R^j$)C(O)O($R^k$), —($C_1$-$C_6$alkylenyl)-N($R^j$)C(O)N($R^j$)$_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (I), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —O$R^h$, —OC(O)$R^i$, —OC(O)N($R^h$)$_2$, —S$R^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^A$, wherein the $C_1$-$C_6$alkyl is optionally substituted with one, two or three substituents independently selected from the group consisting of fluorine, —O$R^h$, —OC(O)$R^i$, —OC(O)N($R^h$)$_2$, —S$R^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$;

m is 0, 1, 2, or 3;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —O$R^j$, —OC(O)N($R^j$)$_2$, —S$R^j$, —C(O)O$R^j$, —C(O)N($R^j$)$_2$, —N($R^j$)$_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —O$R^j$, —OC(O)N($R^j$)$_2$, —S$R^j$, —C(O)O$R^j$, —C(O)N($R^j$)$_2$, —N($R^j$)$_2$, —CN, and $G^E$;

$R^2$ and $R^3$ are each hydrogen;

$R^4$ is hydrogen;

$R^5$ is $C_3$-$C_7$cycloalkyl or phenyl, wherein the phenyl is optionally unsubstituted or substituted with 1, 2, or 3 independently selected $R^u$ groups;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —O$R^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —O$R^j$, —OC(O)$R^k$, —OC(O)N($R^j$)$_2$, —S$R^j$, —S(O)$_2R^j$, —S(O)$_2$N($R^j$)$_2$, —C(O)$R^k$, —C(O)O$R^j$, —C(O)N($R^j$)$_2$, —N($R^j$)$_2$, —N($R^j$)C(O)$R^k$, —N($R^j$)S(O)$_2R^k$, —N($R^j$)C(O)O($R^k$), —N($R^j$)C(O)N($R^j$)$_2$, —($C_1$-$C_6$alkylenyl)-O$R^j$, —($C_1$-$C_6$alkylenyl)-OC(O)$R^k$, —($C_1$-$C_6$alkylenyl)-OC(O)N($R^j$)$_2$, —($C_1$-$C_6$alkylenyl)-S$R^j$, —($C_1$-$C_6$alkylenyl)-S(O)$_2R^j$, —($C_1$-$C_6$alkylenyl)-S(O)$_2$N($R^j$)$_2$, —($C_1$-$C_6$alkylenyl)-C(O)$R^k$, —($C_1$-$C_6$alkylenyl)-C(O)O$R^j$, —($C_1$-$C_6$alkylenyl)-C(O)N($R^j$)$_2$, —($C_1$-$C_6$alkylenyl)-N($R^j$)$_2$, —($C_1$-$C_6$alkylenyl)-N($R^j$)C(O)$R^k$, —($C_1$-$C_6$alkylenyl)-N($R^j$)S(O)$_2R^k$, —($C_1$-$C_6$alkylenyl)-N($R^j$)C(O)O($R^k$), —($C_1$-$C_6$alkylenyl)-N($R^j$)C(O)N($R^j$)$_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (I), $R^1$ is phenyl, wherein the phenyl is optionally substituted with one, two, or three $R^x$ groups, wherein each $R^x$ group is independently selected from $C_1$-$C_6$alkyl, halogen, —O$R^h$, —C(O)$R^i$, and —C(O)O$R^h$, wherein the $C_1$-$C_6$alkyl is optionally substituted with one, two or three substituents independently selected from the group consisting of fluorine and —O$R^h$;

m is 0, 1, 2, or 3;

$R^h$ is hydrogen, $C_1$-$C_6$haloalkyl, or $C_1$-$C_6$alkyl;

$R^i$ is $C_1$-$C_6$haloalkyl, or $C_1$-$C_6$alkyl;

$R^2$ and $R^3$ are each hydrogen;

$R^4$ is hydrogen;

$R^5$ is phenyl; wherein the phenyl is optionally unsubstituted or substituted with 1, 2, or 3 independently selected $R^u$ groups; wherein, $R^u$, at each occurrence, is independently $C_1$-$C_6$alkyl, halogen, $C_1$-$C_6$haloalkyl, —O$R^j$, or —C(O)$R^k$, —C(O)O$R^j$;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —O$R^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (I), $R^1$ is phenyl, wherein the phenyl is optionally substituted with one, two, or three $R^x$ groups, wherein each $R^x$ group is independently selected from $C_1$-$C_6$alkyl, halogen, —O$R^h$, —C(O)$R^i$, and —C(O)O$R^h$, wherein the $C_1$-$C_6$alkyl is optionally substituted with one, two or three substituents independently selected from the group consisting of fluorine and —O$R^h$;

m is 0;

$R^h$ is hydrogen, $C_1$-$C_6$haloalkyl, or $C_1$-$C_6$alkyl;

$R^i$ is $C_1$-$C_6$haloalkyl, or $C_1$-$C_6$alkyl;

$R^2$ and $R^3$ are each hydrogen;

$R^4$ is hydrogen;

$R^5$ is phenyl; wherein the phenyl is optionally unsubstituted or substituted with 1, 2, or 3 independently selected $R^u$ groups; wherein $R^u$, at each occurrence, is independently $C_1$-$C_6$alkyl, halogen, $C_1$-$C_6$haloalkyl, —O$R^j$, or —C(O)$R^k$, —C(O)O$R^j$;

$R^j$, at each occurrence, is independently hydrogen, $C_1$-$C_6$alkyl, or $C_1$-$C_6$haloalkyl;

$R^k$, at each occurrence, is independently $C_1$-$C_6$alkyl or $C_1$-$C_6$haloalkyl;

$R^6$ is hydrogen;

$R^8$, $R^9$, and $R^{10}$ are each hydrogen; and
$R^{11}$ and $R^{12}$ are each halogen.

In one embodiment, in a compound or pharmaceutically acceptable salt of formula (I), $R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$,
wherein the $C_1$-$C_6$alkyl is optionally substituted with one, two or three substituents independently selected from the group consisting of fluorine and —$OR^h$;
m is 0;
$R^h$ is hydrogen, $C_1$-$C_6$haloalkyl, or $C_1$-$C_6$alkyl;
$R^i$ is $C_1$-$C_6$haloalkyl, or $C_1$-$C_6$alkyl;
$R^2$ and $R^3$ are each hydrogen;
$R^4$ is hydrogen;
$R^5$ is phenyl; wherein the phenyl is optionally unsubstituted or substituted with 1, 2, or 3 independently selected $R^u$ groups; wherein
$R^u$, at each occurrence, is independently $C_1$-$C_6$alkyl, halogen, $C_1$-$C_6$haloalkyl, —$OR^j$, —$C(O)R^k$, —$C(O)OR^j$;
$R^j$, at each occurrence, is independently hydrogen, $C_1$-$C_6$alkyl, or $C_1$-$C_6$haloalkyl;
$R^k$, at each occurrence, is independently $C_1$-$C_6$alkyl or $C_1$-$C_6$haloalkyl;
$R^6$ is hydrogen;
$R^8$, $R^9$, and $R^{10}$ are each hydrogen; and
$R^{11}$ and $R^{12}$ are each fluorine.

In one embodiment, the compound or pharmaceutically acceptable salt is a diastereomer of formula (IV),

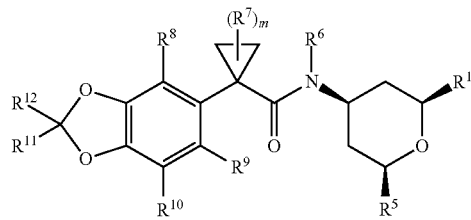

(IV)

$R^1$ is phenyl or phenyl fused to a 4-6-membered heterocycle, wherein the phenyl or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$,
wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$
wherein the 4-6-membered heterocycle of phenyl fused to a 4-6-membered heterocycle is optionally substituted with 1, 2 or 3 independently selected $R^s$ groups;
m is 0, 1, 2, or 3;
$R^s$, at each occurrence, is independently $C_1$-$C_6$alkyl, halogen, —CN, oxo, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, or $G^C$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^D$;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^5$ is $G^F$; wherein $G^F$ is $C_3$-$C_7$cycycloalkyl, aryl or heteroaryl, each of which is independently unsubstituted or substituted with 1, 2, or 3 independently selected $R^u$ groups;
$R^6$ is hydrogen, $C_1$-$C_6$haloalkyl, or $C_1$-$C_6$alkyl;
$R^7$ is an optional substituent on the cyclopropyl ring, and at each occurrence, is independently halogen, $C_1$-$C_6$haloalkyl, or $C_1$-$C_6$alkyl;
$R^8$, $R^9$, and $R^{10}$ are each independently hydrogen, halogen, —$OR^j$, $C_1$-$C_6$haloalkyl, or $C_1$-$C_6$alkyl;
$R^{11}$ and $R^{12}$ are each independently hydrogen, $C_1$-$C_3$alkyl, or halogen;
$G^A$, $G^B$, $G^C$, $G^D$ and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$alkylenyl)-$OR^j$, —($C_1$-$C_6$alkylenyl)-$OC(O)R^k$, —($C_1$-$C_6$alkylenyl)-$OC(O)N(R^j)_2$, —($C_1$-$C_6$alkylenyl)-$SR^j$, —($C_1$-$C_6$alkylenyl)-$S(O)_2R^j$, —($C_1$-$C_6$alkylenyl)-$S(O)_2N(R^j)_2$, —($C_1$-$C_6$alkylenyl)-$C(O)R^k$, —($C_1$-$C_6$alkylenyl)-$C(O)OR^j$, —($C_1$-$C_6$alkylenyl)-$C(O)N(R^j)_2$, —($C_1$-$C_6$alkylenyl)-$N(R^j)_2$, —($C_1$-$C_6$alkylenyl)-$N(R^j)C(O)R^k$, —($C_1$-$C_6$alkylenyl)-$N(R^j)S(O)_2R^k$, —($C_1$-$C_6$alkylenyl)-$N(R^j)C(O)O(R^k)$, —($C_1$-$C_6$alkylenyl)-$N(R^j)C(O)N(R^j)_2$, or —($C_1$-$C_6$alkylenyl)-CN;

$R^j$, at each occurrence, is independently hydrogen, $C_1$-$C_6$alkyl, or $C_1$-$C_6$haloalkyl; and
$R^k$, at each occurrence, is independently $C_1$-$C_6$alkyl or $C_1$-$C_6$haloalkyl.

In one embodiment, in a diastereomer or pharmaceutically acceptable salt of formula (IV),
$R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;

m is 0, 1, 2, or 3;

R$^h$, at each occurrence, is independently hydrogen, $C_1$-$C_6$haloalkyl, $C_1$-$C_6$alkyl, or G$^A$, wherein the $C_1$-$C_6$alkyl is optionally substituted with one, two or three substituents independently selected from the group consisting of fluorine, —OR, —OC(O)N(R$^j$)$_2$, —SR$^j$, —C(O)OR$^j$, —C(O)N(R$^j$)$_2$, —N(R$^j$)$_2$, —CN, and G$^E$;

R$^i$, at each occurrence, is independently $C_1$-$C_6$haloalkyl, $C_1$-$C_6$alkyl, or G$^A$, wherein the $C_1$-$C_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;

R$^5$ is phenyl; wherein, the phenyl is unsubstituted or substituted with 1, 2, or 3 independently selected R$^u$ groups;

R$^6$ is hydrogen, $C_1$-$C_6$haloalkyl, or $C_1$-$C_6$alkyl;

R$^7$ is an optional substituent on the cyclopropyl ring, and at each occurrence, is independently halogen, $C_1$-$C_6$haloalkyl, or $C_1$-$C_6$alkyl;

R$^8$, R$^9$, and R$^{10}$ are each independently hydrogen, halogen, —OR$^j$, $C_1$-$C_6$haloalkyl, or $C_1$-$C_6$alkyl;

R$^{11}$ and R$^{12}$ are each independently hydrogen, $C_1$-$C_3$alkyl, or halogen;

G$^A$, G$^B$ and G$^E$, at each occurrence, are each independently cycloalkyl, cycloalkenyl, heterocycle, aryl, or heteroaryl, each of which is independently unsubstituted or substituted with 1, 2, or 3 independently selected R$^u$ groups; wherein R$^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —($C_1$-$C_6$alkylenyl)-OR$^j$, —($C_1$-$C_6$alkylenyl)-OC(O)R$^k$, —($C_1$-$C_6$alkylenyl)-OC(O)N(R$^j$)$_2$, —($C_1$-$C_6$alkylenyl)-SR$^j$, —($C_1$-$C_6$alkylenyl)-S(O)$_2$R$^j$, —($C_1$-$C_6$alkylenyl)-S(O)$_2$N(R$^j$)$_2$, —($C_1$-$C_6$alkylenyl)-C(O)R$^k$, —($C_1$-$C_6$alkylenyl)-C(O)OR$^j$, —($C_1$-$C_6$alkylenyl)-C(O)N(R$^j$)$_2$, —($C_1$-$C_6$alkylenyl)-N(R$^j$)$_2$, —($C_1$-$C_6$alkylenyl)-N(R$^j$)C(O)R$^k$, —($C_1$-$C_6$alkylenyl)-N(R$^j$)S(O)$_2$R$^k$, —($C_1$-$C_6$alkylenyl)-N(R$^j$)C(O)O(R$^k$), —($C_1$-$C_6$alkylenyl)-N(R$^j$)C(O)N(R$^j$)$_2$, or —($C_1$-$C_6$alkylenyl)-CN;

R$^j$, at each occurrence, is independently hydrogen, $C_1$-$C_6$alkyl, or $C_1$-$C_6$haloalkyl; and R$^k$, at each occurrence, is independently $C_1$-$C_6$alkyl or $C_1$-$C_6$haloalkyl.

In one embodiment, in a diastereomer or pharmaceutically acceptable salt of formula (IV), R$^1$ is phenyl, wherein the phenyl is optionally substituted with, two, or three R$^x$ groups, wherein each R$^x$ group is independently selected from $C_1$-$C_6$alkyl, halogen, —OR$^h$, —C(O)R$^i$, and —C(O)OR$^h$, wherein the $C_1$-$C_6$alkyl is optionally substituted with one, two or three substituents independently selected from the group consisting of fluorine and —OR$^h$;

m is 0;

R$^h$ is hydrogen, $C_1$-$C_6$haloalkyl or $C_1$-$C_6$alkyl;

R$^i$ is $C_1$-$C_6$haloalkyl, or $C_1$-$C_6$alkyl;

R$^5$ is phenyl; wherein the phenyl is optionally unsubstituted or substituted with 1, 2, or 3 independently selected R$^u$ groups; wherein R$^u$, at each occurrence, is independently $C_1$-$C_6$alkyl, halogen, $C_1$-$C_6$haloalkyl, —OR$^j$, —C(O)R$^k$, or —C(O)OR$^j$; and R$^j$, at each occurrence, is independently hydrogen, $C_1$-$C_6$alkyl, or $C_1$-$C_6$haloalkyl;

R$^k$, at each occurrence, is independently $C_1$-$C_6$alkyl or $C_1$-$C_6$haloalkyl;

R$^6$ is hydrogen;

R$^8$, R$^9$, and R$^{10}$ are each hydrogen; and

R$^{11}$ and R$^{12}$ are each halogen.

In one embodiment, in a diastereomer or pharmaceutically acceptable salt of formula (IV), R$^1$ is phenyl, wherein the phenyl is optionally substituted with, two, or three R$^x$ groups, wherein each R$^x$ group is independently selected from $C_1$-$C_6$alkyl, halogen, —OR$^h$, —C(O)R$^i$, and —C(O)OR$^h$, wherein the $C_1$-$C_6$alkyl is optionally substituted with one, two or three substituents independently selected from the group consisting of fluorine and —OR$^h$;

m is 0;

R$^h$ is hydrogen, $C_1$-$C_6$haloalkyl or $C_1$-$C_6$alkyl;

R$^i$ is $C_1$-$C_6$haloalkyl, or $C_1$-$C_6$alkyl;

R$^5$ is phenyl; wherein the phenyl is optionally unsubstituted or substituted with 1, 2, or 3 independently selected R$^u$ groups; wherein R$^u$, at each occurrence, is independently $C_1$-$C_6$alkyl, halogen, $C_1$-$C_6$haloalkyl, —OR$^3$, —C(O)R$^k$, —C(O)OR$^j$; and R$^j$, at each occurrence, is independently hydrogen, $C_1$-$C_6$alkyl, or $C_1$-$C_6$haloalkyl;

R$^k$, at each occurrence, is independently $C_1$-$C_6$alkyl or $C_1$-$C_6$haloalkyl;

R$^6$ is hydrogen;

R$^8$, R$^9$, and R$^{10}$ are each hydrogen; and

R$^{11}$ and R$^{12}$ are each fluorine.

In one embodiment, the compound or pharmaceutically acceptable salt is an enantiomer of formula (IVa), wherein

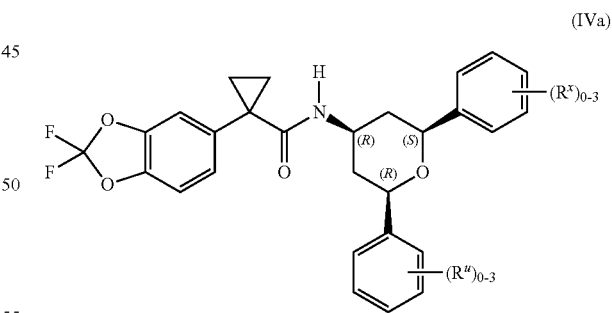

(IVa)

R$^x$ is an optional substituent independently selected at each occurrence from $C_1$-$C_6$alkyl, halogen, —OR$^h$, —C(O)R$^i$, and —C(O)OR$^h$, wherein, the $C_1$-$C_6$alkyl is optionally substituted with one, two or three substituents independently selected from the group consisting of fluorine and —OR$^h$;

R$^h$ is hydrogen, $C_1$-$C_6$haloalkyl, or $C_1$-$C_6$alkyl;

R$^i$ is $C_1$-$C_6$haloalkyl, or $C_1$-$C_6$alkyl;

R$^u$ is an optional substituent independently selected at each occurrence from $C_1$-$C_6$alkyl, halogen, $C_1$-$C_6$haloalkyl, —OR$^j$, —C(O)R$^k$, or —C(O)OR$^j$;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, the compound or pharmaceutically acceptable salt is an enantiomer of formula (IV wherein (IVb)

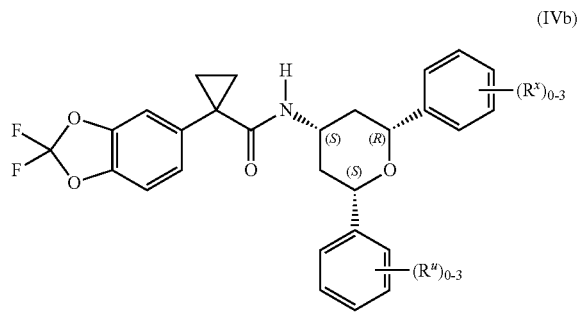

$R^x$ is an optional substituent independently selected at each occurrence from $C_1$-$C_6$alkyl, halogen, —$OR^h$, —C(O)$R^i$, and —C(O)$OR^h$, wherein, the $C_1$-$C_6$alkyl is optionally substituted with one, two or three substituents independently selected from the group consisting of fluorine and —$OR^h$;

$R^h$ is hydrogen, $C_1$-$C_6$haloalkyl, or $C_1$-$C_6$alkyl;

$R^i$ is $C_1$-$C_6$haloalkyl, or $C_1$-$C_6$alkyl;

$R^u$ is an optional substituent independently selected at each occurrence from $C_1$-$C_6$alkyl, halogen, $C_1$-$C_6$haloalkyl, —$OR^j$, —C(O)$R^k$, or —C(O)$OR^j$;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, the compound or pharmaceutically acceptable salt is a diastereomer of formula (V), (V)

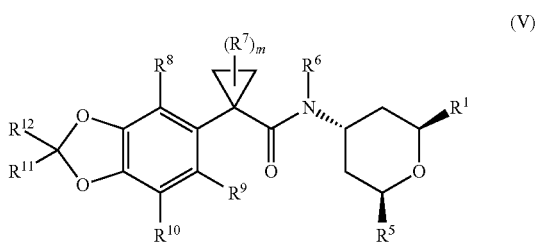

$R^1$ is phenyl or phenyl fused to a 4-6-membered heterocycle, wherein the phenyl or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —$NO_2$, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^A$, wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$;

wherein the 4-6-membered heterocycle of phenyl fused to a 4-6-membered heterocycle is optionally substituted with 1, 2 or 3 independently selected $R^s$ groups;

m is 0, 1, 2, or 3;

$R^s$, at each occurrence, is independently $C_1$-$C_6$alkyl, halogen, —CN, oxo, —$NO_2$, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, or $G^C$, wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^D$;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —OC(O)N($R^j$)$_2$, —$SR^j$, —C(O)$OR^j$, —C(O)N($R^j$)$_2$, —N($R^j$)$_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —OC(O)N($R^j$)$_2$, —$SR^j$, —C(O)$OR^j$, —C(O)N($R^j$)$_2$, —N($R^j$)$_2$, —CN, and $G^E$;

$R^5$ is $G^F$; wherein $G^F$ is $C_3$-$C_7$cycloalkyl, aryl or heteroaryl, each of which is independently unsubstituted or substituted with 1, 2, or 3 independently selected $R^u$ groups;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, $G^C$, $G^D$ and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —OC(O)$R^k$, —OC(O)N($R^j$)$_2$, —$SR^j$, —S(O)$_2R^j$, —S(O)$_2$N($R^j$)$_2$, —C(O)$R^k$, —C(O)$OR^j$, —C(O)N($R^j$)$_2$, —N($R^j$)$_2$, —N($R^j$)C(O)$R^k$, —N($R^j$)S(O)$_2R^k$, —N($R^j$)C(O)O($R^k$), —N($R^j$)C(O)N($R^j$)$_2$, —($C_1$-$C_6$alkylenyl)-$OR^j$, —($C_1$-$C_6$alkylenyl)-OC(O)$R^k$, —($C_1$-$C_6$alkylenyl)-OC(O)N($R^j$)$_2$, —($C_1$-$C_6$alkylenyl)-$SR^j$, —($C_1$-$C_6$alkylenyl)-S(O)$_2R^j$, —($C_1$-$C_6$alkylenyl)-S(O)$_2$N($R^j$)$_2$, —($C_1$-$C_6$alkylenyl)-C(O)$R^k$, —($C_1$-$C_6$alkylenyl)-C(O)$OR^j$, —($C_1$-$C_6$alkylenyl)-C(O)N($R^j$)$_2$, —($C_1$-$C_6$alkylenyl)-N($R^j$)$_2$, —($C_1$-$C_6$alkylenyl)-N($R^j$)C(O)$R^k$, —($C_1$-$C_6$alkylenyl)-N($R^j$)S(O)$_2R^k$, —($C_1$-$C_6$alkylenyl)-N($R^j$)C(O)O($R^k$), —($C_1$-$C_6$alkylenyl)-N($R^j$)C(O)N($R^j$)$_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a diastereomer or pharmaceutically acceptable salt of formula (V), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and $G^A$, wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -$G^B$;

m is 0, 1, 2, or 3;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and $G^E$;

$R^5$ is phenyl; wherein, the phenyl is unsubstituted or substituted with 1, 2, or 3 independently selected $R^u$ groups;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —OR$^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$ and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —($C_1$-$C_6$alkylenyl)-OR$^j$, —($C_1$-$C_6$alkylenyl)-OC(O)R$^k$, —($C_1$-$C_6$alkylenyl)-OC(O)N(R$^j$)$_2$, —($C_1$-$C_6$alkylenyl)-SR$^j$, —($C_1$-$C_6$alkylenyl)-S(O)$_2$R$^j$, —($C_1$-$C_6$alkylenyl)-S(O)$_2$N(R$^j$)$_2$, —($C_1$-$C_6$alkylenyl)-C(O)R$^k$, —($C_1$-$C_6$alkylenyl)-C(O)OR$^j$, —($C_1$-$C_6$alkylenyl)-C(O)N(R$^j$)$_2$, —($C_1$-$C_6$alkylenyl)-N(R$^j$)$_2$, —($C_1$-$C_6$alkylenyl)-N(R$^j$)C(O)R$^k$, —($C_1$-$C_6$alkylenyl)-N(R$^j$)S(O)$_2$R$^k$, —($C_1$-$C_6$alkylenyl)-N(R$^j$)C(O)O(R$^k$), —($C_1$-$C_6$alkylenyl)-N(R$^j$)C(O)N(R$^j$)$_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a diastereomer or pharmaceutically acceptable salt of formula (V), $R^1$ is phenyl, wherein the phenyl is optionally substituted with one, two or three $R^x$ groups, wherein each $R^x$ group is independently selected from $C_1$-$C_6$alkyl, halogen, —OR$^h$, —C(O)R$^i$, and —C(O)OR$^h$, wherein the $C_1$-$C_6$alkyl is optionally substituted with one, two or three substituents independently selected from the group consisting of fluorine and —OR$^h$;

m is 0;

$R^h$ is hydrogen, $C_1$-$C_6$haloalkyl, or $C_1$-$C_6$alkyl;

$R^i$ is $C_1$-$C_6$haloalkyl, or $C_1$-$C_6$alkyl;

$R^2$ and $R^3$ are each hydrogen;

$R^4$ is hydrogen;

$R^5$ is phenyl, wherein the phenyl is optionally unsubstituted or substituted with 1, 2, or 3 independently selected $R^u$ groups; wherein $R^u$, at each occurrence, is independently $C_1$-$C_6$alkyl, halogen, $C_1$-$C_6$haloalkyl, —OR$^j$, —C(O)R$^k$, —C(O)OR$^j$;

$R^j$, at each occurrence, is independently hydrogen, $C_1$-$C_6$alkyl, or $C_1$-$C_6$haloalkyl;

$R^k$, at each occurrence, is independently $C_1$-$C_6$alkyl or $C_1$-$C_6$haloalkyl;

$R^6$ is hydrogen;

$R^8$, $R^9$, and $R^{10}$ are each hydrogen; and $R^{11}$ and $R^{12}$ are each halogen.

In one embodiment, in a diastereomer or pharmaceutically acceptable salt of formula (V), $R^1$ is phenyl, wherein the phenyl is optionally substituted with one, two or three $R^x$ groups, wherein each $R^x$ group is independently selected from $C_1$-$C_6$alkyl, halogen, —OR$^h$, —C(O)R$^i$, and —C(O)OR$^h$, wherein the $C_1$-$C_6$alkyl is optionally substituted with one, two or three substituents independently selected from the group consisting of fluorine and —OR$^h$;

m is 0;

$R^h$ is hydrogen, $C_1$-$C_6$haloalkyl, or $C_1$-$C_6$alkyl;

$R^i$ is $C_1$-$C_6$haloalkyl, or $C_1$-$C_6$alkyl;

$R^2$ and $R^3$ are each hydrogen;

$R^4$ is hydrogen;

$R^5$ is phenyl, wherein the phenyl is optionally unsubstituted or substituted with 1, 2, or 3 independently selected $R^u$ groups; wherein $R^u$, at each occurrence, is independently $C_1$-$C_6$alkyl, halogen, $C_1$-$C_6$haloalkyl, —OR, —C(O)R$^k$, or —C(O)OR$^j$;

$R^j$, at each occurrence, is independently hydrogen, $C_1$-$C_6$alkyl, or $C_1$-$C_6$haloalkyl;

$R^k$, at each occurrence, is independently $C_1$-$C_6$alkyl or $C_1$-$C_6$haloalkyl;

$R^6$ is hydrogen;

$R^8$, $R^9$, and $R^{10}$ are each hydrogen; and $R^{11}$ and $R^{12}$ are each fluorine.

In one embodiment, the compound or pharmaceutically acceptable salt is an enantiomer of formula (Va), wherein (Va)

$R^x$ is an optional substituent independently selected at each occurrence from $C_1$-$C_6$alkyl, halogen, —$OR^h$, —$C(O)R^i$, and —$C(O)OR^h$,
  wherein, the $C_1$-$C_6$alkyl is optionally substituted with one, two or three substituents independently selected from the group consisting of fluorine and —$OR^h$; and
  $R^h$ is hydrogen, $C_1$-$C_6$haloalkyl, or $C_1$-$C_6$alkyl;
$R^i$ is $C_1$-$C_6$haloalkyl, or $C_1$-$C_6$alkyl;
$R^u$ is an optional substituent independently selected at each occurrence from $C_1$-$C_6$alkyl, halogen, $C_1$-$C_6$haloalkyl, —$OR^j$, —$C(O)R^k$, or —$C(O)OR^j$;
$R^j$, at each occurrence, is independently hydrogen, $C_1$-$C_6$alkyl, or $C_1$-$C_6$haloalkyl; and
$R^k$, at each occurrence, is independently $C_1$-$C_6$alkyl or $C_1$-$C_6$haloalkyl.

In one embodiment, the compound or pharmaceutically acceptable salt is an enantiomer of formula (Vb), wherein

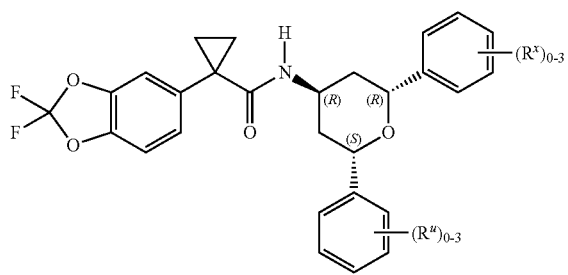

(Vb)

$R^x$ is an optional substituent independently selected at each occurrence from $C_1$-$C_6$alkyl, halogen, —$OR^h$, —$C(O)R^i$, and —$C(O)OR^h$,
  wherein, the $C_1$-$C_6$alkyl is optionally substituted with one, two or three substituents independently selected from the group consisting of fluorine and —$OR^h$; and
  $R^h$ is hydrogen, $C_1$-$C_6$haloalkyl, or $C_1$-$C_6$alkyl;
$R^i$ is $C_1$-$C_6$haloalkyl, or $C_1$-$C_6$alkyl;
$R^u$ is an optional substituent independently selected at each occurrence from $C_1$-$C_6$alkyl, halogen, $C_1$-$C_6$haloalkyl, —$OR^j$, —$C(O)R^k$, and —$C(O)OR^j$;
$R^j$, at each occurrence, is independently hydrogen, $C_1$-$C_6$alkyl, or $C_1$-$C_6$haloalkyl; and
$R^k$, at each occurrence, is independently $C_1$-$C_6$alkyl or $C_1$-$C_6$haloalkyl.

In one embodiment, in a compound or pharmaceutically acceptable salt of formula (I),
$R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$,
  wherein the $C_1$-$C_6$alkyl is optionally substituted with one, two or three substituents independently selected from the group consisting of fluorine and —$OR^h$;
m is 0, 1, 2, or 3;
$R^h$ is hydrogen, $C_1$-$C_6$haloalkyl, or $C_1$-$C_6$alkyl;
$R^i$ is $C_1$-$C_6$haloalkyl, or $C_1$-$C_6$alkyl;
$R^2$ and $R^3$ are each hydrogen;
$R^4$ is hydrogen;
$R^5$ is cycloalkyl, wherein the cycloalkyl is optionally unsubstituted or substituted with 1, 2, or 3 independently selected $R^u$ groups; wherein
  $R^u$, at each occurrence, is independently $C_1$-$C_6$alkyl, halogen, $C_1$-$C_6$haloalkyl, —OR, —$C(O)R^k$, or —$C(O)OR^j$;

$R^6$ is hydrogen, $C_1$-$C_6$haloalkyl, or $C_1$-$C_6$alkyl;
$R^7$ is an optional substituent on the cyclopropyl ring, and at each occurrence, is independently halogen, $C_1$-$C_6$haloalkyl, or $C_1$-$C_6$alkyl;
$R^8$, $R^9$, and $R^{10}$ are each independently hydrogen, halogen, —$OR^j$, $C_1$-$C_6$haloalkyl, or $C_1$-$C_6$alkyl;
$R^{11}$ and $R^{12}$ are each independently hydrogen, $C_1$-$C_3$alkyl, or halogen;
$R^j$, at each occurrence, is independently hydrogen, $C_1$-$C_6$alkyl, or $C_1$-$C_6$haloalkyl; and
$R^k$, at each occurrence, is independently $C_1$-$C_6$alkyl or $C_1$-$C_6$haloalkyl.

In one embodiment, in a compound or pharmaceutically acceptable salt of formula (I),
$R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$,
  wherein the $C_1$-$C_6$alkyl is optionally substituted with one, two or three substituents independently selected from the group consisting of fluorine and —$OR^h$;
m is 0;
$R^h$ is hydrogen, $C_1$-$C_6$haloalkyl, or $C_1$-$C_6$alkyl;
$R^i$ is $C_1$-$C_6$haloalkyl, or $C_1$-$C_6$alkyl;
$R^2$ and $R^3$ are each hydrogen;
$R^4$ is hydrogen;
$R^5$ is cycloalkyl, wherein the cycloalkyl is optionally unsubstituted or substituted with 1, 2, or 3 independently selected $R^u$ groups; wherein
  $R^u$, at each occurrence, is independently $C_1$-$C_6$alkyl, halogen, $C_1$-$C_6$haloalkyl, —OR, —$C(O)R^k$, or —$C(O)OR^j$;
  $R^j$, at each occurrence, is independently hydrogen, $C_1$-$C_6$alkyl, or $C_1$-$C_6$haloalkyl;
  $R^k$, at each occurrence, is independently $C_1$-$C_6$alkyl or $C_1$-$C_6$haloalkyl;
$R^6$ is hydrogen;
$R^8$, $R^9$, and $R^{10}$ are each hydrogen; and
$R^{11}$ and $R^{12}$ are each halogen.

In one embodiment, in a compound or pharmaceutically acceptable salt of formula (I),
$R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$,
  wherein the $C_1$-$C_6$alkyl is optionally substituted with one, two or three substituents independently selected from the group consisting of fluorine and —$OR^h$;
m is 0;
$R^h$ is hydrogen, $C_1$-$C_6$haloalkyl, or $C_1$-$C_6$alkyl;
$R^i$ is $C_1$-$C_6$haloalkyl, or $C_1$-$C_6$alkyl;
$R^2$ and $R^3$ are each hydrogen;
$R^4$ is hydrogen;
$R^5$ cycloalkyl, wherein the cycloalkyl is optionally unsubstituted or substituted with 1, 2, or 3 independently selected $R^u$ groups; wherein
  $R^u$, at each occurrence, is independently $C_1$-$C_6$alkyl, halogen, $C_1$-$C_6$haloalkyl, —OR, —$C(O)R^k$, or —$C(O)OR^j$;
  $R^j$, at each occurrence, is independently hydrogen, $C_1$-$C_6$alkyl, or $C_1$-$C_6$haloalkyl;
  $R^k$, at each occurrence, is independently $C_1$-$C_6$alkyl or $C_1$-$C_6$haloalkyl;
$R^6$ is hydrogen;
$R^8$, $R^9$, and $R^{10}$ are each hydrogen; and
$R^{11}$ and $R^{12}$ are each fluorine.

In one embodiment, in a diastereomer or pharmaceutically acceptable salt of formula (IV), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and $G^A$, wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -$G^B$;

m is 0, 1, 2, or 3;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and $G^E$;

$R^5$ is $C_3$-$C_7$cycloalkyl; wherein, the $C_3$-$C_7$cycloalkyl is unsubstituted or substituted with 1, 2, or 3 independently selected $R^u$ groups;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —OR$^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$ and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —($C_1$-$C_6$alkylenyl)-OR$^j$, —($C_1$-$C_6$alkylenyl)-OC(O)R$^k$, —($C_1$-$C_6$alkylenyl)-OC(O)N(R$^j$)$_2$, —($C_1$-$C_6$alkylenyl)-SR$^j$, —($C_1$-$C_6$alkylenyl)-S(O)$_2$R$^j$, —($C_1$-$C_6$alkylenyl)-S(O)$_2$N(R$^j$)$_2$, —($C_1$-$C_6$alkylenyl)-C(O)R$^k$, —($C_1$-$C_6$alkylenyl)-C(O)OR$^j$, —($C_1$-$C_6$alkylenyl)-C(O)N(R$^j$)$_2$, —($C_1$-$C_6$alkylenyl)-N(R$^j$)$_2$, —($C_1$-$C_6$alkylenyl)-N(R$^j$)C(O)R$^k$, —($C_1$-$C_6$alkylenyl)-N(R$^j$)S(O)$_2$R$^k$, —($C_1$-$C_6$alkylenyl)-N(R$^j$)C(O)O(R$^k$), —($C_1$-$C_6$alkylenyl)-N(R$^j$)C(O)N(R$^j$)$_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a diastereomer or pharmaceutically acceptable salt of formula (IV), $R^1$ is phenyl, wherein the phenyl is optionally substituted with, two, or three $R^x$ groups, wherein each $R^x$ group is independently selected from $C_1$-$C_6$alkyl, halogen, —OR$^h$, —C(O)R$^i$, and —C(O)OR$^h$, wherein the $C_1$-$C_6$alkyl is optionally substituted with one, two or three substituents independently selected from the group consisting of fluorine and —OR$^h$;

m is 0;

$R^h$ is hydrogen, $C_1$-$C_6$haloalkyl or $C_1$-$C_6$alkyl;

$R^i$ is $C_1$-$C_6$haloalkyl, or $C_1$-$C_6$alkyl;

$R^5$ is $C_3$-$C_7$cycloalkyl, wherein the phenyl is optionally unsubstituted or substituted with 1, 2, or 3 independently selected $R^u$ groups; wherein $R^u$, at each occurrence, is independently $C_1$-$C_6$alkyl, halogen, $C_1$-$C_6$haloalkyl, —OR, —C(O)R$^k$, or —C(O)OR$^j$;

$R^j$, at each occurrence, is independently hydrogen, $C_1$-$C_6$alkyl, or $C_1$-$C_6$haloalkyl;

$R^k$, at each occurrence, is independently $C_1$-$C_6$alkyl or $C_1$-$C_6$haloalkyl;

$R^6$ is hydrogen;

$R^8$, $R^9$, and $R^{10}$ are each hydrogen; and $R^{11}$ and $R^{12}$ are each halogen.

In one embodiment, in a diastereomer or pharmaceutically acceptable salt of formula (IV), $R^1$ is phenyl, wherein the phenyl is optionally substituted with, two, or three $R^x$ groups, wherein each $R^x$ group is independently selected from $C_1$-$C_6$alkyl, halogen, —OR$^h$, —C(O)R$^i$, and —C(O)OR$^h$, wherein the $C_1$-$C_6$alkyl is optionally substituted with one, two or three substituents independently selected from the group consisting of fluorine and —OR$^h$;

m is 0;

$R^h$ is hydrogen, $C_1$-$C_6$haloalkyl or $C_1$-$C_6$alkyl;

$R^i$ is $C_1$-$C_6$haloalkyl, or $C_1$-$C_6$alkyl;

$R^5$ is $C_3$-$C_7$cycloalkyl, wherein the phenyl is optionally unsubstituted or substituted with 1, 2, or 3 independently selected $R^u$ groups; wherein $R^u$, at each occurrence, is independently $C_1$-$C_6$alkyl, halogen, $C_1$-$C_6$haloalkyl, —OR$^j$, —C(O)R$^k$, or —C(O)OR$^j$;

$R^j$, at each occurrence, is independently hydrogen, $C_1$-$C_6$alkyl, or $C_1$-$C_6$haloalkyl;

$R^k$, at each occurrence, is independently $C_1$-$C_6$alkyl or $C_1$-$C_6$haloalkyl;

$R^6$ is hydrogen;

$R^8$, $R^9$, and $R^{10}$ are each hydrogen; and $R^{11}$ and $R^{12}$ are each fluorine.

In one embodiment, the compound or pharmaceutically acceptable salt is an enantiomer of formula (IVc), wherein (IVc)

$R^x$ is an optional substituent independently selected at each occurrence from $C_1$-$C_6$alkyl, halogen, —$OR^h$, —C(O)$R^i$, and —C(O)$OR^h$,
wherein, the $C_1$-$C_6$alkyl is optionally substituted with one, two or three substituents independently selected from the group consisting of fluorine and —$OR^h$;
$R^h$ is hydrogen, $C_1$-$C_6$haloalkyl, or $C_1$-$C_6$alkyl;
$R^i$ is $C_1$-$C_6$haloalkyl, or $C_1$-$C_6$alkyl;
$R^u$ is an optional substituent independently selected at each occurrence from $C_1$-$C_6$alkyl, halogen, $C_1$-$C_6$haloalkyl, —$OR^j$, —C(O)$R^k$, and —C(O)$OR^j$;
$R^j$, at each occurrence, is independently hydrogen, $C_1$-$C_6$alkyl, or $C_1$-$C_6$haloalkyl; and
$R^k$, at each occurrence, is independently $C_1$-$C_6$alkyl or $C_1$-$C_6$haloalkyl.

In one embodiment, the compound or pharmaceutically acceptable salt is an enantiomer of formula (IVd), wherein

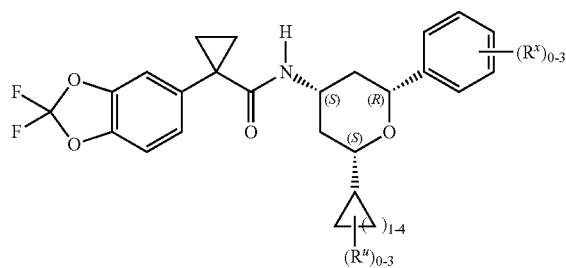

(IVd)

$R^x$ is an optional substituent independently selected at each occurrence from $C_1$-$C_6$alkyl, halogen, —$OR^h$, —C(O)$R^i$, and —C(O)$OR^h$,
wherein, the $C_1$-$C_6$alkyl is optionally substituted with one, two or three substituents independently selected from the group consisting of fluorine and —$OR^h$;
$R^h$ is hydrogen, $C_1$-$C_6$haloalkyl, or $C_1$-$C_6$alkyl;
$R^i$ is $C_1$-$C_6$haloalkyl, or $C_1$-$C_6$alkyl;
$R^u$ is an optional substituent independently selected at each occurrence from $C_1$-$C_6$alkyl, halogen, $C_1$-$C_6$haloalkyl, —$OR^j$, —C(O)$R^k$, and —C(O)$OR^j$;
$R^j$, at each occurrence, is independently hydrogen, $C_1$-$C_6$alkyl, or $C_1$-$C_6$haloalkyl; and
$R^k$, at each occurrence, is independently $C_1$-$C_6$alkyl or $C_1$-$C_6$haloalkyl.

In one embodiment, in a diastereomer or pharmaceutically acceptable salt of formula (V),
$R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^A$,
wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$;
m is 0, 1, 2, or 3;
$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —OC(O)N($R^j$)$_2$, —$SR^j$, —C(O)$OR^j$, —C(O)N($R^j$)$_2$, —N($R^j$)$_2$, —CN, and $G^E$;
$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —OC(O)N($R^j$)$_2$, —$SR^j$, —C(O)$OR^j$, —C(O)N($R^j$)$_2$, —N($R^j$)$_2$, —CN, and $G^E$;
$R^5$ is $C_3$-$C_7$cycloalkyl; wherein, the $C_3$-$C_7$cycloalkyl is unsubstituted or substituted with 1, 2, or 3 independently selected $R^u$ groups;
$R^6$ is hydrogen, $C_1$-$C_6$haloalkyl, or $C_1$-$C_6$alkyl;
$R^7$ is an optional substituent on the cyclopropyl ring, and at each occurrence, is independently halogen, $C_1$-$C_6$haloalkyl, or $C_1$-$C_6$alkyl;
$R^8$, $R^9$, and $R^{10}$ are each independently hydrogen, halogen, —$OR^j$, $C_1$-$C_6$haloalkyl, or $C_1$-$C_6$alkyl;
$R^{11}$ and $R^{12}$ are each independently hydrogen, $C_1$-$C_3$alkyl, or halogen;
$G^A$, $G^B$ and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein
$R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —OC(O)$R^k$, —OC(O)N($R^j$)$_2$, —$SR^j$, —S(O)$_2R^j$, —S(O)$_2$N($R^j$)$_2$, —C(O)$R^k$, —C(O)$OR^j$, —C(O)N($R^j$)$_2$, —N($R^j$)$_2$, —N($R^j$)C(O)$R^k$, —N($R^j$)S(O)$_2R^k$, —N($R^j$)C(O)O($R^k$), —N($R^j$)C(O)N($R^j$)$_2$, —($C_1$-$C_6$alkylenyl)-$OR^j$, —($C_1$-$C_6$alkylenyl)-OC(O)$R^k$, —($C_1$-$C_6$alkylenyl)-OC(O)N($R^j$)$_2$, —($C_1$-$C_6$alkylenyl)-$SR^j$, —($C_1$-$C_6$alkylenyl)-S(O)$_2R^j$, —($C_1$-$C_6$alkylenyl)-S(O)$_2$N($R^j$)$_2$, —($C_1$-$C_6$alkylenyl)-C(O)$R^k$, —($C_1$-$C_6$alkylenyl)-C(O)$OR^j$, —($C_1$-$C_6$alkylenyl)-C(O)N($R^j$)$_2$, —($C_1$-$C_6$alkylenyl)-N($R^j$)$_2$, —($C_1$-$C_6$alkylenyl)-N($R^j$)C(O)$R^k$, —($C_1$-$C_6$alkylenyl)-N($R^j$)S(O)$_2R^k$, —($C_1$-$C_6$alkylenyl)-N($R^j$)C(O)O($R^k$), —($C_1$-$C_6$alkylenyl)-N($R^j$)C(O)N($R^j$)$_2$, or —($C_1$-$C_6$alkylenyl)-CN;
$R^j$, at each occurrence, is independently hydrogen, $C_1$-$C_6$alkyl, or $C_1$-$C_6$haloalkyl; and
$R^k$, at each occurrence, is independently $C_1$-$C_6$alkyl or $C_1$-$C_6$haloalkyl.

In one embodiment, in a diastereomer or pharmaceutically acceptable salt of formula (V),
$R^1$ is phenyl, wherein the phenyl is optionally substituted with, two, or three $R^x$ groups, wherein each $R^x$ group is independently selected from $C_1$-$C_6$alkyl, halogen, —$OR^h$, —C(O)$R^i$, and —C(O)$OR^h$,
wherein the $C_1$-$C_6$alkyl is optionally substituted with one, two or three substituents independently selected from the group consisting of fluorine and —$OR^h$;
m is 0;
$R^h$ is hydrogen, $C_1$-$C_6$haloalkyl or $C_1$-$C_6$alkyl;
$R^i$ is $C_1$-$C_6$haloalkyl, or $C_1$-$C_6$alkyl;
$R^5$ is $C_3$-$C_7$cycloalkyl, wherein the $C_3$-$C_7$cycloalkyl is optionally unsubstituted or substituted with 1, 2, or 3 independently selected $R^u$ groups; wherein
$R^u$, at each occurrence, is independently $C_1$-$C_6$alkyl, halogen, $C_1$-$C_6$haloalkyl, —OR, —C(O)$R^k$, or —C(O)$OR^j$;
$R^j$, at each occurrence, is independently hydrogen, $C_1$-$C_6$alkyl, or $C_1$-$C_6$haloalkyl;
$R^k$, at each occurrence, is independently $C_1$-$C_6$alkyl or $C_1$-$C_6$haloalkyl;
$R^6$ is hydrogen;

$R^8$, $R^9$, and $R^{10}$ are each hydrogen; and $R^{11}$ and $R^{12}$ are each halogen.

In one embodiment, in a diastereomer or pharmaceutically acceptable salt of formula (V), $R^1$ is phenyl, wherein the phenyl is optionally substituted with, two, or three $R^x$ groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$;

m is 0;

$R^h$ is hydrogen, $C_1$-$C_6$haloalkyl or $C_1$-$C_6$alkyl;

$R^i$ is $C_1$-$C_6$haloalkyl, or $C_1$-$C_6$alkyl;

$R^5$ is $C_3$-$C_7$cycloalkyl, wherein the phenyl is optionally unsubstituted or substituted with 1, 2, or 3 independently selected $R^u$ groups; wherein $R^u$, at each occurrence, is independently $C_1$-$C_6$alkyl, halogen, $C_1$-$C_6$haloalkyl, —$OR^j$, —$C(O)R^k$, or —$C(O)OR^j$;

$R^j$, at each occurrence, is independently hydrogen, $C_1$-$C_6$alkyl, or $C_1$-$C_6$haloalkyl;

$R^k$, at each occurrence, is independently $C_1$-$C_6$alkyl or $C_1$-$C_6$haloalkyl;

$R^6$ is hydrogen;

$R^8$, $R^9$, and $R^{10}$ are each hydrogen; and $R^{11}$ and $R^{12}$ are each fluorine.

In one embodiment, the compound or pharmaceutically acceptable salt is an enantiomer of formula (Vc), wherein

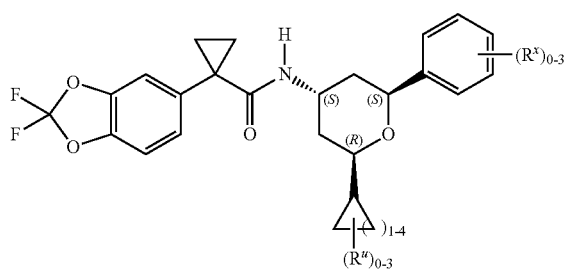

(Vc)

$R^x$ is an optional substituent selected from $C_1$-$C_6$alkyl, halogen, —$OR^h$, —$C(O)R^i$, and —$C(O)OR^h$, wherein, the $C_1$-$C_6$alkyl is optionally substituted with one, two or three substituents independently selected from the group consisting of fluorine and —$OR^h$;

$R^h$ is hydrogen, $C_1$-$C_6$haloalkyl, or $C_1$-$C_6$alkyl;

$R^i$ is $C_1$-$C_6$haloalkyl, or $C_1$-$C_6$alkyl;

$R^u$, at each occurrence, is an optional substituent independently selected from $C_1$-$C_6$alkyl, halogen, $C_1$-$C_6$haloalkyl, —$OR^j$, —$C(O)R^k$, and —$C(O)OR^j$;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, the compound or pharmaceutically acceptable salt is an enantiomer of formula (Vd), wherein

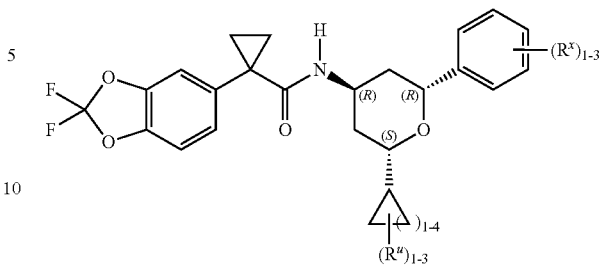

(Vd)

$R^x$ is an optional substituent independently selected at each occurrence from $C_1$-$C_6$alkyl, halogen, —$OR^h$, —$C(O)R^i$, and —$C(O)OR^h$, wherein, the $C_1$-$C_6$alkyl is optionally substituted with one, two or three substituents independently selected from the group consisting of fluorine and —$OR^h$;

$R^h$ is hydrogen, $C_1$-$C_6$haloalkyl, or $C_1$-$C_6$alkyl;

$R^i$ is $C_1$-$C_6$haloalkyl, or $C_1$-$C_6$alkyl;

$R^u$ is an optional substituent independently selected at each occurrence $C_1$-$C_6$alkyl, halogen, $C_1$-$C_6$haloalkyl, —$OR^j$, —$C(O)R^k$, and —$C(O)OR^j$;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (I), $R^1$ is phenyl, phenyl fused to a $C_3$-$C_6$cycloalkyl, or phenyl fused to a 4-6-membered heterocycle, wherein the phenyl, the phenyl of phenyl fused to a $C_3$-$C_6$cycloalkyl, or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;

wherein the $C_3$-$C_6$cycloalkyl of phenyl fused to a $C_3$-$C_6$cycloalkyl or the 4-6-membered heterocycle of phenyl fused to a 4-6-membered heterocycle are each optionally substituted with 1, 2 or 3 independently selected $R^s$ groups;

m is 0, 1, 2, or 3;

$R^s$, at each occurrence, is independently $C_1$-$C_6$alkyl, halogen, —CN, oxo, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, or $G^C$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^D$;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^2$ and $R^3$ are each hydrogen;

$R^4$ is hydrogen;

$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, $G^C$, $G^D$, and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —$(C_1$-$C_6$alkylenyl)-$OR^j$, —$(C_1$-$C_6$alkylenyl)-$OC(O)R^k$, —$(C_1$-$C_6$alkylenyl)-$OC(O)N(R^j)_2$, —$(C_1$-$C_6$alkylenyl)-$SR^j$, —$(C_1$-$C_6$alkylenyl)-$S(O)_2R^j$, —$(C_1$-$C_6$alkylenyl)-$S(O)_2N(R^j)_2$, —$(C_1$-$C_6$alkylenyl)-$C(O)R^k$, —$(C_1$-$C_6$alkylenyl)-$C(O)OR^j$, —$(C_1$-$C_6$alkylenyl)-$C(O)N(R^j)_2$, —$(C_1$-$C_6$alkylenyl)-$N(R^j)_2$, —$(C_1$-$C_6$alkylenyl)-$N(R^j)C(O)R^k$, —$(C_1$-$C_6$alkylenyl)-$N(R^j)S(O)_2R^k$, —$(C_1$-$C_6$alkylenyl)-$N(R^j)C(O)O(R^k)$, —$(C_1$-$C_6$alkylenyl)-$N(R^j)C(O)N(R^j)_2$, or —$(C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (I), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;

m is 0, 1, 2, or 3;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^2$ and $R^3$ are each hydrogen;

$R^4$ is hydrogen;

$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, $G^C$, $G^D$, and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —$(C_1$-$C_6$alkylenyl)-$OR^j$, —$(C_1$-$C_6$alkylenyl)-$OC(O)R^k$, —$(C_1$-$C_6$alkylenyl)-$OC(O)N(R^j)_2$, —$(C_1$-$C_6$alkylenyl)-$SR^j$, —$(C_1$-$C_6$alkylenyl)-$S(O)_2R^j$, —$(C_1$-$C_6$alkylenyl)-$S(O)_2N(R^j)_2$, —$(C_1$-$C_6$alkylenyl)-$C(O)R^k$, —$(C_1$-$C_6$alkylenyl)-$C(O)OR^j$, —$(C_1$-$C_6$alkylenyl)-$C(O)N(R^j)_2$, —$(C_1$-$C_6$alkylenyl)-$N(R^j)_2$, —$(C_1$-$C_6$alkylenyl)-$N(R^j)C(O)R^k$, —$(C_1$-$C_6$alkylenyl)-$N(R^j)S(O)_2R^k$, —$(C_1$-$C_6$alkylenyl)-$N(R^j)C(O)O(R^k)$, —$(C_1$-$C_6$alkylenyl)-$N(R^j)C(O)N(R^j)_2$, or —$(C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (I), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine, and —$OR^h$;

m is 0, 1, 2, or 3;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl;

$R^2$ and $R^3$ are each hydrogen;

$R^4$ is hydrogen;

$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (I), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine, and —$OR^h$;

m is 0;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl;

$R^2$ and $R^3$ are each hydrogen;

$R^4$ is hydrogen;

$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;

$R^6$ is hydrogen;

$R^8$, $R^9$, and $R^{10}$ are each independently hydrogen; and $R^{11}$ and $R^{12}$ are each halogen.

In one embodiment, in a compound or pharmaceutically acceptable salt of formula (I), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine, and —$OR^h$;

m is 0;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl;

$R^2$ and $R^3$ are each hydrogen;

$R^4$ is hydrogen;

$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;

$R^6$ is hydrogen;

$R^8$, $R^9$, and $R^{10}$ are each independently hydrogen; and $R^{11}$ and $R^{12}$ are each fluorine.

In one embodiment, in a compound or pharmaceutically acceptable salt of formula (IV),

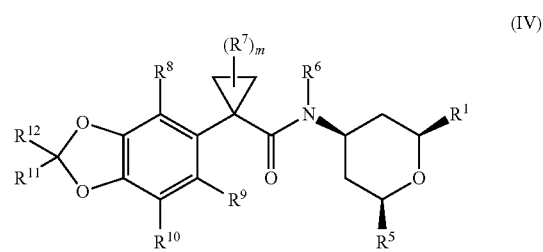

(IV)

$R^1$ is phenyl or phenyl fused to a 4-6-membered heterocycle, wherein the phenyl or the phenyl of phenyl fused to a 4-6-membered heterocycle are independently optionally substituted with one, two or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;

wherein the 4-6-membered heterocycle of phenyl fused to a 4-6-membered heterocycle is optionally substituted with 1, 2 or 3 independently selected $R^s$ groups;

m is 0, 1, 2, or 3;

$R^s$, at each occurrence, is independently $C_1$-$C_6$alkyl, halogen, —CN, oxo, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, or $G^C$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^D$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl or $C_1$-$C_6$alkyl;

$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2$ $N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, $G^C$, and $G^D$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$alkylenyl)-$OR^j$, —($C_1$-$C_6$alkylenyl)-$OC(O)R^k$, —($C_1$-$C_6$alkylenyl)-$OC(O)N(R^j)_2$, —($C_1$-$C_6$alkylenyl)-$SR^j$, —($C_1$-$C_6$alkylenyl)-$S(O)_2R^j$, —($C_1$-$C_6$alkylenyl)-$S(O)_2N(R^j)_2$, —($C_1$-$C_6$alkylenyl)-$C(O)R^k$, —($C_1$-$C_6$alkylenyl)-$C(O)OR^j$, —($C_1$-$C_6$alkylenyl)-$C(O)N(R^j)_2$, —($C_1$-$C_6$alkylenyl)-$N(R^j)_2$, —($C_1$-$C_6$alkylenyl)-$N(R^j)C(O)R^k$, —($C_1$-$C_6$alkylenyl)-$N(R^j)S(O)_2R^k$, —($C_1$-$C_6$alkylenyl)-$N(R^j)C(O)O(R^k)$, —($C_1$-$C_6$alkylenyl)-$N(R^j)C(O)N(R^j)_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (IV), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$,
wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;

m is 0, 1, 2, or 3;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl or $C_1$-$C_6$alkyl;

$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$ and $G^B$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$alkylenyl)-$OR^j$, —($C_1$-$C_6$alkylenyl)-$OC(O)R^k$, —($C_1$-$C_6$alkylenyl)-$OC(O)N(R^j)_2$, —($C_1$-$C_6$alkylenyl)-$SR^j$, —($C_1$-$C_6$alkylenyl)-$S(O)_2R^j$, —($C_1$-$C_6$alkylenyl)-$S(O)_2N(R^j)_2$, —($C_1$-$C_6$alkylenyl)-$C(O)R^k$, —($C_1$-$C_6$alkylenyl)-$C(O)OR^j$, —($C_1$-$C_6$alkylenyl)-$C(O)N(R^j)_2$, —($C_1$-$C_6$alkylenyl)-$N(R^j)_2$, —($C_1$-$C_6$alkylenyl)-$N(R^j)C(O)R^k$, —($C_1$-$C_6$alkylenyl)-$N(R^j)S(O)_2R^k$, —($C_1$-$C_6$alkylenyl)-$N(R^j)C(O)O(R^k)$, —($C_1$-$C_6$alkylenyl)-$N(R^j)C(O)N(R^j)_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a compound or pharmaceutically acceptable salt of formula (IV), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —$OR^h$, —$C(O)R^i$, and —$C(O)OR^h$,
wherein the $C_1$-$C_6$alkyl is optionally substituted with one, two or three substituents independently selected from the group consisting of fluorine and —$OR^h$;

m is 0;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl or $C_1$-$C_6$alkyl;

$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;

$R^6$ is hydrogen;

$R^8$, $R^9$, and $R^{10}$ are each hydrogen; and $R^{11}$ and $R^{12}$ are each halogen. In one embodiment, in a compound or pharmaceutically acceptable salt of formula (IV), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —$OR^h$, —$C(O)R^i$, and —$C(O)OR^h$,
wherein the $C_1$-$C_6$alkyl is optionally substituted with one, two or three substituents independently selected from the group consisting of fluorine and —$OR^h$;

m is 0;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl or $C_1$-$C_6$alkyl;

$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;

$R^6$ is hydrogen;
$R^8$, $R^9$, and $R^{10}$ are each hydrogen; and
$R^{11}$ and $R^{12}$ are each fluorine.

In one embodiment, the compound or pharmaceutically acceptable salt is an enantiomer of formula (IVe), wherein (IVe)

[Chemical structure with $C_1$-$C_6$alkyl, $(R^x)_{0-3}$, and stereochemistry labels (R), (S), (R)]

$R^x$ is an optional substituent selected from $C_1$-$C_6$alkyl, halogen, —$OR^h$, —$C(O)R^i$, and —$C(O)OR^h$,
  wherein, the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl; and
$R^i$, at each occurrence, is independently $C_1$-$C_6$haloalkyl, or $C_1$-$C_6$alkyl.

In one embodiment, the compound or pharmaceutically acceptable salt is an enantiomer of formula (IVf), wherein (IVf)

[Chemical structure with $C_1$-$C_6$alkyl, $(R^x)_{0-3}$, and stereochemistry labels (S), (R), (S)]

$R^x$ is an optional substituent selected from $C_1$-$C_6$alkyl, halogen, —$OR^h$, —$C(O)R$, and —$C(O)OR^h$,
  wherein, the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl; and
$R^i$, at each occurrence, is independently $C_1$-$C_6$haloalkyl, or $C_1$-$C_6$alkyl.

In one embodiment, in a compound or pharmaceutically acceptable salt of formula (V), (V)

[Chemical structure showing formula (V) with substituents $R^1$, $R^5$, $R^6$, $(R^7)_m$, $R^8$, $R^9$, $R^{10}$, $R^{11}$, $R^{12}$]

$R^1$ is phenyl or phenyl fused to a 4-6-membered heterocycle, wherein the phenyl or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$,
  wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;
  wherein the 4-6-membered heterocycle of phenyl fused to a 4-6-membered heterocycle is optionally substituted with 1, 2 or 3 independently selected $R^s$ groups;
m is 0, 1, 2, or 3;
$R^s$, at each occurrence, is independently $C_1$-$C_6$alkyl, halogen, —CN, oxo, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, or $G^C$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^D$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl or $C_1$-$C_6$alkyl;
$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;
$R^6$ is hydrogen, $C_1$-$C_6$haloalkyl, or $C_1$-$C_6$alkyl;
$R^7$ is an optional substituent on the cyclopropyl ring, and at each occurrence, is independently halogen, $C_1$-$C_6$haloalkyl, or $C_1$-$C_6$alkyl;
$R^8$, $R^9$, and $R^{10}$ are each independently hydrogen, halogen, —$OR^j$, $C_1$-$C_6$haloalkyl, or $C_1$-$C_6$alkyl;
$R^{11}$ and $R^{12}$ are each independently hydrogen, $C_1$-$C_3$alkyl, or halogen;
$G^A$, $G^B$, $G^C$, and $G^D$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein
$R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$alkylenyl)-$OR^j$, —($C_1$-$C_6$alkylenyl)-$OC(O)R^k$, —($C_1$-$C_6$alkylenyl)-$OC(O)N(R^j)_2$, —($C_1$-$C_6$alkylenyl)-$SR^j$, —($C_1$-$C_6$alkylenyl)-$S(O)_2R^j$, —($C_1$-$C_6$alkylenyl)-$S(O)_2N(R^j)_2$, —($C_1$-$C_6$alkylenyl)-$C(O)R^k$, —($C_1$-$C_6$alkylenyl)-$C(O)OR^j$, —($C_1$-$C_6$alkylenyl)-$C(O)N(R^j)_2$, —($C_1$-$C_6$alkylenyl)-$N(R^j)_2$, —($C_1$-$C_6$alkylenyl)-$N(R^j)C(O)R^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

In one embodiment, in a compound or pharmaceutically acceptable salt of formula (V), R$^1$ is phenyl, wherein the phenyl is optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;

m is 0, 1, 2, or 3;

R$^h$, at each occurrence, is independently hydrogen, C$_1$-C$_6$haloalkyl, or C$_1$-C$_6$alkyl;

R$^i$, at each occurrence, is independently C$_1$-C$_6$haloalkyl or C$_1$-C$_6$alkyl;

R$^5$ is C$_1$-C$_6$alkyl, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), and —N(R$^h$)C(O)N(R$^h$)$_2$;

R$^6$ is hydrogen, C$_1$-C$_6$haloalkyl, or C$_1$-C$_6$alkyl;

R is an optional substituent on the cyclopropyl ring, and at each occurrence, is independently halogen, C$_1$-C$_6$haloalkyl, or C$_1$-C$_6$alkyl;

R$^8$, R$^9$, and R$^{10}$ are each independently hydrogen, halogen, —OR$^j$, C$_1$-C$_6$haloalkyl, or C$_1$-C$_6$alkyl;

R$^{11}$ and R$^{12}$ are each independently hydrogen, C$_1$-C$_3$alkyl, or halogen;

G$^A$ and G$^B$, at each occurrence, are each independently cycloalkyl, cycloalkenyl, heterocycle, aryl, or heteroaryl, each of which is independently unsubstituted or substituted with 1, 2, or 3 independently selected R$^u$ groups; wherein R$^u$, at each occurrence, is independently C$_1$-C$_6$alkyl, C$_2$-C$_6$alkenyl, C$_2$-C$_6$alkynyl, halogen, C$_1$-C$_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

In one embodiment, in a compound or pharmaceutically acceptable salt of formula (V), R$^1$ is phenyl, wherein the phenyl is optionally substituted with one, two, or three R$^x$ groups, wherein each R$^x$ group is independently selected, at each occurrence, from C$_1$-C$_6$alkyl, halogen, —OR$^h$, —C(O)R$^i$, and —C(O)OR$^h$, wherein the C$_1$-C$_6$alkyl is optionally substituted with one, two or three substituents independently selected from the group consisting of fluorine and —OR$^h$;

m is 0;

R$^h$, at each occurrence, is independently hydrogen, C$_1$-C$_6$haloalkyl, or C$_1$-C$_6$alkyl;

R$^i$, at each occurrence, is independently C$_1$-C$_6$haloalkyl or C$_1$-C$_6$alkyl;

R$^5$ is C$_1$-C$_6$alkyl, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), and —N(R$^h$)C(O)N(R$^h$)$_2$;

R$^6$ is hydrogen;

R$^8$, R$^9$, and R$^{10}$ are each hydrogen; and

R$^{11}$ and R$^{12}$ are each halogen. In one embodiment, in a compound or pharmaceutically acceptable salt of formula (V), R$^1$ is phenyl, wherein the phenyl is optionally substituted with one, two, or three R$^x$ groups, wherein each R$^x$ group is independently selected, at each occurrence, from C$_1$-C$_6$alkyl, halogen, —OR$^h$, —C(O)R$^i$, and —C(O)OR$^h$, wherein the C$_1$-C$_6$alkyl is optionally substituted with one, two or three substituents independently selected from the group consisting of fluorine and —OR$^h$;

m is 0;

R$^h$, at each occurrence, is independently hydrogen, C$_1$-C$_6$haloalkyl, or C$_1$-C$_6$alkyl;

R$^i$, at each occurrence, is independently C$_1$-C$_6$haloalkyl or C$_1$-C$_6$alkyl;

R$^5$ is C$_1$-C$_6$alkyl, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), and —N(R$^h$)C(O)N(R$^h$)$_2$;

R$^6$ is hydrogen;

R$^8$, R$^9$, and R$^{10}$ are each hydrogen; and

R$^{11}$ and R$^{12}$ are each fluorine.

In one embodiment, the compound or pharmaceutically acceptable salt is an enantiomer of formula (Ve), wherein

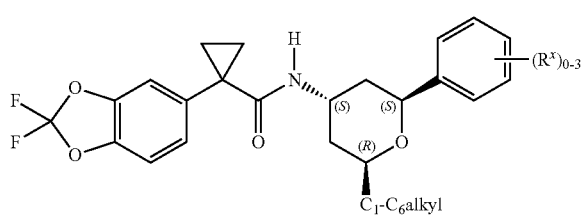

(Ve)

R$^x$ is an optional substituent independently selected at each occurrence from C$_1$-C$_6$alkyl, halogen, —OR$^h$, —C(O)R$^i$, and —C(O)OR$^h$, wherein, the $C_1$-$C_6$alkyl is optionally substituted with one, two or three substituents independently selected from the group consisting of fluorine and —OR$^h$;

R$^h$, at each occurrence, is independently hydrogen, $C_1$-$C_6$haloalkyl, or $C_1$-$C_6$alkyl; and R$^i$, at each occurrence, is independently $C_1$-$C_6$haloalkyl, or $C_1$-$C_6$alkyl.

In one embodiment, the compound or pharmaceutically acceptable salt is an enantiomer of formula (Vf), wherein (Vf)

[Structure: a 2,2-difluoro-1,3-benzodioxole group connected to a cyclopropyl bearing an H, attached via C(=O)NH to a tetrahydropyran ring with (R), (R), (S) stereochemistry, bearing a $C_1$-$C_6$alkyl group and a phenyl ring substituted with $(R^x)_{0-3}$]

R$^x$ is an optional substituent selected from $C_1$-$C_6$alkyl, halogen, —OR$^h$, —C(O)R$^i$, and —C(O)OR$^h$, wherein, the $C_1$-$C_6$alkyl is optionally substituted with one, two or three substituents independently selected from the group consisting of fluorine and —OR$^h$;

R$^h$, at each occurrence, is independently hydrogen, $C_1$-$C_6$haloalkyl, or $C_1$-$C_6$alkyl; and R$^i$, at each occurrence, is independently $C_1$-$C_6$haloalkyl, or $C_1$-$C_6$alkyl.

In one embodiment, in a compound or pharmaceutically acceptable salt of formula (I), R is phenyl, phenyl fused to a $C_3$-$C_6$cycloalkyl, or phenyl fused to a 4-6-membered heterocycle, wherein the phenyl, the phenyl of phenyl fused to a $C_3$-$C_6$cycloalkyl, or the phenyl of phenyl fused to a 4-6-membered heterocycle are independently optionally substituted with one, two, or three R$^x$ groups, wherein each R$^x$ group is independently selected, at each occurrence, from $C_1$-$C_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$, wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;

wherein the $C_3$-$C_6$cycloalkyl of phenyl fused to a $C_3$-$C_6$cycloalkyl or the 4-6-membered heterocycle of phenyl fused to a 4-6-membered heterocycle are each optionally substituted with 1, 2 or 3 independently selected R$^s$ groups;

m is 0, 1, 2, or 3;

R$^s$, at each occurrence, are each independently $C_1$-$C_6$alkyl, halogen, —CN, oxo, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, or G$^C$, wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^D$;

R$^h$, at each occurrence, is independently hydrogen, $C_1$-$C_6$haloalkyl, $C_1$-$C_6$alkyl, or G$^A$, wherein the $C_1$-$C_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;

R$^i$, at each occurrence, is independently $C_1$-$C_6$haloalkyl, $C_1$-$C_6$alkyl, or G$^A$, wherein the $C_1$-$C_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;

R$^2$ and R$^3$ are each hydrogen;

R$^4$ and R$^5$ are each $C_1$-$C_6$alkyl;

R$^6$ is hydrogen, $C_1$-$C_6$haloalkyl, or $C_1$-$C_6$alkyl;

R$^7$ is an optional substituent on the cyclopropyl ring, and at each occurrence, is independently halogen, $C_1$-$C_6$haloalkyl, or $C_1$-$C_6$alkyl;

R$^8$, R$^9$, and R$^{10}$ are each independently hydrogen, halogen, —OR$^j$, $C_1$-$C_6$haloalkyl, or $C_1$-$C_6$alkyl;

R$^{11}$ and R$^{12}$ are each independently hydrogen, $C_1$-$C_3$alkyl, or halogen;

G$^A$, G$^B$, G$^C$, G$^D$, and G$^E$ at each occurrence, are each independently cycloalkyl, cycloalkenyl, heterocycle, aryl, or heteroaryl, each of which is independently unsubstituted or substituted with 1, 2, or 3 independently selected R$^u$ groups; wherein R$^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —($C_1$-$C_6$alkylenyl)-OR$^j$, —($C_1$-$C_6$alkylenyl)-OC(O)R$^k$, —($C_1$-$C_6$alkylenyl)-OC(O)N(R$^j$)$_2$, —($C_1$-$C_6$alkylenyl)-SR$^j$, —($C_1$-$C_6$alkylenyl)-S(O)$_2$R$^j$, —($C_1$-$C_6$alkylenyl)-S(O)$_2$N(R$^j$)$_2$, —($C_1$-$C_6$alkylenyl)-C(O)R$^k$, —($C_1$-$C_6$alkylenyl)-C(O)OR$^j$, —($C_1$-$C_6$alkylenyl)-C(O)N(R$^j$)$_2$, —($C_1$-$C_6$alkylenyl)-N(R$^j$)$_2$, —($C_1$-$C_6$alkylenyl)-N(R$^j$)C(O)R$^k$, —($C_1$-$C_6$alkylenyl)-N(R$^j$)S(O)$_2$R$^k$, —($C_1$-$C_6$alkylenyl)-N(R$^j$)C(O)O(R$^k$), —($C_1$-$C_6$alkylenyl)-N(R$^j$)C(O)N(R$^j$)$_2$, or —($C_1$-$C_6$alkylenyl)-CN;

R$^j$, at each occurrence, is independently hydrogen, $C_1$-$C_6$alkyl, or $C_1$-$C_6$haloalkyl; and R$^k$, at each occurrence, is independently $C_1$-$C_6$alkyl or $C_1$-$C_6$haloalkyl.

In one embodiment, in a compound or pharmaceutically acceptable salt of formula (I), R is phenyl, wherein the phenyl is optionally substituted with one, two, or three R$^x$ groups, wherein each R$^x$ group is independently selected, at each occurrence, from $C_1$-$C_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$, wherein the $C_1$-$C_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;

m is 0, 1, 2, or 3;

R$^h$, at each occurrence, is independently hydrogen, $C_1$-$C_6$haloalkyl, $C_1$-$C_6$alkyl, or G$^A$, wherein the $C_1$-$C_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;

R$^i$, at each occurrence, is independently C$_1$-C$_6$haloalkyl, C$_1$-C$_6$alkyl, or G$^A$, wherein the C$_1$-C$_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;

R$^2$ and R$^3$ are each hydrogen;
R$^4$ and R$^5$ are each C$_1$-C$_6$alkyl;
R$^6$ is hydrogen, C$_1$-C$_6$haloalkyl, or C$_1$-C$_6$alkyl;
R$^7$ is an optional substituent on the cyclopropyl ring, and at each occurrence, is independently halogen, C$_1$-C$_6$haloalkyl, or C$_1$-C$_6$alkyl;
R$^8$, R$^9$, and R$^{10}$ are each independently hydrogen, halogen, —OR$^j$, C$_1$-C$_6$haloalkyl, or C$_1$-C$_6$alkyl;
R$^{11}$ and R$^{12}$ are each independently hydrogen, C$_1$-C$_3$alkyl, or halogen;

G$^A$, G$^B$ and G$^E$, at each occurrence, are each independently cycloalkyl, cycloalkenyl, heterocycle, aryl, or heteroaryl, each of which is independently unsubstituted or substituted with 1, 2, or 3 independently selected R$^u$ groups; wherein R$^u$, at each occurrence, is independently C$_1$-C$_6$alkyl, C$_2$-C$_6$alkenyl, C$_2$-C$_6$alkynyl, halogen, C$_1$-C$_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

In one embodiment, in a compound or pharmaceutically acceptable salt of formula (I), R$^1$ is phenyl, wherein the phenyl is optionally substituted with one, two, or three R$^x$ groups, wherein each R$^x$ group is independently selected from C$_1$-C$_6$alkyl, halogen —C(O)R$^i$, and —C(O)OR$^h$,
   wherein the C$_1$-C$_6$alkyl is optionally substituted with one, two or three substituents independently selected from the group consisting of fluorine and —OR$^h$; and
R$^h$, at each occurrence, is independently hydrogen, C$_1$-C$_6$haloalkyl, or C$_1$-C$_6$alkyl;
R$^i$, at each occurrence, is independently C$_1$-C$_6$haloalkyl or C$_1$-C$_6$alkyl;
m is 0, 1, 2, or 3;
R$^2$ and R$^3$ are each hydrogen;
R$^4$ and R$^5$ are each C$_1$-C$_6$alkyl;
R$^6$ is hydrogen, C$_1$-C$_6$haloalkyl, or C$_1$-C$_6$alkyl;
R$^7$ is an optional substituent on the cyclopropyl ring, and at each occurrence, is independently halogen, C$_1$-C$_6$haloalkyl, or C$_1$-C$_6$alkyl;
R$^8$, R$^9$, and R$^{10}$ are each independently hydrogen, halogen, —OR$^j$, C$_1$-C$_6$haloalkyl, or C$_1$-C$_6$alkyl; and
R$^{11}$ and R$^{12}$ are each independently hydrogen, C$_1$-C$_3$alkyl, or halogen.

In one embodiment, in a compound or pharmaceutically acceptable salt of formula (I), R$^1$ is phenyl, wherein the phenyl is optionally substituted with one, two, or three R$^x$ groups, wherein each R$^x$ group is independently selected from C$_1$-C$_6$alkyl, halogen —C(O)R$^i$, and —C(O)OR$^h$,
   wherein the C$_1$-C$_6$alkyl is optionally substituted with one, two or three substituents independently selected from the group consisting of fluorine and —OR$^h$; and
R$^h$, at each occurrence, is independently hydrogen, C$_1$-C$_6$haloalkyl, or C$_1$-C$_6$alkyl;
R$^i$, at each occurrence, is independently C$_1$-C$_6$haloalkyl or C$_1$-C$_6$alkyl;
m is 0;
R$^2$ and R$^3$ are each hydrogen;
R$^4$ and R$^5$ are each C$_1$-C$_6$alkyl;
R$^6$ is hydrogen;
R$^8$, R$^9$, and R$^{10}$ are each hydrogen; and
R$^{11}$ and R$^{12}$ are each halogen.

In one embodiment, in a compound or pharmaceutically acceptable salt of formula (I), R$^1$ is phenyl, wherein the phenyl is optionally substituted with one, two, or three R$^x$ groups, wherein each R$^x$ group is independently selected from C$_1$-C$_6$alkyl, halogen —C(O)R$^i$, and —C(O)OR$^h$,
   wherein the C$_1$-C$_6$alkyl is optionally substituted with one, two or three substituents independently selected from the group consisting of fluorine and —OR$^h$;
R$^h$, at each occurrence, is independently hydrogen, C$_1$-C$_6$haloalkyl, or C$_1$-C$_6$alkyl;
R$^i$, at each occurrence, is independently C$_1$-C$_6$haloalkyl or C$_1$-C$_6$alkyl;
m is 0;
R$^2$ and R$^3$ are each hydrogen;
R$^4$ and R$^5$ are each C$_1$-C$_6$alkyl;
R$^6$ is hydrogen;
R$^8$, R$^9$, and R$^{10}$ are each hydrogen; and
R$^{11}$ and R$^{12}$ are each fluorine.

In one embodiment, the compound or pharmaceutically acceptable salt is a cis diastereomer of formula (VI), wherein

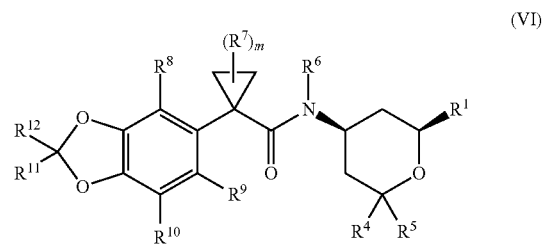

R$^1$ is phenyl or phenyl fused to a 4-6-membered heterocycle, wherein the phenyl or the phenyl of phenyl fused to a 4-6-membered heterocycle are independently optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$,
   wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;
  wherein the 4-6-membered heterocycle of phenyl fused to a 4-6-membered heterocycle is optionally substituted with 1, 2 or 3 independently selected R$^s$ groups;
m is 0, 1, 2, or 3;
R$^s$, at each occurrence, is independently C$_1$-C$_6$alkyl, halogen, —CN, oxo, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, or G$^C$, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^D$;
R$^h$, at each occurrence, is independently hydrogen, C$_1$-C$_6$haloalkyl, C$_1$-C$_6$alkyl, or G$^A$, wherein the C$_1$-C$_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;
R$^i$, at each occurrence, is independently C$_1$-C$_6$haloalkyl, C$_1$-C$_6$alkyl, or G$^A$, wherein the C$_1$-C$_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;
R$^4$ and R$^5$ are each C$_1$-C$_6$alkyl;
R$^6$ is hydrogen, C$_1$-C$_6$haloalkyl, or C$_1$-C$_6$alkyl;
R$^7$ is an optional substituent on the cyclopropyl ring, and at each occurrence, is independently halogen, C$_1$-C$_6$haloalkyl, or C$_1$-C$_6$alkyl;
R$^8$, R$^9$, and R$^{10}$ are each independently hydrogen, halogen, —OR$^j$, C$_1$-C$_6$haloalkyl, or C$_1$-C$_6$alkyl;
R$^{11}$ and R$^{12}$ are each independently hydrogen, C$_1$-C$_3$alkyl, or halogen;
G$^A$, G$^B$, G$^C$, G$^D$ and G$^E$, at each occurrence, are each independently cycloalkyl, cycloalkenyl, heterocycle, aryl, or heteroaryl, each of which is independently unsubstituted or substituted with 1, 2, or 3 independently selected R$^u$ groups; wherein
R$^u$, at each occurrence, is independently C$_1$-C$_6$alkyl, C$_2$-C$_6$alkenyl, C$_2$-C$_6$alkynyl, halogen, C$_1$-C$_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;
R$^j$, at each occurrence, is independently hydrogen, C$_1$-C$_6$alkyl, or C$_1$-C$_6$haloalkyl; and
R$^k$, at each occurrence, is independently C$_1$-C$_6$alkyl or C$_1$-C$_6$haloalkyl.

In one embodiment, in a diastereomer or pharmaceutically acceptable salt of formula (VI),
R$^1$ is phenyl, wherein the phenyl is optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$;
  wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;
m is 0, 1, 2, or 3;
R$^h$, at each occurrence, is independently hydrogen, C$_1$-C$_6$haloalkyl, C$_1$-C$_6$alkyl, or G$^A$, wherein the C$_1$-C$_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;
R$^i$, at each occurrence, is independently C$_1$-C$_6$haloalkyl, C$_1$-C$_6$alkyl, or G$^A$, wherein the C$_1$-C$_6$alkyl is optionally substituted with one, two or three substituents independently selected from the group consisting of fluorine, —OR$^j$, —OC(O)N(R$^j$)$_2$, —SR$^j$, —C(O)OR$^j$, —C(O)N(R$^j$)$_2$, —N(R$^j$)$_2$, —CN, and G$^E$;
R$^4$ and R$^5$ are each C$_1$-C$_6$alkyl;
R$^6$ is hydrogen, C$_1$-C$_6$haloalkyl, or C$_1$-C$_6$alkyl;
R$^7$ is an optional substituent on the cyclopropyl ring, and at each occurrence, is independently halogen, C$_1$-C$_6$haloalkyl, or C$_1$-C$_6$alkyl;
R$^8$, R$^9$, and R$^{10}$ are each independently hydrogen, halogen, —OR$^j$, C$_1$-C$_6$haloalkyl, or C$_1$-C$_6$alkyl;
R$^{11}$ and R$^{12}$ are each independently hydrogen, C$_1$-C$_3$alkyl, or halogen;
G$^A$, G$^B$ and G$^E$, at each occurrence, are each independently cycloalkyl, cycloalkenyl, heterocycle, aryl, or heteroaryl, each of which is independently unsubstituted or substituted with 1, 2, or 3 independently selected R$^u$ groups; wherein
R$^u$, at each occurrence, is independently C$_1$-C$_6$alkyl, C$_2$-C$_6$alkenyl, C$_2$-C$_6$alkynyl, halogen, C$_1$-C$_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;
R$^j$, at each occurrence, is independently hydrogen, C$_1$-C$_6$alkyl, or C$_1$-C$_6$haloalkyl; and
R$^k$, at each occurrence, is independently C$_1$-C$_6$alkyl or C$_1$-C$_6$haloalkyl.

In one embodiment, in a diastereomer or pharmaceutically acceptable salt of formula (VI),
R$^1$ is phenyl, wherein the phenyl is optionally substituted with one, two, or three R$^x$ groups, wherein each R$^x$ group is independently selected from C$_1$-C$_6$alkyl, halogen —C(O)R$^i$, and —C(O)OR$^h$,
  wherein the C$_1$-C$_6$alkyl is optionally substituted with one, two or three substituents independently selected from the group consisting of fluorine and —OR$^h$;
m is 0;
R$^h$, at each occurrence, is independently hydrogen, C$_1$-C$_6$haloalkyl, or C$_1$-C$_6$alkyl;
R$^i$, at each occurrence, is independently C$_1$-C$_6$haloalkyl or C$_1$-C$_6$alkyl;

$R^4$ and $R^5$ are each $C_1$-$C_6$alkyl;
$R^6$ is hydrogen;
$R^8$, $R^9$, and $R^{10}$ are each hydrogen; and
$R^{11}$ and $R^{12}$ are each halogen.

In one embodiment, in a diastereomer or pharmaceutically acceptable salt of formula (VI),
$R^1$ is phenyl, wherein the phenyl is optionally substituted with one, two, or three $R^x$ groups, wherein each $R^x$ group is independently selected from $C_1$-$C_6$alkyl, halogen —C(O)$R^i$, and —C(O)O$R^h$,
  wherein the $C_1$-$C_6$alkyl is optionally substituted with one, two or three substituents independently selected from the group consisting of fluorine and —O$R^h$;
  m is 0;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl or $C_1$-$C_6$alkyl;
$R^4$ and $R^5$ are each $C_1$-$C_6$alkyl;
$R^6$ is hydrogen;
$R^8$, $R^9$, and $R^{10}$ are each hydrogen; and
$R^{11}$ and $R^{12}$ are each fluorine.

In one embodiment, the compound or pharmaceutically acceptable salt is an enantiomer of formula (VIa), wherein

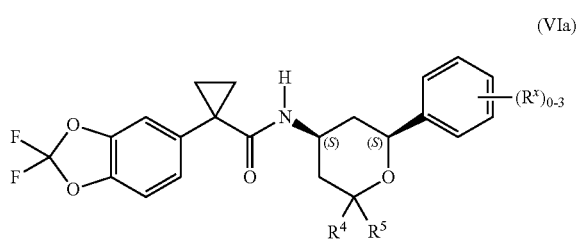

(VIa)

$R^x$, at each occurrence, is an optional substituent independently selected from $C_1$-$C_6$alkyl, halogen, —C(O)$R^i$, and —C(O)O$R^h$,
  wherein, the $C_1$-$C_6$alkyl is optionally substituted with one, two or three substituents independently selected from the group consisting of fluorine and —O$R^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl or $C_1$-$C_6$alkyl; and
$R^4$ and $R^5$ are each $C_1$-$C_6$alkyl.

In one embodiment, the compound or pharmaceutically acceptable salt is an enantiomer of formula (VIb), wherein

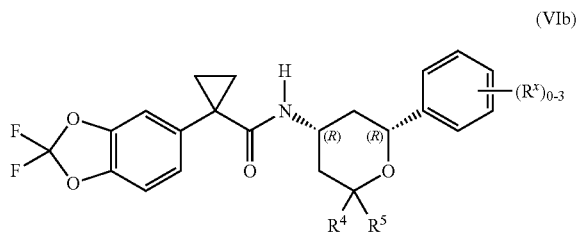

(VIb)

$R^x$, at each occurrence, is an optional substituent independently selected from $C_1$-$C_6$alkyl, halogen, —C(O)$R^i$, and —C(O)O$R^h$,
  wherein, the $C_1$-$C_6$alkyl is optionally substituted with one, two or three substituents independently selected from the group consisting of fluorine and —O$R^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$halo or $C_1$-$C_6$alkyl; and
$R^4$ and $R^5$ are each $C_1$-$C_6$alkyl.

In one embodiment, the compound or pharmaceutically acceptable salt is a cis diastereomer of formula (VII), wherein

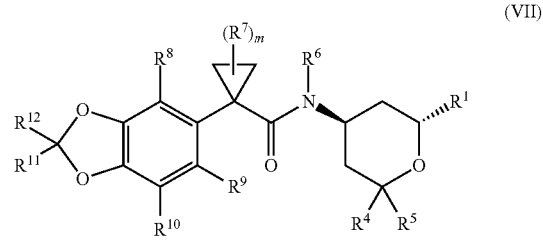

(VII)

$R^1$ is phenyl or phenyl fused to a 4-6-membered heterocycle, wherein the phenyl or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —NO$_2$, —O$R^h$, —OC(O)$R^i$, —OC(O)N($R^h$)$_2$, —S$R^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^A$,
  wherein the $C_1$-$C_6$alkyl is optionally substituted with one, two or three substituents independently selected from the group consisting of fluorine, —O$R^h$, —OC(O)$R^i$, —OC(O)N($R^h$)$_2$, —S$R^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$;
  wherein the 4-6-membered heterocycle of phenyl fused to a 4-6-membered heterocycle is optionally substituted with 1, 2 or 3 independently selected $R^s$ groups;
m is 0, 1, 2, or 3;
$R^s$, at each occurrence, is independently $C_1$-$C_6$alkyl, halogen, —CN, oxo, —NO$_2$, —O$R^h$, —OC(O)$R^i$, —OC(O)N($R^h$)$_2$, —S$R^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, or $G^C$, wherein the $C_1$-$C_6$alkyl is optionally substituted with one, two or three substituents independently selected from the group consisting of fluorine, —O$R^h$, —OC(O)$R^i$, —OC(O)N($R^h$)$_2$, —S$R^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^D$;
$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —O$R^j$, —OC(O)N($R^j$)$_2$, —S$R^j$, —C(O)O$R^j$, —C(O)N($R^j$)$_2$, —N($R^j$)$_2$, —CN, and $G^E$;
$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —OR, —OC(O)N($R^j$)$_2$, —SR, —C(O)O$R^j$, —C(O)N($R^j$)$_2$, —N($R^j$)$_2$, —CN, and $G^E$;
$R^4$ and $R^5$ are each $C_1$-$C_6$alkyl;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$, $G^C$, $G^D$ and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^i$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$alkylenyl)-$OR^j$, —($C_1$-$C_6$alkylenyl)-$OC(O)R^k$, —($C_1$-$C_6$alkylenyl)-$OC(O)N(R^j)_2$, —($C_1$-$C_6$alkylenyl)-$SR^j$, —($C_1$-$C_6$alkylenyl)-$S(O)_2R^j$, —($C_1$-$C_6$alkylenyl)-$S(O)_2N(R^j)_2$, —($C_1$-$C_6$alkylenyl)-$C(O)R^k$, —($C_1$-$C_6$alkylenyl)-$C(O)OR^j$, —($C_1$-$C_6$alkylenyl)-$C(O)N(R^j)_2$, —($C_1$-$C_6$alkylenyl)-$N(R^j)_2$, —($C_1$-$C_6$alkylenyl)-$N(R^j)C(O)R^k$, —($C_1$-$C_6$alkylenyl)-$N(R^j)S(O)_2R^k$, —($C_1$-$C_6$alkylenyl)-$N(R^j)C(O)O(R^k)$, —($C_1$-$C_6$alkylenyl)-$N(R^j)C(O)N(R^j)_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a diastereomer or pharmaceutically acceptable salt of formula (VII), $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;

m is 0, 1, 2, or 3;

$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^4$ and $R^5$ are each $C_1$-$C_6$alkyl;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —$OR^j$, $C_1$-$C_6$haloalkyl, or $C_1$-$C_6$alkyl;

$R^{11}$ and $R^{12}$ are each independently hydrogen, $C_1$-$C_3$alkyl, or halogen;

$G^A$, $G^B$ and $G^E$, at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —($C_1$-$C_6$alkylenyl)-$OR^j$, —($C_1$-$C_6$alkylenyl)-$OC(O)R^k$, —($C_1$-$C_6$alkylenyl)-$OC(O)N(R^j)_2$, —($C_1$-$C_6$alkylenyl)-$SR^j$, —($C_1$-$C_6$alkylenyl)-$S(O)_2R^j$, —($C_1$-$C_6$alkylenyl)-$S(O)_2N(R^j)_2$, —($C_1$-$C_6$alkylenyl)-$C(O)R^k$, —($C_1$-$C_6$alkylenyl)-$C(O)OR^j$, —($C_1$-$C_6$alkylenyl)-$C(O)N(R^j)_2$, —($C_1$-$C_6$alkylenyl)-$N(R^j)_2$, —($C_1$-$C_6$alkylenyl)-$N(R^j)C(O)R^k$, —($C_1$-$C_6$alkylenyl)-$N(R^j)S(O)_2R^k$, —($C_1$-$C_6$alkylenyl)-$N(R^j)C(O)O(R^k)$, —($C_1$-$C_6$alkylenyl)-$N(R^j)C(O)N(R^j)_2$, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

In one embodiment, in a diastereomer or pharmaceutically acceptable salt of formula (VII), $R^1$ is phenyl, wherein the phenyl is optionally substituted with one, two, or three $R^x$ groups, wherein each $R^x$ group is independently selected from $C_1$-$C_6$alkyl, halogen —$C(O)R^i$, and —$C(O)OR^h$, wherein the $C_1$-$C_6$alkyl is optionally substituted with one, two or three substituents independently selected from the group consisting of fluorine and —$OR^h$;

m is 0;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl or $C_1$-$C_6$alkyl;

$R^4$ and $R^5$ are each $C_1$-$C_6$alkyl;

$R^6$ is hydrogen;

$R^8$, $R^9$, and $R^{10}$ are each hydrogen; and $R^{11}$ and $R^{12}$ are each halogen.

In one embodiment, in a diastereomer or pharmaceutically acceptable salt of formula (VII), $R^1$ is phenyl, wherein the phenyl is optionally substituted with one, two, or three $R^x$ groups, wherein each $R^x$ group is independently selected from $C_1$-$C_6$alkyl, halogen —$C(O)R^i$, and —$C(O)OR^h$, wherein the $C_1$-$C_6$alkyl is optionally substituted with one, two or three substituents independently selected from the group consisting of fluorine and —$OR^h$;

m is 0;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl or $C_1$-$C_6$alkyl;

$R^4$ and $R^5$ are each $C_1$-$C_6$alkyl;

$R^6$ is hydrogen;

$R^8$, $R^9$, and $R^{10}$ are each hydrogen; and $R^{11}$ and $R^{12}$ are each fluorine.

In one embodiment, the compound or pharmaceutically acceptable salt is an enantiomer of formula (VIIa), wherein

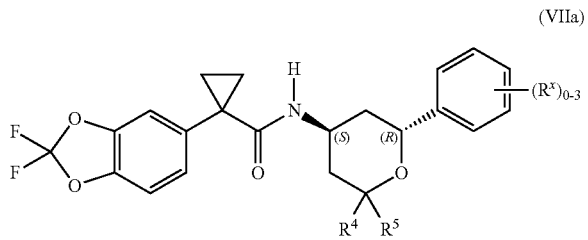

(VIIa)

$R^x$, at each occurrence, is an optional substituent independently selected from $C_1$-$C_6$alkyl, halogen, —C(O)$R^i$, and —C(O)O$R^h$,
  wherein, the $C_1$-$C_6$alkyl is optionally substituted with one, two or three substituents independently selected from the group consisting of fluorine and —O$R^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl or $C_1$-$C_6$alkyl; and
$R^4$ and $R^5$ are each $C_1$-$C_6$alkyl.

In one embodiment, the compound or pharmaceutically acceptable salt is an enantiomer of formula (VIIb), wherein

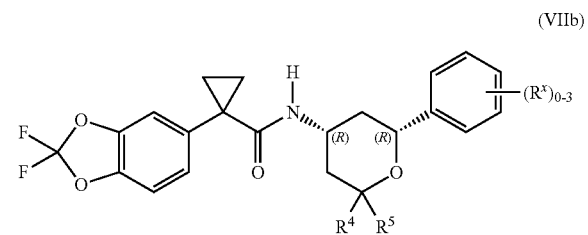

(VIIb)

$R^x$, at each occurrence, is an optional substituent independently selected from $C_1$-$C_6$alkyl, halogen, —C(O)$R^i$, and —C(O)O$R^h$,
  wherein, the $C_1$-$C_6$alkyl is optionally substituted with one, two or three substituents independently selected from the group consisting of fluorine and —O$R^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl or $C_1$-$C_6$alkyl; and
$R^4$ and $R^5$ are each $C_1$-$C_6$alkyl.

Specific embodiments contemplated as part of the invention also include, but are not limited to, compounds or pharmaceutically acceptable salts of formula (I), as defined, for example:
rac-1-(2,2-difluoro-1,3-benzodioxol-5-yl)-N-[(2R,4S)-2-phenyltetrahydro-2H-pyran-4-yl]cyclopropanecarboxamide;
rac-3-[(2R,4S)-4-({[1-(2,2-difluoro-1,3-benzodioxol-5-yl)cyclopropyl]carbonyl}amino)tetrahydro-2H-pyran-2-yl]benzoic acid;
methyl rac-3-[(2R,4S)-4-({[1-(2,2-difluoro-1,3-benzodioxol-5-yl)cyclopropyl]carbonyl}amino)tetrahydro-2H-pyran-2-yl]benzoate;
methyl rac-3-[(2R,4R)-4-({[1-(2,2-difluoro-1,3-benzodioxol-5-yl)cyclopropyl]carbonyl}amino)tetrahydro-2H-pyran-2-yl]benzoate;
rac-3-[(2R,4R)-4-({[1-(2,2-difluoro-1,3-benzodioxol-5-yl)cyclopropyl]carbonyl}amino)tetrahydro-2H-pyran-2-yl]benzoic acid;
rac-1-(2,2-difluoro-1,3-benzodioxol-5-yl)-N-{(2R,4R)-2-[3-(hydroxymethyl)phenyl]tetrahydro-2H-pyran-4-yl}cyclopropanecarboxamide;
rac-1-(2,2-difluoro-1,3-benzodioxol-5-yl)-N-{(2R,4R)-2-[3-(2-hydroxypropan-2-yl)phenyl]tetrahydro-2H-pyran-4-yl}cyclopropanecarboxamide;
rac-N-[(2R,4S)-2-(3-acetylphenyl)tetrahydro-2H-pyran-4-yl]-1-(2,2-difluoro-1,3-benzodioxol-5-yl)cyclopropanecarboxamide;
rac-1-(2,2-difluoro-1,3-benzodioxol-5-yl)-N-{(2R,4S)-2-[3-(hydroxymethyl)phenyl]tetrahydro-2H-pyran-4-yl}cyclopropanecarboxamide;
rac-1-(2,2-difluoro-1,3-benzodioxol-5-yl)-N-{(2R,4S)-2-[3-(2-hydroxypropan-2-yl)phenyl]tetrahydro-2H-pyran-4-yl}cyclopropanecarboxamide;
methyl rac-2-[(2R,4S)-4-({[1-(2,2-difluoro-1,3-benzodioxol-5-yl)cyclopropyl]carbonyl}amino)tetrahydro-2H-pyran-2-yl]benzoate;
rac-2-[(2R,4S)-4-({[1-(2,2-difluoro-1,3-benzodioxol-5-yl)cyclopropyl]carbonyl}amino)tetrahydro-2H-pyran-2-yl]benzoic acid;
methyl rac-4-[(2R,4S)-4-({[1-(2,2-difluoro-1,3-benzodioxol-5-yl)cyclopropyl]carbonyl}amino)tetrahydro-2H-pyran-2-yl]benzoate;
rac-4-[(2R,4S)-4-({[1-(2,2-difluoro-1,3-benzodioxol-5-yl)cyclopropyl]carbonyl}amino)tetrahydro-2H-pyran-2-yl]benzoic acid;
N-[(2S,4R)-2-(1,3-benzodioxol-5-yl)tetrahydro-2H-pyran-4-yl]-1-(2,2-difluoro-1,3-benzodioxol-5-yl)cyclopropanecarboxamide;
methyl 3-[(2S,4R)-4-({[1-(2,2-difluoro-1,3-benzodioxol-5-yl)cyclopropyl]carbonyl}amino)tetrahydro-2H-pyran-2-yl]benzoate;
methyl 3-[(2R,4S)-4-({[1-(2,2-difluoro-1,3-benzodioxol-5-yl)cyclopropyl]carbonyl}amino)tetrahydro-2H-pyran-2-yl]benzoate;
3-[(2S,4R)-4-({[1-(2,2-difluoro-1,3-benzodioxol-5-yl)cyclopropyl]carbonyl}amino)tetrahydro-2H-pyran-2-yl]benzoic acid;
3-[(2R,4S)-4-({[1-(2,2-difluoro-1,3-benzodioxol-5-yl)cyclopropyl]carbonyl}amino)tetrahydro-2H-pyran-2-yl]benzoic acid;
N-[(2R,4R)-2-(4-bromophenyl)tetrahydro-2H-pyran-4-yl]-1-(2,2-difluoro-1,3-benzodioxol-5-yl)cyclopropanecarboxamide;
N-[(2S,4S)-2-(4-bromophenyl)tetrahydro-2H-pyran-4-yl]-1-(2,2-difluoro-1,3-benzodioxol-5-yl)cyclopropanecarboxamide;
methyl rac-3-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoate;
methyl rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoate;
rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;
rac-3-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoic acid;
3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

methyl 4-[(2S,4R)-4-({[1-(2,2-difluoro-1,3-benzodioxol-5-yl)cyclopropyl]carbonyl}amino)tetrahydro-2H-pyran-2-yl]benzoate;

methyl 4-[(2R,4S)-4-({[1-(2,2-difluoro-1,3-benzodioxol-5-yl)cyclopropyl]carbonyl}amino)tetrahydro-2H-pyran-2-yl]benzoate;

4-[(2S,4R)-4-({[1-(2,2-difluoro-1,3-benzodioxol-5-yl)cyclopropyl]carbonyl}amino)tetrahydro-2H-pyran-2-yl]benzoic acid;

4-[(2R,4S)-4-({[1-(2,2-difluoro-1,3-benzodioxol-5-yl)cyclopropyl]carbonyl}amino)tetrahydro-2H-pyran-2-yl]benzoic acid;

methyl rac-4-[(2R,4S)-4-({[1-(2,2-difluoro-1,3-benzodioxol-5-yl)cyclopropyl]carbonyl}amino)-6,6-dimethyltetrahydro-2H-pyran-2-yl]benzoate;

rac-4-[(2R,4S)-4-({[1-(2,2-difluoro-1,3-benzodioxol-5-yl)cyclopropyl]carbonyl}amino)-6,6-dimethyltetrahydro-2H-pyran-2-yl]benzoic acid;

methyl rac-4-[(2R,4R)-4-({[1-(2,2-difluoro-1,3-benzodioxol-5-yl)cyclopropyl]carbonyl}amino)-6,6-dimethyltetrahydro-2H-pyran-2-yl]benzoate rac-4-[(2R,4R)-4-({[1-(2,2-difluoro-1,3-benzodioxol-5-yl)cyclopropyl]carbonyl}amino)-6,6-dimethyltetrahydro-2H-pyran-2-yl]benzoic acid methyl rac-4-[(2R,4S)-4-({[1-(2,2-difluoro-1,3-benzodioxol-5-yl)cyclopropyl]carbonyl}amino)tetrahydro-2H-pyran-2-yl]-3-methylbenzoate;

rac-4-[(2R,4S)-4-({[1-(2,2-difluoro-1,3-benzodioxol-5-yl)cyclopropyl]carbonyl}amino)tetrahydro-2H-pyran-2-yl]-3-methylbenzoic acid;

methyl rac-4-[(2R,6S)-6-cyclopropyl-4-({[1-(2,2-difluoro-1,3-benzodioxol-5-yl)cyclopropyl]carbonyl}amino)tetrahydro-2H-pyran-2-yl]benzoate;

methyl rac-4-[(2R,4S,6R)-4-({[1-(2,2-difluoro-1,3-benzodioxol-5-yl)cyclopropyl]carbonyl}amino)-6-methyltetrahydro-2H-pyran-2-yl]benzoate;

methyl rel-4-[(2S,4R)-4-({[1-(2,2-difluoro-1,3-benzodioxol-5-yl)cyclopropyl]carbonyl}amino)tetrahydro-2H-pyran-2-yl]-3-methylbenzoate;

methyl rel-4-[(2R,4S)-4-({[1-(2,2-difluoro-1,3-benzodioxol-5-yl)cyclopropyl]carbonyl}amino)tetrahydro-2H-pyran-2-yl]-3-methylbenzoate;

rel-4-[(2S,4R)-4-({[1-(2,2-difluoro-1,3-benzodioxol-5-yl)cyclopropyl]carbonyl}amino)tetrahydro-2H-pyran-2-yl]-3-methylbenzoic acid;

rel-4-[(2R,4S)-4-({[1-(2,2-difluoro-1,3-benzodioxol-5-yl)cyclopropyl]carbonyl}amino)tetrahydro-2H-pyran-2-yl]-3-methylbenzoic acid;

4-[6-cyclopropyl-4-({[1-(2,2-difluoro-1,3-benzodioxol-5-yl)cyclopropyl]carbonyl}amino)tetrahydro-2H-pyran-2-yl]benzoic acid;

rac-4-[(2R,4S,6R)-4-({[1-(2,2-difluoro-1,3-benzodioxol-5-yl)cyclopropyl]carbonyl}amino)-6-methyltetrahydro-2H-pyran-2-yl]benzoic acid;

methyl rac-4-[(2R,4R,6R)-4-({[1-(2,2-difluoro-1,3-benzodioxol-5-yl)cyclopropyl]carbonyl}amino)-6-methyltetrahydro-2H-pyran-2-yl]benzoate;

methyl rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoat;

methyl rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoate;

rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoic acid;

rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

dimethyl rac-4,4'-[(2R,4s,6S)-4-({[1-(2,2-difluoro-1,3-benzodioxol-5-yl)cyclopropyl]carbonyl}amino)tetrahydro-2H-pyran-2,6-diyl]dibenzoate;

dimethyl rac-4,4'-[(2R,4r,6S)-4-({[1-(2,2-difluoro-1,3-benzodioxol-5-yl)cyclopropyl]carbonyl}amino)tetrahydro-2H-pyran-2,6-diyl]dibenzoate;

rel-4-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

rel-4-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

methyl rac-4-[(2R,4R,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoate;

rac-4-[(2R,4S,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoic acid;

rac-4-[(2R,4R,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoic acid;

rel-4-[(2S,4R,6S)-4-({[1-(2,2-difluoro-1,3-benzodioxol-5-yl)cyclopropyl]carbonyl}amino)-6-methyltetrahydro-2H-pyran-2-yl]benzoic acid;

rel-4-[(2R,4S,6R)-4-({[1-(2,2-difluoro-1,3-benzodioxol-5-yl)cyclopropyl]carbonyl}amino)-6-methyltetrahydro-2H-pyran-2-yl]benzoic acid;

rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]-3-fluorobenzoic acid;

rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]-3-fluorobenzoic acid;

methyl rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]-3-methylbenzoate;

methyl rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]-3-fluorobenzoate;

rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]-3-methylbenzoic acid;

rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]-3-methylbenzoic acid;

rel-4-[(2R,4R,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoic acid;

rel-4-[(2S,4S,6R)-4-({[1-(2,2-difluoro-1,3-benzodioxol-5-yl)cyclopropyl]carbonyl}amino)-6-(4-methoxyphenyl)tetrahydro-2H-pyran-2-yl]benzoic acid;

ethyl rac-3-[(2R,4R,6S)-4-({[1-(2,2-difluoro-1,3-benzodioxol-5-yl)cyclopropyl]carbonyl}amino)-6-(3-methoxyphenyl)tetrahydro-2H-pyran-2-yl]benzoate;

rac-3-[(2R,4R,6S)-4-({[1-(2,2-difluoro-1,3-benzodioxol-5-yl)cyclopropyl]carbonyl}amino)-6-(3-methoxyphenyl)tetrahydro-2H-pyran-2-yl]benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-4-methylbenzoic acid;

methyl rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-4-methylbenzoate;

ethyl rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-5-methylbenzoate;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-5-methylbenzoic acid;

rel-3-[(2R,4R,6S)-4-({[1-(2,2-difluoro-1,3-benzodioxol-5-yl)cyclopropyl]carbonyl}amino)-6-(3-methoxyphenyl)tetrahydro-2H-pyran-2-yl]benzoic acid;

rel-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-5-methylbenzoic acid; and rel-3-[(2S,4R,6R)-4-({[1-(2,2-difluoro-1,3-benzodioxol-5-yl)cyclopropyl]carbonyl}amino)-6-phenyltetrahydro-2H-pyran-2-yl]-5-methylbenzoic acid.

Compound names are assigned by using Name 2012 naming algorithm by Advanced Chemical Development or Struct=Name naming algorithm as part of CHEMDRAW® ULTRA v. 12.0.2.1076.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^{2}$H and $^{3}$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{5}$O, $^{17}$O and $^{18}$O, phosphorus, such as $^{32}$P, and sulfur, such as $^{35}$S. Certain isotopically-labelled compounds of formula (I), for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection. Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Present compounds may be used in the form of pharmaceutically acceptable salts. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of the invention may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The invention contemplates compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds of the invention can be better understood in connection with the following synthetic schemes and methods which illustrate a means by which the compounds can be prepared.

The compounds of this invention can be prepared by a variety of synthetic procedures. Representative procedures are shown in, but are not limited to, Schemes 1-14. In Schemes 1-14, the variables $R^1$, $R^2$, $R^3$, $R^4$, $R^5$, $R^7$, $R^8$, $R^9$, $R^{10}$, $R^{11}$, $R^{12}$, $R^u$, $R^x$ and m are as described in the Summary.

Abbreviations: $Boc_2O$ for di-tert-butyl dicarbonate; $BF_3 \cdot OEt$ for boron trifluoride diethyl etherate; DMAP for 4-(dimethylamino)pyridine; Et for ethyl; HOAc for acetic acid; Me for methyl; MeOH for methanol; MsCl for methanesulfonyl chloride; NaOAc for sodium acetate; psi for pounds per square inch; Ra—Ni for Raney® nickel; TBAF for tetrabutylammonium fluoride; TBS-OTf for tert-butyldimethylsilyl trifluoromethanesulfonate; and TMSOTf for trimethylsilyl trifluoromethanesulfonate.

Scheme 1

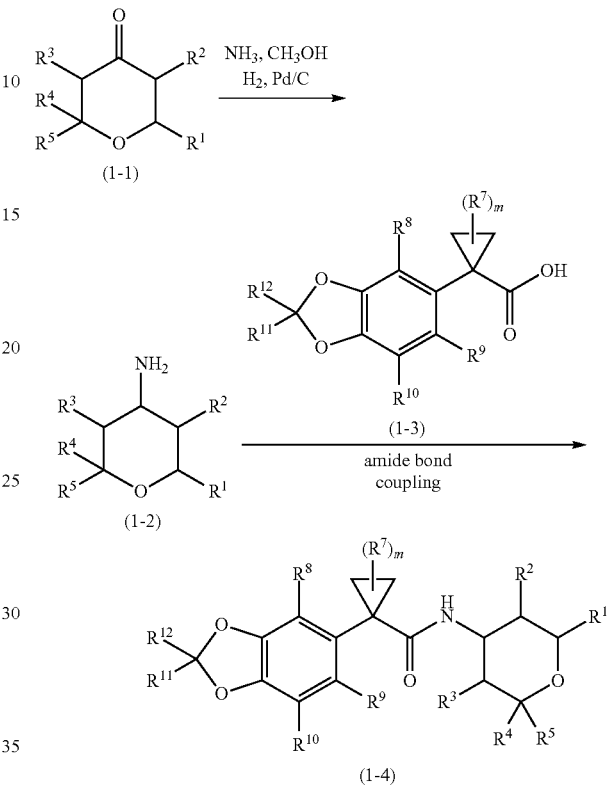

As shown in Scheme 1, compounds of formula (1-4) can be prepared from compounds of formula (1-1). Compounds of formula (1-1) can be reacted with ammonia dissolved in a solvent such as methanol, and the intermediate imine can be reduced by running the reaction in the presence of hydrogen (10-50 psi) and a palladium on carbon catalyst to give compounds of formula (1-2). Compounds of formula (1-2) can be coupled with carboxylic acids of formula (1-3) under amide bond forming conditions to give compounds of formula (1-4). Examples of conditions known to generate amides from a mixture of a carboxylic acid and an amine include but are not limited to adding a coupling reagent such as but not limited to N-(3-dimethylaminopropyl)-N-ethylcarbodiimide or 1-(3-dimethylaminopropyl)-3-ethylcarbodiimide (EDC, EDAC or EDCI), 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, N,N-dimethylacetamide, dimethyl sulfoxide, dichloromethane, and ethyl acetate. Alternatively, carboxylic acids of formula (1-3) can be converted to the corresponding acid chlorides by reaction with thionyl chloride, $PCl_3$, $PCl_5$, cyanuric chloride, or oxalyl chloride. The reactions with thionyl chloride and oxalyl chloride can be catalyzed with N,N-dimethylformamide at ambient temperature in a solvent such as dichloromethane. The resultant acid chlorides can then reacted with amines of formula (1-2) optionally in the presence of a base such as a tertiary amine base such as but not limited to triethylamine or diisopropylethylamine or an aromatic base such as pyridine, at room temperature in a solvent such as dichloromethane to give amides of formula (1-4). Compounds of formula (1-4) are representative of compounds of formula (I).

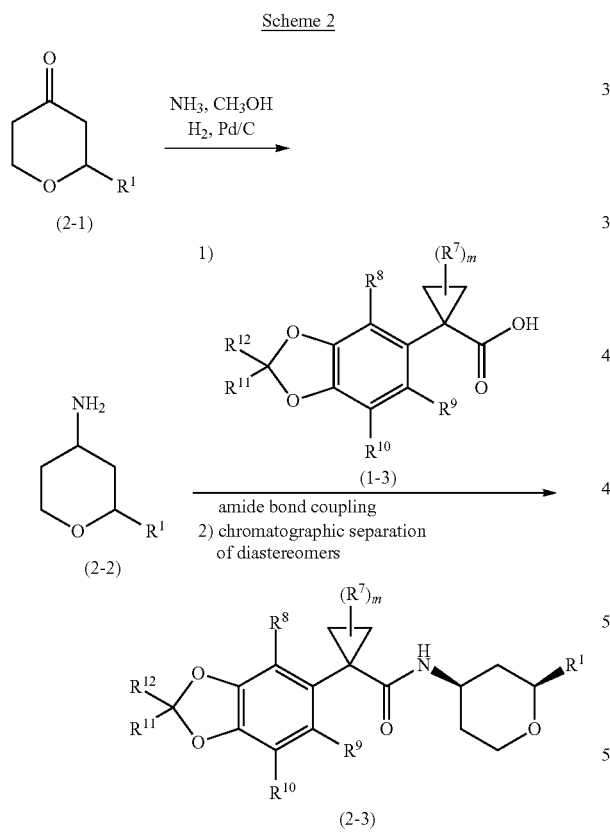

As illustrated in Scheme 2, compounds of formula (2-1) can be converted to compounds of formula (2-3) using the reaction sequence described in Scheme 1. The amides formed by coupling amines of formula (2-2) with carboxylic acids of formula (1-3) can be chromatographically purified to give the individual diastereomers, such as compounds of formula (2-3). Compounds of formula (2-3) are representative of compounds of formula (I).

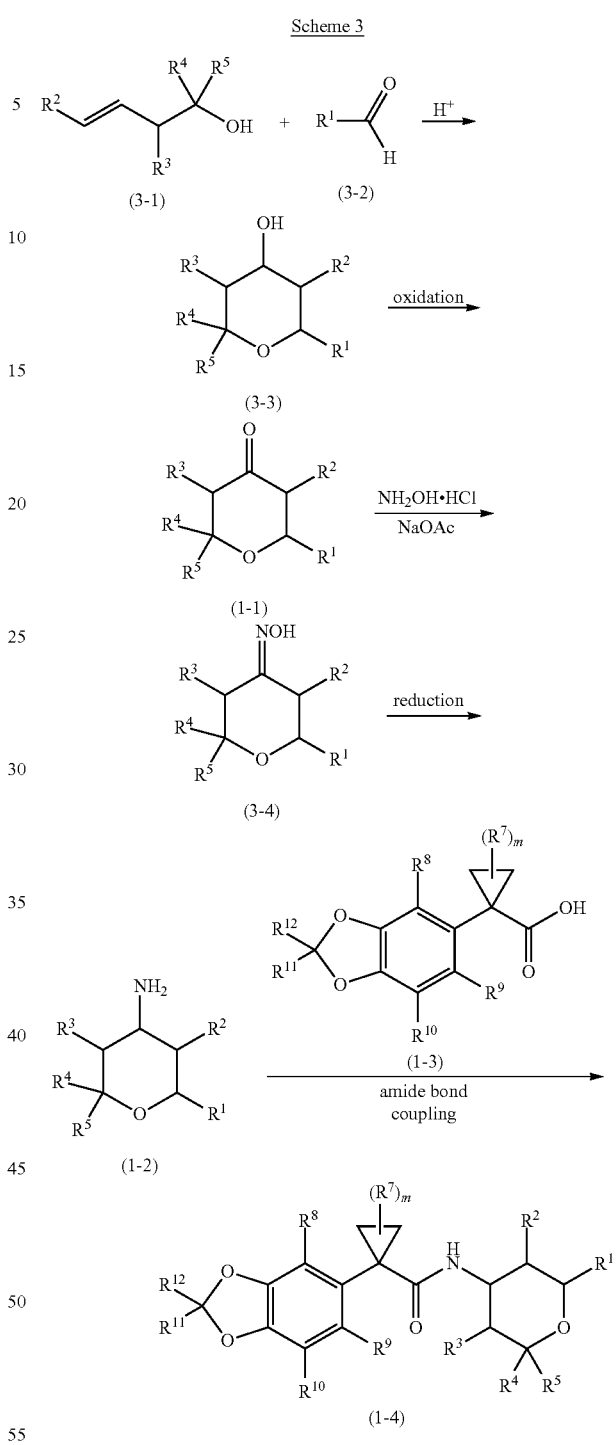

As illustrated in Scheme 3, compounds of formula (1-4) can be prepared starting from compounds of formula (3-1) and compounds of formula (3-2). Accordingly, a chilled (approximately 0° C.) mixture of compounds of formula (3-1) and compounds of formula (3-2) can be treated overnight with an acid such as sulfuric acid with warming to ambient temperature to give compounds of formula (3-3). Then compounds of formula (3-3) can be oxidized with a reagent such as Dess-Martin periodinane in dichloromethane from 1 to 24 hours to give compounds of formula (1-1). Compounds of formula (1-1) can be reacted with hydroxylamine hydrochloride in the presence of sodium acetate in a solvent such as methanol or ethanol overnight at ambient temperature to give compounds of formula (3-4). Compounds of formula (3-4) can then be reduced with hydrogen (20-40 psi) in the presence of a catalyst such as Raney® nickel in a solvent such as methanol from 8-24 hours at room temperature to give compounds of formula (1-2). Compounds of formula (1-2) can be coupled with compounds of formula (1-3) to give compounds of formula (1-4) as described in Scheme 1. Compounds of formula (1-4) are representative of compounds of formula (I).

sequentially to compounds of formula (2-1), formula (4-3), and formula (4-4) using the methodology described in Scheme 3. Compounds of formula (4-4) can be coupled with carboxylic acids of formula (1-3), and the diastereomers of the resultant amide can be chromatographically separated as illustrated with the diastereomer of formula (2-3). Compounds of formula (2-3) are representative of compounds of formula (I).

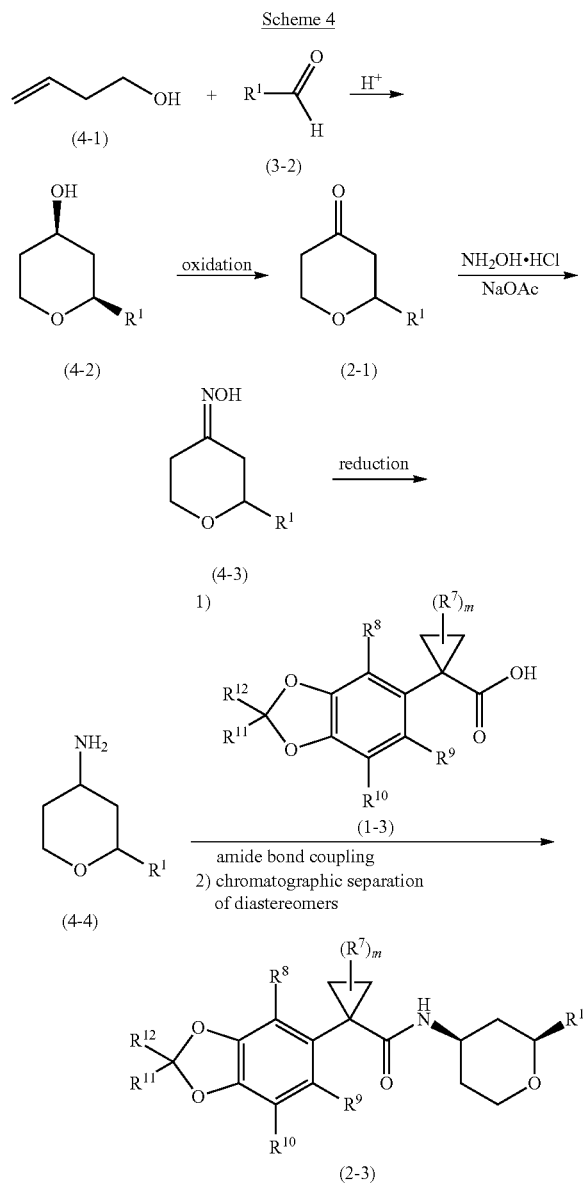

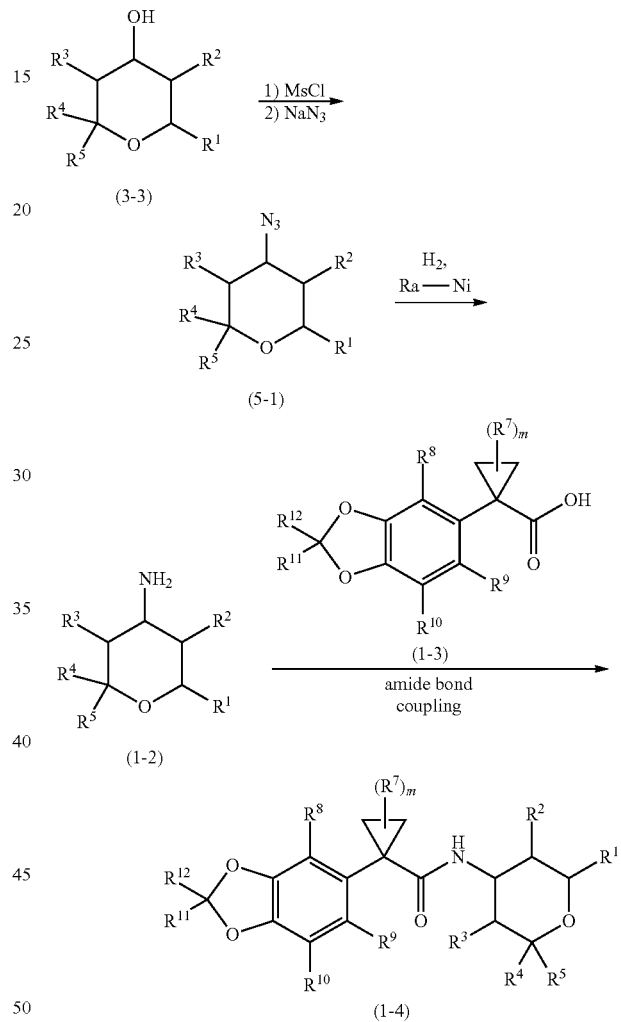

As illustrated in Scheme 4, compounds of formula (2-3) can be prepared starting from compounds of formula (4-1) and compounds of formula (3-2). Accordingly, a chilled (approximately 0° C.) mixture of compounds of formula (4-1) and compounds of formula (3-2) can be treated overnight with an acid such as sulfuric acid with warming to ambient temperature to give cis compounds of formula (4-2). Compounds of formula (4-2) can be converted In an alternative sequence, compounds of formula (1-4) can be prepared from compounds of formula (3-3). Compounds of formula (3-3) can be reacted with a sulfonyl chloride such as methanesulfonyl chloride in the presence of a tertiary amine base such as triethylamine or diisopropylethylamine at ambient temperature in a solvent such as dichloromethane over 15 minutes to 2 hours to give an intermediate sulfonate. The intermediate sulfonate can then be reacted with sodium azide in a solvent such as N,N-dimethylformamide heated from 80-110° C. for 1-8 hours to give compounds of formula (5-1). Azides of formula (5-1) can be reduced with hydrogen (20-40 psi) at ambient temperature in a solvent such as methanol over 1-8 hours to give compounds of formula (1-2). As described in Scheme 1, compounds of formula (1-2) can be coupled with compounds of formula (1-3) to give amides of formula (1-4). Compounds of formula (1-4) are representative of compounds of formula (I).

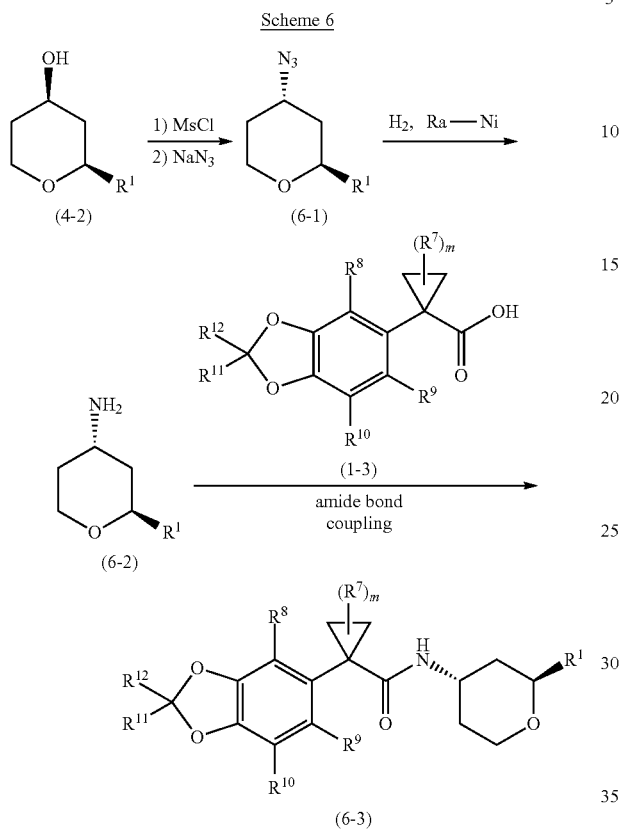

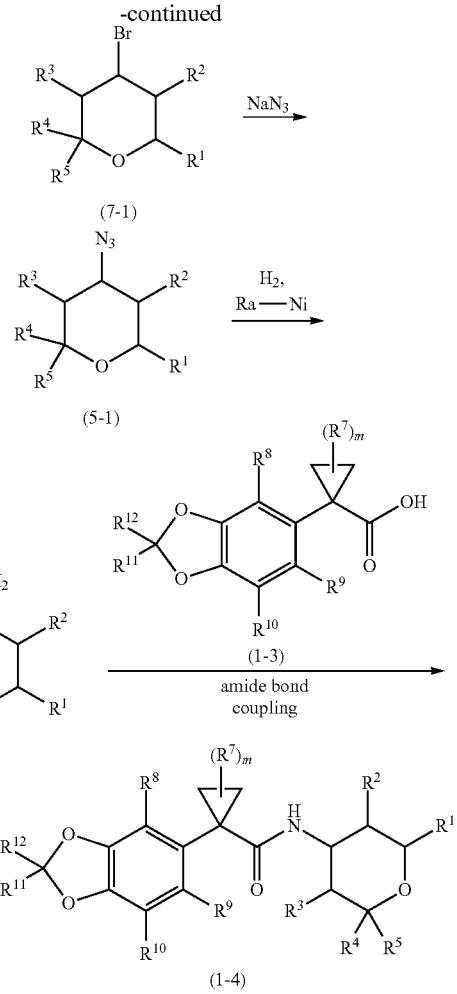

As shown in Scheme 6, compounds of formula (6-3) can be prepared from compounds of formula (4-2). Compounds of formula (4-2) can be converted to the corresponding sulfonate which can then be displaced with azide with inversion to give compounds of formula (6-1) using the methodology described in Scheme 5. Compounds of formula (6-1) can be reduced with hydrogen in the presence of Raney® nickel as described in Scheme 5 to give compounds of formula (6-2). Amines of formula (6-2) can then be coupled with carboxylic acids of formula (1-3) using the conditions described in Scheme 1 to give compounds of formula (6-3). Compounds of formula (6-3) are representative of compounds of formula (I).

Compounds of formula (1-4) can be prepared in an alternative sequence from compounds of formula (3-1) and formula (3-2). Butenols of formula (3-1) and aldehydes of formula (3-2) can be treated with gallium(III) bromide in dichloromethane at ambient temperature for 2-4 days to give compounds of formula (7-1). Compounds of formula (7-1) reacted with sodium azide in a solvent such as N,N-dimethylformamide heated from 80-110° C. for 1-8 hours to give compounds of formula (5-1). Azides of formula (5-1) can be reduced with hydrogen (20-40 psi) at ambient temperature in a solvent such as methanol over 1-8 hours to give compounds of formula (1-2). As described in Scheme 1, compounds of formula (1-2) can be coupled with compounds of formula (1-3) to give amides of formula (1-4). Compounds of formula (1-4) are representative of compounds of formula (I).

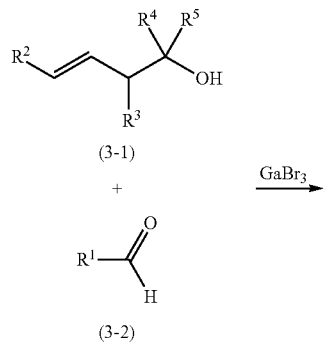

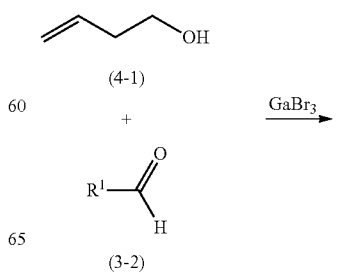

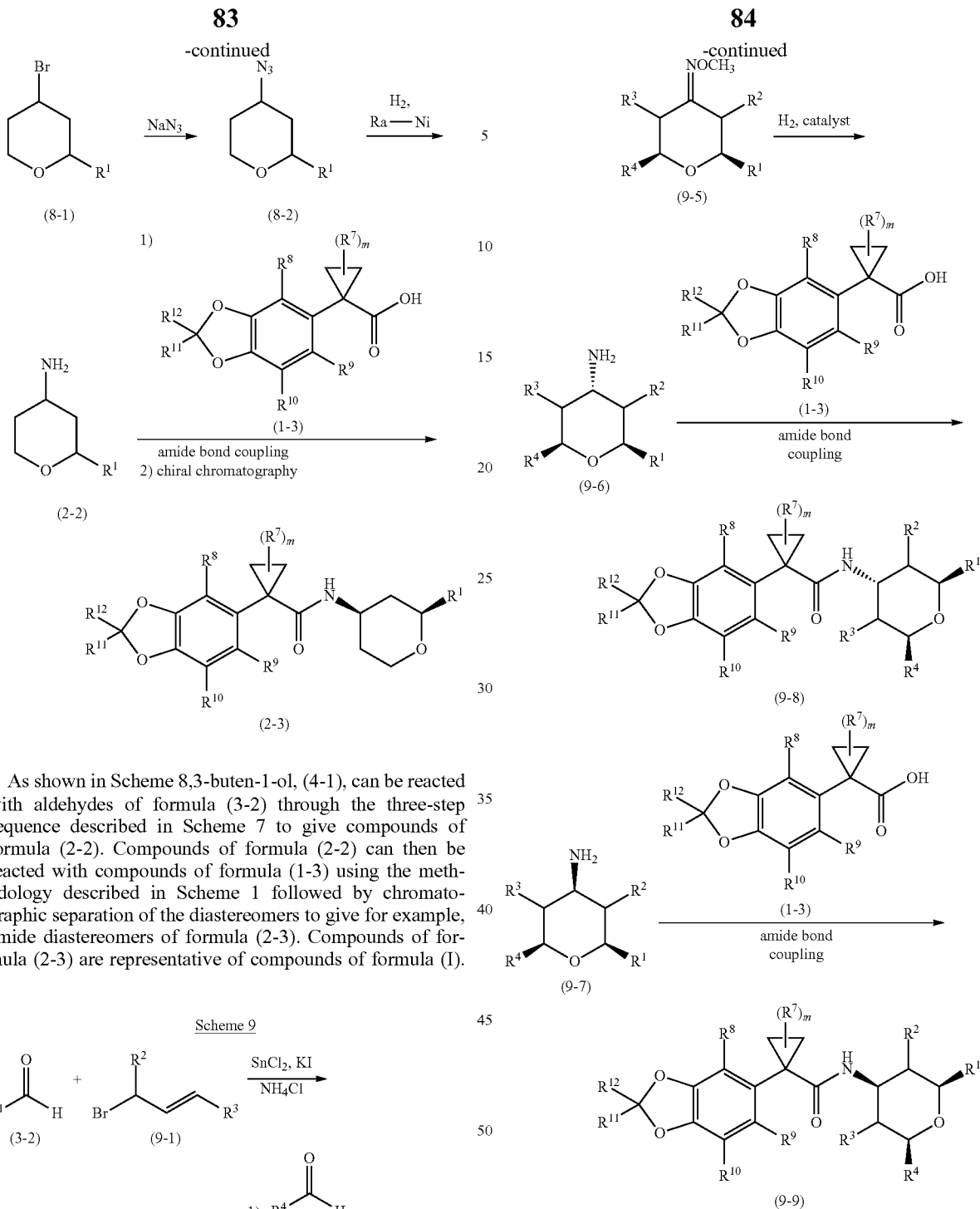

As shown in Scheme 8, 3-buten-1-ol, (4-1), can be reacted with aldehydes of formula (3-2) through the three-step sequence described in Scheme 7 to give compounds of formula (2-2). Compounds of formula (2-2) can then be reacted with compounds of formula (1-3) using the methodology described in Scheme 1 followed by chromatographic separation of the diastereomers to give for example, amide diastereomers of formula (2-3). Compounds of formula (2-3) are representative of compounds of formula (I).

As shown in Scheme 9, compounds of formula (9-8) and formula (9-9) can be prepared from aldehydes of formula (3-2) and bromoalkenes of formula (9-1). Aldehydes of formula (3-2) and bromoalkenes of formula (9-1) can be reacted in the presence of stannous chloride, potassium iodide, and saturated ammonium chloride in water at ambient temperature for 1 to 8 hours to give compounds of formula (9-2). Compounds of formula (9-2) can be reacted with aldehydes of formula (9-3) in the presence of acetic acid and boron trifluoride diethyl etherate in a solvent such as benzene at or near 0° C. for 1 to 8 hours to give compounds of formula (9-4) following removal of the intermediate acetate by treatment with potassium carbonate in methanol. Compounds of formula (9-4) can be oxidized with an oxidant such as pyridinium chlorochromate. The intermediate ketone can be reacted with O-methylhydroxylamine hydrochloride in the presence of sodium acetate in heated (40-64° C.) methanol to give compounds of formula (9-5). Compounds of formula (9-5) can be reduced with hydrogen (15-45 psi) in the presence of a catalyst such as Raney® nickel in a solvent such as methanol at ambient temperature from 4 to 24 hours or with a catalyst such as 5% platinum on carbon in a solvent such as acetic acid at ambient temperature from 8 to 24 hours to give diastereomeric compounds of formula (9-6) and formula (9-7) which can be chromatographically separated. Compounds of formula (9-6) and compounds of formula (9-7) can each be reacted with compounds of formula (1-3) under the amide bond forming conditions described in Scheme 1 to give compounds of formula (9-8) and formula (9-9), respectively. The enantiomers of compounds of formula (9-8) and compounds of formula (9-9) can be separated using supercritical fluid chromatography and an appropriate chiral chromatography column. Compounds of formula (9-8) and compounds of formula (9-9) are representative of compounds of formula (I).

As shown in Scheme 10, compounds of formula (10-5) can be prepared from compounds of formula (10-1). Compounds of formula (10-1) can be reacted with tert-butyldimethylsilyl trifluoromethanesulfonate in a solvent such as tetrahydrofuran initially at 0° C. with warming to ambient temperature over 1 to 8 hours to give compounds of formula (10-2). Compounds of formula (10-2) can be reacted with aldehydes of formula (3-2) in the presence of tris(6,6,7,7,8,8,8-heptafluoro-2,2-dimethyl-3,5-octanedionato)europium (III) in chloroform heated to near the reflux temperature for 4-12 hours to give intermediate silyl enol ethers. The intermediate silyl enol ethers can be converted to the corresponding ketones of formula (10-3) by treatment with tetrabutylammonium fluoride in tetrahydrofuran at room temperature over 30 minutes to 4 hours. The ketones of formula (10-3) can be reacted in a two-step process to give the amines of formula (10-4). In the first step, ketones of formula (10-3) can be reacted with O-methylhydroxylamine hydrochloride in pyridine initially at room temperature and then followed by heating from 50 to 70° C. to give intermediate O-methyl oximes. The intermediate O-methyl oximes can be reduced in a second step with hydrogen (15-45 psi) in the presence of platinum in acetic acid over 12 to 48 hours at ambient temperature to give compounds of formula (10-4). Compounds of formula (10-4) can be reacted with compounds of formula (1-3) under the amide bond forming reaction conditions described in Scheme 1 to give compounds of formula (10-5). Compounds of formula (10-5) are representative of compounds of formula (I).

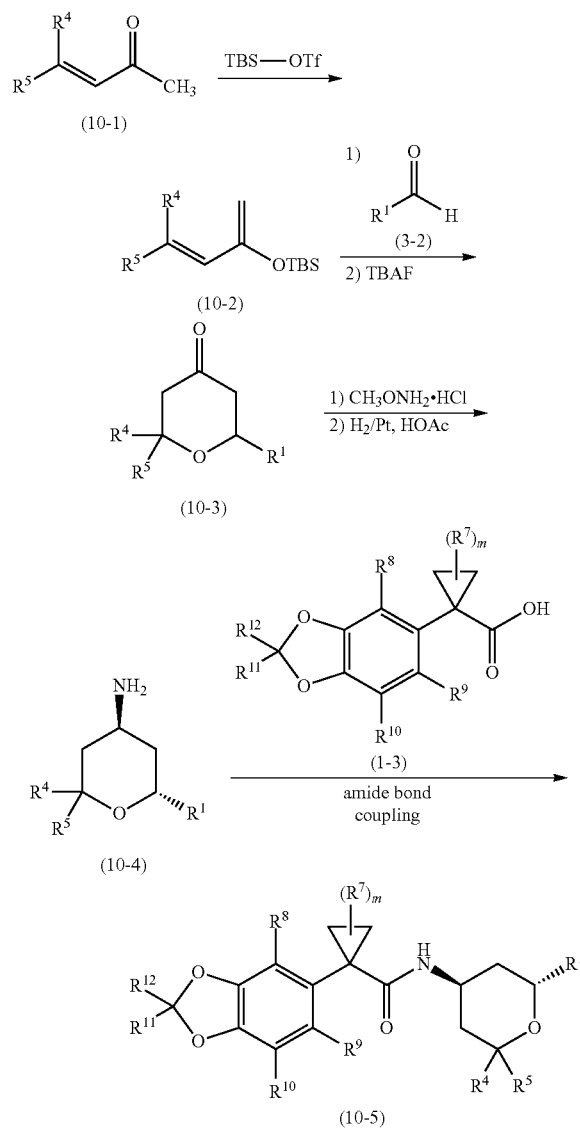

Scheme 10

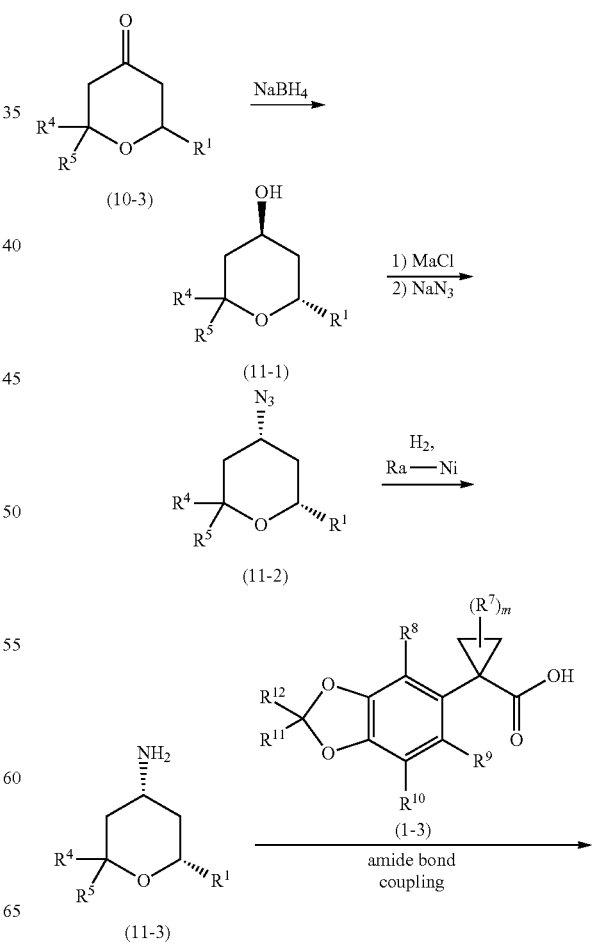

Scheme 11

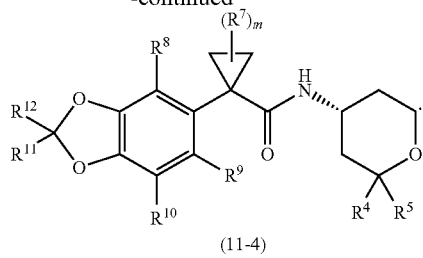

(11-4)

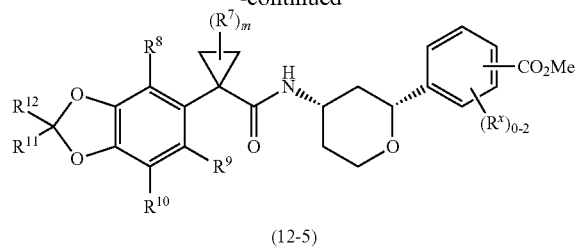

(12-5)

As shown in Scheme 11, compounds of formula (11-4) can be prepared from compounds of formula (10-3) using methodology described in Scheme 6. To that end, compounds of formula (10-3) can be reduced with a reagent such as sodium borohydride in a cooled solvent such as methanol to give compounds of formula (11-1). Compounds of formula (11-1) can be converted to the corresponding sulfonate which can then be displaced with azide with inversion to give compounds of formula (11-2) using the methodology described in Scheme 5. Compounds of formula (11-2) can be reduced with hydrogen in the presence of Raney® nickel as described in Scheme 5 to give compounds of formula (11-3). Amines of formula (11-3) can then be coupled with carboxylic acids of formula (1-3) using the conditions described in Scheme 1 to give compounds of formula (11-4). Compounds of formula (11-4) are representative of compounds of formula (I).

As shown in Scheme 12, compounds of formula (12-5) can be prepared from compounds of formula (12-1). A benzaldehyde of formula (12-1) can be reacted with a 2-(siloxy)-1,3-butadiene in the presence of a catalyst such as boron trifluoride diethyl etherate in a solvent such as toluene cooled to −78 to −40° C. over 1 to 8 hours. The mixture can then be treated with an aqueous acid such as 0.5 N HCl at ambient temperature from 2-24 hours to give compounds of formula (12-2). Compounds of formula (12-2) can be carbonylated with pressurized carbon monoxide in the presence of a base such as triethylamine and a palladium catalyst such as [1,1'-bis(diphenylphosphino)ferrocene]dichloropalladium(II) in a solvent such as methanol heated to about 100° C. to give compounds of formula (12-3). Compounds of formula (12-3) can be reductively aminated with ammonia in the presence of hydrogen and a catalyst such as 5% palladium on carbon in a solvent such as methanol to give compounds of formula (12-4). Compounds of formula (12-4) can be coupled with carboxylic acids of formula (1-3) using the conditions described in Scheme 1 to give compounds of formula (12-5). Compounds of formula (12-5) are representative of compounds of formula (I).

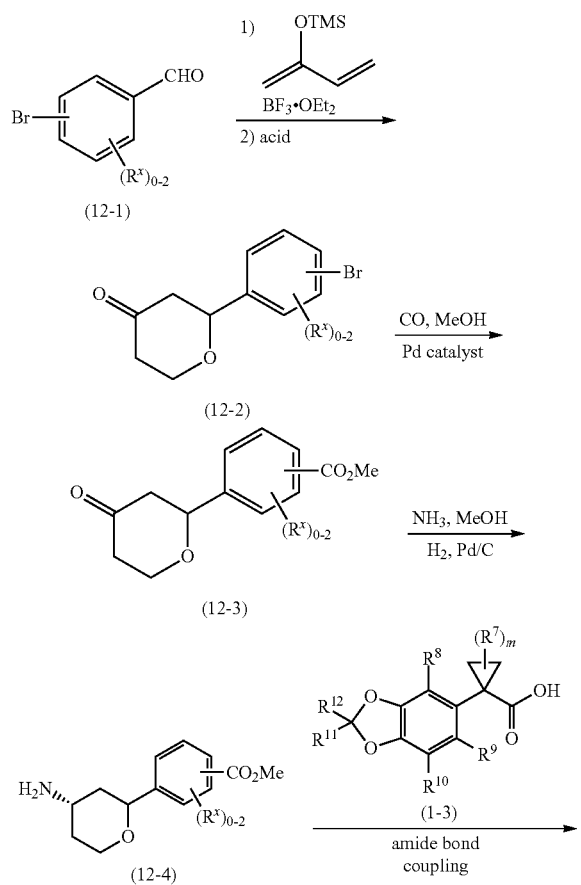

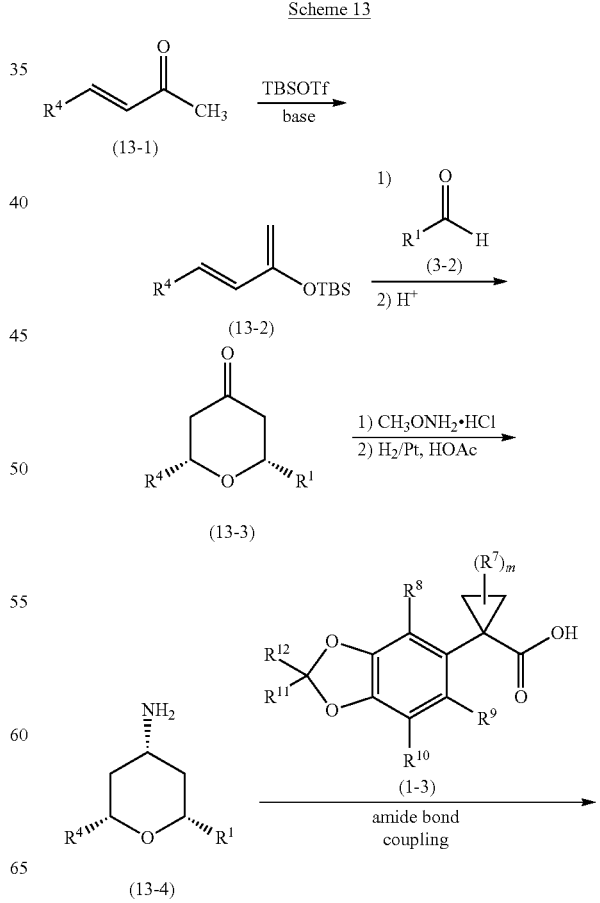

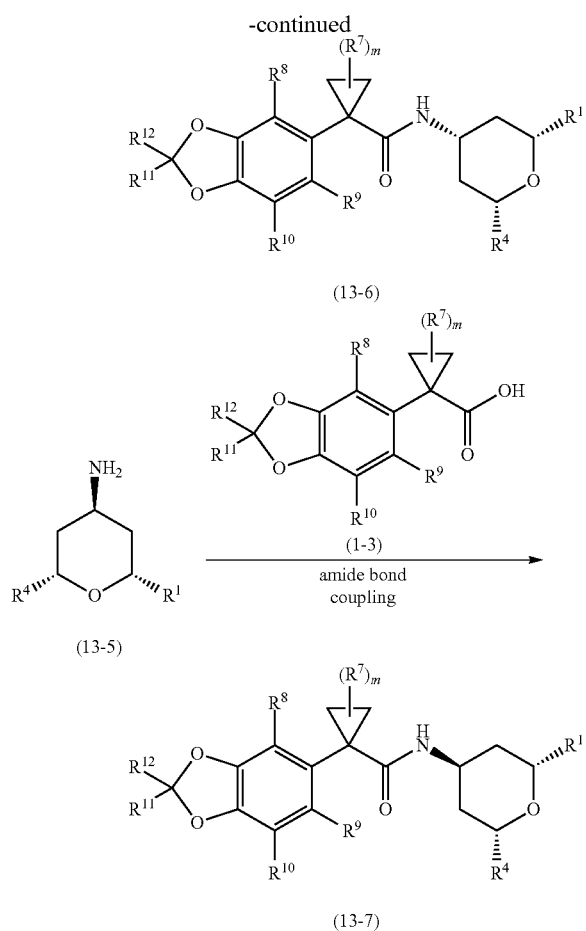

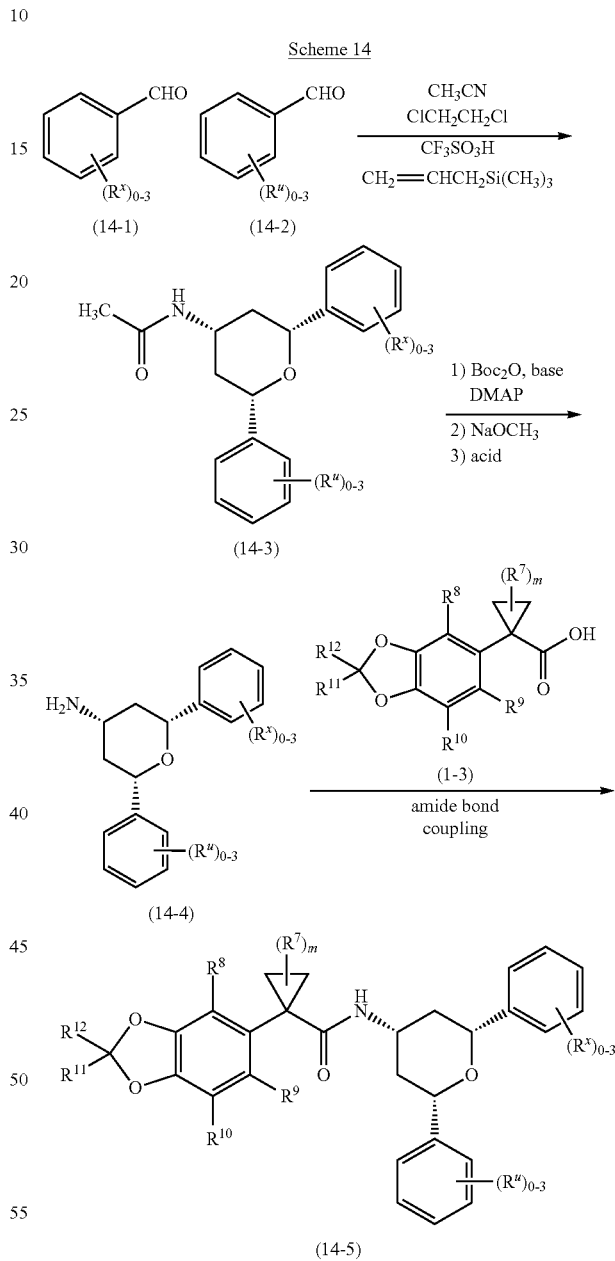

As shown in Scheme 13, compounds of formula (13-6) and compounds of formula (13-7) can be prepared from compounds of formula (13-1). Compounds of formula (13-1) can be reacted with a trialkylsilylsulonate such as tert-butyldimethylsilyl trifluoromethanesulfonate or trimethylsilyl trifluoromethanesulfonate in a solvent such as methylene chloride or tetrahydrofuran initially at −5 to 0° C. with warming to ambient temperature to give compounds of formula (13-2). Compounds of formula (13-2) can be reacted with aldehydes of formula (3-2) in the presence of boron trifluoride diethyl etherate in toluene initially at about −65° C. followed by warming to ambient temperature to give the intermediate silyl enol ethers. The intermediate silyl enol ethers can be converted to the corresponding ketones of formula (13-3) by treatment with an acid such as 1 M hydrochloric acid at room temperature over 8 hours to 24 hours. The ketones of formula (13-3) can be reacted in a two-step process to give the amines of formula (13-4) and (13-5). In the first step, ketones of formula (13-3) can be reacted with O-methylhydroxylamine hydrochloride in the presence of sodium acetate in methanol heated from 50 to 70° C. to give intermediate O-methyl oximes. The intermediate O-methyl oximes can be reduced in a second step with hydrogen in the presence of a 5% platinum on carbon catalyst in acetic acid over 12 to 48 hours at ambient temperature to give compounds of formula (13-4) and compounds of formula (13-5). In some instances compounds of formula (13-4) and formula (13-5) may be separated. In other instances they may be carried on together in the next reaction step. Compounds of formula (13-4) and compounds of (13-5) can be reacted with compounds of formula (1-3) either together or separately under the amide bond forming reaction conditions described in Scheme 1 to give compounds of formula (13-6) and compounds of formula (13-7). Compounds of formula (13-6) and formula (13-7) can be chromatographically separated if formed together in the same reaction. Compounds of formula (13-6) and formula (13-7) are representative of compounds of formula (I).

As shown in Scheme 14, compounds of formula (14-5) can be prepared starting from compounds of formula (14-1) and formula (14-2). Compounds of formula (14-1) and formula (14-2) can be combined with acetonitrile and allyltrimethylsilane in a solvent such as 1,2-dichloroethane in the presence of a catalyst such as trifluoromethanesulfonic acid at −40 to −30° C. to give compounds of formula (14-3). In a three-step process, compounds of formula (14-3) can be converted to compounds of formula (14-4). In the first step, the amide is treated with di-tert-butyl dicarbonate in the presence of a tertiary amine base such as triethylamine or diisopropylethylamine and 4-(dimethylamino)pyridine in a solvent such as heated toluene. The acetyl group can then be removed by treatment of the intermediate acetylated carbamate by treatment with sodium methoxide at about 10° C. In the third step, the tert-butoxycarbonyl group can be removed by treatment under acidic conditions such as trifluoroacetic acid in dichloromethane or hydrochloric acid in dioxane to give compounds of formula (14-4). Compounds of formula (14-4) can be reacted with carboxylic acids of formula (1-3) using the conditions described in Scheme 1 to give compounds of formula (12-5). Compounds of formula (12-5) are representative of compounds of formula (I).

The compounds of formula (1-4), formula (2-3), formula (6-3), formula (9-8), formula (9-9), formula (10-5), formula (11-4), formula (12-5), formula (13-7) and formula (14-5) can contain functional groups that can be further manipulated using methodology described in the examples. For example, $R^1$ can represent a methylbenzoate moiety. The ester functional group is readily hydrolyzed with a base such as sodium hydroxide in a solvent such as ethanol or with aqueous lithium hydroxide in methanol to give a corresponding carboxylic acid. The ester group can also be treated with a reductant such as sodium borohydride in a solvent such as methanol to give the corresponding hydroxymethyl group. Additionally, the ester can be treated with a Grignard reagent in a solvent such as 2-methyltetrahydrofuran to give either the corresponding ketone or tertiary alcohol.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Fumiss, Hannaford, Smith, and Tatchell, pub. Longman Scientific & Technical, Essex CM20 2JE, England.

Many of the compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Pharmaceutical Compositions

This invention also provides for pharmaceutical compositions comprising a therapeutically effective amount of a compound of formula (I), or a pharmaceutically acceptable salt thereof together with a pharmaceutically acceptable carrier, diluent, or excipient thereof. The phrase "pharmaceutical composition" refers to a composition suitable for administration in medical or veterinary use.

The pharmaceutical compositions that comprise a compound of formula (I), alone or in combination with a second therapeutic agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which may serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate), and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula (I). In certain embodiments, the compound of formula (I) may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form may be a capsule, tablet, cachet, or lozenge itself, or it may be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition may, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician may evaluate factors such as the circulating plasma levels of the compound, compound toxicities, and/or the progression of the disease, etc.

For administration, compounds may be administered at a rate determined by factors that may include, but are not limited to, the $LD_{50}$ of the compound, the pharmacokinetic profile of the compound, contraindicated drugs, and the side-effects of the compound at various concentrations, as applied to the mass and overall health of the subject. Administration may be accomplished via single or divided doses.

The compounds utilized in the pharmaceutical method of the invention may be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds with suitable non-irritating carriers or carriers such as cocoa butter, polyethylene glycol, or a suppository wax which are solid at room temperature but liquid at body temperature and therefore melt in the rectum or vaginal cavity and release the active compound.

Compounds may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes may be used. The present compositions in liposome form may contain, in addition to a compound of the invention, stabilizers, preservatives, excipients, and the like. Examples of lipids include, but are not limited to, natural and synthetic phospholipids, and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments, and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

Methods of Use

The compounds and compositions using any amount and any route of administration may be administered to a subject for the treatment or prevention of cystic fibrosis, pancreatic insufficiency, Sjögren's Syndrome (SS), chronic obstructive lung disease (COLD), or chronic obstructive airway disease (COAD).

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, and via implantation. In certain embodiments, the compounds and compositions thereof may be delivered orally. The compounds may also be delivered rectally, bucally, intravaginally, ocularly, or by insufflation. CFTR-modulated disorders and conditions may be treated prophylactically, acutely, and chronically using compounds or pharmaceutically acceptable salts thereof and compositions thereof, depending on the nature of the disorder or condition. Typically, the host or subject in each of these methods is human, although other mammals may also benefit from the administration of compounds or pharmaceutically acceptable salts thereof and compositions thereof as set forth hereinabove.

Compounds of the invention are useful as modulators of CFTR. Thus, the compounds and compositions are particularly useful for treating or lessening the severity or progression of a disease, disorder, or a condition where hyperactivity or inactivity of CFTR is involved. Accordingly, the invention provides a method for treating cystic fibrosis, pancreatic insufficiency, Sjögren's Syndrome (SS), chronic obstructive lung disease (COLD), or chronic obstructive airway disease (COAD) in a subject, wherein the method comprises the step of administering to said subject a therapeutically effective amount of a compound of formula (I) or a pharmaceutically acceptable salt thereof, or a preferred embodiment thereof as set forth above, with or without a pharmaceutically acceptable carrier. Particularly, the method is for the treatment or prevention of cystic fibrosis. In a more particular embodiment, the cystic fibrosis is caused by a Class I, II, III, IV, V, and/or VI mutation.

One embodiment is directed to a compound of the invention or a pharmaceutically acceptable salt thereof, or pharmaceutical compositions comprising a compound of the invention or a pharmaceutically acceptable salt thereof for use in medicine.

One embodiment is directed to a compound according to formula (I) or a pharmaceutically acceptable salt thereof, or pharmaceutical compositions comprising a compound of the invention or pharmaceutically acceptable salt thereof, for use in the treatment of cystic fibrosis, pancreatic insufficiency, Sjögren's Syndrome (SS), chronic obstructive lung disease (COLD) or chronic obstructive airway disease (COAD). In a more particular embodiment, the cystic fibrosis is caused by a Class I, II, III, IV, V, and/or VI mutation.

In one embodiment, the present invention provides pharmaceutical compositions comprising a compound of the invention or a pharmaceutically acceptable salt thereof, and one or more additional therapeutic agents. In a particular embodiment, the additional therapeutic agent is a cystic fibrosis treatment agent other than a compound of the invention. In a more particular embodiment, the cystic fibrosis is caused by a Class I, II, III, IV, V, and/or VI mutation.

The present compounds or pharmaceutically acceptable salts thereof may be administered as the sole active agent or it may be co-administered with one or more additional therapeutic agents, including other compounds that demonstrate the same or a similar therapeutic activity and that are determined to be safe and efficacious for such combined administration. The present compounds may be co-administered to a subject. The term "co-administered" means the administration of two or more different therapeutic agents to a subject by combination in the same pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compounds of the invention or pharmaceutically acceptable salts thereof may be co-administered with a therapeutically effective amount of one or more additional therapeutic agents to treat a CFTR mediated disease, where examples of the therapeutic agents include, but are not limited to, antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), and CFTR amplifiers. In one embodiment, the CFTR mediated disease is cystic fibrosis. In one embodiment, the compounds of the invention or pharmaceutically acceptable salts thereof may be co-administered with one or more additional therapeutic agents selected from the group consisting of CFTR modulators and CFTR amplifiers. In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulators. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In one embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of potentiators include, but are not limited to, Ivacaftor (VX-770), CTP-656, NVS-QBW251, FD1860293, and N-(3-carbamoyl-5,5,7,7-tetramethyl-4,7-dihydro-5H-thieno[2,3-c]pyran-2-yl)-1H-pyrazole-5-carboxamide.

Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, and WO2013038390; and U.S. application Ser. Nos. 14/271,080 and 14/451,619.

In one embodiment, the potentiator can be selected from the group consisting of

Ivacaftor (VX-770, N-(2,4-di-tert-butyl-5-hydroxyphenyl)-4-oxo-1,4-dihydroquinoline-3-carboxamide);
CTP-656;
NVS-QBW251;
FD1860293;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-4,7-dihydro-5H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide
2-(1-hydroxycyclopropanecarboxamido)-5,5,7,7-tetramethyl-5,7-dihydro-4H-thieno[2,3-c]pyran-3-carboxamide;
5,5,7,7-tetramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-5-methyl-1H-pyrazole-3-carboxamide;
N-(3-carbamoyl-5,5,7,7-tetramethyl-5,7-dihydro-4H-thieno[2,3-c]pyran-2-yl)-5-cyclopropyl-1H-pyrazole-3-carboxamide;
N-(3-carbamoyl-5,5,7,7-tetramethyl-5,7-dihydro-4H-thieno[2,3-c]pyran-2-yl)-5-isopropyl-1H-pyrazole-3-carboxamide;

N-(3-carbamoyl-5,5,7,7-tetramethyl-5,7-dihydro-4H-thieno[2,3-c]pyran-2-yl)-5-(trifluoromethyl)-1H-pyrazole-3-carboxamide;

5-tert-butyl-N-(3-carbamoyl-5,5,7,7-tetramethyl-5,7-dihydro-4H-thieno[2,3-c]pyran-2-yl)-1H-pyrazole-3-carboxamide;

N-(3-carbamoyl-5,5,7,7-tetramethyl-5,7-dihydro-4H-thieno[2,3-c]pyran-2-yl)-5-ethyl-1H-pyrazole-3-carboxamide;

N-(3-carbamoyl-5,5,7,7-tetramethyl-5,7-dihydro-4H-thieno[2,3-c]pyran-2-yl)-3-ethyl-4-methyl-1H-pyrazole-5-carboxamide;

2-(2-hydroxypropanamido)-5,5,7,7-tetramethyl-5,7-dihydro-4H-thieno[2,3-c]pyran-3-carboxamide;

N-(3-carbamoyl-5,5,7,7-tetramethyl-5,7-dihydro-4H-thieno[2,3-c]pyran-2-yl)-4-chloro-1H-pyrazole-3-carboxamide;

N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;

4-bromo-N-(3-carbamoyl-5,5,7,7-tetramethyl-5,7-dihydro-4H-thieno[2,3-c]pyran-2-yl)-1H-pyrazole-3-carboxamide;

N-(3-carbamoyl-5,5,7,7-tetramethyl-5,7-dihydro-4H-thieno[2,3-c]pyran-2-yl)-4-chloro-5-methyl-1H-pyrazole-3-carboxamide;

N-(3-carbamoyl-5,5,7,7-tetramethyl-5,7-dihydro-4H-thieno[2,3-c]pyran-2-yl)-4-methyl-1H-pyrazole-3-carboxamide;

2-(2-hydroxy-3,3-dimethylbutanamido)-5,5,7,7-tetramethyl-5,7-dihydro-4H-thieno[2,3-c]pyran-3-carboxamide;

2-[(2-hydroxy-4-methyl-pentanoyl)amino]-5,5,7,7-tetramethyl-4H-thieno[2,3-c]pyran-3-carboxamide;

5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;

N-(3-carbamoyl-5,5,7,7-tetramethyl-4H-thieno[2,3-c]pyran-2-yl)-4-(3-methoxypropyl)-1H-pyrazole-3-carboxamide;

N-(3-carbamoyl-5,5,7,7-tetramethyl-4H-thieno[2,3-c]pyran-2-yl)-4-(2-ethoxyethyl)-1H-pyrazole-3-carboxamide;

2-[[(2S)-2-hydroxy-3,3-dimethyl-butanoyl]amino]-5,5,7,7-tetramethyl-4H-thieno[2,3-c]pyran-3-carboxamide;

2-[[(2R)-2-hydroxy-3,3-dimethyl-butanoyl]amino]-5,5,7,7-tetramethyl-4H-thieno[2,3-c]pyran-3-carboxamide;

2-[(2-hydroxy-2,3,3-trimethyl-butanoyl)amino]-5,5,7,7-tetramethyl-4H-thieno[2,3-c]pyran-3-carboxamide;

[5-[(3-carbamoyl-5,5,7,7-tetramethyl-4H-thieno[2,3-c]pyran-2-yl)carbamoyl]pyrazol-1-yl]methyl dihydrogen phosphate;

[3-[(3-carbamoyl-5,5,7,7-tetramethyl-4H-thieno[2,3-c]pyran-2-yl)carbamoyl]pyrazol-1-yl]methyl dihydrogen phosphate;

N-(3-carbamoyl-5,5,7,7-tetramethyl-4H-thieno[2,3-c]pyran-2-yl)-4-(1,4-dioxan-2-yl)-1H-pyrazole-3-carboxamide;

5,5,7,7-tetramethyl-2-[[(2S)-3,3,3-trifluoro-2-hydroxy-2-methyl-propanoyl]amino]-4H-thieno[2,3-c]pyran-3-carboxamide; and 2-[[(2S)-2-hydroxypropanoyl]amino]-5,5,7,7-tetramethyl-4H-thieno[2,3-c]pyran-3-carboxamide.

Non limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2665, VX-152, VX-440, FDL169, FDL304, FD2052160, and FD2035659. Examples of correctors are also disclosed in publications: US20140274933 and WO2014160478; and U.S. Application 62/073,586.

In one embodiment, the corrector(s) can be selected from the group consisting of Lumacaftor (VX-809);

1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);

VX-983;

GLPG2665;

VX-152;

VX-440;

FDL169

FDL304;

FD2052160;

FD2035659;

rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-4-[(2R,4S)-4-({[1-(2,2-difluoro-1,3-benzodioxol-5-yl)cyclopropyl]carbonyl}amino)tetrahydro-2H-pyran-2-yl]benzoic acid;

3-[(2S,4R)-4-({[1-(2,2-difluoro-1,3-benzodioxol-5-yl)cyclopropyl]carbonyl}amino)tetrahydro-2H-pyran-2-yl]benzoic acid;

3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid; and 4-[(2R,4S)-4-({[1-(2,2-difluoro-1,3-benzodioxol-5-yl)cyclopropyl]carbonyl}amino)tetrahydro-2H-pyran-2-yl]benzoic acid.

In one embodiment, the additional therapeutic agent is a CFTR amplifier. CFTR amplifiers enhance the effect of known CFTR modulators, such as potentiators and correctors. An example of a CFTR amplifier is PTI130. Examples of amplifiers are also disclosed in publications: WO2015138909 and WO2015138934.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., seine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in PCT Publication No. WO2009074575 and U.S. Pat. No. 8,999,976.

In one embodiment, the ENaC inhibitor is VX-371.

This invention also is directed to kits that comprise one or more compounds and/or salts of the invention, and, optionally, one or more additional therapeutic agents.

This invention also is directed to methods of use of the compounds, salts, compositions, and/or kits of the invention to, with or without one or more additional therapeutic agents, for example, modulate the Cystic Fibrosis Transmembrane Conductance Regulator (CFTR) protein, and treat a disease treatable by modulating the Cystic Fibrosis Transmembrane Conductance Regulator (CFTR) protein (including cystic fibrosis, Sjögren's syndrome, pancreatic insufficiency, chronic obstructive lung disease, and chronic obstructive airway disease).

This invention also is directed to a use of one or more compounds and/or salts of the invention in the preparation of a medicament. The medicament optionally can comprise one or more additional therapeutic agents. In some embodiments, the medicament is useful for treating cystic fibrosis, Sjögren's syndrome, pancreatic insufficiency, chronic obstructive lung disease, and chronic obstructive airway disease. In a particular embodiment, the medicament is for use in the treatment of cystic fibrosis. In a more particular embodiment, the cystic fibrosis is caused by a Class I, II, III, IV, V, and/or VI mutation.

This invention also is directed to a use of one or more compounds and/or salts of the invention in the manufacture of a medicament for the treatment of cystic fibrosis, Sjögren's syndrome, pancreatic insufficiency, chronic obstructive lung disease, and chronic obstructive airway disease. The medicament optionally can comprise one or more additional therapeutic agents. In a particular embodiment, the invention is directed to the use of one or more compounds and/or salts of the invention in the manufacture of a medicament for the treatment of cystic fibrosis. In a more particular embodiment, the cystic fibrosis is caused by a Class I, II, III, IV, V, and/or VI mutation.

Further benefits of Applicants' invention will be apparent to one skilled in the art from reading this patent application.

The following Examples may be used for illustrative purposes and should not be deemed to narrow the scope of the invention.

EXAMPLES

Abbreviations: APCI for atmospheric pressure chemical ionization; atm for atmospheres; DCI for desorption chemical ionization; DMAP for 4-(dimethylamino)pyridine; DMF for N,N-dimethylformamide; DMSO for dimethyl sulfoxide; ESI for electrospray ionization; Et for ethyl; EtOAc for ethyl acetate; g for grams; h for hour(s); HATU for N-[(dimethylamino)-1H-1,2,3-triazolo-[4,5-b]pyridin-1-ylmethylene]-N-methylmethanaminium hexafluorophosphate N-oxide or (1-[bis(dimethylamino)methylene]-1H-1,2,3-triazolo [4,5-b]pyridinium 3-oxid hexafluorophosphate; HPLC for high performance liquid chromatography; Hz for hertz; LC/MS for liquid chromatography/mass spectrometry; me for methyl; MeOH for methanol; mg for milligrams; MHz for megahertz; min for minutes; mL for milliliters; mm for millimeter; mmol for millimole; MS for mass spectrometry; NMR for nuclear magnetic resonance; OAc for acetate; ppm for parts per million; psi for pounds per square inch; SFC for supercritical fluid chromatography; TFA for trifluoroacetic acid; THF for tetrahydrofuran; and TLC for thin layer chromatography.

Analytical LC/MS on Thermo MSQ Instruments

Analytical LC/MS was performed on a Thermo MSQ-Plus™ mass spectrometer and Agilent 1100/1200 HPLC system running Xcalibur™ 2.0.7, Open-Access 1.4, and custom login software. The mass spectrometer was operated under positive APCI or ESI ionization conditions dependent on the system used. The HPLC system comprised an Agilent Binary pump, degasser, column compartment, autosampler and diode-array detector, with a Polymer Labs ELS-2100 evaporative light-scattering detector. The column used was a Phenomenex® Kinetex® C8, 2.6 µm 100 Å (2.1 mm×30 mm), at a temperature of 65° C.

A gradient of 5-100% acetonitrile (A) and 0.1% trifluoroacetic acid in water (B) was used, at a flow rate of 1.5 mL/minute (0-0.05 minute 5% A, 0.05-1.2 minutes 5-100% A, 1.2-1.4 minutes 100% A, 1.4-1.5 minutes 100-5% A. 0.25 minute post-run delay).

Example 1 rac-1-(2,2-difluoro-1,3-benzodioxol-5-yl)-N-[(2R,4S)-2-phenyltetrahydro-2H-pyran-4-yl]cyclopropanecarboxamide Step 1: 2-Phenyltetrahydro-4H-pyran-4-one (171 mg, 0.970 mmol) and 7 M ammonia in methanol (10 mL) were added to 5% palladium on carbon (wet) (35 mg, 0.146 mmol) in a 50 mL pressure bottle and shaken for 100 minutes under hydrogen at atmospheric pressure and ambient temperature followed by 16 hours at 30 psi hydrogen and ambient temperature. The reaction mixture was filtered, and the filtrate was concentrated to give 2-phenyltetrahydro-2H-pyran-4-amine (142 mg, 0.801 mmol, 83% yield). $^1$H NMR (400 MHz, CDCl$_3$) δ ppm 7.39-7.30 (m, 5H), 7.29-7.24 (m, 2H), 4.33 (dd, J=11.3, 2.1 Hz, 1H), 4.17 (ddd, J=11.7, 4.7, 1.7 Hz, 1H), 3.60 (td, J=12.2, 2.1 Hz, 1H), 3.05 (tt, J=11.3, 4.2 Hz, 1H), 2.08 (ddt, J=12.7, 4.1, 2.0 Hz, 1H), 2.02-1.92 (m, 1H), 1.51 (td, J=12.1, 4.8 Hz, 1H), 1.41 (dt, J=12.9, 11.4 Hz, 1H); MS (ESI+) m/z 387 (M+H)$^+$.

Step 2: To 1-(2,2-difluorobenzo[d][1,3]dioxol-5-yl)cyclopropanecarboxylic acid (50 mg, 0.206 mmol) (CAS #862574-88-7) in N,N-dimethylformamide (516 µL) was added N-[(dimethylamino)-1H-1,2,3-triazolo-[4,5-b]pyridin-1-ylmethylene]-N-methylmethanaminium hexafluorophosphate N-oxide (HATU, 102 mg, 0.268 mmol). The mixture was stirred for 5 minutes, and then 2-phenyltetrahydro-2H-pyran-4-amine (36.6 mg, 0.206 mmol) from Step 1 was added followed by the dropwise addition of triethylamine (86 µL, 0.619 mmol). After 45 minutes, the mixture was quenched with saturated aqueous sodium bicarbonate, and the aqueous layer was removed with a pipette. The resulting residue was dissolved in dichloromethane and purified chromatographically using a 12 g silica gel cartridge with a gradient of 5-100% ethyl acetate/heptanes to give 52 mg of a mixture of diastereomers. The mixture was purified by preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) for separation of the diastereomers to yield rac-1-(2,2-difluoro-1,3-benzodioxol-5-yl)-N-[(2R,4S)-2-phenyltetrahydro-2H-pyran-4-yl]cyclopropanecarboxamide (22 mg, 0.052 mmol, 25.2% yield). $^1$H NMR (400 MHz, DMSO-d$_6$) δ ppm 7.36-7.21 (m, 7H), 7.14 (dd, J=8.4, 1.7 Hz, 1H), 6.77 (d, J=8.2 Hz, 1H), 4.33 (dd, J=11.4, 2.1 Hz, 1H), 4.06-3.94 (m, 2H), 3.51 (td, J=12.0, 2.3 Hz, 1H), 1.83-1.75 (m, 1H), 1.62 (d, J=11.2 Hz, 1H), 1.49 (tt, J=12.4, 6.2 Hz, 1H), 1.43-1.34 (m, 1H), 1.33 (d, J=3.4 Hz, 2H), 1.02-0.93 (m, 2H); MS (ESI+) m/z 402 (M+H)$^+$. Relative stereochemistry was assigned by $^1$H, H—H COSY, H—H ROESY, H—C HSQC and H—C HMBC NMR experiments.

Example 2 rac-3-[(2R,4S)-4-({[1-(2,2-difluoro-1,3-benzodioxol-5-yl)cyclopropyl]carbonyl}amino)tetrahydro-2H-pyran-2-yl]benzoic acid To a solution methyl rac-3-[(2R,4S)-4-({[1-(2,2-difluoro-1,3-benzodioxol-5-yl)cyclopropyl]carbonyl}amino)tetrahydro-2H-pyran-2-yl]benzoate (20 mg, 0.044 mmol) from Example 3 in methanol (72.6 μL) was added 3 M sodium hydroxide (116 μL, 0.348 mmol), and the reaction mixture was stirred at ambient temperature overnight followed by heating at 50° C. for 2 hours. The volatiles were removed under a stream of nitrogen, and 1N HCl was added dropwise until a white precipitate formed. The precipitate was collected by removing the supernatant, washed with water (0.3 mL), and dried under a stream of nitrogen to give 3-[4-({[1-(2,2-difluoro-1,3-benzodioxol-5-yl)cyclopropyl]carbonyl}amino)tetrahydro-2H-pyran-2-yl]benzoic acid (15 mg, 0.031 mmol, 71.9% yield) with the cis-isomer as the major component and 15% of the trans isomer confirmed by $^1$H NMR experiments. Precipitation from ethyl acetate/n-heptane gave rac-3-[(2R,4S)-4-({[1-(2,2-difluoro-1,3-benzodioxol-5-yl)cyclopropyl]carbonyl}amino)tetrahydro-2H-pyran-2-yl]benzoic acid. $^1$H NMR (400 MHz, DMSO-$d_6$) δ ppm 12.89 (s, 1H), 7.89 (s, 1H), 7.82 (d, J=7.5 Hz, 1H), 7.52 (d, J=7.6 Hz, 1H), 7.44 (d, J=7.7 Hz, 1H), 7.36-7.29 (m, 2H), 7.15 (d, J=8.6 Hz, 1H), 6.77 (d, J=8.2 Hz, 1H), 4.43 (d, J=11.0 Hz, 1H), 4.01 (dq, J=10.9, 6.2, 4.7 Hz, 2H), 3.57-3.48 (m, 1H), 1.86-1.78 (m, 1H), 1.63 (dd, J=12.5, 4.2 Hz, 1H), 1.51 (tt, J=13.3, 6.6 Hz, 1H), 1.45-1.36 (m, 1H), 1.34 (d, J=3.3 Hz, 2H), 0.97 (t, J=8.9 Hz, 2H); MS (ESI+) m/z 446 (M+H)$^+$.

Example 3 methyl rac-3-[(2R,4S)-4-({[1-(2,2-difluoro-1,3-benzodioxol-5-yl)cyclopropyl]carbonyl}amino)tetrahydro-2H-pyran-2-yl]benzoate Step 1: Sulfuric acid (893 μL, 16.75 mmol) was added dropwise at 0° C. to a mixture of but-3-en-1-ol (1.6 mL, 18.28 mmol) and methyl 3-formylbenzoate (1.00 g, 6.09 mmol). After the addition, the mixture was stirred at ambient temperature overnight. The mixture was cooled in an ice bath, made basic with 1 N NaOH and extracted with ethyl acetate. The combined organic extracts were dried over sodium sulfate and concentrated. The crude material was chromatographed using a 24 g silica gel cartridge with a gradient of 5-100% ethyl acetate/heptanes over 30 minutes to give methyl rac-3-[(2R,4S)-4-hydroxytetrahydro-2H-pyran-2-yl]benzoate (522 mg, 2.209 mmol, 36.3% yield). $^1$H NMR (400 MHz, DMSO-$d_6$) δ ppm 7.93 (t, J=1.8 Hz, 1H), 7.85 (dt, J=7.8, 1.5 Hz, 1H), 7.59 (dt, J=7.8, 1.5 Hz, 1H), 7.48 (t, J=7.7 Hz, 1H), 4.84 (d, J=4.8 Hz, 1H), 4.41 (dd, J=11.4, 2.0 Hz, 1H), 4.04 (ddd, J=11.6, 4.8, 1.7 Hz, 1H), 3.86 (s, 3H), 3.82-3.71 (m, 1H), 3.50 (ddd, J=12.9, 11.7, 2.1 Hz, 1H), 2.06 (ddt, J=12.5, 4.3, 2.1 Hz, 1H), 1.82 (ddq, J=12.7, 4.1, 2.0 Hz, 1H), 1.42 (tdd, J=12.5, 10.9, 4.8 Hz, 1H), 1.23 (dt, J=12.3, 11.2 Hz, 1H).

Step 2: To a solution of methyl 3-(4-hydroxytetrahydro-2H-pyran-2-yl)benzoate (317 mg, 1.342 mmol) from Step 1 in dichloromethane (6.7 mL) was added Dess-Martin periodinane (740 mg, 1.744 mmol), and the reaction mixture was stirred at room temperature for 2 hours. The reaction mixture was filtered, the solids were washed with dichloromethane (10 mL), and the combined filtrate and wash were concentrated. The residue was then purified using a 40 g silica gel cartridge eluted with a gradient of 5-50% ethyl acetate/heptanes over 30 minutes to give methyl 3-(4-oxotetrahydro-2H-pyran-2-yl)benzoate (245 mg, 1.046 mmol, 78% yield). $^1$H NMR (400 MHz, DMSO-$d_6$) δ ppm 8.02 (t, J=1.7 Hz, 1H), 7.90 (dt, J=7.8, 1.5 Hz, 1H), 7.66 (dt, J=7.6, 1.3 Hz, 1H), 7.53 (t, J=7.7 Hz, 1H), 4.82 (dd, J=11.3, 3.0 Hz, 1H), 4.34 (ddd, J=11.4, 7.4, 1.4 Hz, 1H), 3.87 (s, 3H), 3.86-3.78 (m, 1H), 2.79-2.67 (m, 1H), 2.62 (ddd, J=14.4, 11.3, 1.0 Hz, 1H), 2.54 (t, J=2.6 Hz, 1H), 2.28 (ddt, J=14.8, 3.1, 1.6 Hz, 1H).

Step 3: Methyl 3-(4-oxotetrahydro-2H-pyran-2-yl)benzoate (150 mg, 0.640 mmol) from Step 2 was treated with hydroxylamine hydrochloride (53.4 mg, 0.768 mmol) and sodium acetate (63.0 mg, 0.768 mmol) in ethanol (3.2 mL) at ambient temperature overnight. Then the mixture was concentrated. The crude material was washed with water (2×1 mL) and dried under a stream of nitrogen to give methyl 3-[4-(hydroxyimino)tetrahydro-2H-pyran-2-yl]benzoate (160 mg, 0.642 mmol, 100% yield). $^1$H NMR showed a mixture of E and Z isomers. MS (ESI+) m/z 250 (M+H)$^+$.

Step 4: Methyl 3-[4-(hydroxyimino)tetrahydro-2H-pyran-2-yl]benzoate (160 mg, 0.642 mmol) from Step 3 and methanol (5 mL) were added to Raney®-nickel 2800, water slurry (300 mg, 2.30 mmol) in a 50 mL pressure bottle, and the mixture was stirred for 16 hours under hydrogen (30 psi) at ambient temperature. The reaction mixture was filtered, and the filtrate was concentrated to give methyl 3-(4-aminotetrahydro-2H-pyran-2-yl)benzoate which was used directly in the next step without further purification. MS (ESI+) m/z 250 (M+H)$^+$.

Step 5: To 1-(2,2-difluorobenzo[d][1,3]dioxol-5-yl)cyclopropanecarboxylic acid (50 mg, 0.206 mmol) in dichloromethane (516 μL) was added half of a solution of oxalyl dichloride (72.3 μL, 0.826 mmol) in 100 μL of dichloromethane followed by 1 drop of N,N-dimethylformamide, and the reaction bubbled vigorously. Then the remainder of the oxalyl chloride solution was added dropwise. The reaction was stirred for 30 minutes, and then the reaction mixture was concentrated under a stream of nitrogen. The residue was taken up in dichloromethane (0.5 mL) and dried under a stream of nitrogen twice. This reagent was taken up in dichloromethane (516 μL) and added to a mixture of methyl 3-(4-aminotetrahydro-2H-pyran-2-yl)benzoate (48.6 mg, 0.206 mmol) from Step 4 and triethylamine (86 μL, 0.619 mmol) in dichloromethane (516 μL). After 15 minutes, the mixture was quenched with saturated aqueous sodium bicarbonate. The aqueous layer was removed, and the organic fraction was concentrated. The residue was dissolved in dichloromethane and purified using a 12 g silica gel cartridge eluted with a gradient of 5-100% ethyl acetate/heptanes over 20 minutes to give a mixture of the two diastereomers. The mixture was precipitated from ether three times to give methyl rac-3-[(2R,4S)-4-({[1-(2,2-difluoro-1,3-benzodioxol-5-yl)cyclopropyl]carbonyl}amino)tetrahydro-2H-pyran-2-yl]benzoate (30 mg, 0.124 mmol, 30% yield). $^1$H NMR (400 MHz, DMSO-$d_6$) δ ppm 7.91 (t, J=1.7 Hz, 1H), 7.87-7.82 (m, 1H), 7.55 (dt, J=7.8, 1.5 Hz, 1H), 7.47 (t, J=7.7 Hz, 1H), 7.34 (d, J=1.7 Hz, 1H), 7.32 (d, J=8.4 Hz, 1H), 7.14 (dd, J=8.3, 1.7 Hz, 1H), 6.77 (d, J=8.2 Hz, 1H), 4.45 (dd, J=11.6, 2.1 Hz, 1H), 4.02 (dd, J=11.9, 4.4 Hz, 1H), 3.84 (s, 3H), 3.53 (td, J=12.1, 2.3 Hz, 1H), 1.85-1.79 (m, 1H), 1.67-1.59 (m, 1H), 1.51 (tt, J=12.4, 6.2 Hz, 1H), 1.44-1.35 (m, 1H), 1.34 (d, J=3.2 Hz, 2H), 1.02-0.94 (m, 2H); MS (ESI+) m/z 460 (M+H)$^+$.

Example 4 methyl rac-3-[(2R,4R)-4-({[1-(2,2-difluoro-1,3-benzodioxol-5-yl)cyclopropyl]carbonyl}amino)tetrahydro-2H-pyran-2-yl]benzoate Step 1: Sulfuric acid (5.36 mL, 101 mmol) was added dropwise at 0° C. to a mixture of but-3-en-1-ol (9.38 mL, 110 mmol) and methyl 3-formylbenzoate (6 g, 36.6 mmol). After the addition, the mixture was stirred at room temperature overnight. The mixture was cooled in an ice bath, made basic with 1 N sodium hydroxide and extracted with ethyl acetate. The combined extracts were dried over sodium sulfate and concentrated. The crude material was chromatographed using a 24 g silica gel cartridge eluted with a gradient of 5-100% ethyl acetate/heptanes over 20 minutes to give methyl rac-3-[(2R,4S)-4-hydroxytetrahydro-2H-pyran-2-yl]benzoate (2.7 g, 11.43 mmol, 31.3% yield). $^1$H NMR (400 MHz, DMSO-$d_6$) δ ppm 7.93 (t, J=1.8 Hz, 1H), 7.85 (dt, J=7.7, 1.5 Hz, 1H), 7.59 (dt, J=7.7, 1.5 Hz, 1H), 7.48 (t, J=7.7 Hz, 1H), 4.84 (d, J=4.8 Hz, 1H), 4.41 (dd, J=11.5, 2.0 Hz, 1H), 4.09-3.99 (m, 1H), 3.86 (s, 3H), 3.76 (dq, J=11.0, 5.4 Hz, 1H), 3.50 (td, J=12.3, 2.2 Hz, 1H), 2.06 (ddt, J=12.5, 4.4, 2.1 Hz, 1H), 1.82 (ddt, J=10.6, 3.9, 1.9 Hz, 1H), 1.41 (tdd, J=12.5, 10.9, 4.8 Hz, 1H), 1.23 (q, J=11.6 Hz, 1H); MS (ESI+) m/z 254 (M+NH$_4$)$^+$.

Step 2: Triethylamine (0.661 mL, 4.74 mmol) was added to a stirred, ice-cooled solution of methyl rac-3-[(2R,4S)-4-hydroxytetrahydro-2H-pyran-2-yl]benzoate (800 mg, 3.39 mmol) from Step 1 in dichloromethane (8 mL). Methanesulfonyl chloride (0.290 mL, 3.72 mmol) was added dropwise from a syringe over 1 minute. After 30 minutes, the reaction mixture was transferred to a separatory funnel with a dichloromethane (40 mL) rinse and washed successively with 1 N citric acid (5 mL) and saturated aqueous sodium bicarbonate (5 mL). The organic phase was concentrated under vacuum to a crude mesylate (780 mg). This crude mesylate was dissolved in N,N-dimethylformamide (3 mL), and sodium azide (991 mg, 15.24 mmol) was added. The mixture was heated at 100° C. under nitrogen for 3 hours. The resulting slurry was cooled to room temperature, diluted with water (50 mL), and extracted with dichloromethane (2×20 mL). The combined organic extracts were concentrated under vacuum leaving a residue that was purified by silica gel chromatography using a 12 g silica gel cartridge eluted with a gradient of 0-80% ethyl acetate/heptanes over 20 minutes to provide methyl rac-3-[(2R,4R)-4-azidotetrahydro-2H-pyran-2-yl]benzoate (665 mg, 2.55 mmol, 75% yield). $^1$H NMR (400 MHz, DMSO-$d_6$) δ ppm 7.92 (t, J=1.8 Hz, 1H), 7.86 (dt, J=7.7, 1.5 Hz, 1H), 7.59 (dt, J=7.6, 1.5 Hz, 1H), 7.48 (t, J=7.7 Hz, 1H), 4.65 (dd, J=11.3, 2.3 Hz, 1H), 4.27 (p, J=3.2 Hz, 1H), 3.90 (dd, J=12.0, 5.3 Hz, 1H), 3.84 (s, 3H), 3.77 (td, J=12.1, 2.2 Hz, 1H), 1.98-1.85 (m, 2H), 1.76 (ddd, J=14.3, 11.3, 3.2 Hz, 1H), 1.66 (dq, J=14.1, 2.1 Hz, 1H); MS (ESI+) m/z 279 (M+NH$_4$)$^+$.

Step 3: Methyl rac-3-[(2R,4R)-4-azidotetrahydro-2H-pyran-2-yl]benzoate (665 mg, 2.55 mmol) from Step 2 and methanol (10 mL) were added to Raney®-nickel 2800, water slurry (890 mg, 6.82 mmol) in a 50 mL pressure bottle and shaken for approximately 2 hours under hydrogen (30 psi) at ambient temperature. The catalyst was removed by filtration, and the filtrate was concentrated to give methyl rac-3-[(2R,4R)-4-aminotetrahydro-2H-pyran-2-yl]benzoate (560 mg, 2.380 mmol, 94% yield). $^1$H NMR (400 MHz, DMSO-$d_6$) δ ppm 7.91 (d, J=1.8 Hz, 1H), 7.83 (dt, J=7.6, 1.6 Hz, 1H), 7.56 (dt, J=7.8, 1.6 Hz, 1H), 7.47 (t, J=7.7 Hz, 1H), 4.87 (dd, J=10.7, 2.9 Hz, 1H), 3.99 (td, J=11.9, 2.4 Hz, 1H), 3.85 (s, 3H), 3.74 (ddd, J=11.3, 5.0, 2.0 Hz, 1H), 1.84-1.73 (m, 1H), 1.72-1.56 (m, 2H), 1.43-1.34 (m, 1H); MS (ESI+) m/z 236 (M+H)$^+$. This material was used for the next step without further purification.

Step 4: To 1-(2,2-difluorobenzo[d][1,3]dioxol-5-yl)cyclopropanecarboxylic acid (500 mg, 2.065 mmol) in dichloromethane (5.162 mL) was added half of a solution of oxalyl dichloride (0.723 mL, 8.26 mmol) in 1 mL of dichloromethane followed by 1 drop of N,N-dimethylformamide, and the reaction bubbled vigorously. Then the remainder of the oxalyl chloride solution was added dropwise. The reaction was stirred for 30 minutes. Then the volatiles were removed under a stream of nitrogen and then chased with dichloromethane (2×1 mL) with drying under a stream of nitrogen. This reagent was taken up in dichloromethane (5.2 mL) and added to a mixture of methyl rac-3-[(2R,4R)-4-aminotetrahydro-2H-pyran-2-yl]benzoate (486 mg, 2.065 mmol) from Step 3 and triethylamine (0.86 mL, 6.19 mmol) in dichloromethane (5.2 mL). After 15 minutes, the mixture was quenched with saturated aqueous sodium bicarbonate, and the organic fraction was separated and then concentrated. The resulting residue was dissolved in dichloromethane and purified using a 24 g silica gel cartridge eluted with a gradient of 5-100% ethyl acetate/heptanes in 20 minutes to give methyl rac-3-[(2R,4R)-4-({[1-(2,2-difluoro-1,3-benzodioxol-5-yl)cyclopropyl]carbonyl}amino)tetrahydro-2H-pyran-2-yl]benzoate (720 mg, 1.567 mmol, 76% yield). $^1$H NMR (400 MHz, DMSO-$d_6$) δ ppm 7.90 (t, J=1.7 Hz, 1H), 7.85 (dt, J=7.6, 1.5 Hz, 1H), 7.56 (dt, J=7.8, 1.5 Hz, 1H), 7.50 (d, J=7.6 Hz, 1H), 7.47 (t, J=1.5 Hz, 1H), 7.39 (d, J=8.3 Hz, 1H), 7.27 (dd, J=8.3, 1.7 Hz, 1H), 7.05 (d, J=6.0 Hz, 1H), 4.56 (dd, J=10.3, 2.6 Hz, 1H), 3.98 (q, J=4.6 Hz, 1H), 3.85 (s, 3H), 3.75 (dt, J=11.7, 3.9 Hz, 1H), 3.60 (td, J=11.4, 2.9 Hz, 1H), 1.90 (dt, J=14.0, 3.3 Hz, 1H), 1.77-1.60 (m, 3H), 1.39 (dt, J=5.7, 2.7 Hz, 2H), 1.11-1.04 (m, 2H); MS (ESI+) m/z 460 (M+H)$^+$.

Example 5 rac-3-[(2R,4R)-4-({[1-(2,2-difluoro-1,3-benzodioxol-5-yl)cyclopropyl]carbonyl}amino)tetrahydro-2H-pyran-2-yl]benzoic acid To a solution of methyl rac-3-[(2R,4R)-4-({[1-(2,2-difluoro-1,3-benzodioxol-5-yl)cyclopropyl]carbonyl}amino)tetrahydro-2H-pyran-2-yl]benzoate (50 mg, 0.109 mmol) from Example 4 in ethanol (1 mL) was added 3 N sodium hydroxide (0.290 mL, 0.871 mmol). The reaction was stirred at room temperature for 16 hours and then quenched with 0.9 mL of 1 N HCl. The addition of water (10 mL) produced a precipitate. The precipitate was collected by filtration and washed with water to give rac-3-[(2R,4R)-4-({[1-(2,2-difluoro-1,3-benzodioxol-5-yl)cyclopropyl]carbonyl}amino)tetrahydro-2H-pyran-2-yl]benzoic acid (46 mg, 0.103 mmol, 95% yield) as a white solid. $^1$H NMR (400 MHz, DMSO-$d_6$) δ 12.93 (s, 1H), 7.89 (d, J=1.9 Hz, 1H), 7.83 (dt, J=7.5, 1.6 Hz, 1H), 7.55-7.49 (m, 1H), 7.49-7.42 (m, 2H), 7.39 (d, J=8.4 Hz, 1H), 7.27 (dd, J=8.3, 1.7 Hz, 1H), 7.03 (d, J=6.0 Hz, 1H), 4.56 (dd, J=10.3, 2.7 Hz, 1H), 3.98 (q, J=4.4 Hz, 1H), 3.74 (dt, J=11.8, 4.0 Hz, 1H), 3.59 (td, J=11.3, 3.0 Hz, 1H), 1.90 (dt, J=13.8, 3.4 Hz, 1H), 1.69 (dddd, J=30.9, 14.0, 10.2, 3.6 Hz, 3H), 1.43-1.35 (m, 2H), 1.11-1.03 (m, 2H); MS (ESI+) m/z 446 (M+H)$^+$.

Example 6 rac-1-(2,2-difluoro-1,3-benzodioxol-5-yl)-N-{(2R,4R)-2-[3-(hydroxymethyl)phenyl]tetrahydro-2H-pyran-4-yl}cyclopropanecarboxamide To a solution of methyl rac-3-[(2R,4R)-4-({[1-(2,2-difluoro-1,3-benzodioxol-5-yl)cyclopropyl]carbonyl}amino)tetrahydro-2H-pyran-2-yl]benzoate (100 mg, 0.218 mmol) from Example 4 in tetrahydrofuran (3 mL) and methanol (1.5 mL) was added sodium tetrahydroborate (124 mg, 3.26 mmol) in 15 portions over 2 days. The reaction was stirred at room temperature, and then the reaction mixture was heated at 65° C. for 2 days. The reaction was quenched with 2 mL of saturated aqueous ammonium acetate. The mixture was then extracted with methyl tert-butyl ether, and the combined organic fractions were concentrated. The residue was purified using a 12 g silica gel cartridge eluted with a gradient of 5-100% ethyl acetate/heptanes over 20 minutes to give rac-1-(2,2-difluoro-1,3-benzodioxol-5-yl)-N-{(2R,4R)-2-[3-(hydroxymethyl)phenyl]tetrahydro-2H-pyran-4-yl}cyclopropanecarboxamide (29 mg, 0.067 mmol, 30.9% yield) as a gummy solid. $^1$H NMR (400 MHz, DMSO-d$_6$) δ ppm 7.46 (d, J=1.7 Hz, 1H), 7.39 (d, J=8.2 Hz, 1H), 7.29-7.24 (m, 3H), 7.18 (d, J=7.6 Hz, 1H), 7.14-7.08 (m, 1H), 6.96 (d, J=6.2 Hz, 1H), 5.15 (t, J=5.6 Hz, 1H), 4.50-4.43 (m, 3H), 3.99 (q, J=4.6, 4.0 Hz, 1H), 3.71 (dt, J=11.8, 4.0 Hz, 1H), 3.56 (td, J=11.4, 2.8 Hz, 1H), 1.85 (dt, J=13.9, 3.6 Hz, 1H), 1.78-1.66 (m, 2H), 1.61 (dd, J=13.9, 3.7 Hz, 1H), 1.38 (q, J=4.1 Hz, 2H), 1.07 (q, J=4.1 Hz, 2H); MS (ESI+) m/z 432 (M+H)$^+$.

Example 7 rac-1-(2,2-difluoro-1,3-benzodioxol-5-yl)-N-{(2R,4R)-2-[3-(2-hydroxypropan-2-yl)phenyl]tetrahydro-2H-pyran-4-yl}cyclopropanecarboxamide To a 0° C. solution of methyl rac-3-[(2R,4R)-4-({[1-(2,2-difluoro-1,3-benzodioxol-5-yl)cyclopropyl]carbonyl}amino)tetrahydro-2H-pyran-2-yl]benzoate (50 mg, 0.109 mmol) from Example 4 in 2-methyl-tetrahydrofuran (0.4 mL) was added 3 M methylmagnesium bromide (0.326 mL, 0.979 mmol) in ether dropwise, maintaining the internal temperature below 6° C. The cold bath was removed, and the reaction mixture was stirred at ambient temperature for 2 hours. The reaction mixture was diluted with 2-methyl-tetrahydrofuran and quenched with saturated aqueous ammonium chloride. The organic fraction was separated, washed with brine, dried over sodium sulfate, and concentrated. The resultant residue was chromatographed using a 12 g silica gel cartridge eluted with a gradient of 5-100% ethyl acetate/hexanes over 20 minutes to give rac-1-(2,2-difluoro-1,3-benzodioxol-5-yl)-N-{(2R,4R)-2-[3-(2-hydroxypropan-2-yl)phenyl]tetrahydro-2H-pyran-4-yl}cyclopropanecarboxamide (9 mg, 0.020 mmol, 18.0% yield). $^1$H NMR (400 MHz, DMSO-d$_6$) δ ppm 7.46 (d, J=1.7 Hz, 1H), 7.42-7.37 (m, 2H), 7.32 (dt, J=7.8, 1.4 Hz, 1H), 7.29-7.21 (m, 2H), 7.08 (d, J=7.5 Hz, 1H), 6.98 (d, J=6.2 Hz, 1H), 4.97 (s, 1H), 4.44 (dd, J=9.8, 2.9 Hz, 1H), 4.00 (q, J=4.2, 3.4 Hz, 1H), 3.71 (dt, J=11.8, 3.9 Hz, 1H), 3.57 (td, J=11.4, 2.8 Hz, 1H), 1.88-1.80 (m, 1H), 1.80-1.74 (m, 1H), 1.70 (dt, J=14.8, 4.2 Hz, 1H), 1.65-1.57 (m, 1H), 1.40 (s, 6H), 1.38 (q, J=3.8 Hz, 2H), 1.07 (q, J=4.0 Hz, 2H); MS (ESI+) m/z 458 (M−H)$^-$.

Example 8 rac-N-[(2R,4S)-2-(3-acetylphenyl)tetrahydro-2H-pyran-4-yl]-1-(2,2-difluoro-1,3-benzodioxol-5-yl)cyclopropanecarboxamide To a 0° C. solution of methyl rac-3-[(2R,4S)-4-({[1-(2,2-difluoro-1,3-benzodioxol-5-yl)cyclopropyl]carbonyl}amino)tetrahydro-2H-pyran-2-yl]benzoate from Example 3 (100 mg, 0.218 mmol) in 2-methyl-tetrahydrofuran (1 mL) was added a half volume of 3 M methylmagnesium bromide (0.653 mL, 1.959 mmol) in ether dropwise. The ice bath was removed, and the second half volume was added. The mixture was diluted with ethyl acetate and quenched with saturated aqueous ammonium chloride. The organic fractions were separated, washed with brine and dried over sodium sulfate. After concentration, the residue (55 mg) was chromatographed using a 12 g silica gel cartridge eluted with a gradient of 5-100% ethyl acetate/hexanes over 20 minutes to give rac-N-[(2R,4S)-2-(3-acetylphenyl)tetrahydro-2H-pyran-4-yl]-1-(2,2-difluoro-1,3-benzodioxol-5-yl)cyclopropanecarboxamide (35 mg, 0.079 mmol, 36.3% yield). $^1$H NMR (500 MHz, DMSO-d$_6$) δ ppm 7.87-7.80 (m, 2H), 7.53 (dt, J=7.8, 1.4 Hz, 1H), 7.46 (t, J=7.5 Hz, 1H), 7.33 (d, J=1.7 Hz, 1H), 7.31 (d, J=8.4 Hz, 1H), 7.13 (dd, J=8.3, 1.7 Hz, 1H), 6.77 (d, J=8.3 Hz, 1H), 4.43 (dd, J=11.5, 2.1 Hz, 1H), 4.01 (ddd, J=11.7, 4.7, 2.2 Hz, 2H), 3.52 (td, J=12.0, 2.2 Hz, 1H), 2.55 (s, 3H), 1.83 (ddt, J=12.7, 4.2, 1.9 Hz, 1H), 1.62 (ddd, J=12.8, 4.5, 2.1 Hz, 1H), 1.57-1.44 (m, 1H), 1.38 (q, J=12.0 Hz, 1H), 1.34-1.29 (m, 2H), 1.01-0.92 (m, 2H); MS (ESI+) m/z 444 (M+H)$^+$.

Example 9 rac-1-(2,2-difluoro-1,3-benzodioxol-5-yl)-N-{(2R,4S)-2-[3-(hydroxymethyl)phenyl]tetrahydro-2H-pyran-4-yl}cyclopropanecarboxamide To a solution of methyl rac-3-[(2R,4S)-4-({[1-(2,2-difluoro-1,3-benzodioxol-5-yl)cyclopropyl]carbonyl}amino)tetrahydro-2H-pyran-2-yl]benzoate (100 mg, 0.218 mmol) from Example 3 in tetrahydrofuran (2 mL) and methanol (2 mL) was added sodium tetrahydroborate (124 mg, 3.26 mmol) in 15 portions over 2 days. The reaction mixture was stirred at room temperature for 1 hour and at 65° C. for 2 days. The reaction mixture was quenched with 2 mL of saturated aqueous ammonium acetate and then extracted with methyl tert-butyl ether. The combined organic fractions were concentrated, and the residue was purified using a 12 g silica gel cartridge eluted with a gradient of 5-100% ethyl acetate/heptanes to give rac-1-(2,2-difluoro-1,3-benzodioxol-5-yl)-N-{(2R,4S)-2-[3-(hydroxymethyl)phenyl]tetrahydro-2H-pyran-4-yl}cyclopropanecarboxamide (27 mg, 0.063 mmol, 28.8% yield). $^1$H NMR (400 MHz, DMSO-d$_6$) δ ppm 7.34 (s, 1H), 7.32 (d, J=8.3 Hz, 1H), 7.28-7.21 (m, 2H), 7.20-7.09 (m, 3H), 6.77 (d, J=8.1 Hz, 1H), 4.46 (s, 2H), 4.32 (d, J=11.2 Hz, 1H), 4.06-3.94 (m, 2H), 3.50 (t, J=12.5 Hz, 1H), 1.78 (d, J=13.3 Hz, 1H), 1.61 (d, J=11.8 Hz, 1H), 1.51 (td, J=12.3, 11.9, 4.6 Hz, 1H), 1.40 (q, J=11.8 Hz, 1H), 1.35-1.30 (m, 2H), 1.03-0.93 (m, 2H); MS (ESI+) m/z 432 (M+H)$^+$.

Example 10 rac-1-(2,2-difluoro-1,3-benzodioxol-5-yl)-N-{(2R,4S)-2-[3-(2-hydroxypropan-2-yl)phenyl]tetrahydro-2H-pyran-4-yl}cyclopropanecarboxamide To a 0° C. solution of methyl rac-3-[(2R,4S)-4-({[1-(2,2-difluoro-1,3-benzodioxol-5-yl)cyclopropyl]

carbonyl}amino)tetrahydro-2H-pyran-2-yl]benzoate from Example 3 (100 mg, 0.218 mmol) in 2-methyl-tetrahydrofuran (1 mL) was added half volume of 3 M methylmagnesium bromide (0.653 mL, 1.959 mmol) in ether dropwise. The ice bath was removed, and the other half volume of methylmagnesium bromide was added. The mixture was diluted with ethyl acetate and quenched with saturated aqueous ammonium chloride. The organic fraction was separated, washed with brine, dried over sodium sulfate, and concentrated. The residue was chromatographed using a 12 g silica gel cartridge eluted with a gradient of 5-100% ethyl acetate/hexanes over 20 minutes to give rac-1-(2,2-difluoro-1,3-benzodioxol-5-yl)-N-{(2R,4S)-2-[3-(2-hydroxypropan-2-yl)phenyl]tetrahydro-2H-pyran-4-yl}cyclopropanecarboxamide (10 mg, 0.022 mmol, 10.00% yield). $^1$H NMR (400 MHz, DMSO-d$_6$) δ ppm 7.41 (t, J=1.7 Hz, 1H), 7.34 (d, J=1.7 Hz, 1H), 7.32 (d, J=2.3 Hz, 1H), 7.30 (d, J=1.9 Hz, 1H), 7.21 (t, J=7.6 Hz, 1H), 7.14 (dd, J=8.3, 1.7 Hz, 1H), 7.08 (dt, J=7.4, 1.4 Hz, 1H), 6.78 (d, J=8.2 Hz, 1H), 4.95 (s, 1H), 4.32 (dd, J=11.3, 2.0 Hz, 1H), 4.06-3.94 (m, 2H), 3.50 (td, J=12.0, 2.2 Hz, 1H), 1.77 (ddd, J=11.5, 4.7, 2.5 Hz, 1H), 1.65-1.57 (m, 1H), 1.51 (td, J=12.1, 4.6 Hz, 1H), 1.44 (m, 1H), 1.39 (s, 6H), 1.33 (d, J=3.3 Hz, 2H), 1.02-0.93 (m, 2H); MS (ESI+) m/z 458 (M−H)$^−$.

Example 11 methyl rac-2-[(2R,4S)-4-({[1-(2,2-difluoro-1,3-benzodioxol-5-yl)cyclopropyl]carbonyl}amino)tetrahydro-2H-pyran-2-yl]benzoate Step 1: Sulfuric acid (4.46 mL, 84 mmol) was added dropwise at 0° C. to a mixture of but-3-en-1-ol (7.82 mL, 91 mmol) and methyl 2-formylbenzoate (5 g, 30.5 mmol). After the addition, the mixture was stirred at ambient temperature overnight. The mixture was cooled in an ice bath. The mixture was made basic with 1 N NaOH (125 mL) and extracted with ethyl acetate. The extracts were dried over sodium sulfate and concentrated. The crude material was chromatographed using a 24 g silica gel cartridge eluted with a gradient of 5-100% ethyl acetate/heptanes over 20 minutes to give methyl 2-(4-hydroxytetrahydro-2H-pyran-2-yl)benzoate (2.1 g, 8.89 mmol, 29.2% yield). $^1$H NMR (400 MHz, DMSO-d$_6$) δ ppm 7.75 (dd, J=7.8, 1.3 Hz, 1H), 7.62 (dd, J=7.9, 1.5 Hz, 1H), 7.57 (td, J=7.5, 1.4 Hz, 1H), 7.38 (td, J=7.4, 1.6 Hz, 1H), 4.90 (dd, J=11.0, 1.8 Hz, 1H), 4.84 (d, J=4.7 Hz, 1H), 4.01 (ddd, J=11.5, 5.0, 1.6 Hz, 1H), 3.83 (s, 3H), 3.73 (ddt, J=15.5, 10.8, 4.7 Hz, 1H), 3.47 (td, J=12.2, 2.2 Hz, 1H), 2.13 (ddt, J=12.3, 4.1, 2.0 Hz, 1H), 1.82 (ddq, J=12.9, 4.0, 1.9 Hz, 1H), 1.41 (tdd, J=12.5, 10.7, 4.9 Hz, 1H), 1.22-1.12 (m, 1H); MS (ESI+) m/z 237 (M+H)$^+$.

Step 2: To a solution of methyl 2-(4-hydroxytetrahydro-2H-pyran-2-yl)benzoate (2.1 g, 8.89 mmol) from Step 1 in dichloromethane (38 mL) was added Dess-Martin periodinane (4.90 g, 11.55 mmol), and the reaction mixture was stirred at room temperature for 16 hours. The mixture was quenched with 1 N sodium thiosulfate (66 mL) and saturated aqueous sodium bicarbonate solution (40 mL), and the mixture was stirred for 15 minutes. The organic layer was separated and concentrated. The residue was then purified using a 24 g silica gel cartridge eluted with 5-60% ethyl acetate/heptanes over 20 minutes to give methyl 2-(4-oxotetrahydro-2H-pyran-2-yl)benzoate (1.6 g, 6.83 mmol, 77% yield). $^1$H NMR (400 MHz, DMSO-d$_6$) δ ppm 7.79 (dd, J=7.8, 1.3 Hz, 1H), 7.74 (dd, J=7.9, 1.2 Hz, 1H), 7.65 (td, J=7.6, 1.4 Hz, 1H), 7.44 (td, J=7.5, 1.3 Hz, 1H), 5.26 (dd, J=10.8, 3.0 Hz, 1H), 4.31 (ddd, J=11.4, 7.6, 1.2 Hz, 1H), 3.83 (s, 3H), 3.79 (td, J=11.9, 2.8 Hz, 1H), 2.72 (ddd, J=14.8, 12.5, 7.6 Hz, 1H), 2.64-2.58 (m, 1H), 2.58-2.53 (m, 1H), 2.27 (ddt, J=14.7, 3.0, 1.4 Hz, 1H); MS (ESI+) m/z 335 (M+H)$^+$.

Step 3: Methyl 2-(4-oxotetrahydro-2H-pyran-2-yl)benzoate (1.45 g, 6.19 mmol) from Step 2 was treated with hydroxylamine hydrochloride (0.602 g, 8.67 mmol) and sodium acetate (0.711 g, 8.67 mmol) in methanol (6 mL). The reaction mixture was stirred at ambient temperature for 20 minutes and then at 80° C. overnight. Additional hydroxylamine hydrochloride (0.602 g, 8.67 mmol) was added, and the mixture was heated at 80° C. over 72 hours. Then the reaction mixture was concentrated and the crude material was partitioned between dichloromethane and water. The organic fraction was separated and concentrated. The residue was purified using a 24 g silica gel cartridge with a gradient of 5-100% ethyl acetate/heptanes over 15 minutes to give methyl 2-(4-(hydroxyimino)tetrahydro-2H-pyran-2-yl)benzoate (1.37 g, 5.50 mmol, 89% yield). $^1$H NMR (400 MHz, DMSO-d$_6$) δ 10.47 (d, J=10.5 Hz, 1H), 7.76 (ddd, J=9.2, 7.7, 1.4 Hz, 1H), 7.69 (d, J=7.8 Hz, 1H), 7.61 (tdd, J=7.7, 3.3, 1.4 Hz, 1H), 7.45-7.39 (m, 1H), 4.97 (ddd, J=36.6, 11.1, 2.6 Hz, 1H), 4.22-4.11 (m, 1H), 3.83 (d, J=1.9 Hz, 3H), 3.62-3.43 (m, 2H), 3.15-2.57 (m, 1H), 2.46-2.22 (m, 1H), 2.22-2.00 (m, 1H); MS (ESI+) m/z 258 (M+CH$_3$OH+Na)$^+$.

Step 4: Methyl 2-(4-(hydroxyimino)tetrahydro-2H-pyran-2-yl)benzoate (1.37 g, 5.50 mmol) from Step 3 and methanol (16 mL) were added to Raney®-nickel 2800, water slurry (0.323 g, 5.50 mmol) in a 50 mL pressure bottle, and the mixture was stirred for 16 hours under hydrogen (30 psi) at ambient temperature. The catalyst was removed by filtration, and the filtrate was concentrated to a residue (1.3 g). Crude NMR indicated a cis/trans ratio of 2:1. The residue was purified using a 24 g silica gel cartridge eluted with a gradient of 1-10% methanol (2 N ammonia)/dichloromethane over 10 minutes to give a first eluting compound, methyl rac-2-[(2R,4R)-4-aminotetrahydro-2H-pyran-2-yl]benzoate (235 mg, 0.999 mmol, 18.17% yield). $^1$H NMR (400 MHz, DMSO-d$_6$) δ ppm 7.67 (dd, J=7.7, 1.3 Hz, 1H), 7.60 (dd, J=7.9, 1.4 Hz, 1H), 7.54 (td, J=7.6, 1.4 Hz, 1H), 7.35 (td, J=7.5, 1.4 Hz, 1H), 5.36 (dd, J=11.1, 2.1 Hz, 1H), 3.98 (ddd, J=13.0, 11.4, 2.3 Hz, 1H), 3.84 (s, 3H), 3.72 (ddd, J=11.3, 5.1, 1.7 Hz, 1H), 1.84-1.76 (m, 1H), 1.76-1.69 (m, 1H), 1.56 (ddd, J=13.2, 11.0, 3.5 Hz, 1H), 1.38 (dp, J=13.5, 2.2 Hz, 1H); MS (ESI+) m/z 236 (M+H)$^+$. A second eluting compound followed, methyl rac-2-[(2R,4S)-4-aminotetrahydro-2H-pyran-2-yl]benzoate, (540 mg, 2.295 mmol, 41.8% yield). $^1$H NMR (400 MHz, DMSO-d$_6$) δ ppm 7.74 (dd, J=7.8, 1.3 Hz, 1H), 7.61 (dd, J=8.0, 1.5 Hz, 1H), 7.57 (td, J=7.5, 1.4 Hz, 1H), 7.37 (td, J=7.4, 1.6 Hz, 1H), 4.91 (dd, J=11.0, 1.9 Hz, 1H), 4.00 (ddd, J=11.5, 4.8, 1.5 Hz, 1H), 3.83 (s, 3H), 3.47 (td, J=12.1, 2.2 Hz, 1H), 2.85 (tt, J=11.1, 4.2 Hz, 1H), 2.02 (ddt, J=12.6, 4.1, 2.0 Hz, 1H), 1.72 (ddq, J=13.0, 3.8, 1.8 Hz, 1H), 1.28 (tdd, J=12.6, 11.0, 4.7 Hz, 1H), 1.05 (dt, J=12.5, 11.0 Hz, 1H); MS (ESI+) m/z 236 (M+H)$^+$.

Step 5: To 1-(2,2-difluorobenzo[d][1,3]dioxol-5-yl)cyclopropanecarboxylic acid (309 mg, 1.275 mmol) in N,N-dimethylformamide (1.2 mL) was added N-[(dimethylamino)-1H-1,2,3-triazolo-[4,5-b]pyridin-1-ylmethylene]-N-methylmethanaminium hexafluorophosphate N-oxide (HATU, 727 mg, 1.913 mmol). The mixture was stirred for 10 minutes, and then methyl rac-2-[(2R,4S)-4-aminotetrahydro-2H-pyran-2-yl]benzoate (300 mg, 1.275 mmol) from Step 4 in 0.5 mL N,N-dimethylformamide was added, followed by N-ethyl-N-isopropylpropan-2-amine (0.444 mL, 2.55 mmol). The mixture was stirred at ambient temperature for 3 hours. Water (10 mL) was added, and the aqueous mixture was decanted. The residue was washed with water, and the resultant residue was purified by flash chromatography using a 24 g silica gel cartridge eluted with a gradient of 5-100% ethyl acetate/heptanes over 20 minutes to provide methyl rac-2-[(2R,4S)-4-({[1-(2,2-difluoro-1,3-benzodioxol-5-yl)cyclopropyl]carbonyl}amino)tetrahydro-2H-pyran-2-yl]benzoate (460 mg, 1.001 mmol, 79% yield). $^1$H NMR (400 MHz, DMSO-$d_6$) δ ppm 7.75 (d, J=7.7 Hz, 1H), 7.57 (d, J=4.2 Hz, 2H), 7.42-7.36 (m, 1H), 7.34 (d, J=1.7 Hz, 1H), 7.31 (d, J=8.3 Hz, 1H), 7.14 (dd, J=8.3, 1.7 Hz, 1H), 6.75 (d, J=8.1 Hz, 1H), 4.94 (dd, J=11.0, 1.9 Hz, 1H), 4.05-3.93 (m, 2H), 3.83 (s, 3H), 3.50 (td, J=12.1, 2.3 Hz, 1H), 1.95-1.86 (m, 1H), 1.67-1.59 (m, 1H), 1.51 (qd, J=12.2, 4.6 Hz, 1H), 1.39-1.30 (m, 3H), 0.97 (qt, J=7.7, 3.8 Hz, 2H); MS (ESI+) m/z 460 (M+H)$^+$.

Example 12 rac-2-[(2R,4S)-4-({[1-(2,2-difluoro-1,3-benzodioxol-5-yl)cyclopropyl]carbonyl}amino)tetrahydro-2H-pyran-2-yl]benzoic acid To a solution of methyl rac-2-[(2R,4S)-4-({[1-(2,2-difluoro-1,3-benzodioxol-5-yl)cyclopropyl]carbonyl}amino)tetrahydro-2H-pyran-2-yl]benzoate (170 mg, 0.370 mmol) from Example 11 in ethanol (3 mL) was added 3 N sodium hydroxide (0.987 mL, 2.96 mmol). The reaction mixture was stirred at room temperature for 16 hours. The reaction was quenched with 0.9 mL of 3 N HCl, and the addition of water (15 mL) produced a white precipitate. The precipitate was collected by filtration and washed with water to give the titled compound (146 mg, 0.328 mmol, 89% yield). $^1$H NMR (400 MHz, DMSO-$d_6$) δ ppm 13.01 (s, 1H), 7.76 (d, J=7.8 Hz, 1H), 7.59-7.48 (m, 2H), 7.38-7.33 (m, 2H), 7.30 (d, J=8.5 Hz, 1H), 7.14 (dd, J=8.3, 1.7 Hz, 1H), 6.73 (d, J=8.3 Hz, 1H), 5.11-5.01 (m, 1H), 3.98 (ddd, J=23.3, 11.6, 5.9 Hz, 2H), 3.55-3.46 (m, 1H), 1.93-1.82 (m, 1H), 1.63 (d, J=11.2 Hz, 1H), 1.51 (tt, J=12.4, 6.2 Hz, 1H), 1.39-1.22 (m, 3H), 0.97 (dtd, J=13.8, 7.3, 3.6 Hz, 2H); MS (ESI+) m/z 446 (M+H)$^+$.

Example 13 methyl rac-4-[(2R,4S)-4-({[1-(2,2-difluoro-1,3-benzodioxol-5-yl)cyclopropyl]carbonyl}amino)tetrahydro-2H-pyran-2-yl]benzoate The titled compound was prepared using the procedures described in Example 11, Steps 1 through 5, substituting methyl 4-formylbenzoate in place of methyl 2-formylbenzoate in Step 1 to provide methyl rac-4-[(2R,4S)-4-({[1-(2,2-difluoro-1,3-benzodioxol-5-yl)cyclopropyl]carbonyl}amino)tetrahydro-2H-pyran-2-yl]benzoate (435 mg, 0.947 mmol, 74.3% yield). $^1$H NMR (400 MHz, DMSO-$d_6$) δ ppm 7.91 (d, J=8.3 Hz, 2H), 7.43 (d, J=8.3 Hz, 2H), 7.34 (d, J=1.7 Hz, 1H), 7.31 (d, J=8.3 Hz, 1H), 7.14 (dd, J=8.3, 1.7 Hz, 1H), 6.78 (d, J=8.2 Hz, 1H), 4.45 (dd, J=11.6, 2.1 Hz, 1H), 4.08-3.96 (m, 2H), 3.84 (s, 3H), 3.53 (td, J=12.1, 2.3 Hz, 1H), 1.84 (ddd, J=12.7, 4.2, 2.1 Hz, 1H), 1.68-1.59 (m, 1H), 1.50 (qd, J=12.4, 4.7 Hz, 1H), 1.41-1.29 (m, 3H), 1.02-0.94 (m, 2H); MS (ESI+) m/z 460 (M+H)$^+$.

Example 14 rac-4-[(2R,4S)-4-({[1-(2,2-difluoro-1,3-benzodioxol-5-yl)cyclopropyl]carbonyl}amino)tetrahydro-2H-pyran-2-yl]benzoic acid To a solution of methyl rac-4-[(2R,4S)-4-({[1-(2,2-difluoro-1,3-benzodioxol-5-yl)cyclopropyl]carbonyl}amino) tetrahydro-2H-pyran-2-yl]benzoate (180 mg, 0.392 mmol) from Example 13 in ethanol (3 mL) was added 3 N sodium hydroxide (1.045 mL, 3.13 mmol). The reaction mixture was stirred at room temperature for 16 hours. The reaction was quenched with 2.8 mL of 1 N HCl and the addition of water (15 mL) produced a white precipitate. The precipitate was collected by filtration and washed with water to give rac-4-[(2R,4S)-4-({[1-(2,2-difluoro-1,3-benzodioxol-5-yl)cyclopropyl]carbonyl}amino)tetrahydro-2H-pyran-2-yl]benzoic acid (142 mg, 0.319 mmol, 81% yield). $^1$H NMR (400 MHz, DMSO-$d_6$) δ ppm 7.87 (d, J=8.2 Hz, 2H), 7.38 (d, J=8.1 Hz, 2H), 7.33 (d, J=1.7 Hz, 1H), 7.30 (d, J=8.3 Hz, 1H), 7.13 (dd, J=8.4, 1.8 Hz, 1H), 6.77 (d, J=8.2 Hz, 1H), 4.42 (dd, J=11.5, 2.1 Hz, 1H), 4.07-3.93 (m, 2H), 3.52 (td, J=12.0, 2.2 Hz, 1H), 1.86-1.77 (m, 1H), 1.61 (dd, J=8.8, 6.1 Hz, 1H), 1.49 (qd, J=12.4, 4.7 Hz, 1H), 1.41-1.28 (m, 3H), 1.01-0.92 (m, 2H); MS (ESI+) m/z 446 (M+H)$^+$.

Example 15

N-[(2S,4R)-2-(1,3-benzodioxol-5-yl)tetrahydro-2H-pyran-4-yl]-1-(2,2-difluoro-1,3-benzodioxol-5-yl) cyclopropanecarboxamide Step 1: To a solution of 3-buten-1-ol (0.239 mL, 2.77 mmol) and piperonal (0.416 g, 2.77 mmol) in dichloromethane (3.00 mL) was added gallium(III) bromide (0.515 g, 1.664 mmol). The reaction mixture was stirred at ambient temperature for 72 hours. The reaction mixture was then washed with water. The organic fraction was separated, dried over anhydrous sodium sulfate, filtered, and concentrated. The residue was purified using a 40 g silica gel cartridge eluted with a gradient of 0-30% ethyl acetate/heptanes over 30 minutes to give 5-(4-bromotetrahydro-2H-pyran-2-yl)-1,3-benzodioxole (0.2405 g, 30%) as a cis:trans (5:3) mixture. $^1$H NMR (500 MHz, CDCl$_3$) δ ppm 2.00-2.11 (m, 1H) 2.11-2.27 (m, 2H) 2.38-2.47 (m, 1H) 3.53-3.61 (m, 1H) 4.08-4.17 (m, 1H) 4.20-4.31 (m, 1H) 4.76-4.85 (m, 1H) 5.92-5.98 (m, 2H) 6.74-6.82 (m, 2H) 6.84-6.88 (m, 1H).

Step 2: To a solution of 5-(4-bromotetrahydro-2H-pyran-2-yl)-1,3-benzodioxole (0.225 g, 0.789 mmol) from Step 1 in N,N-dimethylformamide (3 mL) was added sodium azide (0.205 g, 3.16 mmol), and the reaction mixture was stirred at 100° C. for 4 hours. The reaction mixture was partitioned between dichloromethane and brine. The organic fraction was separated, dried over anhydrous sodium sulfate, and filtered. The filtrate was concentrated, and the residue was purified using a 12 g silica gel cartridge eluted with a gradient of 0-25% ethyl acetate/heptanes over 20 minutes to give 5-(4-azidotetrahydro-2H-pyran-2-yl)-1,3-benzodioxole (169 mg, 87%).

Step 3: A mixture of 5-(4-azidotetrahydro-2H-pyran-2-yl)-1,3-benzodioxole (0.169 g, 0.684 mmol) from Step 2 in tetrahydrofuran (3 mL) was added to Raney®-nickel 2800, water slurry (0.2 g, 1.533 mmol) in a 50 mL pressure bottle, and the mixture was stirred for 4 hours under hydrogen (30 psi) at ambient temperature. The catalyst was removed by filtration, and the filtrate was concentrated. The crude 2-(1, 3-benzodioxol-5-yl)tetrahydro-2H-pyran-4-amine was used in the next step without additional purification.

Step 4: To a suspension of 1-(2,2-difluorobenzo[d][1,3] dioxol-5-yl)cyclopropanecarboxylic acid (0.12 g, 0.496 mmol) in dichloromethane (2.00 mL) was added 2 drops of N,N,-dimethylformamide, and then a 2.0 M solution of oxalyl chloride in dichloromethane (0.496 mL, 0.991 mmol) was added dropwise. The reaction mixture was stirred at ambient temperature for 90 minutes and then concentrated.

The crude material was diluted with 3 mL of dichloromethane, and the resultant solution was added to a solution of 2-(1,3-benzodioxol-5-yl)tetrahydro-2H-pyran-4-amine (0.111 g, 0.502 mmol) from Step 3 and triethylamine (0.175 mL, 1.254 mmol) in dichloromethane (1 mL). The reaction mixture was stirred at ambient temperature for 90 minutes. The reaction mixture was washed with water. The organic fraction was separated, dried over anhydrous sodium sulfate, and filtered. The filtrate was concentrated, and the residue was purified using a 12 g silica gel cartridge eluted with a gradient of 10-60% tert-butyl methyl ether/heptanes over 20 minutes. The racemic material was further purified by preparative supercritical fluid chromatography set to maintain a backpressure at 100 bar using a Chiralcel® OJ-H, 21×250 mm, 5 micron, with the sample at a concentration of 25 mg/mL in methanol using a gradient of 5-30% of 2-propanol (0.1% diethylamine) in $CO_2$ over 10 minutes at a flow rate of 70 mL/minute with a retention time of 6.8 minutes to give N-[(2S,4R)-2-(1,3-benzodioxol-5-yl)tetrahydro-2H-pyran-4-yl]-1-(2,2-difluoro-1,3-benzodioxol-5-yl)cyclopropanecarboxamide (50 mg, 0.112 mmol). $^1$H NMR (400 MHz, $CDCl_3$) δ ppm 0.95-1.07 (m, 2H) 1.11-1.44 (m, 3H) 1.85 (dd, J=12.51, 1.83 Hz, 1H) 2.03 (dd, J=12.51, 1.83 Hz, 1H) 3.09 (s, 1H) 3.49-3.66 (m, 1H) 4.02-4.15 (m, 2H) 4.27 (dd, J=11.14, 1.68 Hz, 1H) 5.09 (d, J=7.93 Hz, 1H) 5.91 (s, 2H) 6.73 (s, 2H) 6.80 (s, 1H) 7.00-7.06 (m, 1H) 7.07-7.16 (m, 2H); MS (ESI+) m/z 446 (M+H)$^+$. Absolute stereochemistry was assigned using X-ray diffraction analysis.

Example 16 methyl 3-[(2S,4R)-4-({[1-(2,2-difluoro-1,3-benzodioxol-5-yl)cyclopropyl]carbonyl}amino)tetrahydro-2H-pyran-2-yl]benzoate The titled compound was prepared from methyl rac-3-[(2R,4S)-4-({[1-(2,2-difluoro-1,3-benzodioxol-5-yl)cyclopropyl]carbonyl}amino)tetrahydro-2H-pyran-2-yl]benzoate from Example 3 by preparative supercritical fluid chromatography set to maintain a backpressure at 100 bar using a WHELK-O® (S,S) column, 21×250 mm, 5 micron, with the sample at a concentration of 20 mg/mL in methanol with a co-solvent of 20% 2-propanol (0.1% diethylamine) in $CO_2$ at a flow rate of 70 mL/minute with a retention time of 6.0 minutes to give the titled compound (125 mg, 0.272 mmol). $^1$H NMR (400 MHz, DMSO-$d_6$) δ ppm 7.91 (t, J=1.7 Hz, 1H), 7.87-7.82 (m, 1H), 7.55 (dt, J=7.8, 1.5 Hz, 1H), 7.47 (t, J=7.7 Hz, 1H), 7.34 (d, J=1.7 Hz, 1H), 7.32 (d, J=8.4 Hz, 1H), 7.14 (dd, J=8.3, 1.7 Hz, 1H), 6.77 (d, J=8.2 Hz, 1H), 4.45 (dd, J=11.6, 2.1 Hz, 1H), 4.02 (dd, J=11.9, 4.4 Hz, 2H), 3.84 (s, 3H), 3.53 (td, J=12.1, 2.3 Hz, 1H), 1.85-1.79 (m, 1H), 1.67-1.59 (m, 1H), 1.51 (tt, J=12.4, 6.2 Hz, 1H), 1.44-1.35 (m, 1H), 1.34 (d, J=3.2 Hz, 2H), 1.02-0.94 (m, 2H); MS (ESI+) m/z 460 (M+H)$^+$; $[α]_D^{25}$ −4.4° (c 2.65, $CH_3OH$).

Example 17 methyl 3-[(2R,4S)-4-({[1-(2,2-difluoro-1,3-benzodioxol-5-yl)cyclopropyl]carbonyl}amino)tetrahydro-2H-pyran-2-yl]benzoate The titled compound was prepared from methyl rac-3-[(2R,4S)-4-({[1-(2,2-difluoro-1,3-benzodioxol-5-yl)cyclopropyl]carbonyl}amino)tetrahydro-2H-pyran-2-yl]benzoate from Example 3 by preparative supercritical fluid chromatography set to maintain a backpressure at 100 bar using a WHELK-O® (S,S) column, 21×250 mm, 5 micron, with the sample at a concentration of 20 mg/mL in methanol using a co-solvent of 20% 2-propanol (0.1% diethylamine) in $CO_2$ at a flow rate of 70 mL/minute with a retention time of 8.2 minutes to give the titled compound (125 mg, 0.272 mmol). $^1$H NMR (400 MHz, DMSO-$d_6$) δ ppm 7.91 (t, J=1.7 Hz, 1H), 7.87-7.82 (m, 1H), 7.55 (dt, J=7.8, 1.5 Hz, 1H), 7.47 (t, J=7.7 Hz, 1H), 7.34 (d, J=1.7 Hz, 1H), 7.32 (d, J=8.4 Hz, 1H), 7.14 (dd, J=8.3, 1.7 Hz, 1H), 6.77 (d, J=8.2 Hz, 1H), 4.45 (dd, J=11.6, 2.1 Hz, 1H), 4.02 (dd, J=11.9, 4.4 Hz, 2H), 3.84 (s, 3H), 3.53 (td, J=12.1, 2.3 Hz, 1H), 1.85-1.79 (m, 1H), 1.67-1.59 (m, 1H), 1.51 (tt, J=12.4, 6.2 Hz, 1H), 1.44-1.35 (m, 1H), 1.34 (d, J=3.2 Hz, 2H), 1.02-0.94 (m, 2H); MS (ESI+) m/z 460 (M+H)$^+$; $[α]_D^{25}$ +4.6° (c 2.60, $CH_3OH$).

Example 18

3-[(2S,4R)-4-({[1-(2,2-difluoro-1,3-benzodioxol-5-yl)cyclopropyl]carbonyl}amino)tetrahydro-2H-pyran-2-yl]benzoic acid The title compound was prepared as described in Example 2 substituting methyl 3-[(2S,4R)-4-({[1-(2,2-difluoro-1,3-benzodioxol-5-yl)cyclopropyl]carbonyl}amino)tetrahydro-2H-pyran-2-yl]benzoate from Example 16 for methyl rac-3-[(2S,4R)-4-({[1-(2,2-difluoro-1,3-benzodioxol-5-yl)cyclopropyl]carbonyl}amino)tetrahydro-2H-pyran-2-yl]benzoate to give the titled compound (78 mg, 87%). $^1$H NMR (400 MHz, DMSO-$d_6$) δ ppm 12.89 (s, 1H), 7.89 (s, 1H), 7.82 (d, J=7.5 Hz, 1H), 7.52 (d, J=7.6 Hz, 1H), 7.44 (d, J=7.7 Hz, 1H), 7.36-7.29 (m, 2H), 7.15 (d, J=8.6 Hz, 1H), 6.77 (d, J=8.2 Hz, 1H), 4.43 (d, J=11.0 Hz, 1H), 4.01 (dq, J=10.9, 6.2, 4.7 Hz, 2H), 3.57-3.48 (m, 1H), 1.86-1.78 (m, 1H), 1.63 (dd, J=12.5, 4.2 Hz, 1H), 1.51 (tt, J=13.3, 6.6 Hz, 1H), 1.45-1.36 (m, 1H), 1.34 (d, J=3.3 Hz, 2H), 0.97 (t, J=8.9 Hz, 2H); MS (ESI+) m/z 446 (M+H)$^+$; $[α]_D^{25}$ −4.4° (c 2.70, $CH_3OH$).

Example 19

3-[(2R,4S)-4-({[1-(2,2-difluoro-1,3-benzodioxol-5-yl)cyclopropyl]carbonyl}amino)tetrahydro-2H-pyran-2-yl]benzoic acid The title compound was prepared as described in Example 2 substituting methyl 3-[(2R,4S)-4-({[1-(2,2-difluoro-1,3-benzodioxol-5-yl)cyclopropyl]carbonyl}amino)tetrahydro-2H-pyran-2-yl]benzoate from Example 17 for methyl rac-3-[(2S,4R)-4-({[1-(2,2-difluoro-1,3-benzodioxol-5-yl)cyclopropyl]carbonyl}amino)tetrahydro-2H-pyran-2-yl]benzoate to give the titled compound (80 mg, 96%). $^1$H NMR (400 MHz, DMSO-$d_6$) δ ppm 12.89 (s, 1H), 7.89 (s, 1H), 7.82 (d, J=7.5 Hz, 1H), 7.52 (d, J=7.6 Hz, 1H), 7.44 (d, J=7.7 Hz, 1H), 7.36-7.29 (m, 2H), 7.15 (d, J=8.6 Hz, 1H), 6.77 (d, J=8.2 Hz, 1H), 4.43 (d, J=11.0 Hz, 1H), 4.01 (dq, J=10.9, 6.2, 4.7 Hz, 2H), 3.57-3.48 (m, 1H), 1.86-1.78 (m, 1H), 1.63 (dd, J=12.5, 4.2 Hz, 1H), 1.51 (tt, J=13.3, 6.6 Hz, 1H), 1.45-1.36 (m, 1H), 1.34 (d, J=3.3 Hz, 2H), 0.97 (t, J=8.9 Hz, 2H); MS (ESI+) m/z 446 (M+H)$^+$; $[α]_D^{25}$ +4.5° (c 2.65, $CH_3OH$).

Example 20

N-[(2R,4R)-2-(4-bromophenyl)tetrahydro-2H-pyran-4-yl]-1-(2,2-difluoro-1,3-benzodioxol-5-yl)cyclopropanecarboxamide Step 1: rac-N-[(2R,4R)-2-(4-Bromophenyl)tetrahydro-2H-pyran-4-yl]-1-(2,2-difluoro-1,3-benzodioxol-5-yl)cyclopropanecarboxamide (1.45 g, 3.02 mmol) was prepared using the procedures described in Example 4, Steps 1 through 4, substituting 4-bromobenzaldehyde for methyl 3-formylbenzoate in Step 1. $^1$H NMR (400 MHz, CDCl$_3$) δ ppm 1.07 (d, J=3.36 Hz, 2H) 1.52 (dd, J=13.89, 2.90 Hz, 1H) 1.58-1.72 (m, 2H) 1.77-1.99 (m, 3H) 3.33-3.45 (m, 1H) 3.78-3.90 (m, 1H) 4.13-4.27 (m, 2H) 5.53 (d, J=6.71 Hz, 1H) 7.09-7.28 (m, 5H) 7.45 (d, J=8.54 Hz, 2H); MS (ESI+) m/z 480 (M+H)$^+$.

Step 2: The title compound was prepared from rac-N-[(2R,4R)-2-(4-bromophenyl)tetrahydro-2H-pyran-4-yl]-1-(2,2-difluoro-1,3-benzodioxol-5-yl)cyclopropanecarboxamide from Step 1 by preparative supercritical fluid chromatography set to maintain a backpressure at 100 bar using a Chiralcel® OJ-H, 21×250 mm, 5 micron, with the sample at a concentration of 15 mg/mL in methanol using 16% methanol in CO$_2$ at a flow rate of 70 mL/minute with a retention time of 2.4 minutes to give N-[(2R,4R)-2-(4-bromophenyl)tetrahydro-2H-pyran-4-yl]-1-(2,2-difluoro-1,3-benzodioxol-5-yl)cyclopropanecarboxamide (430 mg, 0.896 mmol). $^1$H NMR (400 MHz, CDCl$_3$) δ ppm 1.07 (d, J=3.36 Hz, 2H) 1.52 (dd, J=13.89, 2.90 Hz, 1H) 1.58-1.72 (m, 2H) 1.77-1.99 (m, 3H) 3.33-3.45 (m, 1H) 3.78-3.90 (m, 1H) 4.13-4.27 (m, 2H) 5.53 (d, J=6.71 Hz, 1H) 7.09-7.28 (m, 5H) 7.45 (d, J=8.54 Hz, 2H); MS (ESI+) m/z 480 (M+H)$^+$; absolute stereochemistry was assigned by X-ray diffraction analysis.

Example 21

N-[(2S,4S)-2-(4-bromophenyl)tetrahydro-2H-pyran-4-yl]-1-(2,2-difluoro-1,3-benzodioxol-5-yl)cyclopropanecarboxamide The title compound was prepared from rac-N-[(2R,4R)-2-(4-bromophenyl)tetrahydro-2H-pyran-4-yl]-1-(2,2-difluoro-1,3-benzodioxol-5-yl)cyclopropanecarboxamide from Example 20 Step 1 by preparative supercritical fluid chromatography set to maintain a backpressure at 100 bar using a Chiralcel® OJ-H, 21×250 mm, 5 micron, with the sample at a concentration of 15 mg/mL in methanol using 16% methanol in CO$_2$ at a flow rate of 70 mL/minute with a retention time of 3.1 minutes to give the titled compound (466 mg, 0.971 mmol). $^1$H NMR (400 MHz, CDCl$_3$) δ ppm 1.07 (d, J=3.36 Hz, 2H) 1.52 (dd, J=13.89, 2.90 Hz, 1H) 1.58-1.72 (m, 2H) 1.77-1.99 (m, 3H) 3.33-3.45 (m, 1H) 3.78-3.90 (m, 1H) 4.13-4.27 (m, 2H) 5.53 (d, J=6.71 Hz, 1H) 7.09-7.28 (m, 5H) 7.45 (d, J=8.54 Hz, 2H); MS (ESI+) m/z 480 (M+H)$^+$; absolute stereochemistry was assigned by X-ray diffraction analysis.

Example 22 methyl rac-3-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoate Step 1: Methyl 3-formylbenzoate (2.64 g, 16.08 mmol) was added to H$_2$O (40 mL) containing potassium iodide (8.01 g, 48.2 mmol), stannous chloride (4.57 g, 24.12 mmol) and 3-bromoprop-1-ene (2.087 mL, 24.12 mmol). Saturated ammonium chloride (20 mL) was added. The reaction mixture was stirred at ambient temperature for 2 hours and then extracted with CH$_2$Cl$_2$ (2×50 mL). The organic layer was washed with water, dried over sodium sulfate and concentrated. Purification by flash chromatography on a 50 g silica gel cartridge, eluted with ethyl acetate in heptane at 5-30% gradient gave methyl 3-(1-hydroxybut-3-en-1-yl)benzoate (3.0 g, 90% yield). $^1$H NMR (400 MHz, CDCl$_3$) δ ppm 8.02 (d, J=1.8 Hz, 1H), 7.96-7.92 (m, 1H), 7.59-7.54 (m, 1H), 7.42 (t, J=7.7 Hz, 1H), 5.86-5.73 (m, 1H), 5.20-5.16 (m, 1H), 5.14 (s, 1H), 4.80 (dd, J=7.8, 5.0 Hz, 1H), 3.92 (s, 3H), 2.59-2.45 (m, 2H).

Step 2: To methyl 3-(1-hydroxybut-3-en-1-yl)benzoate (1.856 g, 9.0 mmol) from Step 1 in benzene (15 mL) was added benzaldehyde (1.9 mL, 18.00 mmol) and acetic acid (1.65 mL, 28.8 mmol) followed by addition of boron trifluoride diethyl etherate (2.25 mL, 20 mmol) at 0° C. The mixture was stirred at 0° C. for 3 hours and extracted with CH$_2$Cl$_2$. Saturated NaHCO$_3$ (10 mL) was added to the reaction media followed by extraction with ethyl acetate (2×20 mL). The combined organic layers were washed with brine, dried over Na$_2$SO$_4$, filtered and concentrated under reduced pressure. The acetylated intermediate, methyl 3-[4-(acetyloxy)-6-phenyltetrahydro-2H-pyran-2-yl]benzoate, obtained in this reaction was dissolved in CH$_3$OH (10 mL) and K$_2$CO$_3$ (500 mg) was added. The mixture was stirred for 0.5 hour at ambient temperature, and then filtered and concentrated. Purification by flash chromatography on silica gel (50 g), eluted with ethyl acetate in heptane (5-30%) gave methyl rac-3-[(2R,6S)-4-hydroxy-6-phenyltetrahydro-2H-pyran-2-yl]benzoate (865 mg, 30.7% yield). LC/MS (APCI+) m/z 313 (M+H)$^+$.

Step 3: To methyl rac-3-[(2R,6S)-4-hydroxy-6-phenyltetrahydro-2H-pyran-2-yl]benzoate (860 mg, 2.75 mmol) from Step 2 in CH$_2$Cl$_2$ (10 mL) was added pyridinium chlorochromate (593 mg, 2.75 mmol) portionwise at room temperature. The mixture was stirred at room temperature for 3 hours. The reaction mixture was filtered through a pad of diatomaceous earth and extracted with CH$_2$Cl$_2$. The organic layer was washed with water, dried over NaSO$_4$ and concentrated. Purification by flash chromatography on a 25 g silica gel cartridge, eluted with ethyl acetate in heptane (5-20%) yielded methyl rac-3-[(2R,6S)-4-oxo-6-phenyltetrahydro-2H-pyran-2-yl]benzoate (820 mg, 96% yield). $^1$H NMR (400 MHz, CDCl$_3$) δ ppm 8.12 (t, J=1.7 Hz, 1H), 8.00 (dt, J=7.8, 1.4 Hz, 1H), 7.67 (dt, J=7.8, 1.5 Hz, 1H), 7.50-7.44 (m, 3H), 7.43-7.37 (m, 2H), 7.36-7.30 (m, 1H), 4.88 (ddd, J=14.9, 10.6, 3.8 Hz, 2H), 3.93 (s, 3H), 2.82-2.64 (m, 4H).

Step 4: A mixture of methyl rac-3-[(2R,6S)-4-oxo-6-phenyltetrahydro-2H-pyran-2-yl]benzoate (800 mg, 2.58 mmol) from Step 3, sodium acetate (423 mg, 5.16 mmol) and O-methylhydroxylamine hydrochloride (431 mg, 5.16 mmol) in methanol (10 mL) was stirred at 60° C. overnight. The reaction mixture was concentrated under reduced pressure, and the residue was dissolved in ethyl acetate which was washed with brine. The organic layers was dried over MgSO$_4$ and concentrated to give methyl rac-3-[(2R,6S)-4-(methoxyimino)-6-phenyltetrahydro-2H-pyran-2-yl]benzoate (625 mg, 71.4% yield). $^1$H NMR (400 MHz, CDCl$_3$) δ ppm 8.12 (q, J=1.7 Hz, 1H), 7.98 (dt, J=7.9, 1.5 Hz, 1H), 7.68 (ddt, J=12.3, 7.7, 1.5 Hz, 1H), 7.46 (tt, J=7.5, 4.2 Hz, 3H), 7.38 (t, J=7.5 Hz, 2H), 7.33-7.28 (m, 1H), 4.69 (dddd, J=32.8, 14.9, 11.6, 2.7 Hz, 2H), 3.93 (d, J=2.3 Hz, 3H), 3.90 (d, J=1.7 Hz, 3H), 3.57 (ddt, J=14.5, 8.6, 2.2 Hz, 1H), 2.72 (ddt, J=14.1, 4.1, 2.0 Hz, 1H), 2.43 (ddd, J=14.0, 11.6, 8.0 Hz, 1H), 2.08 (dt, J=14.6, 11.2 Hz, 1H); MS (ESI+) m/z 339.9 (M+H)$^+$.

Step 5: To a solution of methyl rac-3-[(2R,6S)-4-(methoxyimino)-6-phenyltetrahydro-2H-pyran-2-yl]benzoate in CH$_3$OH (10 mL) from Step 4 (500 mg, 1.473 mmol) was added Raney®-nickel 2800, water slurry (1.5 g) in a 100 mL pressure bottle. The mixture was charged with 30 psi of hydrogen and stirred at ambient temperature for 16 hours, filtered through a pad of diatomaceous earth, and concentrated under reduced pressure. Purification by chromatography on 100 g silica gel, eluted with $CH_3OH$ in ethyl acetate, with gradient from 0-15% to yield the first eluting fraction (125 mg, 0.401 mmol, 27.2% yield) which contained methyl rac-3-[(2R,4R,6S)-4-amino-6-phenyltetrahydro-2H-pyran-2-yl]benzoate. $^1$H NMR (500 MHz, $CDCl_3$) δ ppm 8.08 (t, J=1.7 Hz, 1H), 7.93 (dt, J=7.7, 1.5 Hz, 1H), 7.66 (dt, J=7.7, 1.5 Hz, 1H), 7.47-7.38 (m, 3H), 7.34 (dd, J=8.4, 6.9 Hz, 2H), 7.28-7.22 (m, 1H), 5.19-5.03 (m, 2H), 3.91 (s, 3H), 3.74 (q, J=4.7, 3.3 Hz, 1H), 1.95 (qt, J=7.0, 3.1 Hz, 4H); MS (ESI+) m/z=311.9 (M+H)$^+$. The second eluting fraction (242 mg, 0.777 mmol, 52.8% yield) contained methyl rac-3-[(2R,4S,6S)-4-amino-6-phenyltetrahydro-2H-pyran-2-yl]benzoate. $^1$H NMR (400 MHz, $CDCl_3$) δ ppm 8.07 (t, J=1.8 Hz, 1H), 7.94 (dt, J=7.7, 1.5 Hz, 1H), 7.65 (dt, J=7.9, 1.5 Hz, 1H), 7.47-7.38 (m, 3H), 7.38-7.32 (m, 2H), 7.30-7.24 (m, 1H), 4.60 (ddd, J=16.3, 11.4, 2.0 Hz, 2H), 3.91 (s, 3H), 3.28 (tt, J=11.3, 4.2 Hz, 1H), 2.20 (dtt, J=12.7, 4.1, 2.0 Hz, 2H), 1.46 (dtd, J=13.0, 11.3, 7.9 Hz, 2H); MS (ESI+) m/z=312 (M+H)$^+$.

Step 6: A mixture of 1-(2,2-difluorobenzo[d][1,3]dioxol-5-yl)cyclopropanecarboxylic acid (62.2 mg, 0.257 mmol) and (1-[bis(dimethylamino)methylene]-1H-1,2,3-triazolo[4,5-b]pyridinium 3-oxid hexafluorophosphate (HATU, 147 mg, 0.385 mmol) in N,N-dimethylformamide (2 mL) was stirred for 5 minutes, and then methyl rac-3-[(2R,4R,6S)-4-amino-6-phenyltetrahydro-2H-pyran-2-yl]benzoate from Step 5 (80 mg, 0.257 mmol) was added followed by addition of N-ethyl-N-isopropylpropan-2-amine (0.179 mL, 1.028 mmol). The mixture was stirred at room temperature for 2 hours. Purification by chromatography on a 25 g silica gel cartridge eluted with a gradient of 5-40% ethyl acetate in heptane yielded methyl rac-3-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoate (130 mg, 47.2% yield). Analytical chiral supercritical fluid chromatography spectrum showed two peaks with ratio 1:1, retention time=1.868 minutes and 2.115 minutes (method: 5-50% $CH_3OH:CO_2$, 10 minutes @3 mL/minute, 150 bar, column: Chiralcel® OJ-H). $^1$H NMR (400 MHz, $CDCl_3$) δ ppm 7.99-7.89 (m, 2H), 7.55 (dt, J=7.9, 1.5 Hz, 1H), 7.41 (td, J=7.6, 0.8 Hz, 1H), 7.34-7.24 (m, 7H), 7.17 (d, J=8.2 Hz, 1H), 5.79 (d, J=7.0 Hz, 1H), 4.43-4.35 (m, 2H), 4.30 (dd, J=9.2, 5.2 Hz, 1H), 3.92 (s, 3H), 2.02-1.83 (m, 4H), 1.70 (d, J=3.3 Hz, 2H), 1.15-1.10 (m, 2H); MS (ESI-) m/z 534.2 (M-H)$^-$.

Example 23 methyl rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoate To 1-(2,2-difluorobenzo[d][1,3]dioxol-5-yl)cyclopropanecarboxylic acid (156 mg, 0.642 mmol) in N,N-dimethylformamide (2 mL) was added (1-[bis(dimethylamino)methylene]-1H-1,2,3-triazolo[4,5-b]pyridinium 3-oxid hexafluorophosphate (HATU, 366 mg, 0.963 mmol). The mixture was stirred for 5 minutes, and then methyl rac-3-[(2R,4S,6S)-4-amino-6-phenyltetrahydro-2H-pyran-2-yl]benzoate from Step 5 of Example 22 (200 mg, 0.642 mmol) and N-ethyl-N-isopropylpropan-2-amine (0.448 mL, 2.57 mmol) were sequentially added. The mixture was stirred at room temperature for 2 hours. The crude material was loaded on 25 g silica gel cartridge without work up and eluted with 5-40% ethyl acetate in heptane to give the titled compound. Analytical chiral supercritical fluid chromatography spectrum showed two peaks with ratio 1:1, retention time=3.268 minutes and 3.940 minutes (method: 5-50% $CH_3OH:CO_2$, 10 minutes @3 mL/minute, 150 bar, column: Chiralcel® OJ-H). $^1$H NMR (400 MHz, $CDCl_3$) δ ppm 8.04 (t, J=1.8 Hz, 1H), 7.93 (dt, J=7.7, 1.6 Hz, 1H), 7.59 (dt, J=8.1, 1.6 Hz, 1H), 7.43-7.29 (m, 5H), 7.28-7.21 (m, 1H), 7.11-7.04 (m, 2H), 7.01 (d, J=8.1 Hz, 1H), 5.12 (d, J=8.0 Hz, 1H), 4.72-4.56 (m, 2H), 4.34 (tdt, J=12.1, 8.2, 4.3 Hz, 1H), 3.91 (d, J=1.4 Hz, 3H), 2.20 (ddd, J=14.8, 9.0, 3.4 Hz, 2H), 1.62 (q, J=3.5 Hz, 2H), 1.27 (d, J=11.3 Hz, 3H), 1.02 (q, J=3.5 Hz, 2H); MS (ESI-) m/z 534.2 (M-H)$^-$.

Example 24 rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid To Example 23 (100 mg, 0.187 mmol) in $CH_3OH$ (4 mL) and water (1.0 mL) was added lithium hydroxide (26.8 mg, 1.120 mmol). The mixture was stirred at 35° C. for 4 hours. The reaction mixture was concentrated under reduced pressure and water (1 mL) was added. Then 2 M HCl was added drop wise to adjust pH to 1-2. The precipitated solid was collected by filtration, washed with water, and dried in a vacuum oven to yield the titled compound (95 mg, 98%). Analytical chiral supercritical fluid chromatography spectrum showed two peaks with ratio 1:1, retention time=7.197 minutes, 7.792 minutes (method: 5-30% $CH_3OH:CO_2$ over 10 minutes @3 mL/minute, 150 bar, column: Whelk-O® 1 (S,S)). $^1$H NMR (400 MHz, $CDCl_3$) δ ppm 8.07 (d, J=43.2 Hz, 2H), 7.62 (s, 1H), 7.32 (d, J=13.4 Hz, 7H), 7.07-6.99 (m, 2H), 5.14 (s, 1H), 4.62 (s, 2H), 4.36 (s, 1H), 2.19 (d, J=30.2 Hz, 2H), 1.64, (s, 2H), 1.26 (s, 2H), 1.06-0.94 (m, 2H); MS (ESI-) m/z 520.2 (M-H)$^-$.

Example 25 rac-3-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoic acid To a mixture of Example 22 (40 mg, 0.037 mmol) in $CH_3OH$ (2 mL) and water (0.5 mL) was added lithium hydroxide (8.94 mg, 0.373 mmol). The mixture was stirred at 35° C. for 4 hours. The reaction mixture was concentrated under reduced pressure and water (1 mL) was added. The mixture was acidified to pH 1~2 with the dropwise addition of 2 M HCl. The precipitated solid was collected by filtration, washed with water, and dried in a vacuum oven to yield the titled compound. The titled compound was further purified (27 mg, 0.026 mmol, 69.3% yield) by preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-1.0 minute 5% A, 1.0-8.5 minutes linear gradient 5-100% A, 8.5-11.0 minutes 100% A, 11.5-12.0 minutes linear gradient 95-5% A). Analytical chiral supercritical fluid chromatography spectrum showed two peaks with ratio 1:1, retention time=7.268 minutes and 7.588 minutes (method: 5-30% $CH_3OH:CO_2$ over 10 minutes @3 mL/minute, 150 bar, column: Whelk-O® 1 (S,S)). $^1$H NMR (400 MHz, $CDCl_3$) δ ppm 8.08-7.96 (m, 2H), 7.61 (dt, J=7.9, 1.5 Hz, 1H), 7.45 (t, J=7.7 Hz, 1H), 7.39-7.26 (m, 7H), 7.18 (d, J=8.2 Hz, 1H), 5.83 (d, J=7.0 Hz, 1H), 4.50-4.22 (m, 4H), 2.02 (d, J=14.0 Hz, 1H), 1.95-1.80 (m, 3H), 1.71 (d, J=3.0 Hz, 2H), 1.18-1.11 (m, 2H); MS (ESI−) m/z 520.2 (M−H)⁻.

Example 26

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid The titled compound was isolated from Example 24 by preparative supercritical fluid chromatography set to maintain a backpressure at 100 bar using a Whelk-O® 1 (S,S) column, 21×250 mm, 5 micron, with the sample at a concentration of 20 mg/mL in methanol with a co-solvent of 20% methanol in $CO_2$ at a flow rate of 70 mL/minute to give the titled compound as the second fraction with a retention time of 7.75 minutes (15.5 mg, 0.030 mmol, 47.7% yield). $^1$H NMR (400 MHz, $CDCl_3$) δ ppm 8.13 (d, J=1.8 Hz, 1H), 8.04-7.94 (m, 1H), 7.65 (d, J=7.6 Hz, 1H), 7.43 (t, J=7.7 Hz, 1H), 7.40-7.30 (m, 4H), 7.25 (d, J=8.8 Hz, 1H), 7.12-6.99 (m, 3H), 5.16 (d, J=8.1 Hz, 1H), 4.74-4.59 (m, 2H), 4.37 (dtd, J=12.0, 7.8, 4.1 Hz, 1H), 2.31-2.13 (m, 2H), 1.65-1.63 (q, J=3.3 Hz, 2H) 1.31 (qd, J=11.8, 2.6 Hz, 2H), 1.04-1.02 (q, J=3.3 Hz, 2H); MS (ESI−) m/z 520.2 (M−H)⁻.

Example 27

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid The titled compound was isolated from Example 24 by preparative supercritical fluid chromatography set to maintain a backpressure at 100 bar using a Whelk-O® 1 (S,S) column, 21×250 mm, 5 micron, with the sample at a concentration of 20 mg/mL in methanol with a co-solvent of 20% methanol in $CO_2$ at a flow rate of 70 mL/minute to give the title compound as the first fraction with a retention time of 6.50 minutes (12.5 mg, 0.024 mmol, 38.5% yield). $^1$H NMR (400 MHz, $CDCl_3$) δ ppm 8.11 (s, 1H), 7.98 (s, 1H), 7.60 (s, 1H), 7.45-7.28 (m, 5H), 7.23 (d, J=7.6 Hz, 1H), 7.10-6.96 (m, 3H), 5.15 (d, J=7.8 Hz, 1H), 4.61 (t, J=12.8 Hz, 2H), 4.34 (s, 1H), 2.31-2.07 (m, 4H), 1.32-1.20 (m, 2H), 1.01 (d, J=3.8 Hz, 2H); MS (ESI−) m/z 520.2 (M−H)⁻.

Example 28 methyl 4-[(2S,4R)-4-({[1-(2,2-difluoro-1,3-benzodioxol-5-yl)cyclopropyl]carbonyl}amino)tetrahydro-2H-pyran-2-yl]benzoate The titled compound was prepared from methyl rac-4-[(2R,4S)-4-({[1-(2,2-difluoro-1,3-benzodioxol-5-yl)cyclopropyl]carbonyl}amino)tetrahydro-2H-pyran-2-yl]benzoate from Example 13 by preparative supercritical fluid chromatography set to maintain a backpressure at 100 bar using a Whelk-O® 1 (S,S) column, 21×250 mm, 5 micron, with the sample at a concentration of 55 mg/mL in methanol with a co-solvent of 30% methanol buffered with 0.1% diethylamine in $CO_2$ at a flow rate of 70 mL/minute with a retention time of 2.8 minutes to give the titled compound (634 mg, 1.380 mmol). $^1$H NMR (400 MHz, DMSO-$d_6$) δ ppm 7.91 (d, J=8.3 Hz, 2H), 7.43 (d, J=8.3 Hz, 2H), 7.34 (d, J=1.7 Hz, 1H), 7.31 (d, J=8.3 Hz, 1H), 7.14 (dd, J=8.3, 1.7 Hz, 1H), 6.78 (d, J=8.2 Hz, 1H), 4.45 (dd, J=11.6, 2.1 Hz, 1H), 4.08-3.96 (m, 2H), 3.84 (s, 3H), 3.53 (td, J=12.1, 2.3 Hz, 1H), 1.84 (ddd, J=12.7, 4.2, 2.1 Hz, 1H), 1.68-1.59 (m, 1H), 1.50 (qd, J=12.4, 4.7 Hz, 1H), 1.41-1.29 (m, 3H), 1.02-0.94 (m, 2H); MS (ESI+) m/z 460 (M+H)⁺; $[α]_D^{25}$ −18.4° (c 5.10, $CH_3OH$).

Example 29 methyl 4-[(2R,4S)-4-({[1-(2,2-difluoro-1,3-benzodioxol-5-yl)cyclopropyl]carbonyl}amino)tetrahydro-2H-pyran-2-yl]benzoate The titled compound was prepared from methyl rac-4-[(2R,4S)-4-({[1-(2,2-difluoro-1,3-benzodioxol-5-yl)cyclopropyl]carbonyl}amino)tetrahydro-2H-pyran-2-yl]benzoate from Example 13 by preparative supercritical fluid chromatography set to maintain a backpressure at 100 bar using a Whelk-O® 1 (S,S) column, 21×250 mm, 5 micron, with the sample at a concentration of 55 mg/mL in methanol with a co-solvent of 30% methanol buffered with 0.1% diethylamine in $CO_2$ at a flow rate of 70 mL/minute with a retention time of 3.35 minutes to give the titled compound (738 mg, 1.606 mmol). $^1$H NMR (400 MHz, DMSO-$d_6$) δ ppm 7.91 (d, J=8.3 Hz, 2H), 7.43 (d, J=8.3 Hz, 2H), 7.34 (d, J=1.7 Hz, 1H), 7.31 (d, J=8.3 Hz, 1H), 7.14 (dd, J=8.3, 1.7 Hz, 1H), 6.78 (d, J=8.2 Hz, 1H), 4.45 (dd, J=11.6, 2.1 Hz, 1H), 4.08-3.96 (m, 2H), 3.84 (s, 3H), 3.53 (td, J=12.1, 2.3 Hz, 1H), 1.84 (ddd, J=12.7, 4.2, 2.1 Hz, 1H), 1.68-1.59 (m, 1H), 1.50 (qd, J=12.4, 4.7 Hz, 1H), 1.41-1.29 (m, 3H), 1.02-0.94 (m, 2H); MS (ESI+) m/z 460 (M+H)⁺; $[α]_D^{25}$ +18.2° (c 5.05, $CH_3OH$). Absolute stereochemistry was assigned by X-ray diffraction analysis.

Example 30

4-[(2S,4R)-4-({[1-(2,2-difluoro-1,3-benzodioxol-5-yl)cyclopropyl]carbonyl}amino)tetrahydro-2H-pyran-2-yl]benzoic acid The title compound was prepared as described in Example 2 substituting methyl 4-[(2S,4R)-4-({[1-(2,2-difluoro-1,3-benzodioxol-5-yl)cyclopropyl]carbonyl}amino)tetrahydro-2H-pyran-2-yl]benzoate from Example 28 for methyl rac-3-[(2R,4S)-4-({[1-(2,2-difluoro-1,3-benzodioxol-5-yl)cyclopropyl]carbonyl}amino)tetrahydro-2H-pyran-2-yl]benzoate to give the titled compound. $^1$H NMR (400 MHz, DMSO-$d_6$) δ ppm 7.87 (d, J=8.2 Hz, 2H), 7.38 (d, J=8.1 Hz, 2H), 7.33 (d, J=1.7 Hz, 1H), 7.30 (d, J=8.3 Hz, 1H), 7.13 (dd, J=8.4, 1.8 Hz, 1H), 6.77 (d, J=8.2 Hz, 1H), 4.42 (dd, J=11.5, 2.1 Hz, 1H), 4.07-3.93 (m, 2H), 3.52 (td, J=12.0, 2.2 Hz, 1H), 1.86-1.77 (m, 1H), 1.61 (dd, J=8.8, 6.1 Hz, 1H), 1.49 (qd, J=12.4, 4.7 Hz, 1H), 1.41-1.28 (m, 3H), 1.01-0.92 (m, 2H); MS (ESI+) m/z 446 (M+H)⁺; $[α]_D^{25}$ −15.6° (c 5.10, $CH_3OH$).

Example 31

4-[(2R,4S)-4-({[1-(2,2-difluoro-1,3-benzodioxol-5-yl)cyclopropyl]carbonyl}amino)tetrahydro-2H-pyran-2-yl]benzoic acid The title compound was prepared as described in Example 2 substituting methyl 4-[(2R,4S)-4-({[1-(2,2-difluoro-1,3-benzodioxol-5-yl)cyclopropyl]carbonyl}amino)tetrahydro-2H-pyran-2-yl]benzoate from Example 29 for methyl rac-3-[(2R,4S)-4-({[1-(2,2-difluoro-1,3-benzodioxol-5-yl)cyclopropyl]carbonyl}amino)tetrahydro-2H-pyran-2-yl]benzoate to give the titled compound. $^1$H NMR (400 MHz, DMSO-d$_6$) δ ppm 7.87 (d, J=8.2 Hz, 2H), 7.38 (d, J=8.1 Hz, 2H), 7.33 (d, J=1.7 Hz, 1H), 7.30 (d, J=8.3 Hz, 1H), 7.13 (dd, J=8.4, 1.8 Hz, 1H), 6.77 (d, J=8.2 Hz, 1H), 4.42 (dd, J=11.5, 2.1 Hz, 1H), 4.07-3.93 (m, 2H), 3.52 (td, J=12.0, 2.2 Hz, 1H), 1.86-1.77 (m, 1H), 1.61 (dd, J=8.8, 6.1 Hz, 1H), 1.49 (qd, J=12.4, 4.7 Hz, 1H), 1.41-1.28 (m, 3H), 1.01-0.92 (m, 2H); MS (ESI+) m/z 446 (M+H)$^+$; [α]$_D^{25}$+16.0° (c 5.10, CH$_3$OH).

Example 32 methyl rac-4-[(2R,4S)-4-({[1-(2,2-difluoro-1,3-benzodioxol-5-yl)cyclopropyl]carbonyl}amino)-6,6-dimethyltetrahydro-2H-pyran-2-yl]benzoate Step 1: To 4-methylpent-3-en-2-one (5.83 mL, 50.9 mmol) in tetrahydrofuran (25.5 mL) at 0° C. was added tert-butyldimethylsilyl trifluoromethanesulfonate (11.71 mL, 50.9 mmol) over 30 minutes via an additional funnel. The solution was stirred and allowed to warm to room temperature over 2 hours. The reaction was quenched with saturated aqueous sodium bicarbonate, and the mixture was extracted with hexane. The organic fraction was concentrated, and the residue (10.5 g) was purified by flash chromatography using a 24 g silica gel cartridge with a gradient of 0-10% ethyl acetate/heptanes over 20 minutes to provide tert-butyl(dimethyl)[(4-methylpenta-1,3-dien-2-yl)oxy]silane (11.2 g, 52.7 mmol, 104% yield). $^1$H NMR (400 MHz, CDCl$_3$) δ ppm 5.57 (s, 1H), 4.32 (s, 1H), 4.17 (s, 1H), 1.91 (s, 3H), 1.78 (s, 3H), 0.95 (s, 9H), 0.17 (d, J=1.0 Hz, 6H); MS (DCI+) m/z 213 (M+H)$^+$.

Step 2: A solution of tert-butyl(dimethyl)[(4-methylpenta-1,3-dien-2-yl)oxy]silane (5.0 g, 23.54 mmol) from Step 1, methyl 4-formylbenzoate (3.86 g, 23.54 mmol) and tris(6,6,7,7,8,8,8-heptafluoro-2,2-dimethyl-3,5-octanedionato)europium(III) (1.221 g, 1.177 mmol) in chloroform (20.83 mL) in a dried vial under nitrogen was heated to 60° C. for 6 hours. The reaction mixture was then allowed to cool to room temperature with continued stirring for 16 hours. The mixture was concentrated, and the residue was purified by flash chromatography using a 40 g silica gel cartridge with a gradient of 0-20% ethyl acetate/heptanes over 20 minutes to provide methyl 4-(4-{[tert-butyl(dimethyl)silyl]oxy}-6,6-dimethyl-3,6-dihydro-2H-pyran-2-yl)benzoate (4.92 g, 13.07 mmol, 55.5% yield). $^1$H NMR (400 MHz, DMSO-d$_6$) δ ppm 7.90 (d, J=8.3 Hz, 2H), 7.50 (d, J=7.8 Hz, 2H), 4.90 (d, J=2.0 Hz, 1H), 4.85 (dd, J=10.4, 3.6 Hz, 1H), 3.81 (s, 3H), 2.14 (dd, J=16.3, 3.7 Hz, 1H), 2.04 (ddd, J=16.3, 10.4, 2.1 Hz, 1H), 1.25 (s, 6H), 0.86 (s, 9H), 0.12 (s, 3H), 0.11 (s, 3H); MS (ESI+) m/z 377 (M+H)$^+$.

Step 3: To a solution of methyl 4-(4-{[tert-butyl(dimethyl)silyl]oxy}-6,6-dimethyl-3,6-dihydro-2H-pyran-2-yl)benzoate (4.92 g, 13.07 mmol) from Step 2 in 1 mL of THF at ambient temperature was added 1 M tetrabutylammonium fluoride in tetrahydrofuran (11.76 mL, 11.76 mmol) dropwise. The mixture was stirred for one hour. The reaction was quenched with 0.1 N HCl, and the mixture was extracted with ethyl acetate. The organic fraction was concentrated, and the residue was purified by flash chromatography using a 12 g silica gel cartridge with a gradient of 0-40% ethyl acetate/heptanes over 20 minutes to provide methyl 4-(6,6-dimethyl-4-oxotetrahydro-2H-pyran-2-yl)benzoate (2.43 g, 9.26 mmol, 70.9% yield). $^1$H NMR (400 MHz, CDCl$_3$) δ ppm 8.08-8.03 (m, 2H), 7.50-7.46 (m, 2H), 4.97 (dd, J=11.4, 3.0 Hz, 1H), 3.93 (s, 3H), 2.64-2.54 (m, 2H), 2.50-2.37 (m, 2H), 1.50 (s, 3H), 1.33 (s, 3H).

Step 4: A mixture of methyl 4-(6,6-dimethyl-4-oxotetrahydro-2H-pyran-2-yl)benzoate (1.24 g, 4.73 mmol) from Step 3 and O-methylhydroxylamine hydrochloride (0.592 g, 7.09 mmol) in pyridine (4.73 mL) was stirred at ambient temperature for 5 minutes and at 65° C. for 1 hour. The reaction mixture was concentrated. The residue was dissolved in 10% methanol/dichloromethane and washed with water. The organic layer was separated and concentrated in vacuo. The resulted solid was rinsed with 10% dichloromethane/hexane and collected by filtration to give methyl 4-[4-(methoxyimino)-6,6-dimethyltetrahydro-2H-pyran-2-yl]benzoate (1.21 g, 4.15 mmol, 88% yield). $^1$H NMR (500 MHz, DMSO-d$_6$) δ ppm 7.95-7.92 (m, 2H), 7.53 (t, J=8.2 Hz, 2H), 4.80 (ddd, J=24.6, 11.6, 3.0 Hz, 1H), 3.84 (s, 3H), 3.76 (s, 3H), 3.22-3.16 (m, 0.5H), 3.06 (dd, J=13.6, 1.6 Hz, 0.5H), 2.48-2.44 (m, 0.5H), 2.30-2.21 (m, 1H), 2.15-2.08 (m, 0.5H), 1.94-1.85 (m, 1H), 1.32 (d, J=14.2 Hz, 3H), 1.19 (d, J=22.6 Hz, 3H); MS (ESI+) m/z 292 (M+H)$^+$.

Step 5: Methyl 4-[4-(methoxyimino)-6,6-dimethyltetrahydro-2H-pyran-2-yl]benzoate (1.2 g, 4.12 mmol) from Step 4 and acetic acid (48.5 mL) were added to platinum (436 mg, 0.923 mmol) in a 50 mL pressure bottle and shaken for 24 hours under 30 psi hydrogen and ambient temperature. The reaction mixture was filtered, and the filtrate was concentrated. The resulting oil was partitioned between dichloromethane and 1 N aqueous sodium bicarbonate. The organic layer was separated and concentrated in vacuo. The residue was purified by flash chromatography using a 12 g silica gel cartridge with a gradient of 1-10% methanol (2 N ammonia)/dichloromethane over 15 minutes to provide methyl rac-4-[(2R,4S)-4-amino-6,6-dimethyltetrahydro-2H-pyran-2-yl]benzoate (0.56 g, 2.127 mmol, 51.6% yield). $^1$H NMR (400 MHz, DMSO-d$_6$) δ ppm 7.94-7.87 (m, 2H), 7.48-7.42 (m, 2H), 5.03 (dd, J=11.2, 2.6 Hz, 1H), 3.82 (s, 3H), 3.41-3.37 (m, 1H), 1.61 (dt, J=13.3, 3.0 Hz, 1H), 1.52 (d, J=3.7 Hz, 2H), 1.46 (m, 4H), 1.15 (s, 3H); MS (ESI+) m/z 264 (M+H)$^+$.

Step 6: To 1-(2,2-difluorobenzo[d][1,3]dioxol-5-yl)cyclopropanecarboxylic acid (506 mg, 2.089 mmol) in N,N-dimethylformamide (3 mL) was added (1-[bis(dimethylamino)methylene]-1H-1,2,3-triazolo[4,5-b]pyridinium 3-oxid hexafluorophosphate (HATU, 1191 mg, 3.13 mmol). The mixture was stirred for 20 minutes, and then methyl rac-4-[(2R,4S)-4-amino-6,6-dimethyltetrahydro-2H-pyran-2-yl]benzoate (550 mg, 2.089 mmol) from Step 5 in 1 mL N,N-dimethylformamide was added, followed by N-ethyl-N-isopropylpropan-2-amine (0.728 mL, 4.18 mmol). The mixture was stirred at ambient temperature for 16 hours. Water (15 mL) was added, and a gel formed. The supernatant was decanted, and the residue was washed with water. The residue was purified by flash chromatography using a 24 g silica gel cartridge with a gradient of 0-2% methanol/dichloromethane over 20 minutes to provide methyl rac-4-[(2R,4S)-4-({[1-(2,2-difluoro-1,3-benzodioxol-5-yl)cyclopropyl]carbonyl}amino)-6,6-dimethyltetrahydro-2H-pyran-2-yl]benzoate (838 mg, 1.719 mmol, 82% yield). $^1$H NMR (400 MHz, DMSO-d$_6$) δ ppm 7.91 (d, J=8.3 Hz, 2H), 7.46 (d, J=1.9 Hz, 1H), 7.44 (d, J=8.4 Hz, 2H), 7.37 (d, J=8.3 Hz, 1H), 7.24 (dd, J=8.3, 1.8 Hz, 1H), 6.75 (d, J=6.1 Hz, 1H), 4.73 (dd, J=11.2, 3.1 Hz, 1H), 3.98 (dd, J=10.7, 4.8 Hz, 1H), 3.82 (s, 3H), 1.83 (dt, J=13.7, 3.6 Hz, 1H), 1.73 (dd, J=13.9, 4.9 Hz, 1H), 1.58 (ddd, J=13.7, 11.2, 5.4 Hz, 1H), 1.50 (dd, J=14.0, 4.7 Hz, 1H), 1.34 (pt, J=4.7, 2.4 Hz, 2H), 1.12 (s, 3H), 1.10-1.02 (m, 2H), 1.02 (s, 3H); MS (ESI+) m/z 488 (M+H)$^+$.

Example 33 rac-4-[(2R,4S)-4-({[1-(2,2-difluoro-1,3-benzodioxol-5-yl)cyclopropyl]carbonyl}amino)-6,6-dimethyltetrahydro-2H-pyran-2-yl]benzoic acid The title compound was prepared as described in Example 2 substituting methyl rac-4-[(2R,4S)-4-({[1-(2,2-difluoro-1,3-benzodioxol-5-yl)cyclopropyl]carbonyl}amino)-6,6-dimethyltetrahydro-2H-pyran-2-yl]benzoate from Example 32 for methyl rac-3-[(2R,4S)-4-({[1-(2,2-difluoro-1,3-benzodioxol-5-yl)cyclopropyl]carbonyl}amino)tetrahydro-2H-pyran-2-yl]benzoate to give the titled compound (42 mg, 0.089 mmol, 96% yield). $^1$H NMR (501 MHz, DMSO-$d_6$) δ ppm 12.79 (bs, 1H), 7.88 (d, J=8.3 Hz, 2H), 7.46 (d, J=1.7 Hz, 1H), 7.41 (d, J=8.3 Hz, 2H), 7.37 (d, J=8.3 Hz, 1H), 7.24 (dd, J=8.3, 1.8 Hz, 1H), 6.74 (d, J=6.2 Hz, 1H), 4.72 (dd, J=11.2, 3.1 Hz, 1H), 3.99 (h, J=5.0 Hz, 1H), 1.82 (dt, J=13.5, 3.4 Hz, 1H), 1.72 (dd, J=13.9, 5.1 Hz, 1H), 1.59 (ddd, J=13.6, 11.2, 5.4 Hz, 1H), 1.50 (dd, J=14.0, 4.7 Hz, 1H), 1.39-1.31 (m, 2H), 1.12 (s, 3H), 1.09-1.02 (m, 2H), 1.02 (s, 3H); MS (ESI+) m/z 474 (M+H)$^+$.

Example 34 methyl rac-4-[(2R,4R)-4-({[1-(2,2-difluoro-1,3-benzodioxol-5-yl)cyclopropyl]carbonyl}amino)-6,6-dimethyltetrahydro-2H-pyran-2-yl]benzoate Step 1: To a solution of methyl 4-(6,6-dimethyl-4-oxotetrahydro-2H-pyran-2-yl)benzoate (1.12 g, 4.27 mmol) from Step 3 of Example 32 in methanol (12 mL) at −78° C. was added sodium tetrahydroborate (0.323 g, 8.54 mmol). The reaction mixture was stirred at −78° C. for 10 minutes, and then allowed to warm up to 0° C. in 1 h. The mixture was quenched with 50 mL of aqueous saturated ammonium chloride, and then it was extracted with ethyl acetate. The organic fraction was concentrated under reduced pressure, and the residue purified using a 24 g silica gel cartridge eluted with a gradient of 5-70% ethyl acetate/heptanes in 20 minutes to provide methyl rac-4-[(2R,4S)-4-hydroxy-6,6-dimethyltetrahydro-2H-pyran-2-yl]benzoate (0.893 g, 3.38 mmol, 79% yield). $^1$H NMR (500 MHz, DMSO-$d_6$) δ ppm 7.95-7.89 (m, 2H), 7.48-7.44 (m, 2H), 5.00-4.93 (m, 1H), 4.81 (d, J=2.6 Hz, 1H), 4.10 (q, J=3.0 Hz, 1H), 3.84 (s, 3H), 1.77 (ddt, J=13.4, 2.9, 1.9 Hz, 1H), 1.67 (ddd, J=14.0, 2.9, 1.9 Hz, 1H), 1.52-1.44 (m, 2H), 1.43 (s, 3H), 1.18 (s, 3H); MS (ESI−) m/z 263 (M−H)$^−$.

Step 2: Triethylamine (1.215 mL, 8.72 mmol) was added to a stirring, ice-cooled solution of methyl rac-4-[(2R,4S)-4-hydroxy-6,6-dimethyltetrahydro-2H-pyran-2-yl]benzoate (768 mg, 2.91 mmol) from Step 1 in dichloromethane (8 mL). Methanesulfonyl chloride (0.453 mL, 5.81 mmol) was then added dropwise over 10 minutes. After 2 hours, the alcohol was almost consumed by TLC (0.5% methanol/dichloromethane). The reaction mixture was transferred to a separatory funnel with a dichloromethane (40 mL) rinse and washed successively with 1 N citric acid (40 mL) and saturated sodium carbonate solution (40 mL). The organic phase was concentrated under vacuum to leave the crude mesylate (820 mg). The crude mesylate intermediate was dissolved in N,N-dimethylformamide (3 mL), and sodium azide (850 mg, 13.08 mmol) was added. The mixture was heated at 100° C. under nitrogen for 3 hours, and the reaction was complete by TLC. The slurry was cooled to ambient temperature, diluted with water (20 mL), and extracted with dichloromethane (2×10 mL). The combined organic extracts were concentrated under vacuum. The residue was purified by chromatography using a 24 g column eluted with a gradient of 0-30% ethyl acetate/heptanes in 20 min to provide methyl rac-4-[(2R,4R)-4-azido-6,6-dimethyltetrahydro-2H-pyran-2-yl]benzoate (460 mg, 1.590 mmol, 54.7% yield). $^1$H NMR (400 MHz, DMSO-$d_6$) δ ppm 7.92 (d, J=8.3 Hz, 1H), 7.48 (d, J=8.4 Hz, 2H), 4.74 (dd, J=11.5, 2.3 Hz, 1H), 4.02 (tt, J=12.1, 4.4 Hz, 1H), 3.83 (d, J=1.5 Hz, 3H), 2.15 (ddd, J=12.1, 4.2, 2.1 Hz, 1H), 1.93 (ddd, J=12.4, 4.4, 1.9 Hz, 1H), 1.31 (t, J=12.5 Hz, 1H), 1.27 (s, 3H), 1.26 (s, 3H), 1.27-1.13 (m, 2H); MS (DCI+) m/z 307 (M+NH$_4$)$^+$.

Step 3: To methyl rac-4-[(2R,4R)-4-azido-6,6-dimethyltetrahydro-2H-pyran-2-yl]benzoate (460 mg, 1.590 mmol) from Step 2 in methanol (20 mL) was added to Raney-Nickel® 2800, water slurry (500 mg, 3.83 mmol) (washed once with methanol) in a 50 mL pressure bottle, and the mixture was shaken under 30 psi of hydrogen at ambient temperature for 4 hours with periodic venting of nitrogen. LC/MS confirmed product formation. The reaction mixture was filtered, and the filtrate was concentrated to give methyl rac-4-[(2R,4R)-4-amino-6,6-dimethyltetrahydro-2H-pyran-2-yl]benzoate (405 mg, 1.538 mmol, 97% yield). It was used for the next step without further purification. $^1$H NMR (501 MHz, DMSO-$d_6$) δ ppm 7.90 (d, J=8.3 Hz, 2H), 7.45 (d, J=8.3 Hz, 2H), 4.65 (dd, J=11.7, 2.1 Hz, 1H), 3.83 (s, 3H), 3.02 (s, 1H), 1.92 (dq, J=12.0, 2.5 Hz, 1H), 1.70 (ddd, J=12.9, 4.1, 1.7 Hz, 1H), 1.23 (s, 3H), 1.22 (s, 3H), 1.05 (t, J=12.1 Hz, 1H), 0.92 (q, J=11.8 Hz, 1H); MS (ESI+) m/z 264 (M+H)$^+$.

Step 4: To 1-(2,2-difluorobenzo[d][1,3]dioxol-5-yl)cyclopropanecarboxylic acid (368 mg, 1.519 mmol) in N,N-dimethylformamide (3 mL) was added (1-[bis(dimethylamino)methylene]-1H-1,2,3-triazolo[4,5-b]pyridinium 3-oxid hexafluorophosphate (HATU 866 mg, 2.278 mmol). The mixture was stirred for 20 minutes, and then methyl rac-4-[(2R,4R)-4-amino-6,6-dimethyltetrahydro-2H-pyran-2-yl]benzoate (400 mg, 1.519 mmol) from Step 3 in 1 mL of N,N-dimethylformamide was added, followed by N-ethyl-N-isopropylpropan-2-amine (0.529 mL, 3.04 mmol). The mixture was stirred at ambient temperature for 16 hours. Water (15 mL) was added, and a gel formed. The supernatant was decanted, and the residue was washed with water. The residue was purified by flash chromatography using a 24 g silica gel cartridge eluted with a gradient of 0-2% methanol/dichloromethane over 20 minutes to provide methyl rac-4-[(2R,4R)-4-({[1-(2,2-difluoro-1,3-benzodioxol-5-yl)cyclopropyl]carbonyl}amino)-6,6-dimethyltetrahydro-2H-pyran-2-yl]benzoate (684 mg, 1.403 mmol, 92% yield). $^1$H NMR (400 MHz, DMSO-$d_6$) δ ppm 7.89 (d, J=8.3 Hz, 2H), 7.46-7.38 (m, 2H), 7.34-7.25 (m, 2H), 7.11 (dd, J=8.3, 1.8 Hz, 1H), 6.65 (d, J=8.2 Hz, 1H), 4.79-4.63 (m, 1H), 4.18 (dtt, J=12.3, 8.2, 4.3 Hz, 1H), 3.82 (s, 3H), 1.85-1.74 (m, 1H), 1.65-1.54 (m, 1H), 1.31 (dt, J=6.8, 2.9 Hz, 2H), 1.26-1.15 (m, 2H), 1.23 (s, 3H), 1.20 (s, 3H), 0.95 (q, J=4.0 Hz, 2H); MS (ESI+) m/z 488 (M+H)$^+$.

Example 35 rac-4-[(2R,4R)-4-({[1-(2,2-difluoro-1,3-benzodioxol-5-yl)cyclopropyl]carbonyl}amino)-6,6-dimethyltetrahydro-2H-pyran-2-yl]benzoic acid The title compound was prepared as described in Example 2 substituting methyl rac-4-[(2R,4R)-4-({[1-(2,2-difluoro-1,3-benzodioxol-5-yl)cyclopropyl]carbonyl}amino)-6,6-dimethyltetrahydro-2H-pyran-2-yl]benzoate from Example 34 for methyl rac-3-[(2R,4S)-4-({[1-(2,2-difluoro-1,3-benzodioxol-5-yl)cyclopropyl]carbonyl}amino)tetrahydro-2H-pyran-2-yl]benzoate to give the titled compound (39 mg, 0.082 mmol, 89% yield). $^1$H NMR (400 MHz, DMSO-d$_6$) δ ppm 12.84 (bs, 1H), 7.86 (d, J=8.2 Hz, 2H), 7.43-7.35 (m, 2H), 7.34-7.25 (m, 2H), 7.11 (dd, J=8.3, 1.8 Hz, 1H), 6.65 (d, J=8.2 Hz, 1H), 4.69 (dd, J=11.7, 2.3 Hz, 1H), 4.17 (tdt, J=12.3, 8.5, 4.3 Hz, 1H), 1.84-1.74 (m, 1H), 1.64-1.54 (m, 1H), 1.34-1.27 (m, 2H), 1.26-1.15 (m, 2H), 1.23 (s, 3H), 1.20 (s, 3H), 0.95 (q, J=3.6 Hz, 2H); MS (ESI−) m/z 472 (M−H)$^−$.

Example 36 methyl rac-4-[(2R,4S)-4-({[1-(2,2-difluoro-1,3-benzodioxol-5-yl)cyclopropyl]carbonyl}amino)tetrahydro-2H-pyran-2-yl]-3-methylbenzoate Step 1: To a solution of 4-bromo-2-methylbenzaldehyde (4 g, 20.10 mmol) in toluene (60 mL) at −67° C. (internal) was added boron trifluoride diethyl etherate (0.505 mL, 4.02 mmol). After 15 min, 2-(trimethylsiloxy)-1,3-butadiene (4.12 mL, 23.39 mmol) was added dropwise in less than 5 minutes. Stirring was continued at −65° C. (internal) for 2 hours; and the internal temperature rose to −45° C. The reaction was quenched with 0.5 N hydrochloric acid (100 mL), and then ethyl acetate (20 mL) was added. The mixture was stirred for 16 hours at ambient temperature, and the solid precipitate was removed by filtration. The filtrate layers were separated. The organic phase was washed with brine, dried (MgSO$_4$), filtered and concentrated to give a residue (7.5 g). The residue was dissolved in 8 mL of tetrahydrofuran at 0° C. and treated with 1 M tetrabutylammonium fluoride/tetrahydrofuran (8.04 mL, 8.04 mmol) with stirring for 1 hour. The mixture was quenched with 0.5 N hydrochloric acid and extracted with ethyl acetate. The residue obtained after concentration was purified by chromatography (24 g silica gel cartridge, 100% dichloromethane in 10 min) to give a crude residue which was re-purified (24 g silica gel cartridge, 0-35% ethyl acetate/heptane in 20 minutes) to give 2-(4-bromo-2-methylphenyl)tetrahydro-4H-pyran-4-one (2 g, 7.43 mmol, 37.0% yield). $^1$H NMR (400 MHz, CDCl$_3$) δ ppm 7.43-7.35 (m, 2H), 7.33 (d, J=0.9 Hz, 0H), 4.76 (dd, J=10.0, 4.0 Hz, 1H), 4.44 (ddd, J=11.6, 7.4, 1.5 Hz, 1H), 3.85 (ddd, J=12.2, 11.6, 2.9 Hz, 1H), 2.75 (dddd, J=14.6, 12.2, 7.4, 0.9 Hz, 1H), 2.65-2.51 (m, 2H), 2.50-2.42 (m, 1H), 2.31 (s, 3H); MS (ESI−) m/z 266.9 (M−H)$^−$.

Step 2: 2-(4-Bromo-2-methylphenyl)tetrahydro-4H-pyran-4-one from Step 1 (2 g, 7.43 mmol) and [1,1′-bis(diphenylphosphino)ferrocene]dichloropalladium(II) (0.109 g, 0.149 mmol) were combined in a 50 mL Hastelloy C reactor. Methanol (25 mL) and triethylamine (2.072 mL, 14.86 mmol) were added, and the mixture was degassed with argon several times. The reaction mixture was placed under carbon monoxide (60 psi) and heated to 100° C. for 16 hours. The mixture was filtered and concentrated in vacuo. The residue was purified using a 24 g silica gel cartridge eluted with a gradient of 0-45% ethyl acetate/heptanes in 20 minutes to give methyl 3-methyl-4-(4-oxotetrahydro-2H-pyran-2-yl)benzoate (490 mg, 1.974 mmol, 26.6% yield). $^1$H NMR (400 MHz, DMSO-d$_6$) δ ppm 7.81-7.77 (m, 1H), 7.74-7.72 (m, 1H), 7.57 (d, J=8.1 Hz, 1H), 4.92 (dd, J=11.3, 2.8 Hz, 1H), 4.27 (ddd, J=11.4, 7.6, 1.4 Hz, 1H), 3.88-3.82 (m, 1H), 3.81 (s, 3H), 2.70 (dddd, J=14.9, 12.3, 7.6, 1.0 Hz, 1H), 2.53 (ddd, J=14.6, 11.3, 1.0 Hz, 1H), 2.42 (dt, J=14.5, 2.7 Hz, 1H), 2.31 (s, 3H), 2.25 (ddt, J=14.9, 3.0, 1.6 Hz, 1H); MS (ESI−) m/z 247 (M−H)$^−$.

Step 3: Methyl 3-methyl-4-(4-oxotetrahydro-2H-pyran-2-yl)benzoate (0.49 g, 1.974 mmol) from Step 2 and 7 M NH$_3$-MeOH (30 mL) were added to 5% Pd/C (wet JM#9) (0.1 g, 0.417 mmol) in a 50 mL pressure bottle, and the mixture was shaken for 100 min under hydrogen (1 psi) followed by 16 hours at 30 psi hydrogen at ambient temperature. The reaction mixture was then filtered through diatomaceous earth, and the filtrate was concentrated. The residue was purified using a 12 g silica gel cartridge with 100% acetone in 15 minutes. The crude fractions 1T and 1B were collected sequentially. The cis fraction 1B was purified using a 12 g silica gel cartridge eluted with a gradient of 0-7% methanol (2 N NH3)/dichloromethane in 20 minutes to give methyl rac-4-[(2R,4S)-4-aminotetrahydro-2H-pyran-2-yl]-3-methylbenzoate (193 mg, 0.774 mmol, 39.2% yield). $^1$H NMR (400 MHz, DMSO-d$_6$) δ ppm 7.76 (dd, J=8.1, 1.9 Hz, 1H), 7.73-7.71 (m, 1H), 7.48 (d, J=8.0 Hz, 1H), 4.48 (dd, J=11.2, 1.9 Hz, 1H), 4.00 (ddd, J=11.5, 4.7, 1.6 Hz, 1H), 3.81 (s, 3H), 3.57-3.45 (m, 1H), 2.87 (tt, J=11.2, 4.2 Hz, 1H), 2.32 (s, 3H), 1.90 (ddd, J=12.9, 4.1, 2.0 Hz, 1H), 1.72 (ddd, J=13.1, 4.4, 2.1 Hz, 1H), 1.68-1.34 (m, 2H), 1.28 (tdd, J=12.8, 11.2, 4.7 Hz, 1H), 1.04 (dt, J=12.9, 11.1 Hz, 1H); MS (ESI+) m/z 266 (M+17)$^+$.

Step 4: To 1-(2,2-difluorobenzo[d][1,3]dioxol-5-yl)cyclopropanecarboxylic acid (185 mg, 0.762 mmol) in N,N-dimethylformamide (2 mL) was added 1-[bis(dimethylamino)methylene]-1H-1,2,3-triazolo[4,5-b]pyridinium 3-oxid hexafluorophosphate (HATU 435 mg, 1.143 mmol), and the mixture was stirred for 20 minutes. Then methyl rac-4-[(2R,4S)-4-aminotetrahydro-2H-pyran-2-yl]-3-methylbenzoate (190 mg, 0.762 mmol) from Step 3 in 1 mL of N,N-dimethylformamide was added followed by N-ethyl-N-isopropylpropan-2-amine (0.265 mL, 1.524 mmol). The mixture was stirred at ambient temperature for 16 hours. Water (15 mL) was added, and a gel formed. The supernatant was decanted, and the residue was washed with water. The residue was purified by flash chromatography using a 24 g silica gel cartridge eluted with a gradient of 0-50% ethyl acetate/heptanes in 20 minutes to give crude titled compound. This material was triturated with 0.5 mL diethyl ether, and the resultant solid was collected by filtration to provide methyl rac-4-[(2R,4S)-4-({[1-(2,2-difluoro-1,3-benzodioxol-5-yl)cyclopropyl]carbonyl}amino)tetrahydro-2H-pyran-2-yl]-3-methylbenzoate (248 mg, 0.524 mmol, 68.7% yield). $^1$H NMR (400 MHz, DMSO-d$_6$) δ ppm 7.73 (dd, J=8.1, 1.8 Hz, 1H), 7.69 (d, J=1.7 Hz, 1H), 7.41 (d, J=8.1 Hz, 1H), 7.30 (d, J=1.7 Hz, 1H), 7.28 (d, J=8.3 Hz, 1H), 7.11 (dd, J=8.3, 1.7 Hz, 1H), 6.73 (d, J=8.2 Hz, 1H), 4.53 (dd, J=11.4, 2.0 Hz, 1H), 4.06-3.92 (m, 2H), 3.79 (s, 3H), 3.53 (td, J=12.2, 2.2 Hz, 1H), 2.29 (s, 3H), 1.77-1.69 (m, 1H), 1.65-1.57 (m, 1H), 1.48 (qd, J=12.4, 4.7 Hz, 1H), 1.37-1.24 (m, 3H), 1.00-0.89 (m, 2H); MS (ESI+) m/z 474 (M+H)$^+$.

Example 37 rac-4-[(2R,4S)-4-({[1-(2,2-difluoro-1,3-benzodioxol-5-yl)cyclopropyl]carbonyl}amino)tetrahydro-2H-pyran-2-yl]-3-methylbenzoic acid To a suspension of methyl rac-4-[(2R,4S)-4-({[1-(2,2-difluoro-1,3-benzodioxol-5-yl)cyclopropyl]carbonyl}amino)tetrahydro-2H-pyran-2-yl]-3-methylbenzoate (40 mg, 0.084 mmol) from Example 36 in ethanol (0.5 mL) was added 3 N sodium hydroxide (0.113 mL, 0.338 mmol). The reaction mixture was stirred at ambient temperature for 16 hours. The reaction was quenched with 0.5 mL of 1 N hydrochloric acid followed by addition of 10 mL of water to give an oily residue. The water was decanted off, and the oily residue was purified using a 12 g silica gel cartridge eluted with a gradient of 4-10% methanol/dichloromethane in 15 minutes to give a crude oil. The crude oil was purified by preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) provided the titled compound (13 mg, 0.028 mmol, 33.5% yield). $^1$H NMR (501 MHz, DMSO-$d_6$) δ ppm 12.78 (bs, 1H), 7.71 (dd, J=8.0, 1.8 Hz, 1H), 7.68 (d, J=1.7 Hz, 1H), 7.39 (d, J=8.1 Hz, 1H), 7.32 (d, J=1.7 Hz, 1H), 7.29 (d, J=8.3 Hz, 1H), 7.12 (dd, J=8.3, 1.8 Hz, 1H), 4.54 (dd, J=11.2, 2.0 Hz, 1H), 4.00 (ddt, J=17.7, 11.3, 2.9 Hz, 2H), 3.54 (td, J=12.1, 2.2 Hz, 1H), 2.29 (s, 3H), 1.78-1.59 (m, 2H), 1.50 (qd, J=12.4, 4.8 Hz, 1H), 1.40-1.27 (m, 3H), 1.02-0.89 (m, 2H); MS (ESI−) m/z 458 (M−H)$^−$.

Example 38 methyl rac-4-[(2R,6S)-6-cyclopropyl-4-({[1-(2,2-difluoro-1,3-benzodioxol-5-yl)cyclopropyl]carbonyl}amino)tetrahydro-2H-pyran-2-yl]benzoate Step 1: Methyl 4-formylbenzoate (CAS#1571-08-0) (2.64 g, 16.08 mmol) was added to H$_2$O (40 mL) containing potassium iodide (8.01 g, 48.2 mmol). Stannous chloride (4.57 g, 24.12 mmol) and 3-bromoprop-1-ene (2.087 mL, 24.12 mmol) were added to give an orange colored solution. The orange solution turns colorless with the addition of saturated ammonium chloride (20 mL). The mixture was stirred at ambient temperature for 2 h. LC/MS showed complete reaction. The mixture was extracted with CH$_2$Cl$_2$ (40 mL×2); and the organic layer was washed with brine, dried over Na$_2$SO$_4$ and concentrated. Purification by flash chromatography on silica gel eluted with ethyl acetate in heptane (1-40%) gave methyl 4-(1-hydroxybut-3-en-1-yl)benzoate (3.01 g, 91%). $^1$H NMR (501 MHz, CDCl$_3$) δ ppm 8.06-7.97 (m, 2H), 7.47-7.39 (m, 2H), 5.86-5.71 (m, 1H), 5.22-5.11 (m, 2H), 4.80 (ddd, J=7.5, 4.8, 2.2 Hz, 1H), 3.91 (s, 3H), 2.61-2.41 (m, 2H), 2.19 (d, J=3.3 Hz, 1H), LC/MS (ESI+) m/z 248 (M+H)$^+$.

Step 2: To methyl 4-(1-hydroxybut-3-en-1-yl)benzoate (2.4 g, 11.64 mmol) from Step 1 in benzene (7 mL) was added cyclopropanecarboxaldehyde (CAS#1489-69-6) (1.74 mL, 23.3 mmol) in one portion and acetic acid (2.13 mL, 37.2 mmol) at room temperature. Then boron trifluoride diethyl etherate (3.16 mL, 25.6 mmol) was added dropwise at 0° C. The mixture was stirred at 0° C. for 3 h. LC/MS showed complete reaction. Saturated NaHCO$_3$ (10 mL) was added followed by extraction with EtOAc. The combined organic layers were washed with water, dried over Na$_2$SO$_4$ and concentrated. The obtained acetylated intermediate was dissolved in methanol (10 mL) and K$_2$CO$_3$ (500 mg) was added. The mixture was stirred for 1 hour, and LC/MS showed complete reaction. The mixture was filtered and concentrated. The residue was purified by flash chromatography on silica gel eluting with EtOAc in heptane (5-30%) to yield methyl rac-4-[(2R,6S)-6-cyclopropyl-4-hydroxytetrahydro-2H-pyran-2-yl]benzoate (955 mg, 29.7%). $^1$H NMR (400 MHz, CDCl$_3$) δ ppm 8.07-7.95 (m, 2H), 7.49-7.38 (m, 2H), 4.36 (dd, J=11.5, 2.0 Hz, 1H), 3.96-3.91 (m, 1H), 3.91 (s, 3H), 2.90 (ddd, J=11.1, 7.6, 1.9 Hz, 1H), 2.17 (dddd, J=14.8, 10.6, 4.5, 2.1 Hz, 2H), 1.51-1.34 (m, 2H), 1.35-1.18 (m, 1H), 1.04 (qt, J=8.0, 4.9 Hz, 1H), 0.64-0.47 (m, 2H), 0.42 (dtd, J=9.1, 4.8, 3.4 Hz, 1H), 0.32-0.21 (m, 1H); LC/MS (ESI+) m/z 277 (M+H)$^+$.

Step 3: To yield methyl rac-4-[(2R,6S)-6-cyclopropyl-4-hydroxytetrahydro-2H-pyran-2-yl]benzoate from Step 2 (950 mg, 3.44 mmol) in CH$_2$Cl$_2$ (6 mL) was added pyridinium chlorochromate (1482 mg, 6.88 mmol) in one portion at ambient temperature, and the mixture was stirred for 3 h, and LC/MS showed complete reaction. CH$_2$Cl$_2$ (20 mL) was added, and the mixture was filtered. The organic filtrate was washed with water and brine, dried over Na$_2$SO$_4$ and concentrated. Purification by flash chromatography on silica gel, eluting with EtOAc in heptane (1-30%) gave methyl rac-4-[(2R,6S)-6-cyclopropyl-4-oxotetrahydro-2H-pyran-2-yl]benzoate (593 mg, 62.9%). $^1$H NMR (400 MHz, CDCl$_3$) δ ppm 8.14-7.92 (m, 2H), 7.55-7.36 (m, 2H), 4.63 (dd, J=11.6, 2.8 Hz, 1H), 3.92 (s, 3H), 3.19 (ddd, J=10.1, 7.4, 3.7 Hz, 1H), 2.70-2.45 (m, 4H), 1.12 (qt, J=8.0, 4.9 Hz, 1H), 0.70-0.53 (m, 2H), 0.49 (dtd, J=9.2, 4.8, 3.6 Hz, 1H), 0.32 (dtd, J=10.1, 4.9, 3.6 Hz, 1H); LC/MS (ESI+) m/z 275 (M+H)$^+$.

Step 4: A mixture of methyl rac-4-[(2R,6S)-6-cyclopropyl-4-oxotetrahydro-2H-pyran-2-yl]benzoate (590 mg, 2.151 mmol), sodium acetate (353 mg, 4.30 mmol) and O-methylhydroxylamine hydrochloride (359 mg, 4.30 mmol) in MeOH (10 mL) was stirred at 60° C. for 2 h. The reaction mixture was concentrated under reduced pressure. The residue was dissolved in EtOAc, and then the mixture was washed with water. The combined organic layers were dried over MgSO$_4$ and then concentrated under reduced pressure to yield methyl rac-4-[(2R,6S)-6-cyclopropyl-4-(methoxyimino)tetrahydro-2H-pyran-2-yl]benzoate (640 mg, 98%). $^1$H NMR (400 MHz, CDCl$_3$) δ ppm 8.03 (d, J=8.0 Hz, 2H), 7.46 (t, J=7.8 Hz, 2H), 4.44 (ddd, J=32.1, 11.7, 2.6 Hz, 1H), 3.91 (s, 3H), 3.86 (d, J=5.2 Hz, 3H), 3.41 (ddt, J=27.5, 14.7, 2.1 Hz, 1H), 2.98 (dddd, J=21.9, 10.9, 7.6, 2.5 Hz, 1H), 2.56 (ddt, J=18.5, 14.2, 2.1 Hz, 1H), 2.27 (ddd, J=16.7, 14.0, 11.4 Hz, 1H), 1.93 (td, J=15.0, 11.6 Hz, 1H), 1.14-0.97 (m, 1H), 0.57 (dtq, J=12.5, 8.3, 4.2 Hz, 2H), 0.45 (dq, J=10.5, 2.9, 1.6 Hz, 1H), 0.38-0.23 (m, 1H); MS (ESI+) m/z 304 (M+H)$^+$.

Step 5: The methyl rac-4-[(2R,6S)-6-cyclopropyl-4-(methoxyimino)tetrahydro-2H-pyran-2-yl]benzoate (200 mg, 0.66 mmol) was reduced to the corresponding amine by hydrogenation using 5% platinum (129 mg, 0.033 mmol) on carbon as catalyst in acetic acid (4 mL). The reaction was run at ambient temperature for 18 h under hydrogen (1 atm), and LC/MS showed complete reaction. The mixture was filtered, and the filtrate was concentrated under reduced pressure. The residue was purified by preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to yield methyl rac-4-[(2R,6S)-4-amino-6-cyclopropyltetrahydro-2H-pyran-2-yl]benzoate as a trifluoroacetate salt (180 mg, 70%). LC/MS (ESI+) m/z 276 (M+H)$^+$.

Step 6: A mixture of 1-(2,2-difluorobenzo[d][1,3]dioxol-5-yl)cyclopropanecarboxylic acid (120 mg, 0.5 mmol) and 1-[bis(dimethylamino)methylene]-1H-1,2,3-triazolo[4,5-b]pyridinium 3-oxid hexafluorophosphate (HATU, 283 mg, 0.74 mmol) in DMF (2 mL) was stirred for 5 min, and then methyl rac-4-[(2R,6S)-4-amino-6-cyclopropyltetrahydro-2H-pyran-2-yl]benzoate trifluoroacetate (166 mg, 0.496 mmol) followed by N-ethyl-N-isopropylpropan-2-amine (0.345 mL, 2.0 mmol) were added. The mixture was stirred at 35° C. for 2 h, and LC/MS showed complete reaction. The reaction mixture was purified without workup by silica gel column chromatography eluted with EtOAc in heptane at 5-40% gradient gave methyl rac-4-[(2R,6S)-6-cyclopropyl-4-({[1-(2,2-difluoro-1,3-benzodioxol-5-yl)cyclopropyl]carbonyl}amino)tetrahydro-2H-pyran-2-yl]benzoate (220 mg, 89% yield). $^1$H NMR (500 MHz, CDCl$_3$) δ ppm 7.19-7.12 (m, 2H), 7.03 (d, J=8.2 Hz, 1H), 6.86 (dd, J=8.5, 1.0 Hz, 1H), 6.44 (dd, J=8.6, 2.6 Hz, 1H), 6.32 (d, J=2.6 Hz, 1H), 5.32 (d, J=8.8 Hz, 1H), 5.26-5.17 (m, 1H), 4.07 (dd, J=11.9, 1.6 Hz, 1H), 3.73 (s, 3H), 3.69 (s, 3H), 2.21 (ddd, J=13.0, 6.2, 1.8 Hz, 1H), 2.08-1.99 (m, 6H), 1.97-1.84 (m, 1H), 1.74 (ddd, J=9.0, 5.4, 2.2 Hz, 1H), 1.69-1.63 (m, 1H), 1.08 (tdd, J=9.6, 6.2, 3.0 Hz, 2H); MS (ESI−) m/z 498 (M−H)$^-$.

Example 39 methyl rac-4-[(2R,4S,6R)-4-({[1-(2,2-difluoro-1,3-benzodioxol-5-yl)cyclopropyl]carbonyl}amino)-6-methyltetrahydro-2H-pyran-2-yl]benzoate Step 1: To a solution of 3-penten-2-one (5 mL, 51.2 mmol) and triethylamine (15.71 mL, 113 mmol) in CH$_2$Cl$_2$ (125 mL) at −8° C. (internal) was added trimethylsilyl trifluoromethanesulfonate (10.23 mL, 56.4 mmol) at such a rate to keep the internal temperature below 0° C. The reaction mixture was stirred for 15 minutes at about −5° C. and then was allowed to warm to ambient temperature, when LC/MS indicated complete reaction. The reaction mixture was washed successively with water (200 mL), saturated NaHCO$_3$ (200 mL), 10% CuSO$_4$ (200 mL×2) and brine (200 mL). The organic fraction was then dried over Na$_2$SO$_4$ and concentrated to yield (E)-trimethyl(penta-1,3-dien-2-yloxy)silane (6.92 g) which used in next step without further purification.

Step 2: To a solution of methyl 4-formylbenzoate (7.27 g, 44.3 mmol) (CAS#1571-08-0) in toluene (100 mL) at −72° C. (internal) was added boron trifluoride diethyl etherate (1.1 mL, 8.85 mmol). After the mixture was stirred for 15 min, (E)-trimethyl(penta-1,3-dien-2-yloxy)silane (6.92 g, 44.3 mmol) from Step 1 was added dropwise. Stirring was continued for 30 min at −65° C. (internal), and then the mixture was allowed to warm slowly to ambient temperature with continued stirring overnight. 1 M Hydrochloric acid (100 mL) was added to the mixture, and this mixture was stirred for 36 h. The organic layer was washed with brine, dried over MgSO$_4$, filtered and concentrated. The residue was then taken up in THF (50 mL) and treated with 1 M tetrabutyl ammonium fluoride in THF (20 mL, 20.00 mmol). After 2 h (for convenience), the reaction was complete. The mixture was partitioned between ether and 1 M HCl. The organic phase was washed with saturated NaHCO$_3$ and brine; then dried over MgSO$_4$, filtered and concentrated. The residue was purified by chromatography (ether/CH$_2$Cl$_2$) to yield methyl rac-4-[(2R,6R)-6-methyl-4-oxotetrahydro-2H-pyran-2-yl]benzoate with purity of about 80%. LC/MS (ESI+) m/z 249 (M+H)$^+$.

Step 3: Methyl rac-4-[(2R,6R)-4-amino-6-methyltetrahydro-2H-pyran-2-yl]benzoate was prepared from methyl rac-4-[(2R,6R)-6-methyl-4-oxotetrahydro-2H-pyran-2-yl]benzoate using the methods described in Steps 4-5 in Example 38. LC/MS (ESI+) m/z 250 (M+H)$^+$.

Step 4: To methyl rac-4-[(2R,6R)-4-amino-6-methyltetrahydro-2H-pyran-2-yl]benzoate from Step 3 (4.0 g, 16.04 mmol) in t-butyl methyl ether (10 mL) was slowly added 4 M HCl in dioxane (8 mL). The precipitated solid was collected by filtration and dried to give methyl rac-4-[(2R,6R)-4-amino-6-methyltetrahydro-2H-pyran-2-yl]benzoate hydrochloride (1.6 g, 35%). LC/MS (ESI+) m/z 250 (M+H)$^+$.

Step 5: To 1-(2,2-difluorobenzo[d][1,3]dioxol-5-yl)cyclopropanecarboxylic acid (170 mg, 0.702 mmol) in DMF (2 mL) was added and 1-[bis(dimethylamino)methylene]-1H-1,2,3-triazolo[4,5-b]pyridinium 3-oxid hexafluorophosphate (HATU, 400 mg, 1.053 mmol). The mixture was stirred for 5 min, and then methyl rac-4-[(2R,6R)-4-amino-6-methyltetrahydro-2H-pyran-2-yl]benzoate hydrochloride (201 mg, 0.70 mmol) from Step 4 was added, followed by addition of N-ethyl-N-isopropylpropan-2-amine (0.489 mL, 2.81 mmol). The mixture was stirred at 35° C. for 2 h, and LC/MS showed complete reaction. The mixture was loaded onto a 24 g silica gel cartridge eluted with EtOAc in heptane using a 5-40% gradient to give the first eluting compound, methyl rac-4-[(2R,4S,6R)-4-({[1-(2,2-difluoro-1,3-benzodioxol-5-yl)cyclopropyl]carbonyl}amino)-6-methyltetrahydro-2H-pyran-2-yl]benzoate (225 mg, 68%). $^1$H NMR (400 MHz, CDCl$_3$) δ ppm 8.04-7.92 (m, 2H), 7.43-7.32 (m, 2H), 7.18-6.96 (m, 3H), 5.08 (d, J=8.0 Hz, 1H), 4.48 (dd, J=11.3, 2.1 Hz, 1H), 4.14 (tdt, J=11.9, 8.1, 4.3 Hz, 1H), 3.90 (s, 3H), 3.68 (dtd, J=12.3, 6.0, 1.8 Hz, 1H), 2.17-2.00 (m, 1H), 1.91 (ddt, J=12.7, 4.1, 2.0 Hz, 1H), 1.63-1.59 (m, 2H), 1.26 (d, J=6.2 Hz, 3H), 1.14-1.05 (m, 1H), 1.03-0.99 (m, 2H), 0.86 (ddt, J=9.9, 6.3, 3.5 Hz, 1H); MS (ESI−) m/z 472 (M−H)$^-$.

The second eluting compound was not pure and was subjected to a second chromatography to give methyl rac-4-[(2R,4R,6R)-4-({[1-(2,2-difluoro-1,3-benzodioxol-5-yl)cyclopropyl]carbonyl}amino)-6-methyltetrahydro-2H-pyran-2-yl]benzoate (15 mg, 4.5%, Example 46). $^1$H NMR (400 MHz, CDCl$_3$) δ ppm 8.09-7.92 (m, 2H), 7.34 (dd, J=25.0, 8.3 Hz, 2H), 7.25-6.99 (m, 3H), 5.64 (d, J=7.1 Hz, 1H), 4.27 (dq, J=6.6, 3.2 Hz, 1H), 4.18 (dd, J=12.1, 2.2 Hz, 1H), 3.90 (d, J=2.7 Hz, 3H), 3.39 (ddt, J=12.6, 6.5, 3.2 Hz, 1H), 1.87 (dq, J=13.8, 2.2 Hz, 1H), 1.67-1.63 (m, 2H), 1.58 (s, 3H), 1.10-1.04 (m, 2H).

Example 40 methyl rel-4-[(2S,4R)-4-({[1-(2,2-difluoro-1,3-benzodioxol-5-yl)cyclopropyl]carbonyl}amino)tetrahydro-2H-pyran-2-yl]-3-methylbenzoate The titled compound was prepared from methyl rac-4-[(2R,4S)-4-({[1-(2,2-difluoro-1,3-benzodioxol-5-yl)cyclopropyl]carbonyl}amino)tetrahydro-2H-pyran-2-yl]-3-methylbenzoate from Example 36 by preparative supercritical fluid chromatography set to maintain a backpressure of 100 bar using a WHELK-O® (S,S) column, 21×250 mm, 5 micron, with the sample at a concentration of 20 mg/mL in methanol with a co-solvent of 20% 2-propanol (0.1% diethylamine) in CO$_2$ at a flow rate of 70 mL/minute with a retention time of 4.7 minutes to give the titled compound (84 mg, 0.177 mmol) with stereochemistry arbitrarily assigned. $^1$H NMR (501 MHz, DMSO-d$_6$) δ ppm 7.74 (dd, J=8.1, 1.8 Hz, 1H), 7.71 (d, J=1.8 Hz, 1H), 7.42 (d, J=8.1 Hz, 1H), 7.32 (d, J=1.7 Hz, 1H), 7.29 (d, J=8.3 Hz, 1H), 7.12 (dd, J=8.3, 1.8 Hz, 1H), 6.75 (d, J=8.2 Hz, 1H), 4.55 (dd, J=11.3, 2.0 Hz, 1H), 4.06-3.96 (m, 2H), 3.81 (s, 3H), 3.54 (td, J=12.0, 2.2 Hz, 1H), 2.30 (s, 3H), 1.80-1.58 (m, 2H), 1.50 (qd, J=12.4, 4.8 Hz, 1H), 1.38-1.27 (m, 3H), 0.96 (dddd, J=12.5, 9.4, 7.4, 2.7 Hz, 2H); MS (ESI+) m/z 474 (M+H)$^+$; [α]$_D^{25}$ −28° (c 2.50, CH$_3$OH).

Example 41 methyl rel-4-[(2R,4S)-4-({[1-(2,2-difluoro-1,3-benzodioxol-5-yl)cyclopropyl]carbonyl}amino)tetrahydro-2H-pyran-2-yl]-3-methylbenzoate The titled compound was prepared from methyl rac-4-[(2R,4S)-4-({[1-(2,2-difluoro-1,3-benzodioxol-5-yl)cyclopropyl]carbonyl}amino)tetrahydro-2H-pyran-2-yl]-3-methylbenzoate from Example 36 by preparative supercritical fluid chromatography set to maintain a backpressure of 100 bar using a WHELK-O® (S,S) column, 21×250 mm, 5 micron, with the sample at a concentration of 20 mg/mL in methanol with a co-solvent of 20% 2-propanol (0.1% diethylamine) in $CO_2$ at a flow rate of 70 mL/minute with a retention time of 5.6 minutes to give the titled compound (84 mg, 0.177 mmol) which is the enantiomer of Example 40, and the stereochemistry is arbitrarily assigned. $^1$H NMR (501 MHz, DMSO-$d_6$) δ ppm 7.74 (dd, J=8.1, 1.8 Hz, 1H), 7.71 (d, J=1.8 Hz, 1H), 7.42 (d, J=8.1 Hz, 1H), 7.32 (d, J=1.7 Hz, 1H), 7.29 (d, J=8.3 Hz, 1H), 7.12 (dd, J=8.3, 1.8 Hz, 1H), 6.75 (d, J=8.2 Hz, 1H), 4.55 (dd, J=11.3, 2.0 Hz, 1H), 4.06-3.96 (m, 2H), 3.81 (s, 3H), 3.54 (td, J=12.0, 2.2 Hz, 1H), 2.30 (s, 3H), 1.80-1.58 (m, 2H), 1.50 (qd, J=12.4, 4.8 Hz, 1H), 1.38-1.27 (m, 3H), 0.96 (dddd, J=12.5, 9.4, 7.4, 2.7 Hz, 2H); MS (ESI+) m/z 474 (M+H)$^+$; $[α]_D^{25}$+29.8° (c 2.50, $CH_3OH$).

Example 42 rel-4-[(2S,4R)-4-({[1-(2,2-difluoro-1,3-benzodioxol-5-yl)cyclopropyl]carbonyl}amino)tetrahydro-2H-pyran-2-yl]-3-methylbenzoic acid To a suspension of methyl rel-4-[(2S,4R)-4-({[1-(2,2-difluoro-1,3-benzodioxol-5-yl)cyclopropyl]carbonyl}amino)tetrahydro-2H-pyran-2-yl]-3-methylbenzoate from Example 40 (58 mg, 0.123 mmol) in ethanol (0.5 mL) was added 1.5 N sodium hydroxide (0.163 mL, 0.245 mmol). The reaction mixture was stirred at room temperature for 16 h. The reaction was quenched by the addition of 0.3 mL of 1 N hydrochloric acid, and then water (3 mL) was added to give a precipitate. The solid was collected by filtration to provide the title compound (45 mg, 0.098 mmol, 80% yield). $^1$H NMR (501 MHz, DMSO-$d_6$) δ ppm 12.78 (s, 1H), 7.71 (dd, J=8.0, 1.8 Hz, 1H), 7.68 (d, J=1.7 Hz, 1H), 7.39 (d, J=8.1 Hz, 1H), 7.32 (d, J=1.7 Hz, 1H), 7.29 (d, J=8.3 Hz, 1H), 7.12 (dd, J=8.3, 1.7 Hz, 1H), 6.75 (d, J=8.2 Hz, 1H), 4.54 (dd, J=11.2, 2.0 Hz, 1H), 4.06-3.95 (m, 2H), 3.54 (td, J=12.1, 2.2 Hz, 1H), 2.29 (s, 3H), 1.77-1.71 (m, 1H), 1.62 (ddd, J=13.1, 4.5, 2.2 Hz, 1H), 1.50 (qd, J=12.4, 4.8 Hz, 1H), 1.38-1.26 (m, 3H), 1.00-0.90 (m, 2H); MS (ESI−) m/z 458 (M−H)$^−$.

Example 43 rel-4-[(2R,4S)-4-({[1-(2,2-difluoro-1,3-benzodioxol-5-yl)cyclopropyl]carbonyl}amino)tetrahydro-2H-pyran-2-yl]-3-methylbenzoic acid To a suspension of methyl rel-4-[(2R,4S)-4-({[1-(2,2-difluoro-1,3-benzodioxol-5-yl)cyclopropyl]carbonyl}amino)tetrahydro-2H-pyran-2-yl]-3-methylbenzoate from Example 41 (56 mg, 0.118 mmol) in ethanol (0.5 mL) was added 1.5 N sodium hydroxide (0.158 mL, 0.237 mmol). The reaction mixture was stirred at room temperature for 16 hours. The reaction was quenched with 0.3 mL of 1 N hydrochloric acid and water (3 mL) was added to give a precipitate. The solid was collected by filtration to provide the title compound (49 mg, 0.107 mmol, 90% yield). $^1$H NMR (501 MHz, DMSO-$d_6$) δ ppm 12.78 (s, 1H), 7.71 (dd, J=8.0, 1.8 Hz, 1H), 7.68 (d, J=1.7 Hz, 1H), 7.39 (d, J=8.1 Hz, 1H), 7.32 (d, J=1.7 Hz, 1H), 7.29 (d, J=8.3 Hz, 1H), 7.12 (dd, J=8.3, 1.7 Hz, 1H), 6.75 (d, J=8.2 Hz, 1H), 4.54 (dd, J=11.2, 2.0 Hz, 1H), 4.06-3.95 (m, 2H), 3.54 (td, J=12.1, 2.2 Hz, 1H), 2.29 (s, 3H), 1.77-1.71 (m, 1H), 1.62 (ddd, J=13.1, 4.5, 2.2 Hz, 1H), 1.50 (qd, J=12.4, 4.8 Hz, 1H), 1.38-1.26 (m, 3H), 1.00-0.90 (m, 2H); MS (ESI−) m/z 458 (M−H)$^−$.

Example 44

4-[6-cyclopropyl-4-({[1-(2,2-difluoro-1,3-benzodioxol-5-yl)cyclopropyl]carbonyl}amino)tetrahydro-2H-pyran-2-yl]benzoic acid A solution of Example 38 (200 mg, 0.400 mmol) in MeOH (4 mL) and 4 N lithium hydroxide aqueous solution (1 mL) was stirred at 35° C. for 2 h, and LC/MS showed complete reaction. The reaction mixture was concentrated under reduced pressure, and water (1 mL) was added. The pH was adjusted with 1 M HCl to pH 1-2. The white solid precipitated was collected by filtration and then further purified by silica gel chromatography eluted with methanol in ethyl acetate using a 0-15% gradient to give the titled compound (150 mg, 77%). $^1$H NMR (501 MHz, $CDCl_3$) δ ppm 8.04 (dd, J=8.2, 5.0 Hz, 2H), 7.39 (d, J=7.9 Hz, 1H), 7.34 (d, J=8.0 Hz, 1H), 7.23-7.17 (m, 1H), 7.14-7.01 (m, 2H), 5.57 (d, J=7.0 Hz, 1H), 5.12 (d, J=8.0 Hz, 0H), 4.41 (d, J=11.1 Hz, 0H), 4.29 (dp, J=6.4, 3.2 Hz, 1H), 4.18-4.07 (m, 1H), 2.92 (ddd, J=10.0, 7.7, 2.0 Hz, 0H), 2.60 (ddd, J=10.4, 7.0, 3.7 Hz, 1H), 2.17-1.97 (m, 1H), 1.94-1.85 (m, 1H), 1.74 (dd, J=14.2, 3.8 Hz, 0H), 1.71-1.60 (m, 3H), 1.22-1.10 (m, 1H), 1.10-0.98 (m, 2H), 0.98 (s, OH), 0.97-0.85 (m, 1H), 0.50 (dtp, J=17.8, 8.9, 4.8 Hz, 2H), 0.43-0.30 (m, 1H), 0.24 (dq, J=9.8, 4.8 Hz, 0H), 0.11-0.06 (m, 1H); MS (ESI−) m/z 484 (M−H)$^−$.

Example 45 rac-4-[(2R,4S,6R)-4-({[1-(2,2-difluoro-1,3-benzodioxol-5-yl)cyclopropyl]carbonyl}amino)-6-methyltetrahydro-2H-pyran-2-yl]benzoic acid To Example 39 (200 mg, 0.422 mmol) in MeOH (3 mL) was added 4 N lithium hydroxide aqueous (1 mL). The mixture was stirred at 35° C. for 2 h, and LC/MS showed complete reaction. The reaction mixture was concentrated, and the residue was adjust to pH 1~2 with 1 M HCl. The precipitate was collected by filtration, washed with water, and dried to yield the titled compound (125 mg, 64.4%). $^1$H NMR (501 MHz, $CDCl_3$) δ ppm 8.08-8.01 (m, 2H), 7.40 (d, J=7.9 Hz, 2H), 7.15-6.99 (m, 3H), 5.10 (d, J=8.0 Hz, 1H), 4.49 (d, J=11.0 Hz, 1H), 4.16 (tdt, J=12.1, 8.3, 4.3 Hz, 1H), 3.69 (dqd, J=12.3, 6.1, 1.9 Hz, 1H), 2.18-2.07 (m, 1H), 1.91 (dd, J=11.6, 4.1 Hz, 1H), 1.63 (q, J=4.3 Hz, 2H), 1.26 (d, J=6.0 Hz, 3H), 1.15-0.97 (m, 4H); MS (ESI−) m/z 458 (M−H)$^−$.

Example 46 methyl rac-4-[(2R,4R,6R)-4-({[1-(2,2-difluoro-1,3-benzodioxol-5-yl)cyclopropyl]carbonyl}amino)-6-methyltetrahydro-2H-pyran-2-yl]benzoate The title compound was obtained as the second eluting compound in Step 5 of Example 39 (15 mg, 4.5%). $^1$H NMR (400 MHz, CDCl$_3$) δ ppm 8.09-7.92 (m, 2H), 7.34 (dd, J=25.0, 8.3 Hz, 2H), 7.25-6.99 (m, 3H), 5.64 (d, J=7.1 Hz, 1H), 4.27 (dq, J=6.6, 3.2 Hz, 1H), 4.18 (dd, J=12.1, 2.2 Hz, 1H), 3.90 (d, J=2.7 Hz, 3H), 3.39 (m, 1H), 1.67-1.63 (m, 2H), 1.58 (s, 3H), 1.10-1.04 (m, 2H); LC/MS (ESI+) m/z 474 (M+H)$^+$.

Example 47 methyl rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoate Step 1: To 1-phenylbut-3-en-1-ol (2 g, 13.5 mmol) in benzene (15 mL) was added methyl 4-formylbenzoate (3.3 g, 20 mmol) in one portion and acetic acid (2.5 mL, 43 mmol) at room temperature followed by the dropwise addition of boron trifluoride diethyl etherate (2.66 mL, 29.6 mmol) at 0° C. The mixture was stirred at 0° C. for 3 h when LC/MS indicated complete reaction. Saturated NaHCO$_3$ (10 mL) was added followed by extraction with EtOAc (30 mL×2), and the combined organic layers were washed with water, dried over Na$_2$SO$_4$ and concentrated. The acetylated intermediate obtained was dissolved in MeOH (20 mL), and to the mixture was added K$_2$CO$_3$ (1.0 g). The mixture was stirred for 1 h, and the mixture was concentrated under reduced pressure. The residue was dissolved in ethyl acetate, washed with water, dried with magnesium sulfate, and concentrated. The residue was purified by flash chromatography on an 80 g silica gel cartridge eluted with EtOAc in heptane (5-30%) to give methyl rac-4-[(2R,6S)-4-hydroxy-6-phenyltetrahydro-2H-pyran-2-yl]benzoate (510 mg, 24%). LC/MS (ESI+) m/z 313 (M+H)$^+$.

Step 2: To methyl rac-4-[(2R,6S)-4-hydroxy-6-phenyltetrahydro-2H-pyran-2-yl]benzoate (1 g, 3.2 mmol) in CH$_2$Cl$_2$ (12 mL) was added pyridinium chlorochromate (1380 mg, 6.4 mmol) in one portion at room temperature. The mixture was stirred at room temperature for 3 h when LC/MS indicated complete reaction. CH$_2$Cl$_2$ (40 mL) was added, and the mixture was filtered. The organic filtrate was washed with water, dried over Na$_2$SO$_4$ and concentrated. Purification by flash chromatography on silica gel eluted with EtOAc in heptane (5-20%) gave methyl rac-4-[(2R,6S)-4-oxo-6-phenyltetrahydro-2H-pyran-2-yl]benzoate (800 mg, 81%). $^1$H NMR (400 MHz, CDCl$_3$) δ ppm 8.07 (dd, J=8.3, 1.4 Hz, 2H), 7.56-7.50 (m, 2H), 7.43 (dtd, J=15.8, 7.3, 1.6 Hz, 4H), 7.38-7.30 (m, 1H), 4.89 (ddd, J=20.1, 11.0, 3.2 Hz, 2H), 3.92 (d, J=1.1 Hz, 3H), 2.81-2.59 (m, 4H); LC/MS (ESI−) m/z 309 (M−H)$^-$.

Step 3: A mixture of methyl rac-4-[(2R,6S)-4-oxo-6-phenyltetrahydro-2H-pyran-2-yl]benzoate (650 mg, 2.1 mmol), sodium acetate (344 mg, 4.2 mmol) and O-methylhydroxylamine hydrochloride (350 mg, 4.2 mmol) in MeOH (10 mL) was stirred at 60° C. for overnight. The mixture was concentrated under reduced pressure. The residue was dissolved in EtOAc, and then the mixture was washed with water. The organic fraction was dried over MgSO$_4$ and concentrated under reduced pressure to give methyl rac-4-[(2R,6S)-4-(methoxyimino)-6-phenyltetrahydro-2H-pyran-2-yl]benzoate (680 mg, 96%). $^1$H NMR (400 MHz, CDCl$_3$) δ ppm 8.11-7.96 (m, 2H), 7.57-7.50 (m, 2H), 7.46 (ddd, J=7.7, 6.4, 1.4 Hz, 2H), 7.39 (dd, J=8.5, 6.7 Hz, 2H), 7.34-7.28 (m, 1H), 4.69 (dddd, J=32.3, 20.3, 11.7, 2.7 Hz, 2H), 3.92 (d, J=1.4 Hz, 3H), 3.90 (d, J=2.0 Hz, 3H), 3.57 (ddt, J=14.5, 5.9, 2.5 Hz, 1H), 2.77-2.66 (m, 1H), 2.40 (dddd, J=21.7, 14.1, 11.6 Hz, 1H), 2.13-1.98 (m, 1H); LC/MS (APCI+) m/z 340 (M+H)$^+$.

Step 4: Methyl rac-4-[(2R,6S)-4-(methoxyimino)-6-phenyltetrahydro-2H-pyran-2-yl]benzoate (677 mg, 1.995 mmol) in MeOH (20 mL) was added to Raney® nickel (3 g, 51.1 mmol) in a 50 mL pressure bottle. The mixture was shaken for 20 hours under hydrogen (30 psi) at room temperature. LC/MS indicated two diastereomers. The mixture was concentrated under reduced pressure, and the residue was purified by chromatography on a 40 g silica gel cartridge eluted with 2 M MeOH/NH$_4$OH (10:1) in ethyl acetate, gradient at 0-20%. The first eluting component was methyl rac-4-[(2R,4R,6S)-4-amino-6-phenyltetrahydro-2H-pyran-2-yl]benzoate (90 mg, 27%). $^1$H NMR (400 MHz, CDCl$_3$) δ ppm 8.01 (d, J=8.0 Hz, 2H), 7.51 (d, J=8.0 Hz, 2H), 7.44 (d, J=7.3 Hz, 2H), 7.35 (t, J=7.5 Hz, 2H), 7.30-7.25 (m, 1H), 5.12 (ddd, J=23.8, 11.4, 2.4 Hz, 2H), 3.90 (s, 3H), 3.66 (q, J=2.8 Hz, 1H), 1.96-1.75 (m, 4H); MS (ESI+) m/z 312 (M+H)$^+$.

The second eluting compound was methyl rac-4-[(2R,4S,6S)-4-amino-6-phenyltetrahydro-2H-pyran-2-yl]benzoate (174 mg, 52.7%). $^1$H NMR (400 MHz, CDCl$_3$) δ ppm 8.07-7.96 (m, 2H), 7.49 (d, J=8.3 Hz, 2H), 7.43 (d, J=7.1 Hz, 2H), 7.36 (dd, J=8.5, 6.7 Hz, 2H), 7.31-7.26 (m, 1H), 4.70-4.50 (m, 2H), 3.91 (s, 3H), 3.26 (tt, J=11.2, 4.1 Hz, 1H), 2.23-2.12 (m, 2H), 2.00 (s, 4H), 1.42 (dq, J=23.6, 11.8 Hz, 2H); MS (ESI+) m/z 312 (M+H)$^+$.

Step 5: To 1-(2,2-difluorobenzo[d][1,3]dioxol-5-yl)cyclopropanecarboxylic acid (72.7 mg, 0.300 mmol) in DMF (2 mL) was added 1-[bis(dimethylamino)methylene]-1H-1,2,3-triazolo[4,5-b]pyridinium 3-oxid hexafluorophosphate (HATU, 156 mg, 0.409 mmol). The mixture was stirred for 5 min, and then methyl rac-4-[(2R,4R,6S)-4-amino-6-phenyltetrahydro-2H-pyran-2-yl]benzoate from Step 4 (85 mg, 0.273 mmol) was added followed by N-ethyl-N-isopropylpropan-2-amine (0.19 mL, 1.1 mmol). The mixture was stirred at ambient temperature for 2 h when LC/MS indicated complete reaction. The reaction mixture was loaded onto a 24 g silica gel cartridge directly without workup and purified by chromatographically eluted with EtOAc in heptane at 5-40% gradient to give methyl rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoate (110 mg, 75%). $^1$H NMR (400 MHz, CDCl$_3$) δ ppm 8.05-7.94 (m, 2H), 7.42-7.27 (m, 9H), 7.25 (d, J=1.6 Hz, 1H), 7.16 (d, J=8.1 Hz, 1H), 5.77 (d, J=7.0 Hz, 1H), 4.38 (ddd, J=8.5, 6.6, 2.9 Hz, 2H), 4.30 (dd, J=9.9, 4.4 Hz, 1H), 3.91 (s, 3H), 2.03 (m, 1H), 1.91-1.75 (m, 3H), 1.69 (q, J=3.7 Hz, 2H), 1.26 (s, 1H), 1.12 (q, J=3.5 Hz, 2H); MS (ESI−) m/z 534 (M−H)$^-$.

Example 48 methyl rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoate To 1-(2,2-difluorobenzo[d][1,3]dioxol-5-yl)cyclopropanecarboxylic acid (145 mg, 0.601 mmol) in DMF (2 mL) was added 1-[bis(dimethylamino)methylene]-1H-1,2,3-triazolo[4,5-b]pyridinium 3-oxid hexafluorophosphate (HATU, 311 mg, 0.819 mmol), and the mixture was stirred for 5 min. Then methyl rac-4-[(2R,4S,6S)-4-amino-6-phenyltetrahydro-2H-pyran-2-yl]benzoate from Step 4 of Example 47 (170 mg, 0.546 mmol) was added following by N-ethyl-N-isopropylpropan-2-amine (0.380 mL, 2.184 mmol). The mixture was stirred at room temperature for 2 h when LC/MS indicated the reaction was complete. The reaction mixture was loaded on a 24 g silica gel cartridge directly without workup and purified by chromatography eluted with EtOAc in heptane at 5-40% gradient give the titled compound (230 mg, 79%). $^1$H NMR (400 MHz, CDCl$_3$) δ ppm 8.04-7.94 (m, 2H), 7.49-7.41 (m, 2H), 7.40-7.30 (m, 4H), 7.29-7.23 (m, 2H), 7.11-6.96 (m, 3H), 5.11 (d, J=8.1 Hz, 1H), 4.66 (ddd, J=20.7, 11.4, 2.2 Hz, 2H), 4.34 (tdt, J=12.0, 8.2, 4.2 Hz, 1H), 3.90 (s, 3H), 2.20 (dddt, J=19.3, 12.8, 4.2, 2.0 Hz, 2H), 1.62 (q, J=3.2 Hz, 2H), 1.28 (dq, J=17.6, 11.9 Hz, 2H), 1.02 (q, J=3.3 Hz, 2H); MS (ESI−) m/z 534 (M−H)−.

Example 49 rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoic acid A mixture of Example 47 (73 mg, 0.136 mmol) in MeOH (2 mL) and aqueous LiOH (2 N, 0.5 mL) was stirred at 35° C. for 2 hours, and the mixture was concentrated under reduced pressure. Water (0.5 mL) was added. The pH was adjusted to 1~2 by adding 2 N HCl. The solid precipitate was collected by filtration. The solid was washed with water and dried in oven to yield the titled compound (60 mg, 0.115 mmol, 84% yield). $^1$H NMR (400 MHz, CDCl$_3$) δ ppm 8.06 (s, 2H), 7.49-7.26 (m, 9H), 7.16 (d, J=8.0 Hz, 1H), 5.80 (s, 1H), 4.42 (d, J=12.3 Hz, 2H), 4.29 (t, J=7.0 Hz, 1H), 2.02 (d, J=13.6 Hz, 1H), 1.89 (s, 2H), 1.71 (s, 3H), 1.13 (s, 2H); MS (ESI−) m/z 522 (M−H)−.

Example 50 rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid To Example 48 (300 mg, 0.56 mmol) in MeOH (8 mL) was added aqueous LiOH (2 N, 2 mL). The mixture was stirred at 35° C. for 2 hours and then concentrated under reduced pressure. Water (1 mL) was added, and the pH was adjusted to 1~2 by adding 2 N HCl. The precipitate was collected by filtration, washed with water and dried in oven to yield the titled compound (270 mg, 92%). $^1$H NMR (400 MHz, CDCl$_3$) δ ppm 8.06 (dd, J=8.5, 2.5 Hz, 2H), 7.58-7.44 (m, 2H), 7.42-7.31 (m, 4H), 7.30-7.27 (m, 1H), 7.13-6.99 (m, 3H), 5.14 (d, J=8.1 Hz, 1H), 4.68 (ddd, J=25.5, 11.4, 2.3 Hz, 2H), 4.37 (tdq, J=12.3, 8.6, 3.8 Hz, 1H), 2.30-2.11 (m, 2H), 1.63 (d, J=3.4 Hz, 2H), 1.29 (dq, J=19.0, 12.0 Hz, 2H), 1.03 (q, J=3.4 Hz, 2H); MS (ESI−) m/z 522 (M−H)−.

Example 51 dimethyl rac-4,4'-[(2R,4s,6S)-4-({[1-(2,2-difluoro-1,3-benzodioxol-5-yl)cyclopropyl]carbonyl}amino)tetrahydro-2H-pyran-2,6-diyl]dibenzoate The titled compounds was prepared using the same procedures in Example 47 from Step 1 through Step 5 substituting methyl 4-(1-hydroxybut-3-en-1-yl)benzoate for 1-phenylbut-3-en-1-ol in Step 1 of Example 47. $^1$H NMR (400 MHz, CDCl$_3$) δ ppm 8.06-7.96 (m, 4H), 7.52-7.40 (m, 4H), 7.12-7.04 (m, 2H), 7.00 (d, J=8.2 Hz, 1H), 5.12 (d, J=8.0 Hz, 2H), 4.69 (dd, J=11.3, 2.0 Hz, 2H), 4.36 (dtd, J=11.9, 7.8, 4.0 Hz, 1H), 3.91 (s, 6H), 2.28-2.14 (m, 2H), 1.62 (q, J=3.8 Hz, 2H), 1.28 (q, J=12.0 Hz, 2H), 1.02 (q, J=3.8 Hz, 2H); MS (ESI−) m/z 592 (M−H)−.

Example 52 dimethyl rac-4,4'-[(2R,4r,6S)-4-({[1-(2,2-difluoro-1,3-benzodioxol-5-yl)cyclopropyl]carbonyl}amino)tetrahydro-2H-pyran-2,6-diyl]dibenzoate The titled compounds was prepared using the procedures described in Example 47, Step 1 through Step 5, substituting methyl 4-(1-hydroxybut-3-en-1-yl)benzoate for 1-phenylbut-3-en-1-ol in Step 1. $^1$H NMR (400 MHz, CDCl$_3$) δ ppm 8.08-7.95 (m, 4H), 7.45-7.33 (m, 4H), 7.32-7.26 (m, 2H), 7.17 (d, J=8.1 Hz, 1H), 5.75 (d, J=6.8 Hz, 1H), 4.46-4.27 (m, 3H), 3.91 (s, 6H), 1.97 (d, J=13.7 Hz, 2H), 1.82 (ddd, J=14.1, 12.0, 3.8 Hz, 2H), 1.70 (q, J=3.8 Hz, 2H), 1.13 (q, J=3.9 Hz, 2H); MS (ESI−) m/z 592 (M−H)−.

Example 53 rel-4-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid The enantiomers of rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid (Example 50) (350 mg, 0.67 mmol) were separated by chiral SFC with the method of 5-50% MeOH:CO$_2$ 10 min at 3 mL/min, 150 bar using a Whelk-O1 (S,S) column. The titled compound (54 mg, 22%) was the latter eluting enantiomer and the stereochemistry has been arbitrarily assigned. $^1$H NMR (500 MHz, CDCl$_3$) δ ppm 8.04 (s, 2H), 7.52-7.39 (m, 2H), 7.34 (dt, J=15.0, 7.6 Hz, 4H), 7.25 (m, J=3.9 Hz, 1H), 7.11-7.02 (m, 2H), 6.99 (d, J=8.1 Hz, 1H), 5.13 (d, J=7.9 Hz, 1H), 4.63 (dd, J=26.0, 11.0 Hz, 2H), 4.34 (s, 1H), 2.18 (dd, J=33.6, 12.2 Hz, 2H), 1.63-1.62 (m, 2H), 1.33-1.19 (m, 2H), 1.10-0.92 (m, 2H); MS (ESI−) m/z 520 (M−H)−.

Example 54 rel-4-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid The titled compound was the first eluting enantiomer from the chiral separation described in Example 53 (54 mg, 21.8%) and the stereochemistry has been arbitrarily assigned. $^1$H NMR (500 MHz, CDCl$_3$) δ ppm 8.06 (d, J=8.2 Hz, 2H), 7.49 (d, J=8.2 Hz, 2H), 7.43-7.32 (m, 4H), 7.29-7.26 (m, 1H), 7.11-7.03 (m, 2H), 7.01 (d, J=8.1 Hz, 1H), 5.14 (d, J=8.0 Hz, 1H), 4.71 (dd, J=11.4, 2.3 Hz, 1H), 4.64 (dd, J=11.3, 2.1 Hz, 1H), 4.36 (tdt, J=11.9, 8.2, 4.2 Hz, 1H), 2.30-2.13 (m, 2H), 1.63 (q, J=3.2 Hz, 2H), 1.35-1.25 (m, 2H), 1.03 (q, J=3.2 Hz, 2H).

Example 55 methyl rac-4-[(2R,4R,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoate Step 1: Methyl rac-4-[(2R,6S)-4-amino-6-(4-methoxyphenyl)tetrahydro-2H-pyran-2-yl]benzoate (160 mg, 87%) was prepared using the methods described in Example 47, Steps 1-4 substituting 1-(4-methoxyphenyl)but-3-en-1-ol for 1-phenylbut-3-en-1-ol and without the separation in Step 4. LC/MS (APCI) m/z 342 (M+H)+.

Step 2: A mixture of 1-(2,2-difluorobenzo[d][1,3]dioxol-5-yl)cyclopropanecarboxylic acid (125 mg, 0.516 mmol) and 1-[bis(dimethylamino)methylene]-1H-1,2,3-triazolo[4,5-b]pyridinium 3-oxid hexafluorophosphate (HATU, 267 mg, 0.7 mmol) in DMF (2 mL) was stirred at ambient temperature for 5 min. Then methyl rac-4-[(2R,6S)-4-amino-6-(4-methoxyphenyl)tetrahydro-2H-pyran-2-yl]benzoate (160 mg, 0.47 mmol) was added to the mixture followed by N-ethyl-N-isopropylpropan-2-amine (0.25 mL, 1.40 mmol), and the resultant mixture was stirred for 2 h when LC/MS showed the reaction was complete. The mixture was loaded onto a 24 g silica gel cartridge directly without workup and purified by chromatography eluting with EtOAc in heptane using a 5-45% gradient. Two diastereomers were obtained. The first eluting diastereomer was methyl rac-4-[(2R,4S,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoate (60 mg, 22.6%). $^1$H NMR (400 MHz, CDCl$_3$) δ ppm 8.01-7.96 (m, 2H), 7.40-7.33 (m, 2H), 7.28 (dd, J=8.1, 1.7 Hz, 1H), 7.26-7.20 (m, 3H), 7.16 (d, J=8.1 Hz, 1H), 6.90-6.85 (m, 2H), 5.76 (d, J=7.0 Hz, 1H), 4.37 (ddd, J=10.3, 5.3, 2.0 Hz, 2H), 4.24 (dd, J=9.8, 4.5 Hz, 1H), 3.90 (s, 3H), 3.80 (s, 3H), 2.02-1.94 (m, 1H), 1.87 (d, J=3.6 Hz, 1H), 1.78 (ddd, J=14.1, 12.1, 3.8 Hz, 1H), 1.69 (q, J=3.7 Hz, 2H), 1.26 (s, 1H), 1.14-1.10 (m, 2H); MS (ESI−) m/z 564 (M−H)⁻.

The second eluting diastereomer was the titled compound, methyl rac-4-[(2R,4R,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoate (104 mg, 39.2%). $^1$H NMR (400 MHz, CDCl$_3$) δ ppm 8.05-7.90 (m, 2H), 7.43 (d, J=8.1 Hz, 2H), 7.34-7.27 (m, 2H), 7.13-7.04 (m, 2H), 7.01 (d, J=8.1 Hz, 1H), 6.91-6.81 (m, 2H), 5.11 (d, J=8.1 Hz, 1H), 4.67 (dd, J=11.2, 2.2 Hz, 1H), 4.58 (dd, J=11.4, 2.2 Hz, 1H), 4.32 (dtd, J=11.9, 7.9, 4.2 Hz, 1H), 3.90 (d, J=1.2 Hz, 3H), 3.79 (d, J=1.3 Hz, 3H), 2.26-2.05 (m, 2H), 1.62 (q, J=3.4 Hz, 2H),1.31-1.23 (m, 2H), 1.02 (q, J=3.4 Hz, 2H); MS (ESI−) m/z 564 (M−H)⁻.

Example 56 rac-4-[(2R,4S,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoic acid The first eluting diastereomer from Step 2 of Example 55, methyl rac-4-[(2R,4S,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoate (55 mg, 0.097 mmol), in MeOH (2 mL) and 2 N lithium hydroxide aqueous solution (0.5 mL) was stirred at ambient temperature for 3 hours when LC/MS showed the reaction was complete. The mixture was concentrated. Water (1 mL) was added to the residue, and the pH was adjusted to 1~2 with 2 N HCl aqueous solution. The solid was collected by filtration and dried in an oven to yield the titled compound (33 mg, 61.5%). $^1$H NMR (400 MHz, CDCl$_3$) δ ppm 8.08-8.01 (m, 2H), 7.43-7.37 (m, 2H), 7.28 (dd, J=8.2, 1.8 Hz, 1H), 7.25 (d, J=1.6 Hz, 1H), 7.24-7.20 (m, 2H), 7.16 (d, J=8.2 Hz, 1H), 6.91-6.84 (m, 2H), 5.78 (d, J=6.9 Hz, 1H), 4.39 (ddd, J=9.0, 7.1, 2.8 Hz, 2H), 4.24 (dd, J=10.4, 3.8 Hz, 1H), 3.80 (s, 3H), 2.06-1.73 (m, 4H), 1.74-1.65 (m, 2H), 1.15-1.08 (m, 2H); MS (ESI−) m/z 550 (M−H)⁻.

Example 57 rac-4-[(2R,4R,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoic acid A solution of the second eluting diastereomer from Step 2 of Example 55, methyl rac-4-[(2R,4R,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoate (90 mg, 0.159 mmol) in MeOH (4 mL) and 2 N lithium hydroxide aqueous solution (1 mL) was stirred at room temperature for 3 h when LC/MS showed the reaction was complete. The reaction mixture was concentrated. Water was added (2 mL) to the residue, and the pH was adjusted to 1~2 with 2 N HCl. The resultant solid was collected by filtration and dried in an oven to yield titled compound (63 mg, 72%). $^1$H NMR (400 MHz, CDCl$_3$) δ ppm 8.05 (d, J=8.0 Hz, 2H), 7.47 (d, J=8.1 Hz, 2H), 7.34-7.26 (m, 2H), 7.14-6.96 (m, 3H), 6.92-6.82 (m, 2H), 5.14 (d, J=8.0 Hz, 1H), 4.73-4.45 (m, 2H), 4.34 (dtd, J=12.8, 8.2, 4.4 Hz, 1H), 3.79 (s, 3H), 2.36-2.08 (m, 2H), 1.27 (dq, J=23.8, 11.9 Hz, 2H), 1.02 (q, J=3.5 Hz, 2H); MS (ESI−) m/z 550 (M−H)⁻.

Example 58 rel-4-[(2S,4R,6S)-4-({[1-(2,2-difluoro-1,3-benzodioxol-5-yl)cyclopropyl]carbonyl}amino)-6-methyltetrahydro-2H-pyran-2-yl]benzoic acid rac-4-[(2R,4S,6R)-4-({[1-(2,2-Difluoro-1,3-benzodioxol-5-yl)cyclopropyl]carbonyl}amino)-6-methyltetrahydro-2H-pyran-2-yl]benzoic acid (Example 45, 106 mg, 0.231 mmol) was separated by chiral SFC with the method of 5-50% MeOH:CO$_2$ 10 min @3 mL/min, 150 bar and using a Whelk-O1 (S,S) column. The first eluting enantiomer was the titled compound (50 mg, 47%) and the stereochemistry was arbitrarily assigned. $^1$H NMR (400 MHz, CDCl$_3$) δ ppm 8.03 (d, J=7.8 Hz, 2H), 7.39 (d, J=7.9 Hz, 2H), 7.14-7.05 (m, 2H), 7.03 (d, J=8.1 Hz, 1H), 5.10 (d, J=7.9 Hz, 1H), 4.53-4.42 (m, 1H), 4.15 (dtt, J=14.7, 10.8, 5.5 Hz, 1H), 3.68 (ddt, J=13.4, 7.1, 3.5 Hz, 1H), 2.12 (dd, J=11.5, 3.7 Hz, 1H), 1.96-1.85 (m, 1H), 1.63 (q, J=4.3 Hz, 2H), 1.25 (d, J=6.0 Hz, 3H), 1.17-0.92 (m, 4H); MS (ESI+) m/z 460 (M+H)⁺.

Example 59 rel-4-[(2R,4S,6R)-4-({[1-(2,2-difluoro-1,3-benzodioxol-5-yl)cyclopropyl]carbonyl}amino)-6-methyltetrahydro-2H-pyran-2-yl]benzoic acid The titled compound was the second eluting enantiomer from the chiral SFC separation described in Example 58 (41 mg, 38%) and the stereochemistry was arbitrarily assigned. $^1$H NMR (400 MHz, CDCl$_3$) δ ppm 8.03 (d, J=7.9 Hz, 2H), 7.39 (d, J=8.0 Hz, 2H), 7.14-7.06 (m, 2H), 7.03 (d, J=8.1 Hz, 1H), 5.10 (d, J=7.9 Hz, 1H), 4.52-4.44 (m, 1H), 4.15 (tdt, J=12.0, 8.1, 4.6 Hz, 1H), 3.69 (ddd, J=11.2, 6.2, 2.0 Hz, 1H), 2.12 (dd, J=12.9, 3.7 Hz, 1H), 1.97-1.85 (m, 1H), 1.72-1.52 (m, 2H), 1.26 (d, J=6.0 Hz, 3H), 1.16-0.96 (m, 4H); MS (ESI+) m/z 460 (M+H)⁺.

Example 60 rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]-3-fluorobenzoic acid Methyl rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]-3-fluorobenzoate (32 mg, 0.058 mmol, Example 63) in a mixture of MeOH (2 mL) and 2 N lithium hydroxide aqueous solution (0.5 mL) was stirred at ambient temperature for 3 h when LC/MS showed the reaction was complete. The reaction mixture was concentrated. Water (2 mL) was added to the residue, and the pH was adjusted to 1~2 with 2 N HCl. The resultant solid was collected by filtration and dried in an oven to yield the titled compound (28 mg, 90%). $^1$H NMR (501 MHz, CDCl$_3$) δ ppm 7.88 (dd, J=8.0, 1.6 Hz, 1H), 7.76-7.61 (m, 2H), 7.42-7.30 (m, 4H), 7.30-7.26 (m, 1H), 7.12-7.04 (m, 2H), 7.00 (d, J=8.1 Hz, 1H), 5.13 (d, J=8.1 Hz, 1H), 4.97 (dd, J=11.3, 2.1 Hz, 1H), 4.66 (dd, J=11.4, 2.2 Hz, 1H), 4.37 (tdt, J=12.1, 8.4, 4.2 Hz, 1H), 2.31-2.17 (m, 2H), 1.67-1.60 (m, 2H), 1.29 (dq, J=40.5, 11.9 Hz, 2H), 1.06-0.99 (m, 2H); MS (ESI+) m/z 540 (M+H)$^+$.

Example 61 rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]-3-fluorobenzoic acid Methyl rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]-3-fluorobenzoate (60 mg, 0.11 mmol) from Example 63 in MeOH (2 mL) and 2 N lithium hydroxide aqueous solution (0.5 mL) were stirred at room temperature for 3 hours when LC/MS showed the reaction was complete. The mixture was concentrated. Water (1 mL) was added, and the pH was adjusted to 1~2 with 2 N HCl. The precipitate was collected by filtration and dried in oven to yield titled compound (40 mg, 68%). $^1$H NMR (501 MHz, CDCl$_3$) δ ppm 7.89 (d, J=8.2 Hz, 1H), 7.78-7.57 (m, 2H), 7.40-7.25 (m, 7H), 7.16 (d, J=8.2 Hz, 1H), 5.80 (d, J=6.9 Hz, 1H), 4.65 (d, J=11.8 Hz, 1H), 4.38 (d, J=12.3 Hz, 2H), 2.04 (d, J=13.9 Hz, 1H), 1.99-1.81 (m, 2H), 1.76 (d, J=13.4 Hz, 3H), 1.21-1.04 (m, 2H); MS (ESI+) m/z 540 (M+H)$^+$.

Example 62 methyl rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]-3-methylbenzoate Step 1: The intermediate methyl rac-4-[(2R,6S)-4-amino-6-phenyltetrahydro-2H-pyran-2-yl]-3-methylbenzoate was prepared using the procedures described in Example 47 from Step 1 through Step 4 without the separation described in Step 4, replacing methyl 4-formyl-benzoate with methyl 4-formyl-3-methylbenzoate in Step 1.

Step 2: A mixture of 1-(2,2-difluorobenzo[d][1,3]dioxol-5-yl)cyclopropanecarboxylic acid (216 mg, 0.891 mmol) and 1-[bis(dimethylamino)methylene]-1H-1,2,3-triazolo[4,5-b]pyridinium 3-oxid hexafluorophosphate (HATU, 508 mg, 1.337 mmol) in DMF (2 mL) was stirred for 5 min, and then methyl rac-4-[(2R,6S)-4-amino-6-phenyltetrahydro-2H-pyran-2-yl]-3-methylbenzoate (290 mg, 0.891 mmol) from Step 1 was added followed by N-ethyl-N-isopropyl-propan-2-amine (0.466 mL, 2.67 mmol). The mixture was stirred at room temperature for 2 h when LC/MS showed the reaction was complete. The reaction mixture was loaded onto a 24 g silica gel cartridge directly without workup and purified by chromatography eluting with EtOAc in heptane at 5-45% gradient to give methyl rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]-3-methylbenzoate as the first eluting diastereomer (128.5 mg, 26.2%). $^1$H NMR (400 MHz, CDCl$_3$) δ ppm 7.87 (dd, J=8.1, 1.8 Hz, 1H), 7.78 (d, J=2.1 Hz, 1H), 7.60 (d, J=8.2 Hz, 1H), 7.38-7.31 (m, 4H), 7.31-7.26 (m, 3H), 7.16 (d, J=8.2 Hz, 1H), 5.75 (d, J=6.7 Hz, 1H), 4.50 (dd, J=11.6, 2.1 Hz, 1H), 4.40 (dd, J=12.1, 2.3 Hz, 1H), 4.34 (dq, J=6.4, 3.3 Hz, 1H), 3.89 (s, 3H), 2.11 (s, 3H), 2.08-2.01 (m, 1H), 1.92-1.80 (m, 2H), 1.78-1.72 (m, 1H), 1.69 (td, J=4.1, 2.1 Hz, 2H), 1.18-1.06 (m, 2H); MS (ESI−) m/z 548 (M−H)$^−$.

The titled compound, methyl rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]-3-methylbenzoate was obtained as the second eluting diastereomer (290 mg, 0.528 mmol, 59.2% yield). $^1$H NMR (400 MHz, CDCl$_3$) δ ppm 7.86 (dd, J=8.2, 1.7 Hz, 1H), 7.80 (d, J=1.6 Hz, 1H), 7.60 (d, J=8.1 Hz, 1H), 7.41-7.29 (m, 4H), 7.29-7.23 (m, 2H), 7.11-7.04 (m, 2H), 7.00 (d, J=8.1 Hz, 1H), 5.12 (d, J=8.1 Hz, 1H), 4.81 (dd, J=11.2, 2.0 Hz, 1H), 4.65 (dd, J=11.3, 2.1 Hz, 1H), 4.34 (tdt, J=12.1, 8.3, 4.2 Hz, 1H), 3.89 (d, J=0.7 Hz, 3H), 2.37 (s, 3H), 2.18 (dddt, J=26.5, 12.9, 4.0, 1.9 Hz, 2H), 1.61 (t, J=3.3 Hz, 2H), 1.30-1.17 (m, 2H), 1.02 (q, J=3.6 Hz, 2H); MS (ESI−) m/z 548 (M−H)$^−$.

Example 63 methyl rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]-3-fluorobenzoate Step 1: The intermediate methyl rac-4-[(2R,6S)-4-amino-6-phenyltetrahydro-2H-pyran-2-yl]-3-fluorobenzoate was prepared using the procedures described in Example 47 from Step 1 through Step 4 without the separation described in Step 4, replacing methyl 4-formyl-benzoate with methyl 4-formyl-3-fluorolbenzoate in Step 1.

Step 2: To 1-(2,2-difluorobenzo[d][1,3]dioxol-5-yl)cyclopropanecarboxylic acid (162 mg, 0.668 mmol) in DMF (2 mL) was added 1-[bis(dimethylamino)methylene]-1H-1,2,3-triazolo[4,5-b]pyridinium 3-oxid hexafluorophosphate (HATU, 381 mg, 1.0 mmol). The mixture was stirred for 5 min, and then methyl rac-4-[(2R,6S)-4-amino-6-phenyltetrahydro-2H-pyran-2-yl]-3-fluorobenzoate (220 mg, 0.668 mmol) was added followed N-ethyl-N-isopropylpropan-2-amine (0.349 mL, 2.004 mmol). The mixture was stirred at room temperature for 2 h when LC/MS showed the reaction was complete. The reaction mixture was loaded onto a 24 g silica gel cartridge directly without workup and purified by chromatography eluting with EtOAc in heptane at 5-45% gradient. The second eluting diastereomer was the title compound, methyl rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]-3-fluorobenzoate (90 mg, 24.3%). $^1$H NMR (400 MHz, CDCl$_3$) δ ppm 7.81 (dd, J=8.1, 1.6 Hz, 1H), 7.70-7.58 (m, 2H), 7.42-7.31 (m, 4H), 7.30-7.26 (m, 1H), 7.12-7.03 (m, 2H), 7.00 (d, J=8.1 Hz, 1H), 5.10 (d, J=8.0 Hz, 1H), 4.99-4.89 (m, 1H), 4.65 (dd, J=11.5, 2.1 Hz, 1H), 4.35 (tdt, J=12.0, 8.2, 4.3 Hz, 1H), 3.91 (s, 3H), 2.31-2.16 (m, 2H), 1.62 (q, J=3.7, 3.2 Hz, 2H), 1.28 (dq, J=31.2, 11.9 Hz, 2H), 1.01 (q, J=3.9 Hz, 2H); MS (ESI+) m/z 554 (M+H)$^+$.

The first eluting diastereomer was methyl rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]-3-fluorobenzoate (70 mg, 18.93%). $^1$H NMR (400 MHz, CDCl$_3$) δ ppm 7.83 (dd, J=8.1, 1.5 Hz, 1H), 7.68-7.59 (m, 2H), 7.38-7.27 (m, 6H), 7.25 (d, J=1.6 Hz, 1H), 7.16 (d, J=8.2 Hz, 1H), 5.78 (d, J=6.9 Hz, 1H), 4.68-4.58 (m, 1H), 4.41-4.29 (m, 2H), 3.91 (s, 3H), 2.04 (dq, J=14.3, 2.4 Hz, 1H), 1.96-1.64 (m, 5H), 1.19-1.05 (m, 2H); MS (ESI+) m/z 554 (M+H)+.

Example 64 rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]-3-methylbenzoic acid A solution of methyl rac-4-[(2R,4R,6S)-4-({[1-(2,2-difluoro-1,3-benzodioxol-5-yl)cyclopropyl]carbonyl}amino)-6-phenyltetrahydro-2H-pyran-2-yl]-3-methylbenzoate from Example 62 (126 mg, 0.229 mmol) in MeOH (2 mL) and 2 N lithium hydroxide aqueous solution (0.5 mL) was stirred at ambient temperature for 3 h when LC/MS showed the reaction was complete, and then the mixture was concentrated. Water was added (2 mL) to the residue, and the pH was adjusted to 1~2 with 2 N HCl. The precipitate was collected by filtration and dried in oven to yield the titled compound (103 mg, 84%). $^1$H NMR (501 MHz, CDCl$_3$) δ ppm 7.94 (d, J=8.5 Hz, 1H), 7.83 (s, 1H), 7.61 (d, J=8.1 Hz, 1H), 7.34 (h, J=5.9 Hz, 4H), 7.30-7.26 (m, 3H), 7.16 (d, J=8.1 Hz, 1H), 5.77 (d, J=6.7 Hz, 1H), 4.54-4.46 (m, 1H), 4.42-4.30 (m, 2H), 2.11 (s, 3H), 2.03 (d, J=14.1 Hz, 1H), 1.92-1.78 (m, 2H), 1.77-1.64 (m, 3H), 1.19-1.04 (m, 2H); MS (ESI+) m/z 536 (M+H)+.

Example 65 rac-4-[(2S,4R,6S)-4-({[1-(2,2-difluoro-1,3-benzodioxol-5-yl)cyclopropyl]carbonyl}amino)-6-phenyltetrahydro-2H-pyran-2-yl]-3-methylbenzoic acid A solution of methyl rac-4-[(2R,4S,6S)-4-({[1-(2,2-difluoro-1,3-benzodioxol-5-yl)cyclopropyl]carbonyl}amino)-6-phenyltetrahydro-2H-pyran-2-yl]-3-methylbenzoate from Example 62 (270 mg, 0.491 mmol) in MeOH (10 mL) and 2 N LiOH aqueous solution (3 mL) was stirred at 35° C. for 4 h when LC/MS showed the reaction was complete, and then the mixture was concentrated. Water (2 mL) was added to the residue, and the pH was adjusted to 1~2 with 2 N HCl. The solid precipitate was collected by filtration and dried in oven to yield the titled compound (222 mg, 84%). $^1$H NMR (400 MHz, CDCl$_3$) δ ppm 7.96 (d, J=8.2 Hz, 1H), 7.89 (s, 1H), 7.67 (d, J=8.1 Hz, 1H), 7.49-7.31 (m, 4H), 7.29 (s, 1H), 7.19-6.95 (m, 3H), 5.17 (d, J=8.0 Hz, 1H), 4.85 (d, J=10.9 Hz, 1H), 4.68 (d, J=11.1 Hz, 1H), 4.38 (s, 1H), 2.42 (s, 3H), 2.22 (dd, J=19.8, 13.4 Hz, 2H), 1.66 (q, J=3.8 Hz, 2H), 1.32 (dq, J=36.9, 11.9 Hz, 2H), 1.05 (q, J=3.8 Hz, 2H); MS (ESI+) m/z 536 (M+H)+.

Example 66 rel-4-[(2R,4R,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoic acid The enantiomers of Example 57, rac-4-[(2R,4R,6S)-4-({[1-(2,2-difluoro-1,3-benzodioxol-5-yl)cyclopropyl]carbonyl}amino)-6-(4-methoxyphenyl)tetrahydro-2H-pyran-2-yl]benzoic acid (50 mg, 0.091 mmol), were separated by chiral SFC with the method of 5-30% MeOH:CO$_2$ 10 min @3 mL/min, 150 bar, on a Whelk-O1 (S,S) column. The titled compound (19 mg, 38%) was the second enantiomer to elute and the stereochemistry was arbitrarily assigned. $^1$H NMR (501 MHz, CDCl$_3$) δ ppm 8.02 (s, 2H), 7.43 (d, J=7.3 Hz, 2H), 7.29 (d, J=8.3 Hz, 2H), 7.11-7.03 (m, 2H), 7.00 (d, J=8.1 Hz, 1H), 6.86 (d, J=8.4 Hz, 2H), 5.12 (d, J=7.9 Hz, 1H), 4.60 (dd, J=45.7, 10.9 Hz, 2H), 4.31 (s, 1H), 3.78 (s, 3H), 2.16 (dd, J=43.8, 12.4 Hz, 2H), 1.62 (d, J=3.6 Hz, 2H), 1.25 (tt, J=23.5, 11.8 Hz, 2H), 1.01 (d, J=3.6 Hz, 2H); MS (ESI-) m/z 550 (M-H)-.

Example 67 rel-4-[(2S,4S,6R)-4-({[1-(2,2-difluoro-1,3-benzodioxol-5-yl)cyclopropyl]carbonyl}amino)-6-(4-methoxyphenyl)tetrahydro-2H-pyran-2-yl]benzoic acid The titled compound (21 mg, 42%) was the first enantiomer to elute from the chiral SFC separation in Example 66 and the stereochemistry was arbitrarily assigned. $^1$H NMR (501 MHz, CDCl$_3$) δ ppm 8.03 (s, 2H), 7.44 (d, J=6.8 Hz, 2H), 7.29 (d, J=8.3 Hz, 2H), 7.11-7.04 (m, 2H), 7.00 (d, J=8.1 Hz, 1H), 6.86 (d, J=8.7 Hz, 2H), 5.13 (d, J=7.7 Hz, 1H), 4.66 (d, J=11.0 Hz, 1H), 4.56 (d, J=11.1 Hz, 1H), 4.32 (s, 1H), 3.78 (s, 3H), 2.17 (dd, J=45.5, 12.4 Hz, 2H), 1.62 (d, J=3.6 Hz, 2H), 1.34-1.19 (m, 2H), 1.01 (d, J=3.3 Hz, 2H); MS (ESI-) m/z 550 (M-H)-.

Example 68 ethyl rac-3-[(2R,4R,6S)-4-({[1-(2,2-difluoro-1,3-benzodioxol-5-yl)cyclopropyl]carbonyl}amino)-6-(3-methoxyphenyl)tetrahydro-2H-pyran-2-yl]benzoate Step 1: To a mixture of methyl 3-formylbenzoate (1.0 g, 6.1 mmol) in acetonitrile (5 mL) and ClCH$_2$CH$_2$Cl (5.00 mL) at -40° C. was added 3-methoxybenzaldehyde (1.25 g, 9.2 mmol) and trifluoromethanesulfonic acid (1.1 mL, 12.2 mmol) followed by the addition of allyltrimethylsilane (2.9 mL, 18.3 mmol) dropwise, keeping the internal temperature lower than -30° C. After addition, stirring was continued for another 10 min when LC/MS showed the reaction was complete. The mixture was poured into saturated aqueous NaHCO$_3$ solution (30 mL) with vigorous stirring, and then the mixture was extracted with EtOAc (30 mL×2). The combined organic fractions were washed with brine, dried over Na$_2$SO$_4$ and concentrated. The residue was purified by chromatography on a 40 g silica gel cartridge eluted with EtOAc in heptane 5-50% to yield methyl rac-3-[(2R,4R,6S)-4-(acetylamino)-6-(3-methoxyphenyl)tetrahydro-2H-pyran-2-yl]benzoate (805 mg, 34.5%). LC/MS (APCI+) m/z 384 (M+H)+.

Step 2: A mixture of methyl rac-3-[(2R,4R,6S)-4-(acetylamino)-6-(3-methoxyphenyl)tetrahydro-2H-pyran-2-yl]benzoate (800 mg, 2.1 mmol) from Step 1, diisopropylethylamine (4.1 mL, 23.5 mmol), di-tert-butyl dicarbonate (8 mL, 35.5 mmol), and DMAP (1.912 g, 15.65 mmol) in toluene (55 mL) was heated to 100° C. After 40 min when LC/MS showed the reaction was complete, the mixture was cooled to 10° C. followed by the addition of sodium methoxide (3.6 mL, 15.7 mmol) at 10° C. After addition, the reaction was immediately complete as indicated by LC/MS. The reaction mixture was partitioned between water (55 mL) and EtOAc (55 mL). The organic layer was washed with 2 N HCl (55 mL) and brine (20 mL). The organic layer was dried over Na$_2$SO$_4$ and concentrated. The residue was purified by chromatography on a 40 g silica gel cartridge eluted with EtOAc in heptane 5-50% to yield methyl rac-3-[(2R, 4R,6S)-4-[(tert-butoxycarbonyl)amino]-6-(3-methoxyphenyl)tetrahydro-2H-pyran-2-yl]benzoate (365 mg, 39.6%). LC/MS (APCI+) m/z 442 (M+H)$^+$.

Step 3: To methyl rac-3-[(2R,4R,6S)-4-[(tert-butoxycarbonyl)amino]-6-(3-methoxyphenyl)tetrahydro-2H-pyran-2-yl]benzoate (360 mg, 0.79 mmol) in dichloromethane (8 mL) was added trifluoroacetic acid (0.61 mL, 7.9 mmol), and the mixture was stirred at ambient for 90 min when LC/MS showed the reaction was complete. The mixture was concentrated, toluene (20 mL) was added, and then this mixture was concentrated again to remove trifluoroacetic acid. The residue was partitioned between EtOAc (50 mL) and 2 N HCl (2.6 mL, 31 mmol). The organic fraction was washed with saturated aqueous NaHCO$_3$ (50 mL) and brine (20 mL), dried over MgSO4, and concentrated to give ethyl rac-3-[(2R,4R,6S)-4-amino-6-(3-methoxyphenyl)tetrahydro-2H-pyran-2-yl]benzoate which was used in the next step without further purification. LC/MS (APCI+) m/z 356 (M+H)$^+$.

Step 4: A mixture of 1-(2,2-difluorobenzo[d][1,3]dioxol-5-yl)cyclopropanecarboxylic acid (100 mg, 0.413 mmol) and 1-[bis(dimethylamino)methylene]-1H-1,2,3-triazolo[4,5-b]pyridinium 3-oxid hexafluorophosphate (HATU, 236 mg, 0.619 mmol) in DMF (2 mL) was stirred for 5 min. Then ethyl rac-3-[(2R,4R,6S)-4-amino-6-(3-methoxyphenyl)tetrahydro-2H-pyran-2-yl]benzoate (147 mg, 0.413 mmol) from Step 3 was added followed by N-ethyl-N-isopropylpropan-2-amine (0.216 mL, 1.239 mmol). The mixture was stirred at ambient temperature for 2 h when LC/MS showed the reaction was complete. The reaction mixture was loaded onto a 24 g silica gel cartridge directly without workup and purified by chromatography eluting with EtOAc in heptane at 5-45% gradient to give ethyl rac-3-[(2R,4R,6S)-4-({[1-(2,2-difluoro-1,3-benzodioxol-5-yl)cyclopropyl]carbonyl}amino)-6-(3-methoxyphenyl)tetrahydro-2H-pyran-2-yl]benzoate (150 mg, 62.7%). $^1$H NMR (400 MHz, CDCl$_3$) δ ppm 8.04 (s, 1H), 7.94 (d, J=7.8 Hz, 1H), 7.59 (d, J=7.5 Hz, 1H), 7.39 (t, J=7.7 Hz, 1H), 7.24 (s, 1H), 7.11-7.04 (m, 2H), 7.01 (d, J=8.1 Hz, 1H), 6.98-6.90 (m, 2H), 6.83-6.74 (m, 1H), 5.12 (d, J=8.2 Hz, 1H), 4.63 (ddt, J=19.6, 10.5, 5.2 Hz, 2H), 4.41-4.35 (m, 2H), 4.35-4.25 (m, 1H), 3.80 (d, J=2.8 Hz, 3H), 2.27-2.13 (m, 2H), 1.39 (t, J=7.1 Hz, 3H), 1.1.62 (m, 2H), 1.35-1.25 (m, 2H); MS (ESI-) m/z 578 (M-H)$^-$.

Example 69 rac-3-[(2R,4R,6S)-4-({[1-(2,2-difluoro-1,3-benzodioxol-5-yl)cyclopropyl]carbonyl}amino)-6-(3-methoxyphenyl)tetrahydro-2H-pyran-2-yl]benzoic acid A mixture of ethyl rac-3-[(2R,4R,6S)-4-({[1-(2,2-difluoro-1,3-benzodioxol-5-yl)cyclopropyl]carbonyl}amino)-6-(3-methoxyphenyl)tetrahydro-2H-pyran-2-yl]benzoate (Example 68, 130 mg, 0.224 mmol) in MeOH (4 mL) and 2 N LiOH aqueous solution (1 mL) was stirred at 35° C. for 2 h when LC/MS showed the reaction was complete, and then the mixture was concentrated. Water (1 mL) was added to the residue, and the pH was adjusted to 1~2 by adding 2 M HCl. The precipitate was collected by filtration, washed with water, and dried in an oven to yield the titled compound (115 mg, 93%). $^1$H NMR (400 MHz, CDCl$_3$) δ ppm 8.13 (s, 1H), 8.01 (dt, J=7.8, 1.5 Hz, 1H), 7.65 (dt, J=7.6, 1.5 Hz, 1H), 7.43 (t, J=7.7 Hz, 1H), 7.29-7.19 (m, 2H), 7.11-7.05 (m, 2H), 7.01 (d, J=8.2 Hz, 1H), 6.98-6.92 (m, 2H), 6.84-6.75 (m, 1H), 5.16 (d, J=8.1 Hz, 1H), 4.66 (ddd, J=26.1, 11.3, 2.1 Hz, 2H), 4.37 (tdt, J=12.2, 8.5, 4.4 Hz, 1H), 3.80 (s, 3H), 2.22 (dddt, J=30.4, 12.7, 4.3, 2.1 Hz, 2H), 1.64 (q, J=3.1 Hz, 2H), 1.31 (q, J=12.0 Hz, 2H), 1.03 (q, J=3.1 Hz, 2H); MS (ESI+) m/z 552 (M+H)$^+$.

Example 70 rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-4-methylbenzoic acid A mixture of methyl rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-4-methylbenzoate (Example 71, 260 mg, 0.47 mmol) in MeOH (4 mL) and aqueous 2 N lithium hydroxide (1 mL) was stirred at 35° C. for 2 h when LC/MS showed the reaction was complete, and then the mixture was concentrated. Water (1 mL) was added to the residue, and the pH was adjusted to 1~2 by adding 2 M HCl. The precipitate was collected by filtration, washed with water, and dried in an oven to yield the titled compound (230 mg, 91% yield). $^1$H NMR (400 MHz, CDCl$_3$) δ ppm 8.24 (s, 1H), 7.90 (dd, J=7.9, 1.8 Hz, 1H), 7.44-7.29 (m, 4H), 7.29-7.17 (m, 2H), 7.15-6.97 (m, 3H), 5.18 (d, J=8.1 Hz, 1H), 4.81 (d, J=10.8 Hz, 1H), 4.65 (d, J=10.9 Hz, 1H), 4.36 (dq, J=11.6, 7.4, 5.7 Hz, 1H), 2.41 (s, 3H), 2.18 (dd, J=24.2, 12.9 Hz, 2H), 1.62 (q, J=2.9 Hz, 2H). 1.36 (qd, J=11.8, 5.6 Hz, 2H), 1.03 (q, J=2.9 Hz, 2H); MS (ESI-) m/z 534 (M-H)$^-$.

Example 71 methyl rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-4-methylbenzoate Step 1: rac-N-[(2R,4S,6S)-2-(5-Bromo-2-methylphenyl)-6-phenyltetrahydro-2H-pyran-4-yl]acetamide was prepared using the procedure in Example 68-Step 1, substituting 5-bromo-2-methylbenzaldehyde for 3-methoxybenzaldehyde and benzaldehyde for methyl-3-formylbenzoate. LC/MS (APCI+) m/z 388 (M+H)$^+$.

Step 2: rac-N-[(2R,4S,6S)-2-(5-Bromo-2-methylphenyl)-6-phenyltetrahydro-2H-pyran-4-yl]acetamide (2.1 g, 5.41 mmol, Step 1), dichloro[1,1'-ferrocenylbis(diphenylphosphane)]palladium(II) dichloromethane ([PdCl$_2$(dppf)]*CH$_2$Cl$_2$, 0.079 g, 0.108 mmol), methanol (30 mL) and triethylamine (1.508 mL, 10.82 mmol) were combined in a 50 mL pressure bottle and degassed several times with argon. The reaction mixture was placed under an atmosphere of carbon monoxide (60 psi) and heated to 100° C. for 16 h. LC/MS confirmed carbonylation. The reaction mixture was concentrated under reduced pressure, and the residue was purified by chromatography on an 80 g silica gel cartridge eluted with 5-60% EtOAc in heptane gave methyl rac-3-[(2R,4S,6S)-4-(acetylamino)-6-phenyltetrahydro-2H-pyran-2-yl]-4-methylbenzoate (375 mg, 1.021 mmol, 18.87% yield) that was used without further purification in the next step. LC/MS (APCI+) m/z 368 (M+H)$^+$.

Step 3: Methyl rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-4-methylbenzoate was prepared using the procedures described in Example 68-Steps 2-4, substituting methyl rac-3-[(2R,4S,6S)-4-(acetylamino)-6-phenyltetrahydro-2H-pyran-2-yl]-4-methylbenzoate from Step 2 for methyl rac-3-[(2R,4R,6S)-4-(acetylamino)-6-(3-methoxyphenyl)tetrahydro-2H-pyran-2-yl]benzoate from Step 1 of Example 68 (280 mg, 64%). ¹H NMR (400 MHz, CDCl₃) δ ppm 8.16 (d, J=2.1 Hz, 1H), 7.82 (dd, J=7.9, 1.8 Hz, 1H), 7.43-7.28 (m, 4H), 7.29-7.22 (m, 1H), 7.18 (d, J=7.9 Hz, 1H), 7.15-6.95 (m, 3H), 5.15 (d, J=8.1 Hz, 1H), 4.79 (dd, J=11.3, 2.1 Hz, 1H), 4.64 (dd, J=11.3, 2.1 Hz, 1H), 4.34 (tdt, J=12.1, 8.4, 4.2 Hz, 1H), 3.90 (s, 3H), 2.39 (s, 3H), 2.16 (dddt, J=34.3, 12.8, 4.0, 2.0 Hz, 2H), 1.62 (q, J=3.4 Hz, 2H), 1.35 (qd, J=11.7, 5.3 Hz, 2H), 1.02 (q, J=3.4 Hz, 2H); MS (ESI−) m/z 548 (M−H)⁻.

Example 72 ethyl rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-5-methylbenzoate Step 1: rac-N-[(2R,4S,6S)-2-(3-Bromo-5-methylphenyl)-6-phenyltetrahydro-2H-pyran-4-yl]acetamide was prepared using the procedure described in Example 68-Step 1, substituting 3-bromo-5-methylbenzaldehyde for 3-methoxybenzaldehyde and benzaldehyde for methyl-3-formylbenzoate. LC/MS (APCI+) m/z 388 (M+H)⁺.

Step 2: Methyl rac-3-[(2R,4S,6S)-4-(acetylamino)-6-phenyltetrahydro-2H-pyran-2-yl]-5-methylbenzoate was prepared according to Example 71-Step 2, substituting rac-N-[(2R,4S,6S)-2-(3-bromo-5-methylphenyl)-6-phenyltetrahydro-2H-pyran-4-yl]acetamide from Step 1 for rac-N-[(2R,4S,6S)-2-(5-bromo-2-methylphenyl)-6-phenyltetrahydro-2H-pyran-4-yl]acetamide from Step 2 of Example 71. LC/MS (APCI+) m/z 368 (M+H)⁺.

Step 3: Ethyl rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-5-methylbenzoate was prepared using the same procedure in Example 68, following Steps 2 to 4, substituting methyl rac-3-[(2R,4S,6S)-4-(acetylamino)-6-phenyltetrahydro-2H-pyran-2-yl]-5-methylbenzoate from Step 2 for methyl rac-3-[(2R,4R,6S)-4-(acetylamino)-6-(3-methoxyphenyl)tetrahydro-2H-pyran-2-yl]benzoate from Step 1 of Example 68 (62% yield). ¹H NMR (400 MHz, CDCl₃) δ ppm 7.83 (s, 1H), 7.75 (q, J=1.4 Hz, 1H), 7.42-7.36 (m, 3H), 7.33 (ddd, J=7.6, 6.6, 1.3 Hz, 2H), 7.29-7.24 (m, 1H), 7.12-7.04 (m, 2H), 7.01 (d, J=8.2 Hz, 1H), 5.11 (d, J=8.0 Hz, 1H), 4.63 (ddd, J=11.3, 5.2, 2.1 Hz, 2H), 4.35 (m, J=7.3 Hz, 3H), 2.19 (dtd, J=12.0, 4.7, 4.0, 2.1 Hz, 2H), 1.62 (q, J=3.7 Hz, 2H), 1.39 (t, J=7.1 Hz, 3H), 1.35-1.26 (m, 2H), 1.01 (q, J=3.7 Hz, 2H); MS (ESI−) m/z 562 (M−H)⁻.

Example 73 rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-5-methylbenzoic acid A solution of Example 72 (430 mg, 0.76 mmol) in MeOH (6 mL) and aqueous 2 N NaOH (2 mL) was stirred at 35° C. for 4 h when LC/MS showed the reaction was complete, and then the mixture was concentrated under reduced pressure. Water was added to the residue, and the pH was adjusted to 1~2 with aqueous 2 N HCl. The precipitate was collected by filtration, washed with water, and dried to yield the titled compound (250 mg, 61% yield). ¹H NMR (400 MHz, CDCl₃) δ ppm 7.91 (d, J=1.6 Hz, 1H), 7.82 (d, J=1.7 Hz, 1H), 7.45 (s, 1H), 7.41-7.30 (m, 4H), 7.29-7.23 (m, 1H), 7.12-7.05 (m, 2H), 7.01 (d, J=8.2 Hz, 1H), 5.15 (d, J=8.1 Hz, 1H), 4.64 (ddd, J=11.4, 9.5, 2.0 Hz, 2H), 4.36 (tdt, J=12.1, 8.2, 4.2 Hz, 1H), 2.40 (s, 3H), 2.28-2.12 (m, 2H), 1.67-1.61 (m, 2H), 1.31 (q, J=11.9 Hz, 2H), 1.02 (q, J=3.4 Hz, 2H); MS (ESI−) m/z 534 (M−H)⁻.

Example 74 rel-3-[(2R,4R,6S)-4-({[1-(2,2-difluoro-1,3-benzodioxol-5-yl)cyclopropyl]carbonyl}amino)-6-(3-methoxyphenyl)tetrahydro-2H-pyran-2-yl]benzoic acid The enantiomers of Example 69, rac-3-[(2R,4R,6S)-4-({[1-(2,2-difluoro-1,3-benzodioxol-5-yl)cyclopropyl]carbonyl}amino)-6-(3-methoxyphenyl)tetrahydro-2H-pyran-2-yl]benzoic acid (93 mg, 0.169 mmol), were separated by chiral SFC using 5-50% MeOH:CO₂, 10 min @3 mL/min, 150 bar, Column: Whelk-O1 (S,S) to yield the titled compound (33 mg, 35.5%) as the first enantiomer to elute. The stereochemistry was arbitrarily assigned. ¹H NMR (400 MHz, CDCl₃) δ ppm 8.12 (s, 1H), 8.00 (d, J=7.7 Hz, 1H), 7.65 (d, J=7.6 Hz, 1H), 7.43 (t, J=7.7 Hz, 1H), 7.24 (d, J=7.8 Hz, 1H), 7.12-7.05 (m, 2H), 7.01 (d, J=8.3 Hz, 1H), 6.95 (dd, J=5.1, 3.2 Hz, 2H), 6.88-6.75 (m, 1H), 5.16 (d, J=8.1 Hz, 1H), 4.66 (dd, J=27.1, 11.1 Hz, 2H), 4.46-4.28 (m, 1H), 3.80 (d, J=1.4 Hz, 3H), 2.22 (dd, J=33.5, 12.6 Hz, 2H), 1.64 (q, J=3.0 Hz, 2H), 1.27 (d, J=11.9 Hz, 2H), 1.03 (q, J=3.0 Hz, 2H); MS (ESI+) m/z 552 (M+H)⁺.

Example 75 rel-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-5-methylbenzoic acid The enantiomers of Example 73, rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]-5-methylbenzoic acid (248 mg, 0.463 mmol), were separated by chiral SFC with 5-50% MeOH:CO₂ 10 min @3 mL/min, 150 bar, Column: Whelk-O1 (S,S). The second enantiomer to elute was the titled compound (85 mg, 34%). The stereochemistry was arbitrarily assigned. ¹H NMR (400 MHz, CDCl₃) δ ppm 7.90 (s, 1H), 7.81 (s, 1H), 7.43 (s, 1H), 7.38 (d, J=7.6 Hz, 2H), 7.32 (t, J=7.5 Hz, 2H), 7.25 (d, J=3.0 Hz, 1H), 7.13-7.04 (m, 2H), 7.01 (d, J=8.1 Hz, 1H), 5.14 (d, J=8.0 Hz, 1H), 4.63 (t, J=10.4 Hz, 2H), 4.25 (m, 1H), 2.38 (s, 3H), 2.20 (t, J=15.0 Hz, 2H), 1.63 (d, J=3.3 Hz, 2H), 1.33-1.23 (m, 2H), 1.02 (q, J=3.4 Hz, 2H).

Example 76 rel-3-[(2S,4R,6R)-4-({[1-(2,2-difluoro-1,3-benzodioxol-5-yl)cyclopropyl]carbonyl}amino)-6-phenyltetrahydro-2H-pyran-2-yl]-5-methylbenzoic acid The titled compound was the first enantiomer to elute in the chiral separation of Example 75 (30 mg, 12.1%). The stereochemistry was arbitrarily assigned. ¹H NMR (400 MHz, CDCl₃) δ ppm 7.92 (s, 1H), 7.82 (s, 1H), 7.45 (s, 1H), 7.41-7.29 (m, 4H), 7.27 (d, J=5.8 Hz, 2H), 7.14-6.96 (m, 3H), 5.15 (d, J=8.1 Hz, 1H), 4.71-4.55 (m, 2H), 4.35 (m, 1H), 2.39 (s, 3H), 2.27-2.10 (m, 2H), 1.63 (m, 2H), 1.30 (m, 2H), 1.02 (q, J=3.4 Hz, 2H); MS (ESI+) m/z 536 (M+H)⁺.

Determination of Biological Activity

Cellular Assays
Cell Surface Expression-Horse Radish Peroxidase (CSE-HRP) Assay:
A cellular assay for measuring the F508delCFTR cell surface expression after correction with test compounds was developed in human lung derived epithelial cell line (CFBE41o-) (Veit G et al, (2012) Mol Biol Cell. 23(21): 4188-4202). This was achieved by expressing the F508delCFTR mutation along with a horseradish peroxidase (HRP) in the fourth exofacial loop and then measuring the HRP activity using luminescence readout from these cells, CFBE41o-F508delCFTR-HRP, that were incubated overnight with the test corrector compounds. Briefly, for this primary assay, the CFBE41o-F508delCFTR-HRP cells were plated in 384-well plates (Greiner Bio-one; Cat 781080) at 4,000 cells/well along with 0.5 µg/mL doxycycline to induce the F508delCFTR-HRP expression and further incubated at 37° C., 5% $CO_2$ for 72 hours. The test compounds were then added at the required concentrations and further incubated for 18-24 hours at 33° C. The highest concentration tested was 20 µM with an 8-point concentration response curve using a 3-fold dilution. Three replicate plates were run to determine one $EC_{50}$. All plates contained negative controls (dimethyl sulfoxide, DMSO) and positive controls (3 µM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) as well as on-plate concentration response of the positive control. Post incubation, the plates were washed 5× times with Dulbecco's phosphate buffered saline (DPBS), followed by the addition of the HRP substrate, luminol (50 µL), and measuring the HRP activity using luminescence readout on EnVision® Multilabel Plate Reader (Perkin Elmer; product number 2104-0010). The raw counts from the experiment are analyzed using Accelrys® Assay Explorer v3.3.

Z' greater than 0.5 was used as passing quality control criteria for the plates.

The Z' is defined as:

$$1-[3*SD_{Positive\ Control}+3*SD_{Negative\ Control}/\text{Absolute}(\text{Mean}_{Positive\ Control}-\text{Mean}_{Negative\ Control})],$$

wherein "SD" is standard deviation.

The % activity measured at each of the 8 test concentrations of the test compound was normalized to the on-plate positive control using the following formula:

$$\%\ activity=[(\text{test compound response}-\text{DMSO response})/(\text{positive control response}-\text{DMSO response})]*100$$

The maximum % activity achieved for the test compound at any tested concentration is presented in Table 1 along with the $EC_{50}$ calculated using the following general sigmoidal curve with variable Hill slope equation (described as Model 42 in the Accelrys® Assay Explorer v3.3 software):

$$y=(a-d)/(1+(x/c)^b)+d$$

General sigmoidal curve with concentration, response, top, bottom, $EC_{50}$ and Hill slope.

This model describes a sigmoidal curve with an adjustable baseline, a. The equation can be used to fit curves where response is either increasing or decreasing with respect to the independent variable, "x".

"x" is a concentration of drug under test.

"y" is the response.

"a" is the maximum response, and "d" is the minimum response

"c" is the inflection point ($EC_{50}$) for the curve. That is, "y" is halfway between the lower and upper asymptotes when x=c.

"b" is the slope-factor or Hill coefficient. The sign of b is positive when the response increases with increasing dose and is negative when the response decreases with increasing dose (inhibition).

TABLE 1

| | CSE-HRP data | |
|---|---|---|
| Example | $EC_{50}$ (µM) | Maximum % activity (%) |
| 1 | 1.7 | 62 |
| 2 | 0.85 | 71 |
| 3 | 1.41 | 64 |
| 4 | 3.11 | 23 |
| 5 | 20 | 13 |
| 6 | 5.15 | 32 |
| 7 | 5.56 | 27 |
| 8 | 1.39 | 57 |
| 9 | 2.26 | 61 |
| 10 | 2.09 | 58 |
| 11 | 0.9 | 116 |
| 12 | 7.63 | 108 |
| 13 | 1.16 | 110 |
| 14 | 2.86 | 113 |
| 15 | 6.7 | 75 |
| 16 | 2.62 | 44 |
| 17 | 1.11 | 81 |
| 18 | 20 | 3 |
| 19 | 2.23 | 100 |
| 20 | 7.3 | 45 |
| 21 | 7.72 | 59 |
| 22 | 2.18 | 63 |
| 23 | 0.85 | 104 |
| 24 | 0.5 | 109 |
| 25 | 2.02 | 108 |
| 26 | 20 | 16 |
| 27 | 0.28 | 109 |
| 28 | 3.31 | 73 |
| 29 | 1.05 | 107 |
| 30 | 9.57 | 26 |
| 31 | 0.77 | 102 |
| 32 | 4.12 | 69 |
| 33 | 3.89 | 102 |
| 34 | 1.61 | 105 |
| 35 | 2.87 | 89 |
| 36 | 0.57 | 100 |
| 37 | 0.47 | 115 |
| 38 | 2.48 | 84 |
| 39 | 1.64 | 90 |
| 40 | 2.10 | 60 |
| 41 | 0.41 | 104 |
| 42 | 6.87 | 36 |
| 43 | 0.32 | 119 |
| 44 | 2.58 | 88 |
| 45 | 2.00 | 101 |
| 46 | 4.56 | 67 |
| 47 | 6.47 | 73 |
| 48 | 0.83 | 100 |
| 49 | 3.08 | 77 |
| 50 | 0.52 | 92 |
| 51 | 0.76 | 103 |
| 52 | 1.80 | 70 |
| 53 | 0.30 | 81 |
| 54 | 1.71 | 71 |
| 55 | 0.86 | 104 |
| 56 | 1.90 | 89 |
| 57 | 0.58 | 90 |
| 58 | 7.37 | 63 |
| 59 | 0.98 | 90 |
| 60 | 0.27 | 97 |
| 61 | 2.54 | 82 |
| 62 | 0.88 | 111 |
| 63 | 0.86 | 105 |
| 64 | 2.40 | 53 |
| 65 | 0.37 | 100 |
| 66 | 0.32 | 79 |
| 67 | 2.41 | 54 |
| 68 | 1.04 | 108 |
| 69 | 0.42 | 85 |
| 70 | 0.91 | 92 |
| 71 | 1.31 | 92 |
| 72 | 1.16 | 106 |
| 73 | 0.41 | 90 |
| 74 | 0.24 | 89 |

TABLE 1-continued

CSE-HRP data

| Example | EC$_{50}$ (µM) | Maximum % activity (%) |
|---|---|---|
| 75 | 0.22 | 105 |
| 76 | 1.59 | 38 |

Transepithelial Clamp Circuit on Human Bronchial Epithelial Cells Conductance Assay:

A cell based assay using the primary human bronchial epithelial cells (hBE) was used as a secondary assay to test novel F508delCFTR correctors for their activity on primary hBE cells with F508del/F508del CFTR mutation. The assay used a TECC-24 (Transepithelial Clamp Circuit for 24 wells) instrument that measures the functionality of the mutated channel by measuring the equivalent short circuit current (Ieq) generated by the polarized epithelial cells. The instrument works by measuring the transepithelial potential difference (Vt) and transepithelial resistance (Rt) in an open circuit format, and the Ieq is calculated by using Ohms law (Ieq=Vt/Rt). The assay was run in a 24-well format and all 24-wells were measured at the same time point giving a higher throughput for this assay.

Primary human bronchial epithelial (hBE) cells from F508del/F508delCFTR patients were expanded from 1×10$^6$ to 250×10$^6$ cells (Neuberger T, Burton B, Clark H and VanGoor F; *Cystic Fibrosis*, Methods in Mole Biol 741; eds. Amaral M D and Kunzelmann K, 2011). For this purpose, cells isolated from CF patients with the homozygous mutation were seeded onto 24 well Corning (Cat #3378) filter plates that were coated with 3T3 conditioned media and grown at an air-liquid interface for 35 days using an Ultroser® G supplemented differentiation media. Apical surface mucus was removed 72 hours before the experiment using 3 mM dithiothreitol (DTT) in phosphate buffered saline (PBS). The apical surface was washed again 24 hours before the experiment using PBS. The cells were incubated with the desired dose response of the corrector compounds 18-24 hours at 37° C., 5% CO$_2$. The corrector compounds are only added on the basolateral side of the epithelial cells.

On the day of measuring the corrector activity on the TECC, the cells were switched into a bicarbonate and serum free F-12 Coon's medium and allowed to equilibrate for 90 minutes in a CO$_2$ free incubator. At the time of measurement, the apical and basolateral sides of the filter were bathed with the F-12 Coon's modification media (with 20 mM 4-(2-hydroxyethyl)-1-piperazineethanesulfonic acid (HEPES), pH 7.4 (using 1 M tris(hydroxymethyl)aminomethane (Tris)), and the measurements were made at 36.5° C. Transepithelial voltage (Vt) and transepithelial resistance (Rt) were measured using a 24 channel transepithelial current clamp (TECC-24). Current responses to the sequential addition of benzamil (apical 6 M addition; for inhibiting epithelial ENaC channel), forskolin (apical and basolateral 10 M addition; for activating the CFTR channel), control potentiator (N-(3-carbamoyl-5,5,7,7-tetramethyl-4,7-dihydro-5H-thieno[2,3-c]pyran-2-yl)-1H-pyrazole-5-carboxamide; apical and basolateral 1 M addition; for potentiating the CFTR channel) and bumetanide (basolateral 20 µM addition; for inhibiting the Na:2Cl:K co-transporter, an indirect measure of inhibiting the Cl-secretion driven by CFTR channel) were measured.

All plates contained negative controls (dimethyl sulfoxide, DMSO) which coupled with the control potentiator (N-(3-carbamoyl-5,5,7,7-tetramethyl-4,7-dihydro-5H-thieno[2,3-c]pyran-2-yl)-1H-pyrazole-5-carboxamide) sets the null response and positive controls (3 µM of 3-[(2R,4R)-4-({[1-(2,2-difluoro-1,3-benzodioxol-5-yl)cyclopropyl] carbonyl}amino)-7-methoxy-3,4-dihydro-2H-chromen-2-yl]benzoic acid) coupled with the control potentiator sets the 100% response to measure the correction of the mutated CFTR channel. The maximum percent activity is reported relative to the positive control value.

The % activity measured at each of the 6 test concentrations of the test compound was normalized to the on-plate positive control using the following formula:

% activity=[(test compound response−DMSO response)/(positive control response−DMSO response)]*100

The following log(agonist) vs response using a four parameters variable slope was used to calculate EC$_{50}$ (4 PL in Prism v 5 software):

$$F(x)=D+(A-D)/(1+(x/C)^{\wedge}B)$$

Where:

"x" is a concentration of drug under test.

"F(x)" is the response.

"A" is the maximum response, and "D" is the minimum response

"C" is the inflection point (EC$_{50}$) for the curve. That is, "F(x)" is halfway between the lower and upper asymptotes when x=C.

"B" is the slope-factor or Hill coefficient. The sign of B is positive when the response increases with increasing dose and is negative when the response decreases with increasing dose (inhibition).

The maximum percent activity and EC$_{50}$ values for tested corrector compounds are presented in Table 2.

TABLE 2 hBE-TECC data

| Example | EC$_{50}$ (µM) | Maximum % Activity (%) |
|---|---|---|
| 14 | 1.34 | 73 |
| 19 | 1.03 | 87 |
| 24 | 0.34 | 76 |
| 27 | 0.1 | 94 |
| 31 | 1.03 | 65 |
| 53 | 0.26 | 73 |
| 60 | 0.14 | 83 |
| 65 | 0.20 | 84 |
| 73 | 0.33 | 91 |

It is understood that the foregoing detailed description and accompanying examples are merely illustrative and are not to be taken as limitations upon the scope of the invention, which is defined solely by the appended claims and their equivalents. Various changes and modifications to the described embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

We claim:

1. A compound having formula (I) or a pharmaceutically acceptable salt thereof, or a diastereomer thereof, or an enantiomer thereof,

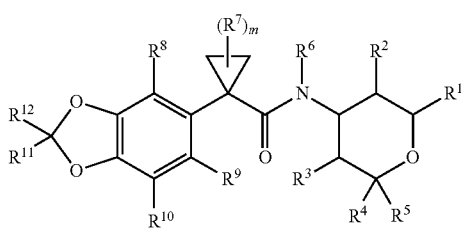

(I)

wherein:

R¹ is phenyl, phenyl fused to a $C_3$-$C_6$cycloalkyl, or phenyl fused to a 4-6-membered heterocycle, wherein the phenyl, the phenyl of phenyl fused to a $C_3$-$C_6$cycloalkyl, or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —NO₂, —OR$^h$, —OC(O)R$^i$, —OC(O)N(R$^h$)₂, —SR$^h$, —S(O)₂R$^h$, —S(O)₂N(R$^h$)₂, —C(O)R$^i$, —C(O)OR$^h$, —C(O) N(R$^h$)₂, —N(R$^h$)₂, —N(R$^h$)C(O)R$^i$, —N(R$^h$)S(O)₂R$^i$, —N(R$^h$)C(O)O(R$^i$), —N(R$^h$)C(O)N(R$^h$)₂, and G$^A$, wherein the $C_1$-$C_6$alkyl is optionally substituted with one, two or three substituents independently selected from the group consisting of fluorine, —OR$^h$, —OC(O)R$^i$, —OC(O)N(R$^h$)₂, —SR$^h$, —S(O)₂R$^h$, —S(O)₂N(R$^h$)₂, —C(O)R$^i$, —C(O)OR$^h$, —C(O)N(R$^h$)₂, —N(R$^h$)₂, —N(R$^h$)C(O)R$^i$, —N(R$^h$)S(O)₂R$^i$, —N(R$^h$)C(O)O(R$^i$), —N(R$^h$)C(O)N(R$^h$)₂, and -G$^B$;

wherein the $C_3$-$C_6$cycloalkyl of phenyl fused to a $C_3$-$C_6$cycloalkyl or the 4-6-membered heterocycle of phenyl fused to a 4-6-membered heterocycle are each optionally substituted with 1, 2 or 3 independently selected $R^s$ groups;

m is 0, 1, 2, or 3;

$R^s$ and $R^t$, at each occurrence, are each independently $C_1$-$C_6$alkyl, halogen, —CN, oxo, —NO₂, —OR$^h$, —OC(O)R$^i$, —OC(O)N(R$^h$)₂, —SR$^h$, —S(O)₂R$^h$, —S(O)₂N(R$^h$)₂, —C(O)R$^i$, —C(O)OR$^h$, —C(O)N(R$^h$)₂, —N(R$^h$)₂, —N(R$^h$)C(O)R$^i$, —N(R$^h$)S(O)₂R$^i$, —N(R$^h$)C(O)O(R$^i$), —N(R$^h$)C(O)N(R$^h$)₂, or G$^C$, wherein the $C_1$-$C_6$alkyl is optionally substituted with one, two or three substituents independently selected from the group consisting of fluorine, —OR$^h$, —OC(O)R$^i$, —OC(O)N(R$^h$)₂, —SR$^h$, —S(O)₂R$^h$, —S(O)₂N(R$^h$)₂, —C(O)R$^i$, —C(O)OR$^h$, —C(O)N(R$^h$)₂, —N(R$^h$)₂, —N(R$^h$)C(O)R$^i$, —N(R$^h$)S(O)₂R$^i$, —N(R$^h$)C(O)O(R$^i$), —N(R$^h$)C(O)N(R$^h$)₂, and G$^D$;

$R^h$, at each occurrence, is independently hydrogen, $C_1$-$C_6$haloalkyl, $C_1$-$C_6$alkyl, or G$^A$, wherein the $C_1$-$C_6$alkyl is optionally substituted with one, two or three substituents independently selected from the group consisting of fluorine, —OR$^j$, —OC(O)N(R$^j$)₂, —SR$^j$, —C(O)OR$^j$, —C(O)N(R$^j$)₂, —N(R$^j$)₂, —CN, and G$^E$;

$R^i$, at each occurrence, is independently $C_1$-$C_6$haloalkyl, $C_1$-$C_6$alkyl, or G$^A$, wherein the $C_1$-$C_6$alkyl is optionally substituted with one, two or three substituents independently selected from the group consisting of fluorine, —OR$^j$, —OC(O)N(R$^j$)₂, —SR$^j$, —C(O)OR$^j$, —C(O)N(R$^j$)₂, —N(R$^j$)₂, —CN, and G$^E$;

$R^2$ and $R^3$ are each independently hydrogen, $C_1$-$C_6$haloalkyl, or $C_1$-$C_6$alkyl;

$R^4$ and $R^5$ are each independently hydrogen, $C_1$-$C_6$haloalkyl, $C_1$-$C_6$alkyl or G$^F$, wherein the $C_1$-$C_6$alkyl is optionally substituted with one, two or three substituents independently selected from the group consisting of fluorine, —OR$^h$, —OC(O)R$^i$, —OC(O)N(R$^h$)₂, —SR$^h$, —S(O)₂R$^h$, —S(O)₂N(R$^h$)₂, —C(O)R$^i$, —C(O)OR$^h$, —C(O)N(R$^h$)₂, —N(R$^h$)₂, —N(R$^h$)C(O)R$^i$, —N(R$^h$)S(O)₂R$^i$, —N(R$^h$)C(O)O(R$^i$), and —N(R$^h$)C(O)N(R$^h$)₂; or $R^4$ and $R^5$ together with the carbon atom to which they are attached, form a $C_3$-$C_6$cycloalkyl or a 4-6-membered heterocycle; wherein the $C_3$-$C_6$cycloalkyl and the 4-6-membered heterocycle are each optionally substituted with 1, 2, or 3 independently selected $R^t$ groups;

$R^6$ is hydrogen, $C_1$-$C_6$haloalkyl, or $C_1$-$C_6$alkyl;

$R^7$ is an optional substituent on the cyclopropyl ring, and at each occurrence, is independently halogen, $C_1$-$C_6$haloalkyl, or $C_1$-$C_6$alkyl;

$R^8$, $R^9$, and $R^{10}$ are each independently hydrogen, halogen, —OR$^j$, $C_1$-$C_6$haloalkyl, or $C_1$-$C_6$alkyl;

$R^{11}$ and $R^{12}$ are each independently hydrogen, $C_1$-$C_3$alkyl, or halogen;

G$^A$, G$^B$, G$^C$, G$^D$, G$^E$, and G$^F$ at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —NO₂, —OR$^j$, —OC(O)R$^k$, —OC(O)N(R$^j$)₂, —SR$^j$, —S(O)₂R$^j$, —S(O)₂N(R$^j$)₂, —C(O)R$^k$, —C(O)OR$^j$, —C(O)N(R$^j$)₂, —N(R$^j$)₂, —N(R$^j$)C(O)R$^k$, —N(R$^j$)S(O)₂R$^k$, —N(R$^j$)C(O)O(R$^k$), —N(R$^j$)C(O)N(R$^j$)₂, —($C_1$-$C_6$alkylenyl)-OR$^j$, —($C_1$-$C_6$alkylenyl)-OC(O)R$^k$, —($C_1$-$C_6$alkylenyl)-OC(O)N(R$^j$)₂, —($C_1$-$C_6$alkylenyl)-SR$^j$, —($C_1$-$C_6$alkylenyl)-S(O)₂R$^j$, —($C_1$-$C_6$alkylenyl)-S(O)₂N(R$^j$)₂, —($C_1$-$C_6$alkylenyl)-C(O)R$^k$, —($C_1$-$C_6$alkylenyl)-C(O)OR$^j$, —($C_1$-$C_6$alkylenyl)-C(O)N(R$^j$)₂, —($C_1$-$C_6$alkylenyl)-N(R$^j$)₂, —($C_1$-$C_6$alkylenyl)-N(R$^j$)C(O)R$^k$, —($C_1$-$C_6$alkylenyl)-N(R$^j$)S(O)₂R$^k$, —($C_1$-$C_6$alkylenyl)-N(R$^j$)C(O)O(R$^k$), —($C_1$-$C_6$alkylenyl)-N(R$^j$)C(O)N(R$^j$)₂, or —($C_1$-$C_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

2. The compound or pharmaceutically acceptable salt of claim 1, wherein $R^2$, $R^3$, $R^4$ and $R^5$ are each hydrogen.

3. The compound or pharmaceutically acceptable salt of claim 2, wherein $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —NO₂, —OR$^h$, —OC(O)R$^i$, —OC(O)N(R$^h$)₂, —SR$^h$, —S(O)₂R$^h$, —S(O)₂N(R$^h$)₂, —C(O)R$^i$, —C(O)OR$^h$, —C(O)N(R$^h$)₂, —N(R$^h$)₂, —N(R$^h$)C(O)R$^i$, —N(R$^h$)S(O)₂R$^i$, —N(R$^h$)C(O)O(R$^i$), —N(R$^h$)C(O)N(R$^h$)₂, and G$^A$, wherein the $C_1$-$C_6$alkyl is optionally substituted with one, two or three substituents independently selected from the group consisting of fluorine, —OR$^h$, —OC(O)R$^i$, —OC(O)N(R$^h$)₂, —SR$^h$, —S(O)₂R$^h$, —S(O)₂N(R$^h$)₂, —C(O)R$^i$, —C(O)OR$^h$, —C(O)N(R$^h$)₂, —N(R$^h$)₂, —N(R$^h$)C(O)R$^i$, —N(R$^h$)S(O)₂R$^i$, —N(R$^h$)C(O)O(R$^i$), —N(R$^h$)C(O)N(R$^h$)₂, and -G$^B$.

4. The compound or pharmaceutically acceptable salt of claim 3, wherein $R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl; and $R^i$, at each occurrence, is independently $C_1$-$C_6$haloalkyl, or $C_1$-$C_6$alkyl.

5. The compound or pharmaceutically acceptable salt of claim 4, wherein $R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl $R^6$ is hydrogen;

m is 0;

$R^8$, $R^9$, and $R^{10}$ are each hydrogen; and $R^{11}$ and $R^{12}$ are each halogen.

6. The compound or pharmaceutically acceptable salt of claim 5, wherein $R^{11}$ and $R^{12}$ are each fluorine.

7. The compound or pharmaceutically acceptable salt of claim 2, wherein the compound or pharmaceutically acceptable salt is a cis diastereomer of formula (II), wherein

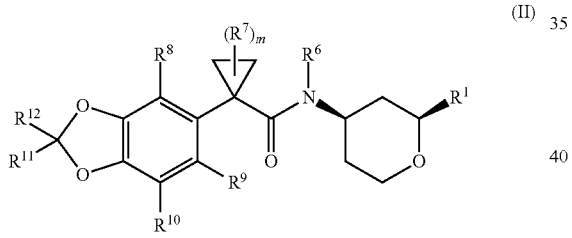

(II)

$R^1$ is phenyl or phenyl fused to a 4-6-membered heterocycle, wherein the phenyl or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$; and wherein the 4-6-membered heterocycle of phenyl fused to a 4-6-membered heterocycle is optionally substituted with 1, 2 or 3 independently selected $R^5$ groups.

8. The compound or pharmaceutically acceptable salt of claim 7, wherein, $R^1$ is phenyl fused to a 4-6-membered heterocycle, wherein the phenyl of phenyl fused to a 4-6-membered heterocycle is optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$; and wherein the 4-6-membered heterocycle of phenyl fused to a 4-6-membered heterocycle is optionally substituted with 1, 2 or 3 independently selected $R^s$ groups.

9. The compound or pharmaceutically acceptable salt of claim 8, wherein $R^1$ is phenyl fused to a 4-6-membered heterocycle, wherein the phenyl of phenyl fused to a 4-6-membered heterocycle is optionally substituted with one, two or three IV groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$; and wherein the 4-6-membered heterocycle of phenyl fused to a 4-6-membered heterocycle is optionally substituted with 1, 2 or 3 independently selected $R^s$ groups;

$R^s$, at each occurrence, is independently $C_1$-$C_6$alkyl, halogen, —CN, oxo, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, or $G^C$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$S(O)_2R^h$, —$SR^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^D$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)OR^j$, —$C(O)N(R^j)_2$, —$N(R^j)_2$, —CN, and $G^E$;

$R^6$ is hydrogen;

m is 0;

$R^8$, $R^9$, and $R^{10}$ are each hydrogen;

$R^{11}$ and $R^{12}$ are each halogen;

$G^A$, $G^C$, $G^D$ and $G^E$ at each occurrence, are each independently cycloalkyl, cycloalkenyl, heterocycle, aryl, or heteroaryl, each of which is independently unsubstituted or substituted with 1, 2, or 3 independently selected $R^u$ groups; wherein $R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —$OC(O)R^k$, —$OC(O)N(R^j)_2$, —$SR^j$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, —$N(R^j)C(O)N(R^j)_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

10. The compound or pharmaceutically acceptable salt of claim 9, wherein R$^{11}$ and R$^{12}$ are each fluorine.

11. The compound or pharmaceutically acceptable salt of claim 1, wherein the compound or pharmaceutically acceptable salt is an enantiomer of formula (IIa)

(IIa)

12. The compound or pharmaceutically acceptable salt of claim 1, wherein the compound or pharmaceutically acceptable salt is an enantiomer of formula (IIb)

(IIb)

13. The compound or pharmaceutically acceptable salt of claim 7, wherein, R$^1$ is phenyl, wherein the phenyl is optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O) N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^1$, —C(O)OR$^h$, —C (O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$.

14. The compound or pharmaceutically acceptable salt of claim 13, wherein

R$^1$ is phenyl, wherein the phenyl is optionally substituted with one, two, or three R$^x$ groups, wherein each R$^x$ group is independently selected from C$_1$-C$_6$alkyl, halogen, —OR$^h$, —C(O)R$^i$, and —C(O)OR$^h$, wherein the C$_1$-C$_6$alkyl is optionally substituted with one, two or three substituents independently selected from the group consisting of fluorine and —OR$^h$;

R$^h$, at each occurrence, is independently hydrogen, C$_1$-C$_6$haloalkyl, or C$_1$-C$_6$alkyl;

R$^i$, at each occurrence, is independently C$_1$-C$_6$haloalkyl, or C$_1$-C$_6$alkyl;

R$^6$ is hydrogen;

m is 0;

R$^8$, R$^9$, and R$^{10}$, are each hydrogen; and

R$^{11}$ and R$^{12}$ are each halogen.

15. The compound or pharmaceutically acceptable salt of claim 14, wherein R$^{11}$ and R$^{12}$ are each fluorine.

16. The compound or pharmaceutically acceptable salt of claim 15, wherein the compound or pharmaceutically acceptable salt is an enantiomer of formula (IIc), wherein (IIc)

each R$^x$ is an optional substituent independently selected from C$_1$-C$_6$alkyl, halogen, —OR$^h$, —C(O)R$^i$, and —C(O)OR$^h$, wherein, the C$_1$-C$_6$alkyl is optionally substituted with one, two or three substituents independently selected from the group consisting of fluorine and —OR$^h$;

R$^h$, at each occurrence, is independently hydrogen, C$_1$-C$_6$haloalkyl, or C$_1$-C$_6$alkyl; and R$^i$, at each occurrence, is independently C$_1$-C$_6$haloalkyl, or C$_1$-C$_6$alkyl.

17. The compound or pharmaceutically acceptable salt of claim 1, wherein the compound or pharmaceutically acceptable salt is an enantiomer of formula (IId), wherein (IId)

each R$^x$ is an optional substituent independently selected from C$_1$-C$_6$alkyl, halogen, —OR$^h$, —C(O)R$^i$, and —C(O)OR$^h$, wherein, the C$_1$-C$_6$alkyl is optionally substituted with one, two or three substituents independently selected from the group consisting of fluorine and —OR$^h$;

R$^h$, at each occurrence, is independently hydrogen, C$_1$-C$_6$haloalkyl, or C$_1$-C$_6$alkyl; and R$^i$, at each occurrence, is independently C$_1$-C$_6$haloalkyl, or C$_1$-C$_6$alkyl.

18. The compound or pharmaceutically acceptable salt of claim 2, wherein the compound or pharmaceutically acceptable salt is a trans diastereomer of formula (III), wherein (III)

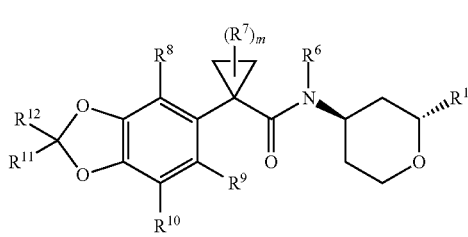

R[1] is phenyl or phenyl fused to a 4-6-membered heterocycle, wherein the phenyl or the phenyl of phenyl fused to a 4-6-membered heterocycle are independently optionally substituted with one, two, or three IV groups, wherein each IV group is independently selected, at each occurrence, from $C_1$-$C_6$alkyl, halogen, —CN, —$NO_2$, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)O$R^h$, —C(O)N($R^h$)$_2$, —N($R^h$)$_2$, —N($R^h$) C(O)$R^i$, —N($R^h$)S(O)$_2R^i$, —N($R^h$)C(O)O($R^i$), —N($R^h$)C(O)N($R^h$)$_2$, and $G^A$, wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)O$R^h$, —C (O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$.

19. The compound or pharmaceutically acceptable salt of claim 18, wherein,

R[1] is phenyl, wherein the phenyl is optionally substituted with one, two, or three IV groups,
wherein each IV group is independently selected, at each occurrence, from $C_1$-$C_6$alkyl, halogen, —CN, —$NO_2$, —$OR^h$, —OC(O)$R^i$, —OC(O)N($R^h$)$_2$, —$SR^h$, —S(O)$_2$ $R^h$, —S(O)$_2$N($R^h$)$_2$, —C(O)$R^i$, —C(O)O$R^h$, —C(O) N($R^h$)$_2$, —N($R^h$)$_2$, —N($R^h$)C(O)$R^1$, —N($R^h$)S(O)$_2R^1$, —N($R^h$)C(O)O($R^i$), —N($R^h$)C(O)N($R^h$)$_2$, and $G^A$,
  wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)O$R^h$, —C (O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$.

20. The compound or pharmaceutically acceptable salt of claim 19, wherein

R[1] is phenyl, wherein the phenyl is optionally substituted with one, two, or three $R^x$ groups, wherein each $R^x$ group is independently selected from $C_1$-$C_6$alkyl, halogen, —$OR^h$, —C(O)$R^i$, and —C(O)O$R^h$,
wherein the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl, or $C_1$-$C_6$alkyl;
$R^6$ is hydrogen;
m is 0;
$R^8$, $R^9$, and $R^{10}$ are each hydrogen; and
$R^{11}$ and $R^{12}$ are each halogen.

21. The compound or pharmaceutically acceptable salt of claim 20, wherein $R^{11}$ and $R^{12}$ are each fluorine.

22. The compound or pharmaceutically acceptable salt of claim 21, wherein the compound or pharmaceutically acceptable salt is an enantiomer of formula (IIIa), wherein (IIIa)

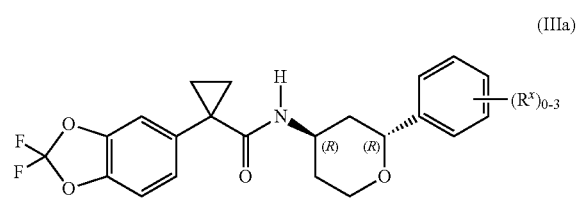

each $R^x$ is an optional substituent independently selected from $C_1$-$C_6$alkyl,
halogen, —$OR^h$, —C(O)$R^i$, and —C(O)O$R^h$,
wherein, the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl; and
$R^i$, at each occurrence, is independently $C_1$-$C_6$haloalkyl, or $C_1$-$C_6$alkyl.

23. The compound or pharmaceutically acceptable salt of claim 1, wherein the compound or pharmaceutically acceptable salt is an enantiomer of formula (IIIb), wherein (IIIb)

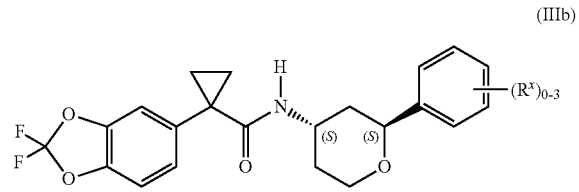

each $R^x$ is an optional substituent independently selected from $C_1$-$C_6$alkyl, halogen, —$OR^h$, —C(O)$R^i$, and —C(O)O$R^h$,
wherein, the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl; and
$R^i$, at each occurrence, is independently $C_1$-$C_6$haloalkyl, or $C_1$-$C_6$alkyl.

24. The compound or pharmaceutically acceptable salt of claim 1, wherein $R^2$, $R^3$, and $R^4$ are hydrogen and $R^5$ is $G^F$; wherein, $G^F$ is $C_3$-$C_7$cycloalkyl, $C_5$-$C_7$cycloalkenyl, heterocycle, aryl or heteroaryl, each of which is independently unsubstituted or substituted with 1, 2, or 3 independently selected $R^u$ groups; wherein
$R^u$, at each occurrence, is independently $C_1$-$C_6$alkyl, $C_2$-$C_6$alkenyl, $C_2$-$C_6$alkynyl, halogen, $C_1$-$C_6$haloalkyl, —CN, oxo, —$NO_2$, —$OR^j$, —OC(O)$R^k$, —OC(O)N ($R^j$)$_2$, —$SR^j$, —S(O)$_2R^j$, —S(O)$_2$N($R^j$)$_2$, —C(O)$R^k$, —C(O)O$R^j$, —C(O)N ($R^j$)$_2$, —N($R^j$)$_2$, —N($R^j$)C(O) $R^k$, —N($R^j$)S(O)$_2R^k$, —N($R^j$)C(O)O($R^k$), —N($R^j$)C (O)N($R^j$)$_2$, —($C_1$-$C_6$alkylenyl)-O$R^j$, —($C_1$-$C_6$alkylenyl)-OC(O)$R^k$, —($C_1$-$C_6$alkylenyl)-OC(O)N ($R^j$)$_2$, —($C_1$-$C_6$alkylenyl)-S$R^j$, —($C_1$-$C_6$alkylenyl)-S (O)$_2R^j$, —($C_1$-$C_6$alkylenyl)-S(O)$_2$N($R^j$)$_2$, —($C_1$-$C_6$alkylenyl)-C(O)$R^k$, —($C_1$-$C_6$alkylenyl)-C(O)O$R^j$, —($C_1$-$C_6$alkylenyl)-C(O)N($R^j$)$_2$, —($C_1$-$C_6$alkylenyl)-

N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

25. The compound or pharmaceutically acceptable salt of claim 24, wherein,

R$^1$ is phenyl, wherein the phenyl is optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;

R$^5$ is C$_3$-C$_7$cycloalkyl or phenyl, wherein the C$_3$-C$_7$cycloalkyl and the phenyl are optionally unsubstituted or substituted with 1, 2, or 3 independently selected R$^u$ groups; wherein R$^u$, at each occurrence, is independently C$_1$-C$_6$alkyl, C$_2$-C$_6$alkenyl, C$_2$-C$_6$alkynyl, halogen, C$_1$-C$_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

26. The compound or pharmaceutically acceptable salt of claim 25, wherein

R$^1$ is phenyl, wherein the phenyl is optionally substituted with one, two, or three R$^x$ groups, wherein each R$^x$ group is independently selected from C$_1$-C$_6$alkyl, halogen, —OR$^h$, —C(O)R$^i$, and —C(O)OR$^h$, wherein the C$_1$-C$_6$alkyl is optionally substituted with one, two or three substituents independently selected from the group consisting of fluorine and —OR$^h$;

R$^h$, at each occurrence, is independently hydrogen, C$_1$-C$_6$haloalkyl, or C$_1$-C$_6$alkyl;

R$^i$, at each occurrence, is independently C$_1$-C$_6$haloalkyl, or C$_1$-C$_6$alkyl;

R$^5$ is phenyl, wherein the phenyl is optionally unsubstituted or substituted with 1, 2, or 3 independently selected R$^u$ groups; wherein, R$^u$, at each occurrence, is independently C$_1$-C$_6$alkyl, halogen, C$_1$-C$_6$haloalkyl, —OR$^j$, —C(O)R$^k$, or —C(O)OR$^j$;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

27. The compound or pharmaceutically acceptable salt of claim 26, wherein

R$^1$ is phenyl, wherein the phenyl is optionally substituted with one, two, or three R$^x$ groups, wherein each R$^x$ group is independently selected from C$_1$-C$_6$alkyl, halogen, —OR$^h$, —C(O)R$^i$, and —C(O)OR$^h$, wherein the C$_1$-C$_6$alkyl is optionally substituted with one, two or three substituents independently selected from the group consisting of fluorine and —OR$^h$;

R$^h$, at each occurrence, is independently hydrogen, C$_1$-C$_6$haloalkyl, or C$_1$-C$_6$alkyl;

R$^i$, at each occurrence, is independently C$_1$-C$_6$haloalkyl, or C$_1$-C$_6$alkyl;

R$^5$ is phenyl, wherein the phenyl is optionally unsubstituted or substituted with 1, 2, or 3 independently selected R$^u$ groups; wherein R$^u$, at each occurrence, is independently C$_1$-C$_6$alkyl, halogen, C$_1$-C$_6$haloalkyl, —OR$^j$, —C(O)R$^k$, or —C(O)OR$^j$;

R$^j$, at each occurrence, is independently hydrogen, C$_1$-C$_6$alkyl, or C$_1$-C$_6$haloalkyl;

R$^k$, at each occurrence, is independently C$_1$-C$_6$alkyl or C$_1$-C$_6$haloalkyl;

R$^6$ is hydrogen;

m is 0;

R$^8$, R$^9$, and R$^{10}$ are each hydrogen; and

R$^{11}$ and R$^{12}$ are each halogen.

28. The compound or pharmaceutically acceptable salt of claim 27, wherein R$^{11}$ and R$^{12}$ are each fluorine.

29. The compound or pharmaceutically acceptable salt of claim 24, wherein the compound or pharmaceutically acceptable salt is a diastereomer of formula (IV), wherein

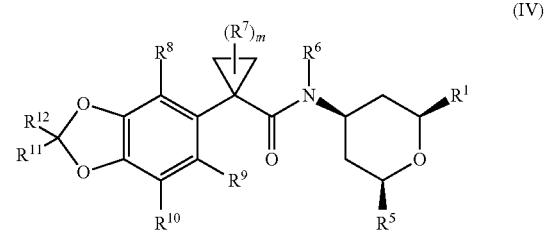

(IV)

R$^1$ is phenyl or phenyl fused to a 4-6-membered heterocycle, wherein the phenyl or the phenyl of phenyl fused to a 4-6-membered heterocycle are independently optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;

wherein the 4-6-membered heterocycle of phenyl fused to a 4-6-membered heterocycle is optionally substituted with 1, 2 or 3 independently selected R$^s$ groups;

R$^5$ is G$^F$; wherein,

G$^F$ is C$_3$-C$_7$cycloalkyl, aryl or heteroaryl, each of which is independently unsubstituted or substituted with 1, 2, or 3 independently selected R$^u$ groups; wherein R$^u$, at each occurrence, is independently C$_1$-C$_6$alkyl, C$_2$-C$_6$alkenyl, C$_2$-C$_6$alkynyl, halogen, C$_1$-C$_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N (R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

30. The compound or pharmaceutically acceptable salt of claim 29, wherein,

R$^1$ is phenyl, wherein the phenyl is optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;

R$^5$ is phenyl; wherein, the phenyl is unsubstituted or substituted with 1, 2, or 3 independently selected R$^u$ groups; wherein R$^u$, at each occurrence, is independently C$_1$-C$_6$alkyl, C$_2$-C$_6$alkenyl, C$_2$-C$_6$alkynyl, halogen, C$_1$-C$_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N (R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

31. The compound or pharmaceutically acceptable salt of claim 30, wherein

R$^1$ is phenyl, wherein the phenyl is optionally substituted with one, two, or three R$^x$ groups, wherein each R$^x$ group is independently selected from C$_1$-C$_6$alkyl, halogen, —OR$^h$, —C(O)R$^i$, and —C(O)OR$^h$, wherein the C$_1$-C$_6$alkyl is optionally substituted with one, two or three substituents independently selected from the group consisting of fluorine and —OR$^h$;

R$^h$, at each occurrence, is independently hydrogen, C$_1$-C$_6$haloalkyl, or C$_1$-C$_6$alkyl;

R$^i$, at each occurrence, is independently C$_1$-C$_6$haloalkyl, or C$_1$-C$_6$alkyl;

R$^5$ is phenyl, wherein the phenyl is optionally unsubstituted or substituted with 1, 2, or 3 independently selected R$^u$ groups; wherein R$^u$, at each occurrence, is independently C$_1$-C$_6$alkyl, halogen, C$_1$-C$_6$haloalkyl, —OR$^j$, —C(O)R$^k$, or —C(O)OR$^j$;

R$^j$, at each occurrence, is independently hydrogen, C$_1$-C$_6$alkyl, or C$_1$-C$_6$haloalkyl;

R$^k$, at each occurrence, is independently C$_1$-C$_6$alkyl or C$_1$-C$_6$haloalkyl;

R$^6$ is hydrogen;

m is 0;

R$^8$, R$^9$, and R$^{10}$ are each hydrogen; and

R$^{11}$ and R$^{12}$ are each halogen.

32. The compound or pharmaceutically acceptable salt of claim 31, wherein R$^{11}$ and R$^{12}$ are each fluorine.

33. The compound or pharmaceutically acceptable salt of claim 32, wherein the compound or pharmaceutically acceptable salt is an enantiomer of formula (IVa), wherein

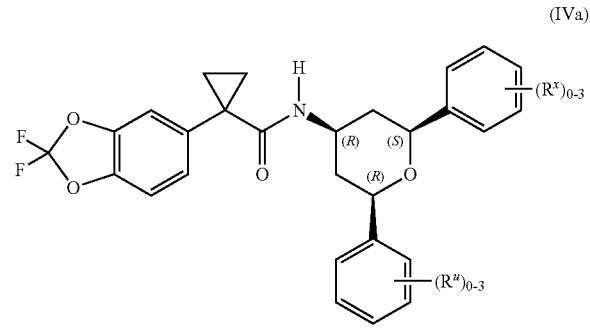

(IVa)

R$^x$ is an optional substituent independently selected at each occurrence from C$_1$-C$_6$alkyl, halogen, —OR$^h$, —C(O)R$^i$, and —C(O)OR$^h$, wherein, the C$_1$-C$_6$alkyl is optionally substituted with one, two or three substituents independently selected from the group consisting of fluorine and —OR$^h$;

R$^h$ is hydrogen, C$_1$-C$_6$haloalkyl, or C$_1$-C$_6$alkyl;

R$^i$ is C$_1$-C$_6$haloalkyl, or C$_1$-C$_6$alkyl;

R$^u$ is an optional substituent independently selected at each occurrence from C$_1$-C$_6$alkyl, halogen, C$_1$-C$_6$haloalkyl, —OR$^j$, —C(O)R$^k$, or —C(O)OR$^j$;

R$^j$, at each occurrence, is independently hydrogen, C$_1$-C$_6$alkyl, or C$_1$-C$_6$haloalkyl; and R$^k$, at each occurrence, is independently C$_1$-C$_6$alkyl or C$_1$-C$_6$haloalkyl.

34. The compound or pharmaceutically acceptable salt of claim 1, wherein the compound or pharmaceutically acceptable salt is an enantiomer of formula (IVb), wherein

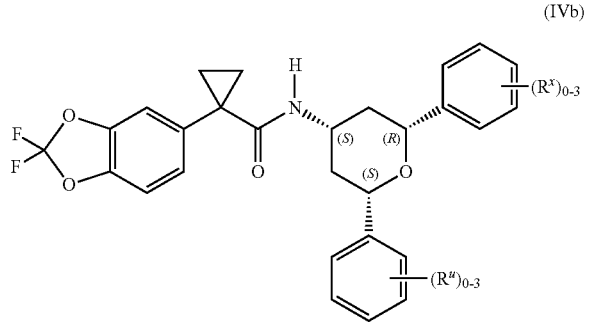

(IVb)

R$^x$ is an optional substituent independently selected at each occurrence from C$_1$-C$_6$alkyl, halogen, —OR$^h$, —C(O)R$^i$, and —C(O)OR$^h$,
wherein, the C$_1$-C$_6$alkyl is optionally substituted with one, two or three substituents independently selected from the group consisting of fluorine and —OR$^h$;
R$^h$, at each occurrence, is independently hydrogen, C$_1$-C$_6$haloalkyl, or C$_1$-C$_6$alkyl;
R$^i$, at each occurrence, is independently C$_1$-C$_6$haloalkyl, or C$_1$-C$_6$alkyl;
R$^u$ is an optional substituent independently selected at each occurrence from C$_1$-C$_6$alkyl, halogen, C$_1$-C$_6$haloalkyl, —OR$^j$, —C(O)R$^k$, or —C(O)OR$^j$;
R$^j$, at each occurrence, is independently hydrogen, C$_1$-C$_6$alkyl, or C$_1$-C$_6$haloalkyl; and
R$^k$, at each occurrence, is independently C$_1$-C$_6$alkyl or C$_1$-C$_6$haloalkyl.

35. The compound or pharmaceutically acceptable salt of claim 24, wherein the compound or pharmaceutically acceptable salt is a diastereomer of formula (V), wherein

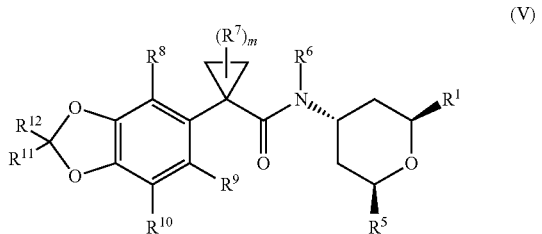

(V)

R$^1$ is phenyl or phenyl fused to a 4-6-membered heterocycle, wherein the phenyl or the phenyl of phenyl fused to a 4-6-membered heterocycle are independently optionally substituted with one, two or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O) N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$,
wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C (O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;
wherein the 4-6-membered heterocycle of phenyl fused to a 4-6-membered heterocycle is optionally substituted with 1, 2 or 3 independently selected R$^s$ groups;
R$^5$ is G$^F$; wherein,
G$^F$ is C$_3$-C$_7$cycloalkyl, aryl or heteroaryl, each of which is independently unsubstituted or substituted with 1, 2, or 3 independently selected R$^u$ groups; wherein
R$^u$, at each occurrence, is independently C$_1$-C$_6$alkyl, C$_2$-C$_6$alkenyl, C$_2$-C$_6$alkynyl, halogen, C$_1$-C$_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N (R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;
R$^j$, at each occurrence, is independently hydrogen, C$_1$-C$_6$alkyl, or C$_1$-C$_6$haloalkyl; and
R$^k$, at each occurrence, is independently C$_1$-C$_6$alkyl or C$_1$-C$_6$haloalkyl.

36. The compound or pharmaceutically acceptable salt of claim 35, wherein,
R$^1$ is phenyl, wherein the phenyl is optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O) N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$,
wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C (O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;
R$^5$ is phenyl; wherein, the phenyl is unsubstituted or substituted with 1, 2, or 3 independently selected R$^u$ groups; wherein
R$^u$, at each occurrence, is independently C$_1$-C$_6$alkyl, C$_2$-C$_6$alkenyl, C$_2$-C$_6$alkynyl, halogen, C$_1$-C$_6$haloalkyl, —CN, oxo, —NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^k$, —C(O)OR$^j$, —C(O)N (R$^j$)$_2$, —N(R$^j$)$_2$, —N(R$^j$)C(O) R$^k$, —N(R$^j$)S(O)$_2$R$^k$, —N(R$^j$)C(O)O(R$^k$), —N(R$^j$)C(O)N(R$^j$)$_2$, —(C$_1$-C$_6$alkylenyl)-OR$^j$, —(C$_1$-C$_6$alkylenyl)-OC(O)R$^k$, —(C$_1$-C$_6$alkylenyl)-OC(O)N(R$^j$)$_2$, —(C$_1$-C$_6$alkylenyl)-SR$^j$, —(C$_1$-C$_6$alkylenyl)-S(O)$_2$R$^j$, —(C$_1$-C$_6$alkylenyl)-S(O)$_2$N(R$^j$)$_2$, —(C$_1$-C$_6$alkylenyl)-C(O)R$^k$, —(C$_1$-C$_6$alkylenyl)-C(O)OR$^j$, —(C$_1$-C$_6$alkylenyl)-C(O)N(R$^j$)$_2$, —(C$_1$-C$_6$alkylenyl)-N(R$^j$)$_2$, —(C$_1$-C$_6$alkylenyl)-N(R$^j$)C(O)R$^k$, —(C$_1$-C$_6$alkylenyl)-N(R$^j$)S(O)$_2$R$^k$, —(C$_1$-C$_6$alkylenyl)-N(R$^j$)C(O)O(R$^k$), —(C$_1$-C$_6$alkylenyl)-N(R$^j$)C(O)N(R$^j$)$_2$, or —(C$_1$-C$_6$alkylenyl)-CN;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

37. The compound or pharmaceutically acceptable salt of claim 36, wherein $R^1$ is phenyl, wherein the phenyl is optionally substituted with one, two or three $R^x$ groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl;

$R^5$ is phenyl, wherein the phenyl is optionally unsubstituted or substituted with 1, 2, or 3 independently selected $R^u$ groups; wherein $R^u$, at each occurrence, is independently $C_1$-$C_6$alkyl, halogen, $C_1$-$C_6$haloalkyl, —$OR^j$, —$C(O)R^k$, or —$C(O)OR^j$;

$R^j$, at each occurrence, is independently hydrogen, $C_1$-$C_6$alkyl, or $C_1$-$C_6$haloalkyl;

$R^k$, at each occurrence, is independently $C_1$-$C_6$alkyl or $C_1$-$C_6$haloalkyl;

$R^6$ is hydrogen;

m is 0;

$R^8$, $R^9$, and $R^{10}$ are each hydrogen; and $R^{11}$ and $R^{12}$ are each halogen.

38. The compound or pharmaceutically acceptable salt of claim 37, wherein $R^{11}$ and $R^{12}$ are each fluorine.

39. The compound or pharmaceutically acceptable salt of claim 38, wherein the compound or pharmaceutically acceptable salt is an enantiomer of formula (Va), wherein

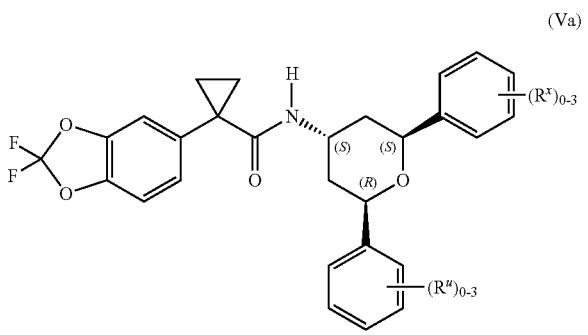

(Va)

$R^x$ is an optional substituent independently selected at each occurrence from $C_1$-$C_6$alkyl, halogen, —$OR^h$, —$C(O)R^i$, and —$C(O)OR^h$, wherein, the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl;

$R^u$ is an optional substituent independently selected at each occurrence from $C_1$-$C_6$alkyl, halogen, $C_1$-$C_6$haloalkyl, —$OR^j$, —$C(O)R^k$, or —$C(O)OR^j$;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

40. The compound or pharmaceutically acceptable salt of claim 1, wherein the compound or pharmaceutically acceptable salt is an enantiomer of formula (Vb), wherein

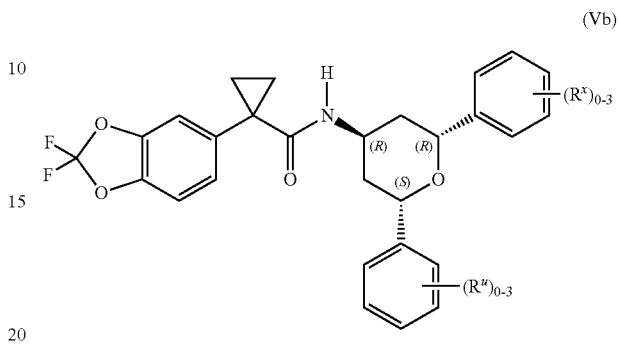

(Vb)

$R^x$ is an optional substituent independently selected at each occurrence from $C_1$-$C_6$alkyl, halogen, —$OR^h$, —$C(O)R^i$, and —$C(O)OR^h$, wherein, the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl;

$R^u$ is an optional substituent independently selected at each occurrence from $C_1$-$C_6$alkyl, halogen, $C_1$-$C_6$haloalkyl, —$OR^j$, —$C(O)R^k$, and —$C(O)OR^j$;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

41. The compound or pharmaceutically acceptable salt of claim 25, wherein $R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl;

$R^5$ is cycloalkyl, wherein the cycloalkyl is optionally unsubstituted or substituted with 1, 2, or 3 independently selected $R^u$ groups; wherein $R^u$, at each occurrence, is independently $C_1$-$C_6$alkyl, $C_1$-$C_6$haloalkyl, —$C(O)R^k$, or —$C(O)OR^j$;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

42. The compound or pharmaceutically acceptable salt of claim 41, wherein $R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl, or $C_1$-$C_6$alkyl;
$R^5$ is cycloalkyl, wherein the cycloalkyl is optionally unsubstituted or substituted with 1, 2, or 3 independently selected $R^u$ groups; wherein
$R^u$, at each occurrence, is independently $C_1$-$C_6$alkyl, $C_1$-$C_6$haloalkyl, —$C(O)R^k$, or —$C(O)OR^j$;
$R^j$, at each occurrence, is independently hydrogen, $C_1$-$C_6$alkyl, or $C_1$-$C_6$haloalkyl;
$R^k$, at each occurrence, is independently $C_1$-$C_6$alkyl or $C_1$-$C_6$haloalkyl;
$R^6$ is hydrogen;
m is 0;
$R^8$, $R^9$, and $R^{10}$ are each hydrogen; and
$R^{11}$ and $R^{12}$ are each halogen.
43. The compound or pharmaceutically acceptable salt of claim 42, wherein $R^{11}$ and $R^{12}$ are each fluorine.
44. The compound or pharmaceutically acceptable salt of claim 29, wherein,
$R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$,
wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;
$R^5$ is $C_3$-$C_7$cycloalkyl; wherein, the $C_3$-$C_7$cycloalkyl is unsubstituted or substituted with 1, 2, or 3 independently selected $R^u$ groups; wherein
$R^u$, at each occurrence, is independently $C_1$-$C_6$alkyl, $C_1$-$C_6$haloalkyl, —$C(O)R^k$, or —$C(O)OR^j$;
$R^j$, at each occurrence, is independently hydrogen, $C_1$-$C_6$alkyl, or $C_1$-$C_6$haloalkyl; and
$R^k$, at each occurrence, is independently $C_1$-$C_6$alkyl or $C_1$-$C_6$haloalkyl.
45. The compound or pharmaceutically acceptable salt of claim 44, wherein
$R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$,
wherein the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl, or $C_1$-$C_6$alkyl;
$R^5$ is $C_3$-$C_7$cycloalkyl, wherein the $C_3$-$C_7$cycloalkyl is optionally unsubstituted or substituted with 1, 2, or 3 independently selected $R^u$ groups; wherein
$R^u$, at each occurrence, is independently $C_1$-$C_6$alkyl, $C_1$-$C_6$haloalkyl, —$C(O)R^k$, or —$C(O)OR^j$;
$R^j$, at each occurrence, is independently hydrogen, $C_1$-$C_6$alkyl, or $C_1$-$C_6$haloalkyl;
$R^k$, at each occurrence, is independently $C_1$-$C_6$alkyl or $C_1$-$C_6$haloalkyl;
$R^6$ is hydrogen;
m is 0;
$R^8$, $R^9$, and $R^{10}$ are each hydrogen; and
$R^{11}$ and $R^{12}$ are each halogen.
46. The compound or pharmaceutically acceptable salt of claim 45, wherein $R^{11}$ and $R^{12}$ are each fluorine.
47. The compound or pharmaceutically acceptable salt of claim 46, wherein the compound or pharmaceutically acceptable salt is an enantiomer of formula (IVc), wherein

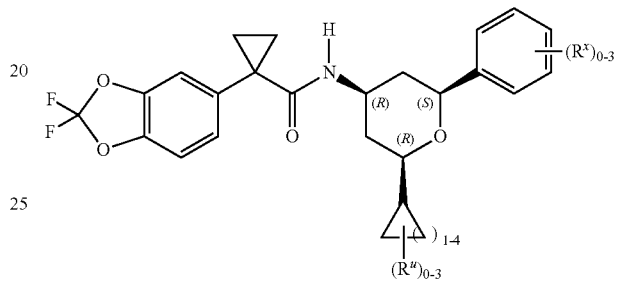

(IVc)

$R^x$ is an optional substituent independently selected at each occurrence from $C_1$-$C_6$alkyl, halogen, —$OR^h$, —$C(O)R^i$, and —$C(O)OR^h$,
wherein, the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl, or $C_1$-$C_6$alkyl;
$R^u$ is an optional substituent independently selected at each occurrence from $C_1$-$C_6$alkyl, $C_1$-$C_6$haloalkyl, —$C(O)R^k$, and —$C(O)OR^j$;
$R^j$, at each occurrence, is independently hydrogen, $C_1$-$C_6$alkyl, or $C_1$-$C_6$haloalkyl; and
$R^k$, at each occurrence, is independently $C_1$-$C_6$alkyl or $C_1$-$C_6$haloalkyl.
48. The compound or pharmaceutically acceptable salt of claim 1, wherein the compound or pharmaceutically acceptable salt is an enantiomer of formula (IVd), wherein

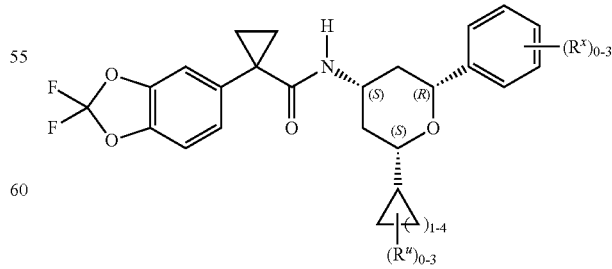

(IVd)

$R^x$ is an optional substituent independently selected at each occurrence from $C_1$-$C_6$alkyl, halogen, —$OR^h$, —$C(O)R^i$, and —$C(O)OR^h$, wherein, the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl;

$R^u$ is an optional substituent independently selected at each occurrence from $C_1$-$C_6$alkyl, $C_1$-$C_6$haloalkyl, —$C(O)R^k$, and —$C(O)OR^j$;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

49. The compound or pharmaceutically acceptable salt of claim 35, wherein, $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;

$R^5$ is $C_3$-$C_7$cycloalkyl; wherein, the $C_3$-$C_7$cycloalkyl is unsubstituted or substituted with 1, 2, or 3 independently selected $R^u$ groups; wherein $R^u$, at each occurrence, is independently $C_1$-$C_6$alkyl, $C_1$-$C_6$haloalkyl, —$C(O)R^k$, or —$C(O)OR^j$;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

50. The compound or pharmaceutically acceptable salt of claim 49, wherein $R^1$ is phenyl, wherein the phenyl is optionally substituted with one, two or three $R^x$ groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl;

$R^5$ is $C_3$-$C_7$cycloalkyl; wherein, the $C_3$-$C_7$cycloalkyl is unsubstituted or substituted with 1, 2, or 3 independently selected $R^u$ groups; wherein $R^u$, at each occurrence, is independently $C_1$-$C_6$alkyl, $C_1$-$C_6$haloalkyl, —$C(O)R^k$, or —$C(O)OR^j$;

$R^j$, at each occurrence, is independently hydrogen, $C_1$-$C_6$alkyl, or $C_1$-$C_6$haloalkyl;

$R^k$, at each occurrence, is independently $C_1$-$C_6$alkyl or $C_1$-$C_6$haloalkyl;

m is 0;

$R^8$, $R^9$, and $R^{10}$ are each hydrogen; and $R^{11}$ and $R^{12}$ are each halogen.

51. The compound or pharmaceutically acceptable salt of claim 50, wherein $R^{11}$ and $R^{12}$ are each fluorine.

52. The compound or pharmaceutically acceptable salt of claim 51, wherein the compound or pharmaceutically acceptable salt is an enantiomer of formula (Vc), wherein

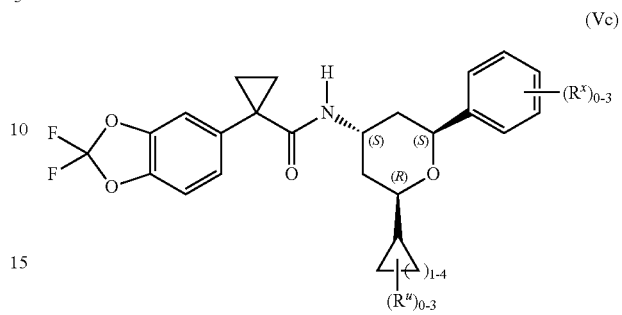

$R^x$, at each occurrence, is an optional substituent independently selected from $C_1$-$C_6$alkyl, halogen, —$OR^h$, —$C(O)R^i$, and —$C(O)OR^h$, wherein, the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl;

$R^u$, at each occurrence, is independently $C_1$-$C_6$alkyl, $C_1$-$C_6$haloalkyl, —$C(O)R^k$, or —$C(O)OR^j$;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

53. The compound or pharmaceutically acceptable salt of claim 1, wherein the compound or pharmaceutically acceptable salt is an enantiomer of formula (Vd), wherein

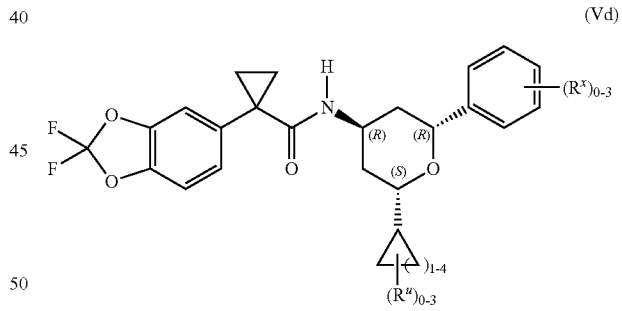

$R^x$, at each occurrence, is an optional substituent independently selected from $C_1$-$C_6$alkyl, halogen, —$OR^h$, —$C(O)R^i$, and —$C(O)OR^h$, wherein, the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl;

$R^u$, at each occurrence, is an optional substituent independently selected from $C_1$-$C_6$alkyl, $C_1$-$C_6$haloalkyl, —$C(O)R^k$, and —$C(O)OR^j$;

$R^j$, at each occurrence, is independently hydrogen, $C_1$-$C_6$alkyl, or $C_1$-$C_6$haloalkyl; and $R^k$, at each occurrence, is independently $C_1$-$C_6$alkyl or $C_1$-$C_6$haloalkyl.

54. The compound or pharmaceutically acceptable salt of claim 1, wherein $R^2$, $R^3$, and $R^4$ are hydrogen and $R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$.

55. The compound or pharmaceutically acceptable salt of claim 54, wherein,
$R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^D$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$,
wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;
$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;
$R^h$, at each occurrence, is independently hydrogen, $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$C(O)OR^j$, —$C(O)N(R^j)_2$, —$N(R^j)_2$, —CN, and $G^E$; and
$R^i$, at each occurrence, is independently $C_1$-$C_6$haloalkyl, $C_1$-$C_6$alkyl, or $G^A$, wherein the $C_1$-$C_6$alkyl is optionally substituted with one, two or three substituents independently selected from the group consisting of fluorine, —$OR^j$, —$OC(O)N(R^j)_2$, —$SR^j$, —$C(O)N(R^j)_2$, —$N(R^j)_2$, —CN, and $G^E$.

56. The compound or pharmaceutically acceptable salt of claim 55, wherein
$R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$,
wherein the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl or $C_1$-$C_6$alkyl; and
$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$.

57. The compound or pharmaceutically acceptable salt of claim 56, wherein
$R^1$ is phenyl, wherein the phenyl is optionally substituted with one, two, or three $R^x$ groups, wherein each $R^x$ group is independently selected from $C_1$-$C_6$alkyl, halogen, —$OR^h$, —$C(O)R^i$, and —$C(O)OR^h$,
wherein the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl or $C_1$-$C_6$alkyl;
$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;
$R^6$ is hydrogen;
m is 0;
$R^8$, $R^9$, and $R^{10}$ are each hydrogen; and
$R^{11}$ and $R^{12}$ are each halogen.

58. The compound or pharmaceutically acceptable salt of claim 57, wherein $R^{11}$ and $R^{12}$ are each fluorine.

59. The compound or pharmaceutically acceptable salt of claim 54, wherein the compound or pharmaceutically acceptable salt is a diastereomer of formula (IV), wherein

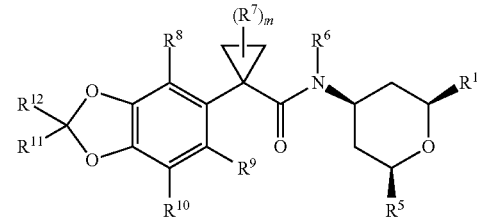

(IV)

$R^1$ is phenyl or phenyl fused to a 4-6-membered heterocycle, wherein the phenyl or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$,
wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;
wherein the 4-6-membered heterocycle of phenyl fused to a 4-6-membered heterocycle is optionally substituted with 1, 2 or 3 independently selected $R^s$ groups;
$R^h$, at each occurrence, is independently hydrogen, $C_1$-$C_6$haloalkyl, or $C_1$-$C_6$alkyl;

R$^i$, at each occurrence, is independently C$_1$-C$_6$haloalkyl or C$_1$-C$_6$alkyl; and R$^5$ is C$_1$-C$_6$alkyl, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), and —N(R$^h$)C(O)N(R$^h$)$_2$.

60. The compound or pharmaceutically acceptable salt of claim 59, wherein,

R$^1$ is phenyl, wherein the phenyl is optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;

R$^h$, at each occurrence, is independently hydrogen, C$_1$-C$_6$haloalkyl, or C$_1$-C$_6$alkyl;

R$^i$, at each occurrence, is independently C$_1$-C$_6$haloalkyl or C$_1$-C$_6$alkyl; and R$^5$ is C$_1$-C$_6$alkyl, wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), and —N(R$^h$)C(O)N(R$^h$)$_2$.

61. The compound or pharmaceutically acceptable salt of claim 60, wherein

R$^1$ is phenyl, wherein the phenyl is optionally substituted with one, two, or three R$^x$ groups, wherein each R$^x$ group is independently selected from C$_1$-C$_6$alkyl, halogen, —OR$^h$, —C(O)R$^i$, and —C(O)OR$^h$, wherein the C$_1$-C$_6$alkyl is optionally substituted with one, two or three substituents independently selected from the group consisting of fluorine and —OR$^h$;

R$^h$, at each occurrence, is independently hydrogen, C$_1$-C$_6$haloalkyl, or C$_1$-C$_6$alkyl;

R$^i$, at each occurrence, is independently C$_1$-C$_6$haloalkyl or C$_1$-C$_6$alkyl;

R$^5$ is C$_1$-C$_6$alkyl, wherein the C$_1$-C$_6$alkyl is is optionally substituted with one, two or three substituents independently selected from the group consisting of fluorine, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), and —N(R$^h$)C(O)N(R$^h$)$_2$;

R$^6$ is hydrogen;

m is 0;

R$^8$, R$^9$, and R$^{10}$ are each hydrogen; and

R$^{11}$ and R$^{12}$ are each halogen.

62. The compound or pharmaceutically acceptable salt of claim 61, wherein R$^{11}$ and R$^{12}$ are each fluorine.

63. The compound or pharmaceutically acceptable salt of claim 62, wherein the compound or pharmaceutically acceptable salt is an enantiomer of formula (IVe), wherein

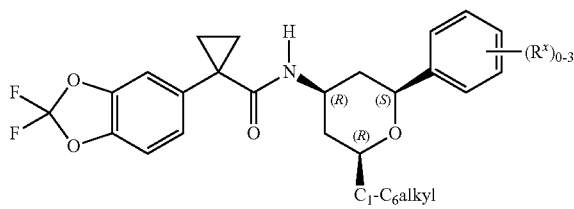

(IVe)

R$^x$, at each occurrence, is an optional substituent independently selected from C$_1$-C$_6$alkyl, halogen, —OR$^h$, —C(O)R$^i$, and —C(O)OR$^h$, wherein, the C$_1$-C$_6$alkyl is optionally substituted with one, two or three substituents independently selected from the group consisting of fluorine and —OR$^h$;

R$^h$, at each occurrence, is independently hydrogen, C$_1$-C$_6$haloalkyl, or C$_1$-C$_6$alkyl; and R$^i$, at each occurrence, is independently C$_1$-C$_6$haloalkyl, or C$_1$-C$_6$alkyl.

64. The compound or pharmaceutically acceptable salt of claim 1, wherein the compound or pharmaceutically acceptable salt is an enantiomer of formula (IVf), wherein

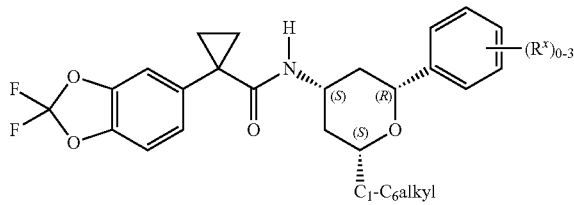

(IVf)

R$^x$, at each occurrence, is an optional substituent independently selected from C$_1$-C$_6$alkyl, halogen, —OR$^h$, —C(O)R$^i$, and —C(O)OR$^h$, wherein, the C$_1$-C$_6$alkyl is optionally substituted with one, two or three substituents independently selected from the group consisting of fluorine and —OR$^h$;

R$^h$, at each occurrence, is independently hydrogen, C$_1$-C$_6$haloalkyl, or C$_1$-C$_6$alkyl; and R$^i$, at each occurrence is independently is C$_1$-C$_6$haloalkyl, or C$_1$-C$_6$alkyl.

65. The compound or pharmaceutically acceptable salt of claim 54, wherein the compound or pharmaceutically acceptable salt is a diastereomer of formula (V), wherein

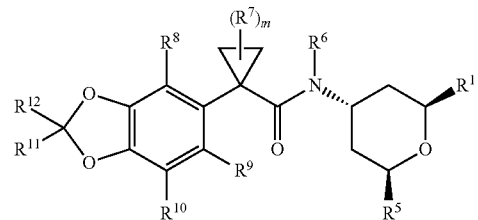

(V)

R$^1$ is phenyl or phenyl fused to a 4-6-membered heterocycle, wherein the phenyl or the phenyl of phenyl fused to a 4-6-membered heterocycle are independently optionally substituted with one, two or three R$^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;

wherein the 4-6-membered heterocycle of phenyl fused to a 4-6-membered heterocycle is optionally substituted with 1, 2 or 3 independently selected $R^s$ groups;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl or $C_1$-$C_6$alkyl; and $R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$.

66. The compound or pharmaceutically acceptable salt of claim 65, wherein, $R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and $G^A$, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^i$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, —$N(R^h)C(O)N(R^h)_2$, and -$G^B$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl or $C_1$-$C_6$alkyl; and $R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$.

67. The compound or pharmaceutically acceptable salt of claim 66, wherein $R^1$ is phenyl, wherein the phenyl is optionally substituted with one, two or three $R^x$ groups, wherein each $R^x$ group is independently selected from $C_1$-$C_6$alkyl, halogen, —$OR^h$, —$C(O)R^i$, and —$C(O)OR^h$, wherein the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl or $C_1$-$C_6$alkyl;

$R^5$ is $C_1$-$C_6$alkyl, wherein the $C_1$-$C_6$alkyl is optionally substituted with one, two or three substituents independently selected from the group consisting of fluorine, —$OR^h$, —$OC(O)R^i$, —$OC(O)N(R^h)_2$, —$SR^h$, —$S(O)_2R^h$, —$S(O)_2N(R^h)_2$, —$C(O)R^i$, —$C(O)OR^h$, —$C(O)N(R^h)_2$, —$N(R^h)_2$, —$N(R^h)C(O)R^i$, —$N(R^h)S(O)_2R^i$, —$N(R^h)C(O)O(R^i)$, and —$N(R^h)C(O)N(R^h)_2$;

$R^6$ is hydrogen;

m is 0;

$R^8$, $R^9$, and $R^{10}$ are each hydrogen; and $R^{11}$ and $R^{12}$ are each halogen.

68. The compound or pharmaceutically acceptable salt of claim 67, wherein $R^{11}$ and $R^{12}$ are each fluorine.

69. The compound or pharmaceutically acceptable salt of claim 68, wherein the compound or pharmaceutically acceptable salt is an enantiomer of formula (Ve), wherein

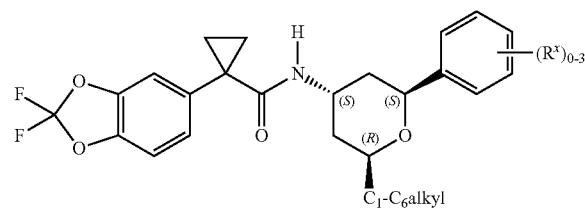

(Ve)

$R^x$, at each occurrence, is an optional substituent independently selected from $C_1$-$C_6$alkyl, halogen, —$OR^h$, —$C(O)R^i$, and —$C(O)OR^h$, wherein, the $C_1$-$C_6$alkyl is optionally substituted with one, two or three substituents independently selected from the group consisting of fluorine and —$OR^h$;

$R^h$ is hydrogen, $C_1$-$C_6$haloalkyl, or $C_1$-$C_6$alkyl; and $R^i$, at each occurrence, is independently $C_1$-$C_6$haloalkyl or $C_1$-$C_6$alkyl.

70. The compound or pharmaceutically acceptable salt of claim 1, wherein the compound or pharmaceutically acceptable salt is an enantiomer of formula (Vf), wherein

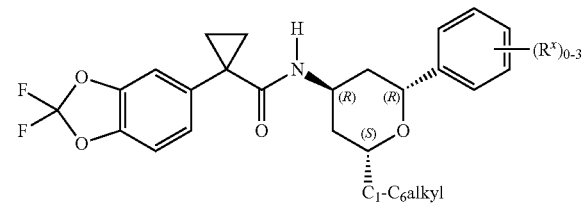

(Vf)

$R^x$, at each occurrence, is an optional substituent independently selected from $C_1$-$C_6$alkyl, halogen, —$OR^h$, —$C(O)R^i$, and —$C(O)OR^h$, wherein, the $C_1$-$C_6$alkyl is optionally substituted with one, two or three substituents independently selected from the group consisting of fluorine and —$OR^h$;

$R^h$, at each occurrence, is independently hydrogen, $C_1$-$C_6$haloalkyl, or $C_1$-$C_6$alkyl; and $R^i$, at each occurrence, is independently $C_1$-$C_6$haloalkyl or $C_1$-$C_6$alkyl.

71. The compound or pharmaceutically acceptable salt of claim 1, wherein $R^2$ and $R^3$ are each hydrogen and $R^4$ and $R^5$ are each $C_1$-$C_6$alkyl.

72. The compound or pharmaceutically acceptable salt of claim 71, wherein,
$R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —OC(O)$R^i$, —OC(O)N($R^h$)$_2$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^A$,
wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$.

73. The compound or pharmaceutically acceptable salt of claim 72, wherein
$R^1$ is phenyl, wherein the phenyl is optionally substituted with one, two, or three $R^x$ groups, wherein each $R^x$ group is independently selected from $C_1$-$C_6$alkyl, halogen —C(O)$R^i$, and —C(O)$OR^h$,
wherein the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl; and
$R^i$, at each occurrence, is independently $C_1$-$C_6$haloalkyl or $C_1$-$C_6$alkyl.

74. The compound or pharmaceutically acceptable salt of claim 73, wherein
$R^1$ is phenyl, wherein the phenyl is optionally substituted with one, two, or three $R^x$ groups, wherein each $R^x$ group is independently selected from $C_1$-$C_6$alkyl, halogen —C(O)$R^i$, and —C(O)$OR^h$,
wherein the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl or $C_1$-$C_6$alkyl;
$R^6$ is hydrogen;
m is 0;
$R^8$, $R^9$, and $R^{10}$ are each hydrogen; and
$R^{11}$ and $R^{12}$ are each halogen.

75. The compound or pharmaceutically acceptable salt of claim 74, wherein $R^{11}$ and $R^{12}$ are each fluorine.

76. The compound or pharmaceutically acceptable salt of claim 71, wherein the compound or pharmaceutically acceptable salt is a cis diastereomer of formula (VI), wherein

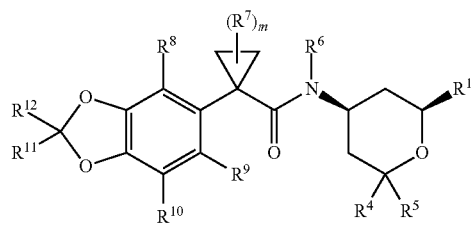

(VI)

$R^1$ is phenyl or phenyl fused to a 4-6-membered heterocycle, wherein the phenyl or the phenyl of phenyl fused to a 4-6-membered heterocycle are independently optionally substituted with one, two, or three $R^x$ groups, wherein each $R^x$ group is independently selected, at each occurrence, from $C_1$-$C_6$alkyl, halogen, —CN, —$NO_2$, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^A$;
wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —$SR^h$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$;
wherein the 4-6-membered heterocycle of phenyl fused to a 4-6-membered heterocycle is optionally substituted with 1, 2 or 3 independently selected $R^s$ groups; and
$R^4$ and $R^5$ are each $C_1$-$C_6$alkyl.

77. The compound or pharmaceutically acceptable salt of claim 76, wherein,
$R^1$ is phenyl, wherein the phenyl is optionally substituted with one, two, or three $R^x$ groups, wherein each $R^x$ group is independently selected, at each occurrence, from $C_1$-$C_6$alkyl, halogen, —CN, —$NO_2$, —$OR^h$, —OC(O)$R^i$, —OC(O)N($R^h$)$_2$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and $G^A$,
wherein the $C_1$-$C_6$alkyl is optionally substituted with one, two or three substituents independently selected from the group consisting of fluorine, —$OR^h$, —OC(O)$R^i$, —OC(O)N($R^h$)$_2$, —S(O)$_2R^h$, —S(O)$_2$N($R^h$)$_2$, —C(O)$R^i$, —C(O)$OR^h$, —C(O)N($R^h$)$_2$, —N($R^h$)$_2$, —N($R^h$)C(O)$R^i$, —N($R^h$)S(O)$_2R^i$, —N($R^h$)C(O)O($R^i$), —N($R^h$)C(O)N($R^h$)$_2$, and -$G^B$.

78. The compound or pharmaceutically acceptable salt of claim 77, wherein
$R^1$ is phenyl, wherein the phenyl is optionally substituted with one, two, or three $R^x$ groups, wherein each $R^x$ group is independently selected from $C_1$-$C_6$alkyl, halogen, —C(O)$R^i$, and —C(O)$OR^h$,
wherein the $C_1$-$C_6$alkyl is optionally substituted with one, two or three substituents independently selected from the group consisting of fluorine and —$OR^h$;
$R^h$, at each occurrence, is independently hydrogen, $C_1$-$C_6$haloalkyl, or $C_1$-$C_6$alkyl;
$R^i$, at each occurrence, is independently $C_1$-$C_6$haloalkyl or $C_1$-$C_6$alkyl;
$R^6$ is hydrogen;
m is 0;
$R^8$, $R^9$, and $R^{10}$ are each hydrogen; and
$R^{11}$ and $R^{12}$ are each halogen.

79. The compound or pharmaceutically acceptable salt of claim 78, wherein $R^{11}$ and $R^{12}$ are each fluorine.

80. The compound or pharmaceutically acceptable salt of claim 79, wherein the compound or pharmaceutically acceptable salt is an enantiomer of formula (VIa), wherein

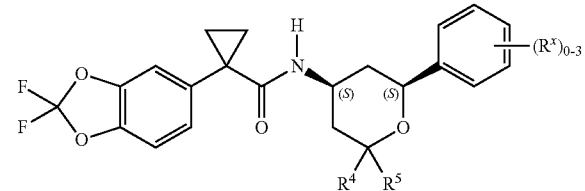

(VIa)

R$^x$, at each occurrence, is an optional substituent independently selected from C$_1$-C$_6$alkyl, halogen, —C(O)R$^i$, and —C(O)OR$^h$,
wherein, the C$_1$-C$_6$alkyl is optionally substituted with one, two or three substituents independently selected from the group consisting of fluorine and —OR$^h$;
R$^h$, at each occurrence, is independently hydrogen, C$_1$-C$_6$haloalkyl, or C$_1$-C$_6$alkyl;
R$^i$, at each occurrence, is independently C$_1$-C$_6$haloalkyl or C$_1$-C$_6$alkyl; and
R$^4$ and R$^5$ are each C$_1$-C$_6$alkyl.

81. The compound or pharmaceutically acceptable salt of claim 1, wherein the compound or pharmaceutically acceptable salt is an enantiomer of formula (VIb), wherein

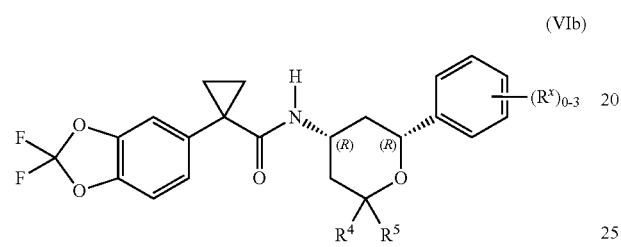

(VIb)

R$^x$, at each occurrence, is an optional substituent independently selected from C$_1$-C$_6$alkyl, halogen, —C(O)R$^i$, and —C(O)OR$^h$,
wherein, the C$_1$-C$_6$alkyl is optionally substituted with one, two or three substituents independently selected from the group consisting of fluorine and —OR$^h$;
R$^h$, at each occurrence, is independently hydrogen, C$_1$-C$_6$haloalkyl, or C$_1$-C$_6$alkyl;
R$^i$, at each occurrence, is independently C$_1$-C$_6$haloalkyl, or C$_1$-C$_6$alkyl; and
R$^4$ and R$^5$ are each C$_1$-C$_6$alkyl.

82. The compound or pharmaceutically acceptable salt of claim 71, wherein the compound or pharmaceutically acceptable salt is a trans diastereomer of formula (VII), wherein

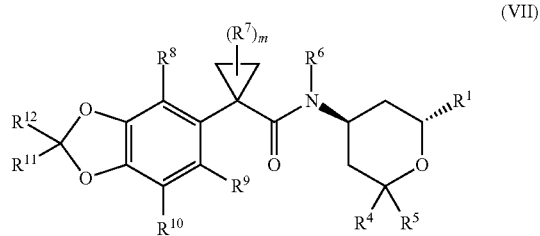

(VII)

R$^1$ is phenyl or phenyl fused to a 4-6-membered heterocycle, wherein the phenyl or the phenyl of phenyl fused to a 4-6-membered heterocycle are independently optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —SR$^h$, —S(O)$_2$R$^h$, —S(O)$_2$N(R$^h$)$_2$, —C(O)R$^i$, —C(O)OR$^h$, —C(O) N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$;
wherein, the C$_1$-C$_6$alkyl is optionally substituted with one, two or three substituents independently selected from the group consisting of fluorine, —OR$^h$, —OC(O)R$^i$, —OC(O)N(R$^h$)$_2$, —S(O)$_2$R$^h$, —S(O)$_2$N(R$^h$)$_2$, —C(O)R$^i$, —C(O)OR$^h$, —C (O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$;
wherein, the 4-6-membered heterocycle of phenyl fused to a 4-6-membered heterocycle is optionally substituted with 1, 2 or 3 independently selected R$^s$ groups; and
R$^4$ and R$^5$ are each C$_1$-C$_6$alkyl.

83. The compound or pharmaceutically acceptable salt of claim 82, wherein,
R$^1$ is phenyl, wherein the phenyl is optionally substituted with one, two, or three R$^x$ groups, wherein each R$^x$ group is independently selected, at each occurrence, from C$_1$-C$_6$alkyl, halogen, —CN, —NO$_2$, —OR$^h$, —OC(O)R$^i$, —OC(O)N(R$^h$)$_2$, —S(O)$_2$R$^h$, —S(O)$_2$N (R$^h$)$_2$, —C(O)R$^i$, —C(O)OR$^h$, —C(O) N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and G$^A$,
wherein the C$_1$-C$_6$alkyl is optionally substituted with one, two or three substituents independently selected from the group consisting of fluorine, —OR$^h$, —OC(O)R$^i$, —OC(O)N(R$^h$)$_2$, —S(O)$_2$R$^h$, —S(O)$_2$N(R$^h$)$_2$, —C(O)R$^i$, —C(O)OR$^h$, —C(O)N(R$^h$)$_2$, —N(R$^h$)$_2$, —N(R$^h$)C(O)R$^i$, —N(R$^h$)S(O)$_2$R$^i$, —N(R$^h$)C(O)O(R$^i$), —N(R$^h$)C(O)N(R$^h$)$_2$, and -G$^B$.

84. The compound or pharmaceutically acceptable salt of claim 83, wherein
R$^1$ is phenyl, wherein the phenyl is optionally substituted with one, two, or three R$^x$ groups, wherein each R$^x$ group is independently selected from C$_1$-C$_6$alkyl, halogen, —C(O)R$^i$, and —C(O)OR$^h$,
wherein the C$_1$-C$_6$alkyl is optionally substituted with one, two or three substituents independently selected from the group consisting of fluorine and —OR$^h$;
R$^h$, at each occurrence, is independently hydrogen, C$_1$-C$_6$haloalkyl, or C$_1$-C$_6$alkyl;
R$^i$, at each occurrence, is independently C$_1$-C$_6$haloalkyl, or C$_1$-C$_6$alkyl;
R$^6$ is hydrogen;
m is 0;
R$^8$, R$^9$, and R$^{10}$ are each hydrogen; and
R$^{11}$ and R$^{12}$ are each halogen.

85. The compound or pharmaceutically acceptable salt of claim 84, wherein R$^{11}$ and R$^{12}$ are each fluorine.

86. The compound or pharmaceutically acceptable salt of claim 85, wherein the compound or pharmaceutically acceptable salt is an enantiomer of formula (VIIa), wherein

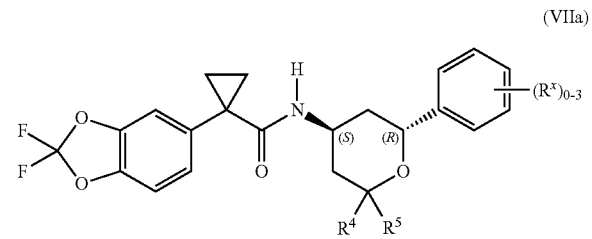

(VIIa)

R$^x$, at each occurrence, is an optional substituent independently selected from C$_1$-C$_6$alkyl, halogen, —C(O)R$^i$, and —C(O)OR$^h$,
wherein, the C$_1$-C$_6$alkyl is optionally substituted with one, two or three substituents independently selected from the group consisting of fluorine and —OR$^h$;

$R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl; and $R^4$ and $R^5$ are each $C_1$-$C_6$alkyl.

87. The compound or pharmaceutically acceptable salt of claim 1, wherein the compound or pharmaceutically acceptable salt is an enantiomer of formula (VIIb), wherein (VIIb)

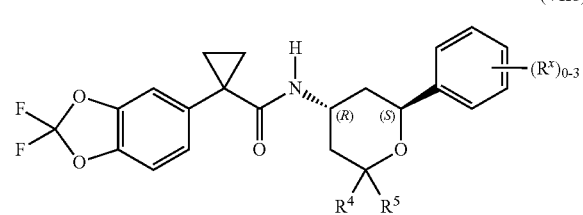

$R^x$, at each occurrence, is an optional substituent independently selected from $C_1$-$C_6$alkyl, halogen, —C(O)$R^i$, and —C(O)O$R^h$, wherein, the $C_1$-$C_6$alkyl is optionally substituted with one, two or three substituents independently selected from the group consisting of fluorine and —O$R^h$; and $R^h$, at each occurrence, is independently hydrogen, $C_1$-$C_6$haloalkyl, or $C_1$-$C_6$alkyl;

$R^i$, at each occurrence, is independently $C_1$-$C_6$haloalkyl, or $C_1$-$C_6$alkyl; and $R^4$ and $R^5$ are each $C_1$-$C_6$alkyl.

88. The compound or pharmaceutically acceptable salt of claim 1, selected from:

rac-1-(2,2-difluoro-1,3-benzodioxol-5-yl)-N-[(2R,4S)-2-phenyltetrahydro-2H-pyran-4-yl]cyclopropanecarboxamide;

rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

methyl rac-3-[(2R,4S)-4-({[1-(2,2-difluoro-1,3-benzodioxol-5-yl)cyclopropyl]carbonyl}amino)tetrahydro-2H-pyran-2-yl]benzoate;

methyl rac-3-[(2R,4R)-4-({[1-(2,2-difluoro-1,3-benzodioxol-5-yl)cyclopropyl]carbonyl}amino)tetrahydro-2H-pyran-2-yl]benzoate;

rac-3-[(2R,4R)-4-({[1-(2,2-difluoro-1,3-benzodioxol-5-yl)cyclopropyl]carbonyl}amino)tetrahydro-2H-pyran-2-yl]benzoic acid;

rac-1-(2,2-difluoro-1,3-benzodioxol-5-yl)-N-{(2R,4R)-2-[3-(hydroxymethyl)phenyl]tetrahydro-2H-pyran-4-yl}cyclopropanecarboxamide;

rac-1-(2,2-difluoro-1,3-benzodioxol-5-yl)-N-{(2R,4R)-2-[3-(2-hydroxypropan-2-yl)phenyl]tetrahydro-2H-pyran-4-yl}cyclopropanecarboxamide;

rac-N-[(2R,4S)-2-(3-acetylphenyl)tetrahydro-2H-pyran-4-yl]-(2,2-difluoro-1,3-benzodioxol-5-yl)cyclopropanecarboxamide;

rac-1-(2,2-difluoro-1,3-benzodioxol-5-yl)-N-{(2R,4S)-2-[3-(hydroxymethyl)phenyl]tetrahydro-2H-pyran-4-yl}cyclopropanecarboxamide;

rac-1-(2,2-difluoro-1,3-benzodioxol-5-yl)-N-{(2R,4S)-2-[3-(2-hydroxypropan-2-yl)phenyl]tetrahydro-2H-pyran-4-yl}cyclopropanecarboxamide;

methyl rac-2-[(2R,4S)-4-({[1-(2,2-difluoro-1,3-benzodioxol-5-yl)cyclopropyl]carbonyl}amino)tetrahydro-2H-pyran-2-yl]benzoate;

rac-2-[(2R,4S)-4-({[1-(2,2-difluoro-1,3-benzodioxol-5-yl)cyclopropyl]carbonyl}amino)tetrahydro-2H-pyran-2-yl]benzoic acid;

methyl rac-4-[(2R,4S)-4-({[1-(2,2-difluoro-1,3-benzodioxol-5-yl)cyclopropyl]carbonyl}amino)tetrahydro-2H-pyran-2-yl]benzoate;

rac-4-[(2R,4S)-4-({[1-(2,2-difluoro-1,3-benzodioxol-5-yl)cyclopropyl]carbonyl}amino)tetrahydro-2H-pyran-2-yl]benzoic acid;

N-[(2S,4R)-2-(1,3-benzodioxol-5-yl)tetrahydro-2H-pyran-4-yl]-(2,2-difluoro-1,3-benzodioxol-5-yl)cyclopropanecarboxamide;

methyl 3-[(2S,4R)-4-({[1-(2,2-difluoro-1,3-benzodioxol-5-yl)cyclopropyl]carbonyl}amino)tetrahydro-2H-pyran-2-yl]benzoate;

methyl 3-[(2R,4S)-4-({[1-(2,2-difluoro-1,3-benzodioxol-5-yl)cyclopropyl]carbonyl}amino)tetrahydro-2H-pyran-2-yl]benzoate;

3-[(2S,4R)-4-({[1-(2,2-difluoro-1,3-benzodioxol-5-yl)cyclopropyl]carbonyl}amino)tetrahydro-2H-pyran-2-yl]benzoic acid;

3-[(2R,4S)-4-({[1-(2,2-difluoro-1,3-benzodioxol-5-yl)cyclopropyl]carbonyl}amino)tetrahydro-2H-pyran-2-yl]benzoic acid;

N-[(2R,4R)-2-(4-bromophenyl)tetrahydro-2H-pyran-4-yl]-(2,2-difluoro-1,3-benzodioxol-5-yl)cyclopropanecarboxamide;

N-[(2S,4S)-2-(4-bromophenyl)tetrahydro-2H-pyran-4-yl]-(2,2-difluoro-1,3-benzodioxol-5-yl)cyclopropanecarboxamide;

methyl rac-3-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoate;

methyl rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoate;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

rac-3-[(2R,4R,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

methyl 4-[(2S,4R)-4-({[1-(2,2-difluoro-1,3-benzodioxol-5-yl)cyclopropyl]carbonyl}amino)tetrahydro-2H-pyran-2-yl]benzoate;

methyl 4-[(2R,4S)-4-({[1-(2,2-difluoro-1,3-benzodioxol-5-yl)cyclopropyl]carbonyl}amino)tetrahydro-2H-pyran-2-yl]benzoate;

4-[(2S,4R)-4-({[1-(2,2-difluoro-1,3-benzodioxol-5-yl)cyclopropyl]carbonyl}amino)tetrahydro-2H-pyran-2-yl]benzoic acid;

4-[(2R,4S)-4-({[1-(2,2-difluoro-1,3-benzodioxol-5-yl)cyclopropyl]carbonyl}amino)tetrahydro-2H-pyran-2-yl]benzoic acid;

methyl rac-4-[(2R,4S)-4-({[1-(2,2-difluoro-1,3-benzodioxol-5-yl)cyclopropyl]carbonyl}amino)-6,6-dimethyltetrahydro-2H-pyran-2-yl]benzoate;

rac-4-[(2R,4S)-4-({[1-(2,2-difluoro-1,3-benzodioxol-5-yl)cyclopropyl]carbonyl}amino)-6,6-dimethyltetrahydro-2H-pyran-2-yl]benzoic acid;

methyl rac-4-[(2R,4R)-4-({[1-(2,2-difluoro-1,3-benzodi-oxol-5-yl)cyclopropyl]carbonyl}amino)-6, 6-dimethyl-tetrahydro-2H-pyran-2-yl]benzoate
rac-4-[(2R,4R)-4-({[1-(2,2-difluoro-1,3-benzodioxol-5-yl)cyclopropyl]carbonyl}amino)-6,6-dimethyltetra-hydro-2H-pyran-2-yl]benzoic acid
methyl rac-4-[(2R,4S)-4-({[1-(2,2-difluoro-1,3-benzodi-oxol-5-yl)cyclopropyl]carbonyl}amino)tetrahydro-2H-pyran-2-yl]-methylbenzoate;
rac-4-[(2R,4S)-4-({[1-(2,2-difluoro-1,3-benzodioxol-5-yl)cyclopropyl]carbonyl}amino)tetrahydro-2H-pyran-2-yl]-methylbenzoic acid;
methyl rac-4-[(2R,6S)-6-cyclopropyl-4-({[1-(2,2-dif-luoro-1,3-benzodioxol-5-yl)cyclopropyl]carbonyl}amino)tetrahydro-2H-pyran-2-yl]benzoate;
methyl rac-4-[(2R,4S,6R)-4-({[1-(2,2-difluoro-1,3-ben-zodioxol-5-yl)cyclopropyl]carbonyl}amino)-6-methyl-tetrahydro-2H-pyran-2-yl]benzoate;
methyl rel-4-[(2S,4R)-4-({[1-(2,2-difluoro-1,3-benzodi-oxol-5-yl)cyclopropyl]carbonyl}amino)tetrahydro-2H-pyran-2-yl]-methylbenzoate;
methyl rel-4-[(2R,4S)-4-({[1-(2,2-difluoro-1,3-benzodi-oxol-5-yl)cyclopropyl]carbonyl}amino)tetrahydro-2H-pyran-2-yl]-methylbenzoate;
rel-4-[(2S,4R)-4-({[1-(2,2-difluoro-1,3-benzodioxol-5-yl)cyclopropyl]carbonyl}amino)tetrahydro-2H-pyran-2-yl]-methylbenzoic acid;
rel-4-[(2R,4S)-4-({[1-(2,2-difluoro-1,3-benzodioxol-5-yl)cyclopropyl]carbonyl}amino)tetrahydro-2H-pyran-2-yl]-methylbenzoic acid;
4-[6-cyclopropyl-4-({[1-(2,2-difluoro-1,3-benzodioxol-5-yl)cyclopropyl]carbonyl}amino)tetrahydro-2H-pyran-2-yl]benzoic acid;
rac-4-[(2R,4S,6R)-4-({[1-(2,2-difluoro-1,3-benzodioxol-5-yl)cyclopropyl]carbonyl}amino)-6-methyltetra-hydro-2H-pyran-2-yl]benzoic acid;
methyl rac-4-[(2R,4R,6R)-4-({[1-(2,2-difluoro-1,3-ben-zodioxol-5-yl)cyclopropyl]carbonyl}amino)-6-methyl-tetrahydro-2H-pyran-2-yl]benzoate;
methyl rac-4-[(2R,4R,6S)-4-({[1-(2,2-difluoro-1,3-ben-zodioxol-5-yl)cyclopropyl]carbonyl}amino)-6-phe-nyltetrahydro-2H-pyran-2-yl]benzoate;
methyl rac-4-[(2R,4S,6S)-4-({[1-(2,2-difluoro-1,3-ben-zodioxol-5-yl)cyclopropyl]carbonyl}amino)-6-phe-nyltetrahydro-2H-pyran-2-yl]benzoate;
rac-4-[(2R,4R,6S)-4-({[1-(2,2-difluoro-1,3-benzodioxol-5-yl)cyclopropyl]carbonyl}amino)-6-phenyltetra-hydro-2H-pyran-2-yl]benzoic acid;
rac-4-[(2R,4S,6S)-4-({[1-(2,2-difluoro-1,3-benzodioxol-5-yl)cyclopropyl]carbonyl}amino)-6-phenyltetra-hydro-2H-pyran-2-yl]benzoic acid;
dimethyl rac-4,4'-[(2R,4S,6S)-4-({[1-(2,2-difluoro-1,3-benzodioxol-5-yl)cyclopropyl]carbonyl}amino)tetra-hydro-2H-pyran-2,6-diyl]dibenzoate;
dimethyl rac-4,4'-[(2R,4r,6S)-4-({[1-(2,2-difluoro-1,3-benzodioxol-5-yl)cyclopropyl]carbonyl}amino)tetra-hydro-2H-pyran-2,6-diyl]dibenzoate;
rel-4-[(2R,4S,6S)-4-({[1-(2,2-difluoro-1,3-benzodioxol-5-yl)cyclopropyl]carbonyl}amino)-6-phenyltetra-hydro-2H-pyran-2-yl]benzoic acid;
rel-4-[(2S,4R,6R)-4-({[1-(2,2-difluoro-1,3-benzodioxol-5-yl)cyclopropyl]carbonyl}amino)-6-phenyltetra-hydro-2H-pyran-2-yl]benzoic acid;
methyl rac-4-[(2R,4R,6S)-4-({[1-(2,2-difluoro-1,3-ben-zodioxol-5-yl)cyclopropyl]carbonyl}amino)-6-(4-methoxyphenyl)tetrahydro-2H-pyran-2-yl]benzoate;
rac-4-[(2R,4S,6S)-4-({[1-(2,2-difluoro-1,3-benzodioxol-5-yl)cyclopropyl]carbonyl}amino)-6-(4-methoxyphe-nyl)tetrahydro-2H-pyran-2-yl]benzoic acid;
rac-4-[(2R,4R,6S)-4-({[1-(2,2-difluoro-1,3-benzodioxol-5-yl)cyclopropyl]carbonyl}amino)-6-(4-methoxyphe-nyl)tetrahydro-2H-pyran-2-yl]benzoic acid;
rel-4-[(2S,4R,6S)-4-({[1-(2,2-difluoro-1,3-benzodioxol-5-yl)cyclopropyl]carbonyl}amino)-6-methyltetra-hydro-2H-pyran-2-yl]benzoic acid;
rel-4-[(2R,4S,6R)-4-({[1-(2,2-difluoro-1,3-benzodioxol-5-yl)cyclopropyl]carbonyl}amino)-6-methyltetra-hydro-2H-pyran-2-yl]benzoic acid;
rac-4-[(2R,4S,6S)-4-({[1-(2,2-difluoro-1,3-benzodioxol-5-yl)cyclopropyl]carbonyl}amino)-6-phenyltetra-hydro-2H-pyran-2-yl]-fluorobenzoic acid;
rac-4-[(2R,4R,6S)-4-({[1-(2,2-difluoro-1,3-benzodioxol-5-yl)cyclopropyl]carbonyl}amino)-6-phenyltetra-hydro-2H-pyran-2-yl]-fluorobenzoic acid;
methyl rac-4-[(2R,4S,6S)-4-({[1-(2,2-difluoro-1,3-ben-zodioxol-5-yl)cyclopropyl]carbonyl}amino)-6-phe-nyltetrahydro-2H-pyran-2-yl]-methylbenzoate;
methyl rac-4-[(2R,4S,6S)-4-({[1-(2,2-difluoro-1,3-ben-zodioxol-5-yl)cyclopropyl]carbonyl}amino)-6-phe-nyltetrahydro-2H-pyran-2-yl]-3-fluorobenzoate;
rac-4-[(2R,4R,6S)-4-({[1-(2,2-difluoro-1,3-benzodioxol-5-yl)cyclopropyl]carbonyl}amino)-6-phenyltetra-hydro-2H-pyran-2-yl]-3-methylbenzoic acid;
rac-4-[(2R,4R,6S)-4-({[1-(2,2-difluoro-1,3-benzodioxol-5-yl)cyclopropyl]carbonyl}amino)-6-phenyltetra-hydro-2H-pyran-2-yl]-3-methylbenzoic acid;
rel-4-[(2R,4R,6S)-4-({[1-(2,2-difluoro-1,3-benzodioxol-5-yl)cyclopropyl]carbonyl}amino)-6-(4-methoxyphe-nyl)tetrahydro-2H-pyran-2-yl]benzoic acid;
rel-4-[(2S,4S,6R)-4-({[1-(2,2-difluoro-1,3-benzodioxol-5-yl)cyclopropyl]carbonyl}amino)-6-(4-methoxyphe-nyl)tetrahydro-2H-pyran-2-yl]benzoic acid;
ethyl rac-3-[(2R,4R,6S)-4-({[1-(2,2-difluoro-1,3-benzo-dioxol-5-yl)cyclopropyl]carbonyl}amino)-6-(3-methoxyphenyl)tetrahydro-2H-pyran-2-yl]benzoate;
rac-3-[(2R,4R,6S)-4-({[1-(2,2-difluoro-1,3-benzodioxol-5-yl)cyclopropyl]carbonyl}amino)-6-(3-methoxyphe-nyl)tetrahydro-2H-pyran-2-yl]benzoic acid;
rac-3-[(2R,4S,6S)-4-({[1-(2,2-difluoro-1,3-benzodioxol-5-yl)cyclopropyl]carbonyl}amino)-6-phenyltetra-hydro-2H-pyran-2-yl]-4-methylbenzoic acid;
methyl rac-3-[(2R,4S,6S)-4-({[1-(2,2-difluoro-1,3-ben-zodioxol-5-yl)cyclopropyl]carbonyl}amino)-6-phe-nyltetrahydro-2H-pyran-2-yl]-4-methylbenzoate;
ethyl rac-3-[(2R,4S,6S)-4-({[1-(2,2-difluoro-1,3-benzo-dioxol-5-yl)cyclopropyl]carbonyl}amino)-6-phenyltet-rahydro-2H-pyran-2-yl]-5-methylbenzoate;
rac-3-[(2R,4S,6S)-4-({[1-(2,2-difluoro-1,3-benzodioxol-5-yl)cyclopropyl]carbonyl}amino)-6-phenyltetra-hydro-2H-pyran-2-yl]-5-methylbenzoic acid;
rel-3-[(2R,4R,6S)-4-({[1-(2,2-difluoro-1,3-benzodioxol-5-yl)cyclopropyl]carbonyl}amino)-6-(3-methoxyphe-nyl)tetrahydro-2H-pyran-2-yl]benzoic acid;
rel-3-[(2R,4S,6S)-4-({[1-(2,2-difluoro-1,3-benzodioxol-5-yl)cyclopropyl]carbonyl}amino)-6-phenyltetra-hydro-2H-pyran-2-yl]-5-methylbenzoic acid; and
rel-3-[(2S,4R,6R)-4-({[1-(2,2-difluoro-1,3-benzodioxol-5-yl)cyclopropyl]carbonyl}amino)-6-phenyltetra-hydro-2H-pyran-2-yl]-5-methylbenzoic acid.

89. A pharmaceutical composition comprising a therapeutically effective amount of a compound of formula (I) according to claim 1, or a pharmaceutically acceptable salt thereof, in combination with a pharmaceutically acceptable carrier.

90. A method for alleviating cystic fibrosis in a subject comprising administering a therapeutically effective amount of a compound of formula (I) according to claim 1 or a pharmaceutically acceptable salt thereof, to a subject in need thereof.

91. A pharmaceutical composition comprising a compound of claim 1 or a pharmaceutically acceptable salt thereof, and one or more additional therapeutic agents.

92. The pharmaceutical composition of claim 91 wherein the additional therapeutic agents are selected from the group consisting of CFTR modulators and CFTR amplifiers.

93. The pharmaceutical composition of claim 92 wherein the additional therapeutic agents are CFTR modulators.

94. A pharmaceutical composition comprising a compound of claim 1 or a pharmaceutically acceptable salt thereof, one potentiator, and one or more correctors.

95. A method for alleviating cystic fibrosis in a subject comprising administering a compound of claim 1 or a pharmaceutically acceptable salt thereof, and one or more additional therapeutic agents.

96. The method of claim 95 wherein the additional therapeutic agents are selected from the group consisting of CFTR modulators and CFTR amplifiers.

97. The method of claim 95 wherein the additional therapeutic agents are CFTR modulators.

98. A method for alleviating cystic fibrosis in a subject comprising administering a compound of claim 1 or a pharmaceutically acceptable salt thereof, one potentiator, and one or more correctors.

* * * * *